(12) United States Patent
Kang et al.

(10) Patent No.: US 10,319,918 B2
(45) Date of Patent: Jun. 11, 2019

(54) ORGANIC ELECTROLUMINESCENT COMPOUND AND ORGANIC ELECTROLUMINESCENT DEVICE COMPRISING THE SAME

(71) Applicant: Rohm and Haas Electronic Materials Korea Ltd., Cheonan (KR)

(72) Inventors: Hyun-Ju Kang, Gwangmyeong (KR); Hee-Ryong Kang, Seoul (KR); Young-Gil Kim, Cheonan (KR); Chi-Sik Kim, Hwaseong (KR); Seon-Woo Lee, Osan (KR); Jeong-Eun Yang, Suwon (KR); Hee-Choon Ahn, Seoul (KR); Kyoung-Jin Park, Seongnam (KR); Tae-Jin Lee, Seoul (KR)

(73) Assignee: ROHM AND HAAS ELECTRONIC MATERIALS KOREA LTD, Cheonan (KR)

( * ) Notice: Subject to any disclaimer, the term of this patent is extended or adjusted under 35 U.S.C. 154(b) by 0 days.

(21) Appl. No.: 15/671,365

(22) Filed: Aug. 8, 2017

(65) Prior Publication Data

US 2017/0352814 A1 Dec. 7, 2017

Related U.S. Application Data

(62) Division of application No. 15/311,539, filed as application No. PCT/KR2015/005322 on May 27, 2015, now Pat. No. 9,768,394.

(30) Foreign Application Priority Data

May 27, 2014 (KR) .................. 10-2014-0063792
May 22, 2015 (KR) .................. 10-2015-0072071

(51) Int. Cl.
| | | |
|---|---|---|
| *C07D 491/147* | (2006.01) | |
| *H01L 51/00* | (2006.01) | |
| *C09K 11/02* | (2006.01) | |
| *H01L 51/50* | (2006.01) | |

(52) U.S. Cl.
CPC ...... *H01L 51/0071* (2013.01); *C07D 491/147* (2013.01); *C09K 11/025* (2013.01); *H01L 51/0072* (2013.01); *H01L 51/0052* (2013.01); *H01L 51/0085* (2013.01); *H01L 51/5016* (2013.01)

(58) Field of Classification Search
CPC .................................................. C07D 491/147
See application file for complete search history.

(56) References Cited

U.S. PATENT DOCUMENTS

| | | |
|---|---|---|
| 9,859,507 B2 | 1/2018 | Kang et al. |
| 2014/0191225 A1 | 7/2014 | Inoue et al. |
| 2015/0228909 A1 | 8/2015 | Kim et al. |

FOREIGN PATENT DOCUMENTS

WO 2013154325 A1 10/2013

OTHER PUBLICATIONS

Eom, et al. (Document No. 161:575416, CAPLUS); retrieved from STN; Sep. 23, 2014.*
Chinese Search Report for application No. 201580026103.8: dated May 27, 2015.

* cited by examiner

*Primary Examiner* — Shawquia Jackson
(74) *Attorney, Agent, or Firm* — S. Matthew Cairns

(57) ABSTRACT

The present disclosure relates to an organic electroluminescent compound and an organic electroluminescent device comprising the same. By using the organic electroluminescent compound according to the present disclosure, it is possible to produce an organic electroluminescent device which has a low driving voltage, excellent current and power efficiencies, and improved operation lifespan.

7 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent (EL) device is a self-light-emitting device which has advantages in that it provides a wider viewing angle, a greater contrast ratio, and a faster response time. An organic EL device was first developed by Eastman Kodak, by using small aromatic diamine molecules and aluminum complexes as materials to form a light-emitting layer [Appl. Phys. Lett. 51, 913, 1987].

The most important factor determining luminous efficiency in the organic EL device is light-emitting materials. Until now, fluorescent materials have been widely used as light-emitting material. However, in view of electroluminescent mechanisms, since phosphorescent materials theoretically enhance luminous efficiency by four (4) times compared to fluorescent materials, phosphorescent light-emitting materials have been widely researched. Iridium(III) complexes have been widely known as phosphorescent materials, including bis(2-(2'-benzothienyl)-pyridinato-N,C-3')iridium(acetylacetonate) ((acac)Ir(btp)$_2$), tris(2-phenylpyridine)iridium (Ir(ppy)$_3$) and bis(4,6-difluorophenylpyridinato-N,C2)picolinate iridium (Firpic) as red-, green-, and blue-emitting materials, respectively.

At present, 4,4'-N,N'-dicarbazol-biphenyl (CBP) is the most widely known host material for phosphorescent materials. Recently, Pioneer (Japan) et al., developed a high performance organic EL device using bathocuproine (BCP) and aluminum(III) bis(2-methyl-8-quinolinate)(4-phenylphenolate) (BAlq) etc., as host materials, which were known as hole blocking materials.

Although these materials provide good luminous characteristics, they have the following disadvantages: (1) Due to their low glass transition temperature and poor thermal stability, their degradation may occur during a high-temperature deposition process in a vacuum, which results in poor lifespan. (2) The power efficiency of the organic EL device is given by [(π/voltage)×current efficiency], and the power efficiency is inversely proportional to the voltage. Although the organic EL device comprising phosphorescent host materials provides higher current efficiency (cd/A) than one comprising fluorescent materials, a significantly high driving voltage is necessary. Thus, there is no merit in terms of power efficiency (lm/W). (3) Furthermore, the operational lifespan of the organic EL device is short, and luminous efficiency is still required to be improved.

Korean Patent No. 955993 discloses an indolocarbazole derivative substituted with a nitrogen-containing heterocycle. However, it fails to disclose an indolocarbazole derivative fused with a benzofuran or benzothiophene.

DISCLOSURE OF THE INVENTION

Problems to be Solved

The objective of the present disclosure is to provide an organic electroluminescent compound, which can provide an organic electroluminescent device showing long lifespan, low driving voltage, and good luminos efficiency such as current and power efficiencies, and an organic electroluminescent device comprising the same.

Solution to Problems

The present inventors found that the above objective can be achieved by an organic electroluminescent compound represented by the following formula 1.

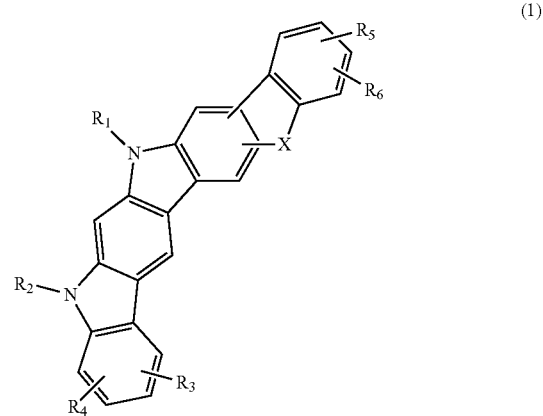

(1)

wherein

X represents —O— or —S—;

$R_1$ to $R_6$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent(s) to form a (3- to 30-membered), mono- or polycyclic, alicyclic or aromatic ring whose carbon atom(s) may be replaced with at least one hetero atom selected from nitrogen, oxygen, and sulfur; and the heteroaryl contains at least one hetero atom selected from B, N, O, S, Si, and P.

Effects of the Invention

The organic electroluminescent compound of the present disclosure can provide an organic electroluminescent device having a low driving voltage, excellent current and power efficiencies, and remarkably improved operation lifespan.

EMBODIMENTS OF THE INVENTION

Hereinafter, the present disclosure will be described in detail. However, the following description is intended to explain the invention, and is not meant in any way to restrict the scope of the invention.

The present disclosure provides the organic electroluminescent compound of formula 1 above, an organic electroluminescent material comprising the organic electroluminescent compound, and an organic electroluminescent device comprising the organic electroluminescent compound.

The details of the organic electroluminescent compound of formula 1 are as follows.

Herein, "alkyl" includes methyl, ethyl, n-propyl, isopropyl, n-butyl, isobutyl, tert-butyl, etc. "Cycloalkyl" includes cyclopropyl, cyclobutyl, cyclopentyl, cyclohexyl, etc. "(3- to 7-membered)heterocycloalkyl" indicates a cycloalkyl having 3 to 7 ring backbone atoms including at least one hetero atom selected from B, N, O, S, Si, and P, preferably O, S, and N, and includes tetrahydrofuran, pyrrolidine, thiolan, tetrahydropyran, etc. Furthermore, "aryl(ene)" indicates a monocyclic or fused ring derived from an aromatic hydrocarbon, and includes a spiro compound in which two rings are connected through one atom. The aryl includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "(3- to 30-membered)heteroaryl(ene)" indicates an aryl group having 3 to 30 ring backbone atoms including at least one, preferably 1 to 4, hetero atom selected from the group consisting of B, N, O, S, Si, and P, preferably O, S, and N; may be a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidyl, pyridazinyl, etc., and a fused ring-type heteroaryl such as benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, dihydroacridinyl, etc. Furthermore, "halogen" includes F, Cl, Br, and I.

Herein, "substituted" in the expression, "substituted or unsubstituted," means that a hydrogen atom in a certain functional group is replaced with another atom or group, i.e. a substituent. The substituents for the substituted alkyl, the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted mono- or polycyclic, alicyclic or aromatic ring of $R_1$ to $R_6$, $L_1$, $L_2$, $A_1$, $A_2$, M, $L_4$, L, $Y_1$, $Y_2$, $R_{21}$ to $R_{27}$, $R_{31}$ to $R_{33}$, $R_{100}$ to $R_{109}$, $R_{111}$ to $R_{127}$, and $R_{201}$ to $R_{211}$, each independently, are at least one selected from the group consisting of deuterium, a halogen, a cyano, a carboxy, a nitro, a hydroxy, a (C1-C30)alkyl, a halo(C1-C30)alkyl, a (C1-C30)alkoxy, a (C1-C30)alkylthio, a (C3-C30)cycloalkyl, a 3- to 7-membered heterocycloalkyl, a (C6-C30)aryloxy, a (C6-C30)arylthio, a 3- to 30-membered heteroaryl unsubstituted or substituted with a (C6-C30)aryl or a di(C6-C30)arylamino, a (C6-C30)aryl unsubstituted or substituted with a 3- to 30-membered heteroaryl or a di(C6-C30)arylamino, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

Specifically, the compound represented by formula 1 may be represented by any one of the following formulae 2 to 7; and more specifically, may be represented by formula 2 or 7.

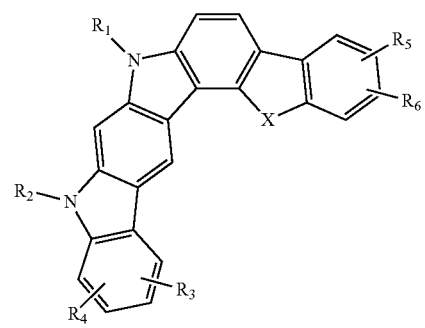

(2)

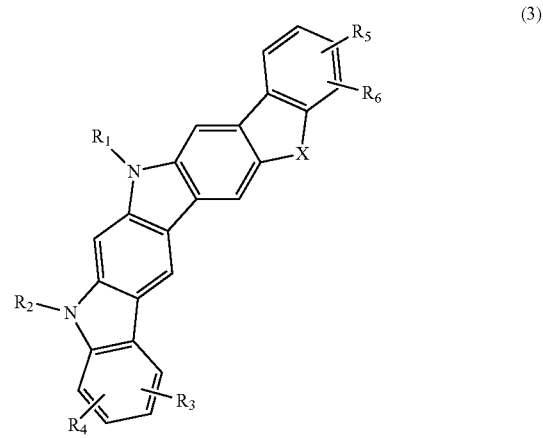

(3)

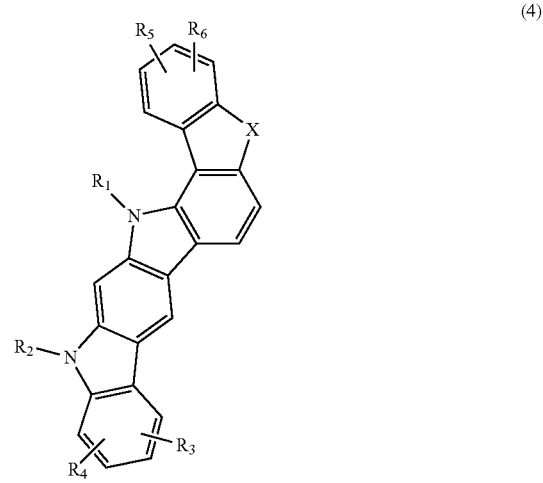

(4)

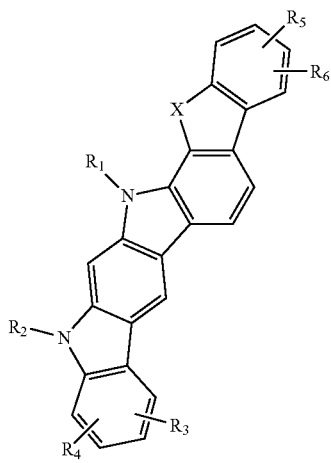
(5)

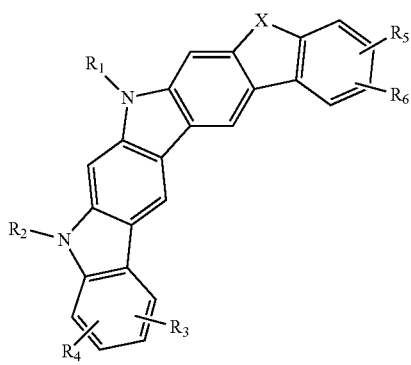
(6)

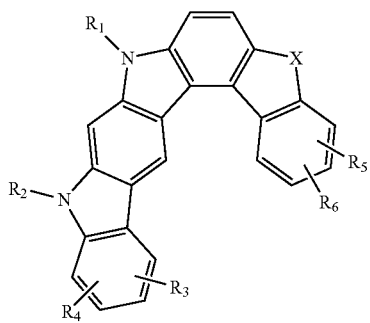
(7)

wherein X, and $R_1$ to $R_6$ are as defined in formula 1.

Specifically, $R_1$ and $R_2$, each independently, may represent hydrogen, a substituted or unsubstituted (C6-C30)aryl, or a substituted or unsubstituted 5- to 30-membered heteroaryl. More specifically, $R_1$ may be hydrogen or the group represented by the following formula 8; and $R_2$ may be hydrogen, or the group represented by the following formula 9.

*-$L_1$-$Ar_1$  (8)

*-$L_2$-$Ar_2$  (9)

wherein
$L_1$ and $L_2$, each independently, represent a single bond, a substituted or unsubstituted (C6-C30)arylene, or a substituted or unsubstituted 3- to 30-membered heteroarylene;

$Ar_1$ and $Ar_2$, each independently, represent a substituted or unsubstituted (C6-C30)aryl, or a substituted or unsubstituted 3- to 30-membered heteroaryl;

the heteroaryl contains at least one hetero atom selected from B, N, O, S, Si, and P; and

* represents a bonding site.

Specifically, $L_1$ and $L_2$, each independently, may represent a single bond, or a substituted or unsubstituted (C6-C20)arylene. More specifically, $L_1$ and $L_2$, each independently, may represent a single bond, a substituted or unsubstituted phenylene, a substituted or unsubstituted biphenylene, a substituted or unsubstituted terphenylene, a substituted or unsubstituted naphthylene, a substituted or unsubstituted binaphthylene, a substituted or unsubstituted phenanthrenylene, a substituted or unsubstituted anthracenylene, a substituted or unsubstituted triphenylenylene, a substituted or unsubstituted fluoranthenylene, a substituted or unsubstituted pyrenylene, a substituted or unsubstituted tetracenylene, a substituted or unsubstituted perylenylene, a substituted or unsubstituted chrysenylene, or a substituted or unsubstituted fluorenylene.

Specifically, $Ar_1$ and $Ar_2$, each independently, may represent a substituted or unsubstituted (C6-C20)aryl; or a substituted or unsubstituted nitrogen-containing 5- to 20-membered heteroaryl. More specifically, $Ar_1$ and $Ar_2$, each independently, may represent a substituted or unsubstituted phenyl, a substituted or unsubstituted biphenyl, a substituted or unsubstituted terphenyl, a substituted or unsubstituted naphthyl, a substituted or unsubstituted binaphthyl, a substituted or unsubstituted phenanthrenyl, a substituted or unsubstituted anthracenyl, a substituted or unsubstituted triphenylenyl, a substituted or unsubstituted fluoranthenyl, a substituted or unsubstituted pyrenyl, a substituted or unsubstituted tetracenyl, a substituted or unsubstituted perylenyl, or a substituted or unsubstituted chrysenyl, a substituted or unsubstituted fluorenyl, a substituted or unsubstituted benzofluorenyl, a substituted or unsubstituted dibenzofluorenyl, a substituted or unsubstituted pyridyl, a substituted or unsubstituted pyrazinyl, a substituted or unsubstituted pyrimidyl, a substituted or unsubstituted pyridazinyl, a substituted or unsubstituted triazinyl, a substituted or unsubstituted quinolyl, a substituted or unsubstituted isoquinolyl, a substituted or unsubstituted cinnolinyl, a substituted or unsubstituted quinazolinyl, a substituted or unsubstituted quinoxalinyl, or a substituted or unsubstituted phthalazinyl. Specifically, the substituent of the substituted group of $Ar_1$ and $Ar_2$, each independently, may be selected from the group consisting of a (C1-C10)alkyl, a (C6-C20) aryl, and a 5- to 20-membered heteroaryl.

More specifically, the group represented by formula 8 and the group represented by formula 9, each independently, may be selected from the following.

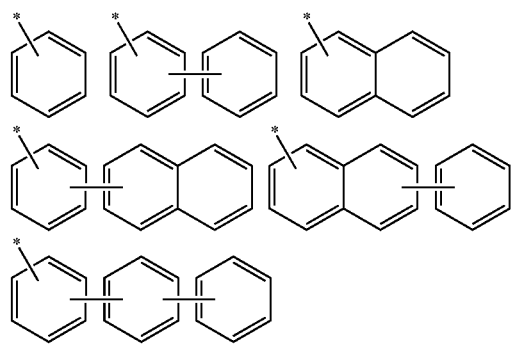

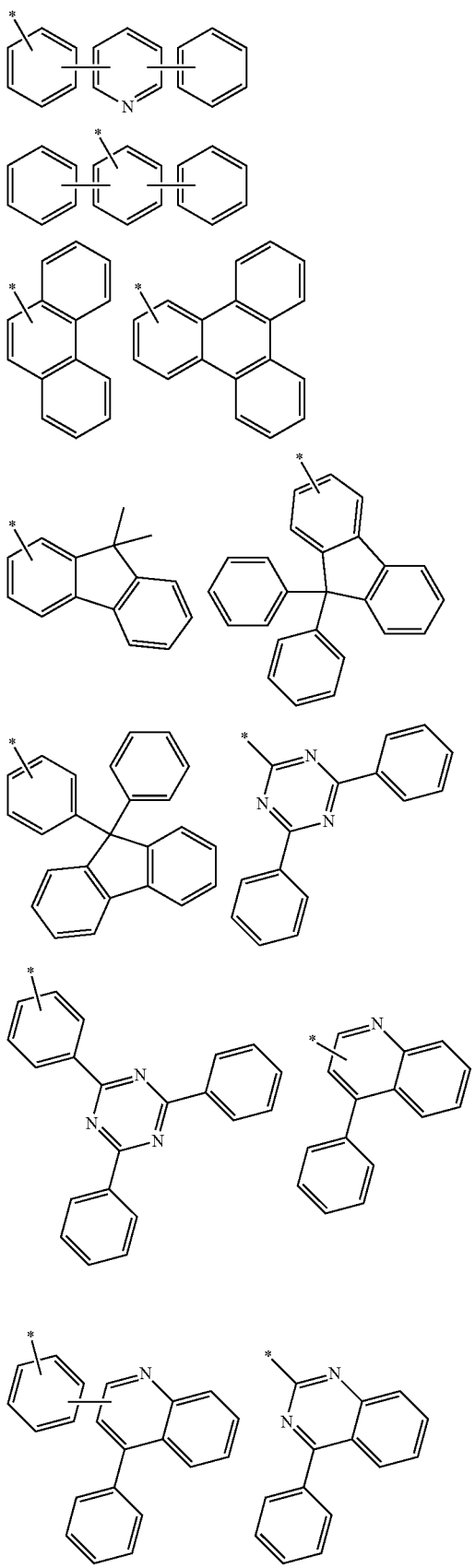

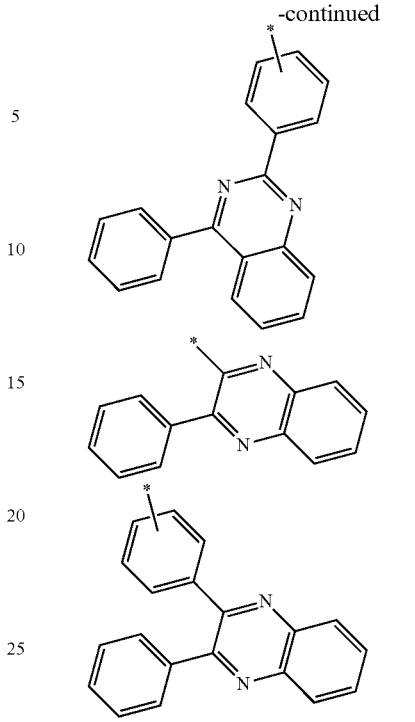

Specifically, $R_3$ to $R_6$, each independently, may represent hydrogen, deuterium, a halogen, a cyano, a substituted or unsubstituted (C1-C10)alkyl, a substituted or unsubstituted (C6-C18)aryl, or a substituted or unsubstituted 5- to 18-membered heteroaryl, or may be linked to an adjacent substituent(s) to form a mono- or polycyclic 5- to 18-membered aromatic ring whose carbon atom(s) may be replaced with at least one hetero atom selected from nitrogen, oxygen, and sulfur. More specifically, $R_3$ to $R_6$, each independently, may represent hydrogen, a substituted or unsubstituted (C6-C18)aryl, or a substituted or unsubstituted 5- to 18-membered heteroaryl, or may be linked to an adjacent substituent(s) to form a mono- or polycyclic 5- to 18-membered aromatic ring.

More specifically, the organic electroluminescent compound of the present disclosure includes the following, but is not limited thereto:

A-1

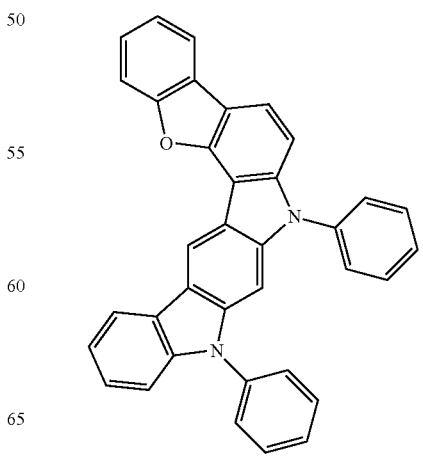

A-2
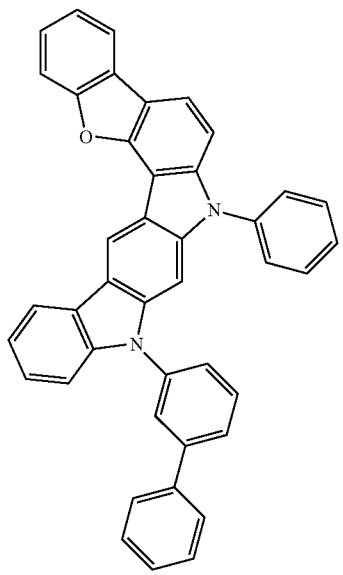
A-3
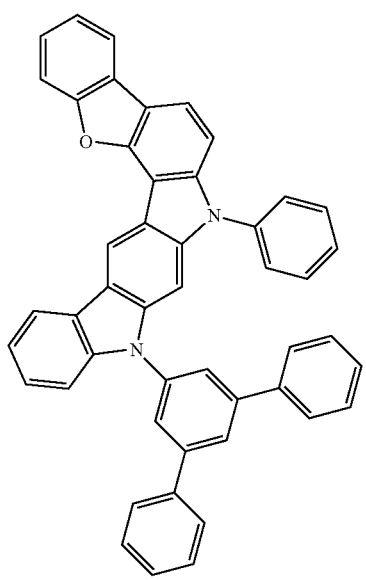
A-4
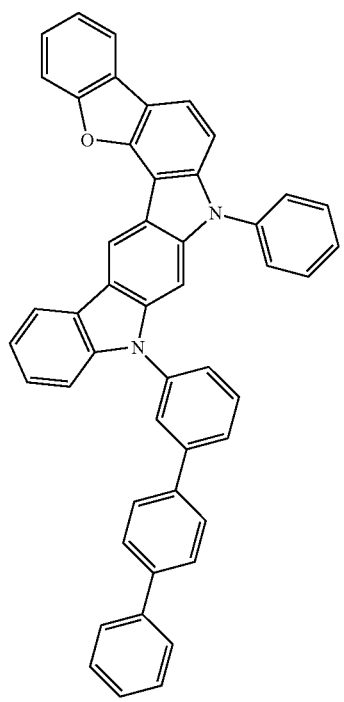
A-5
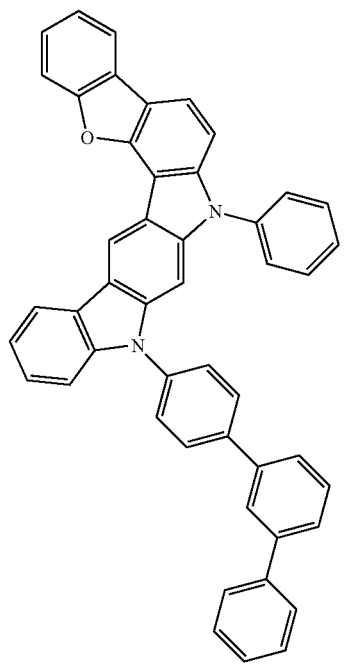

A-6
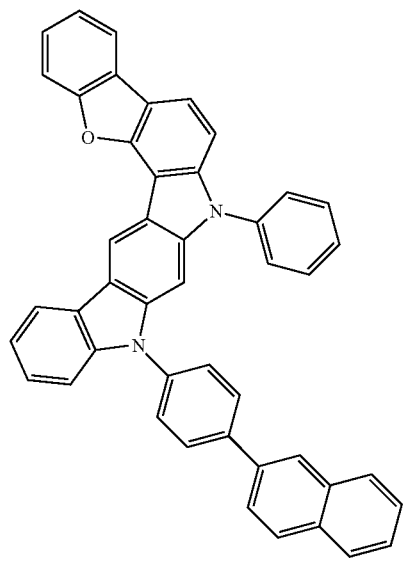
A-7
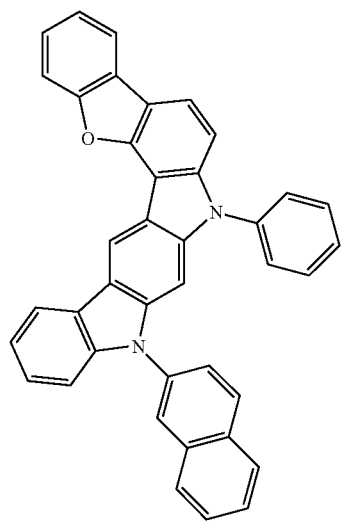
A-8
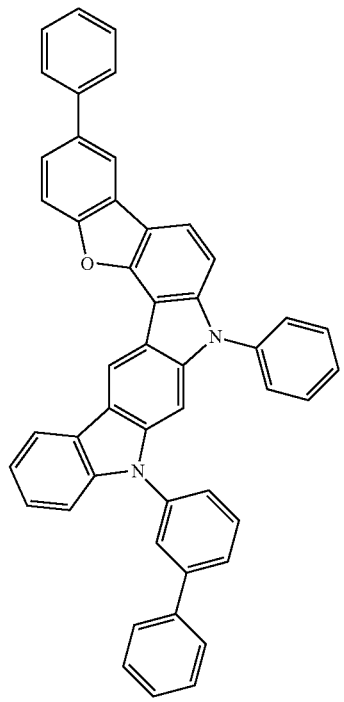
A-9
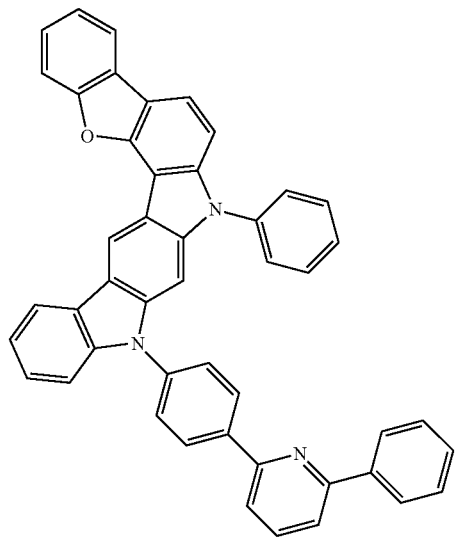

A-10
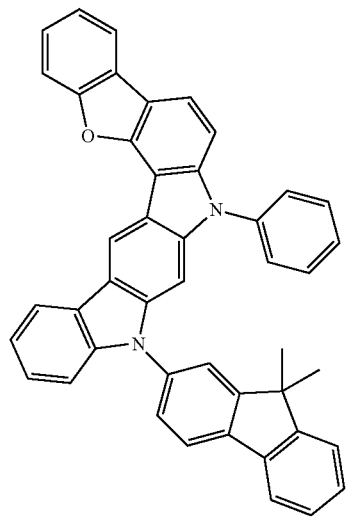
A-11
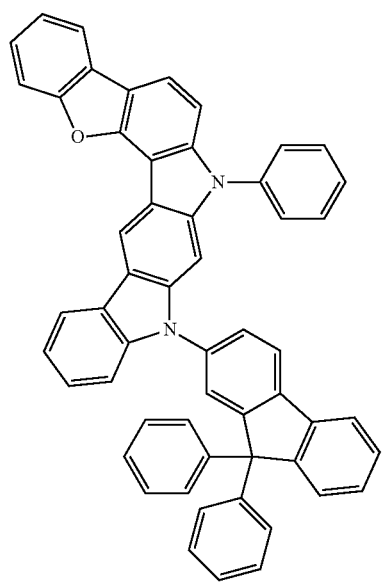
A-12
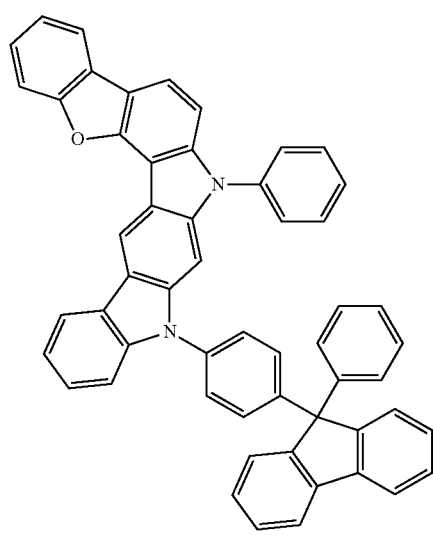
A-13
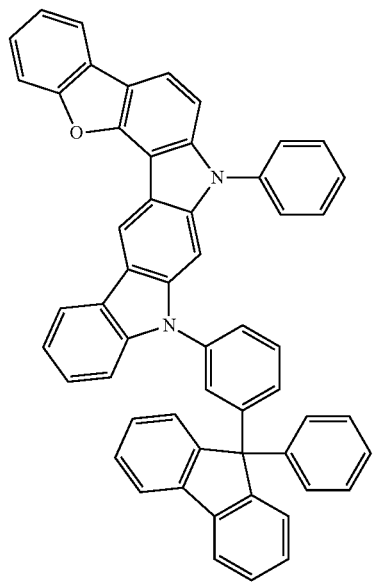
A-14
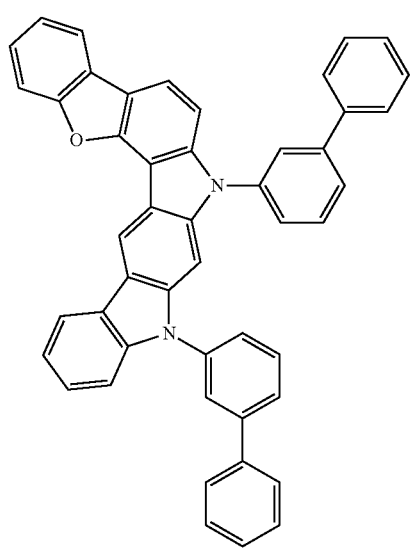
A-15
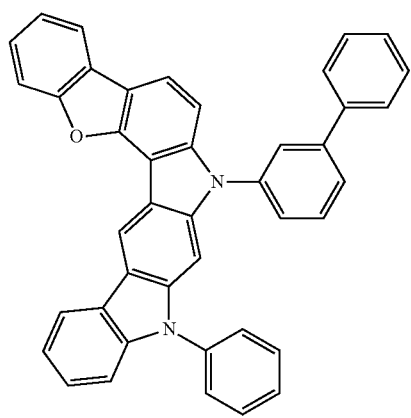

A-16
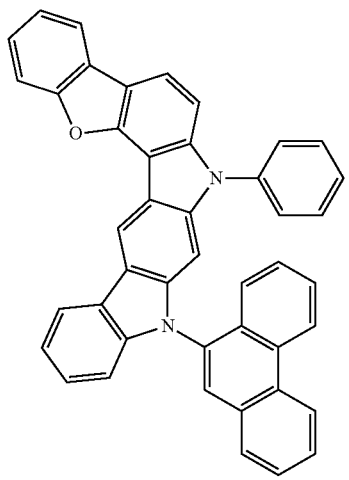
A-17
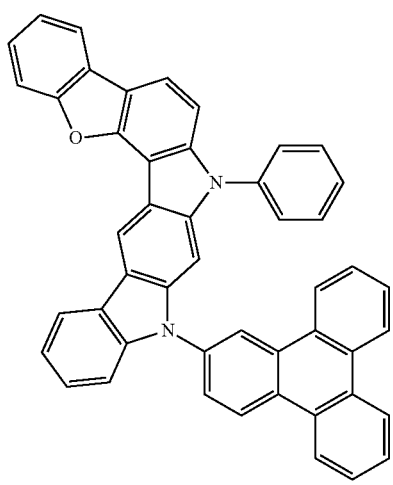
A-18
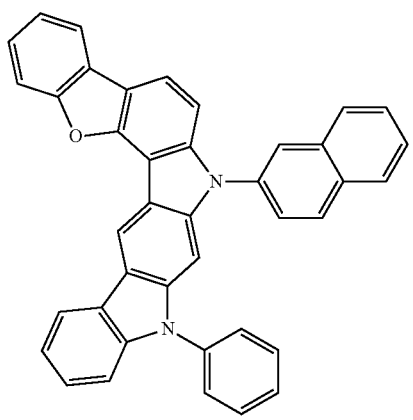
A-19
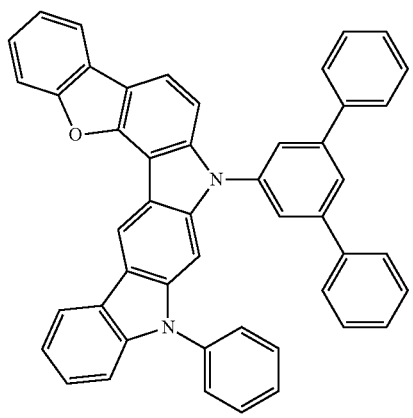
A-20
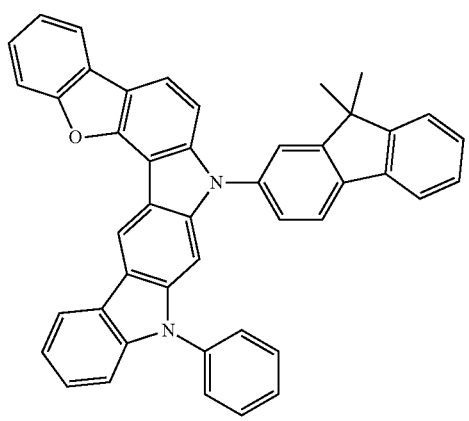
A-21
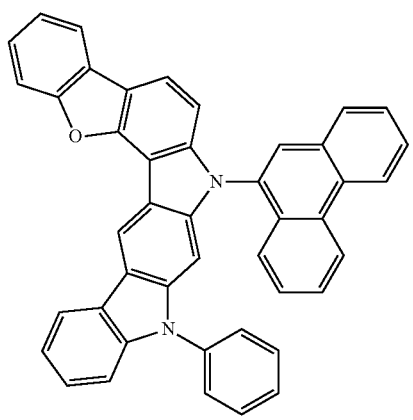

A-22
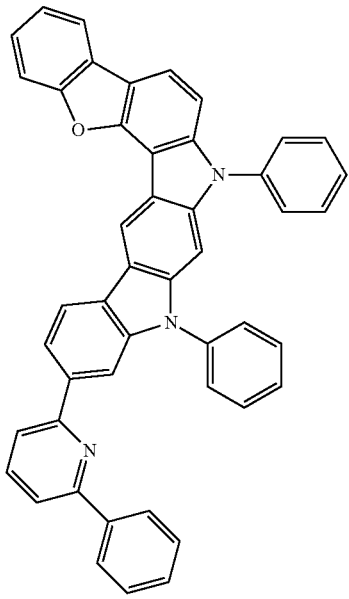
A-23
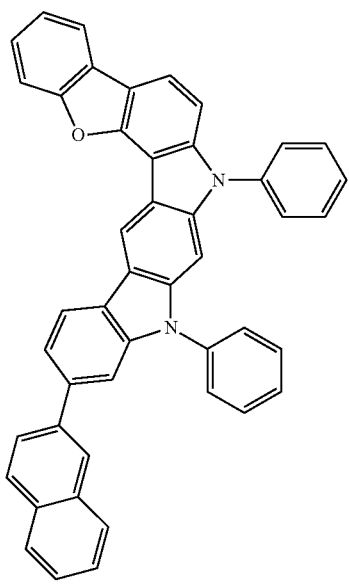
A-24
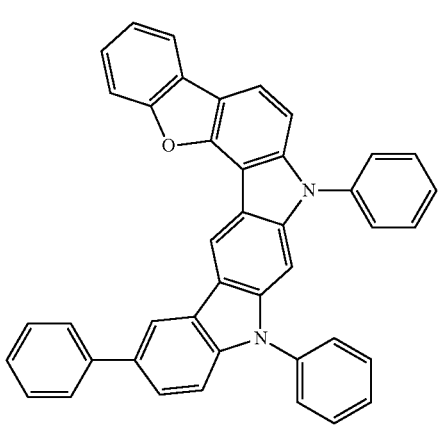
A-25
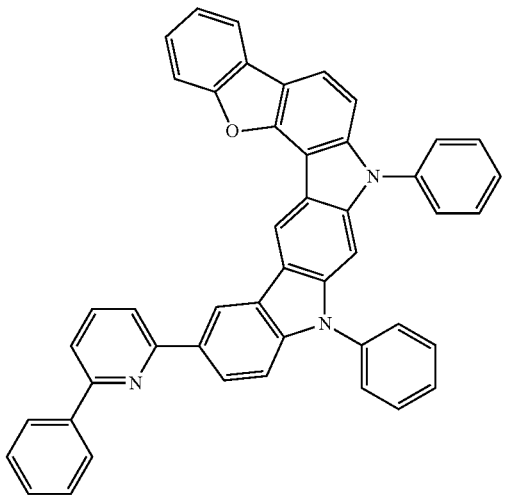
A-26
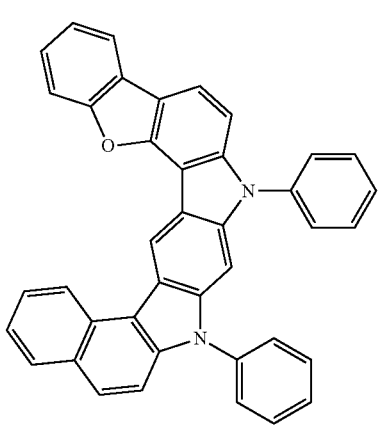
A-27
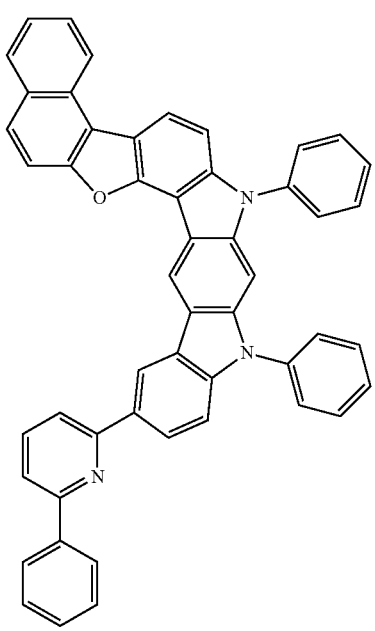

-continued
A-28
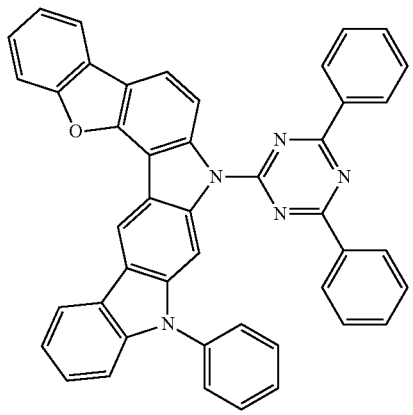
A-29
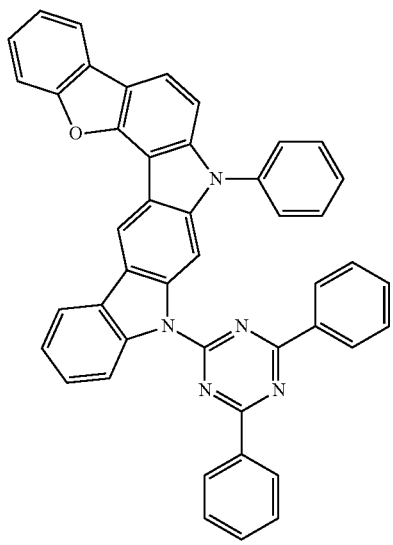
A-30
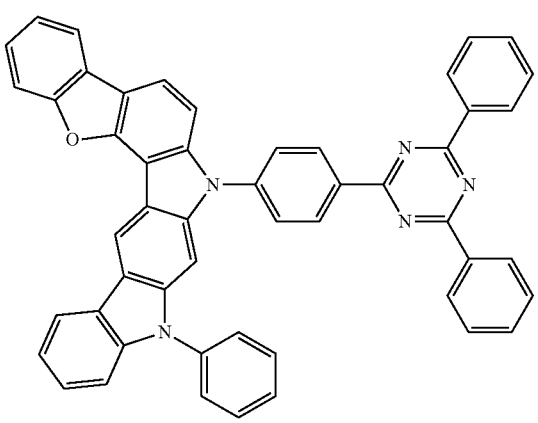
-continued
A-31
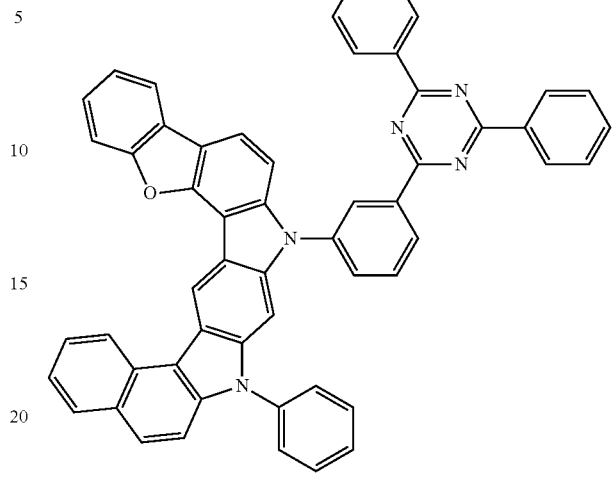
A-32
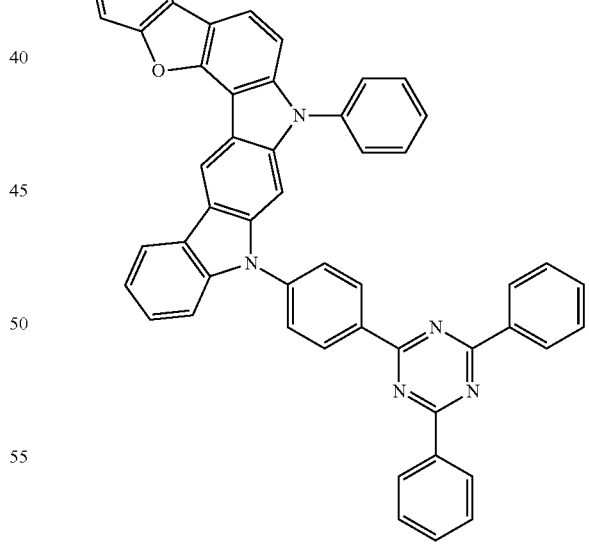

A-33
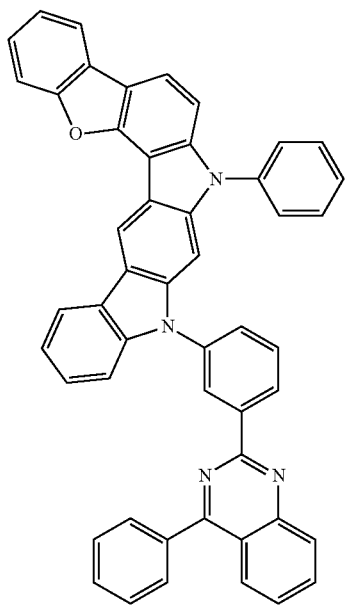
A-34
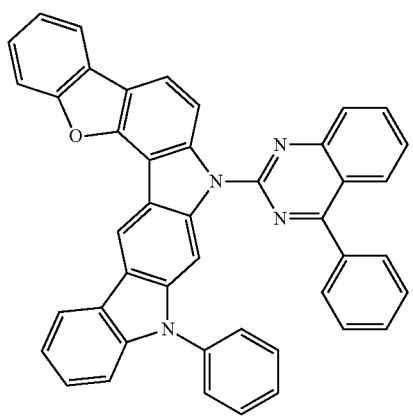
A-35
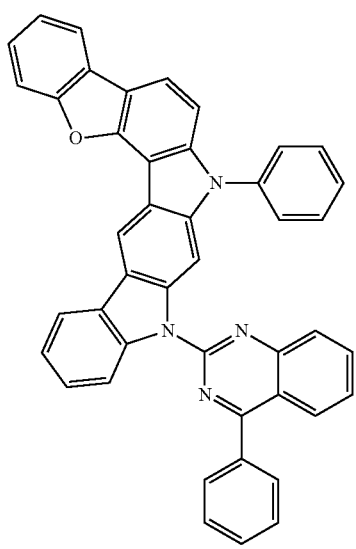
A-36
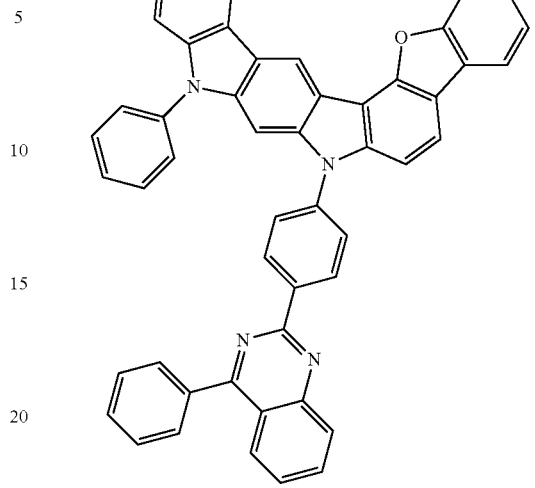
A-37
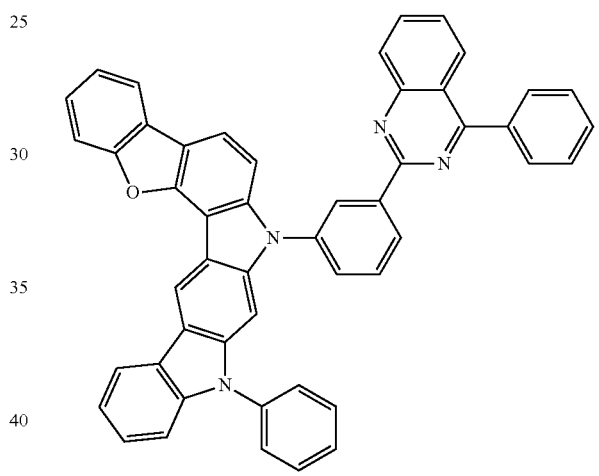
A-38
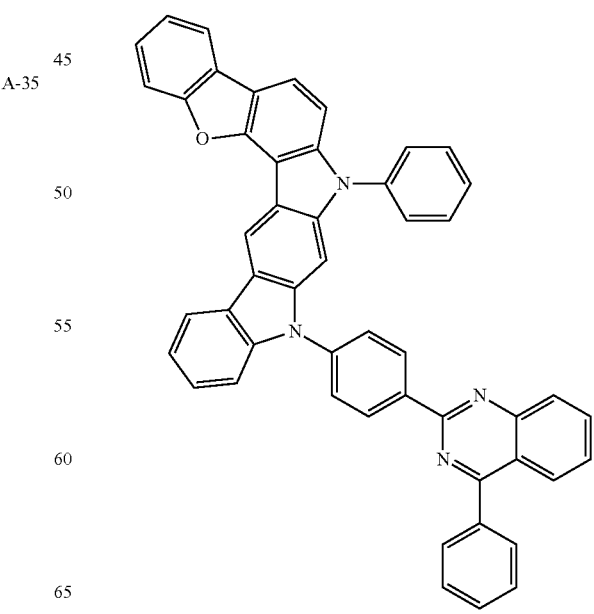

A-39
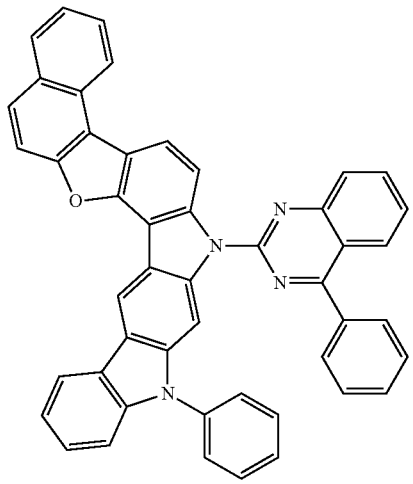
A-40
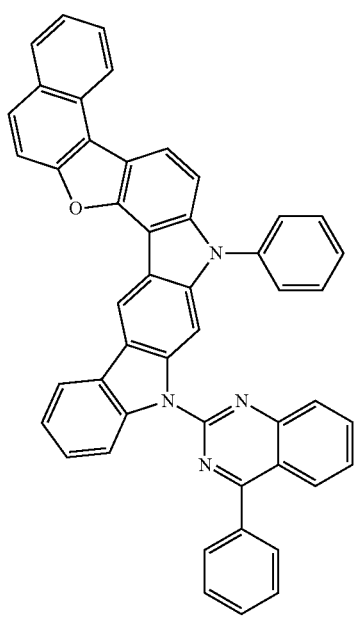
A-41
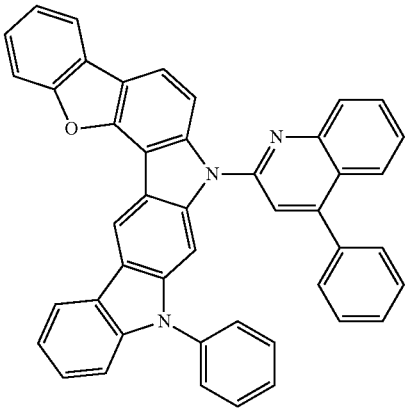
A-42
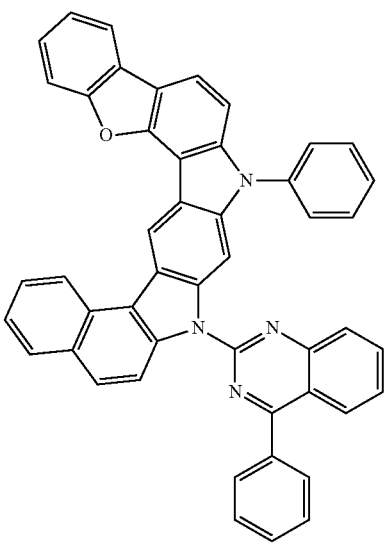
A-43
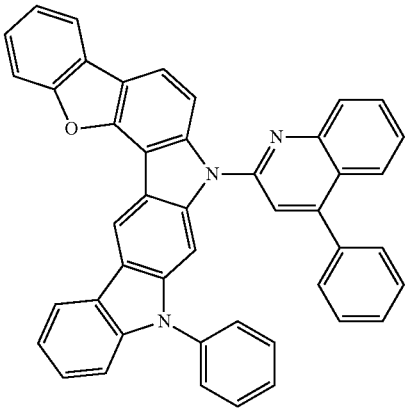
A-44
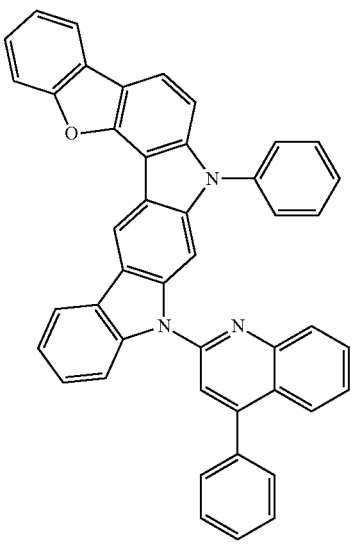

A-45
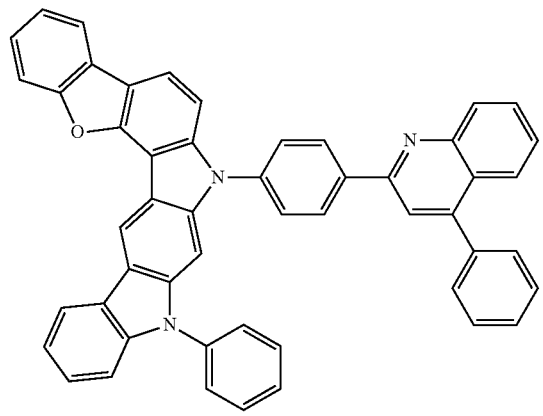
A-46
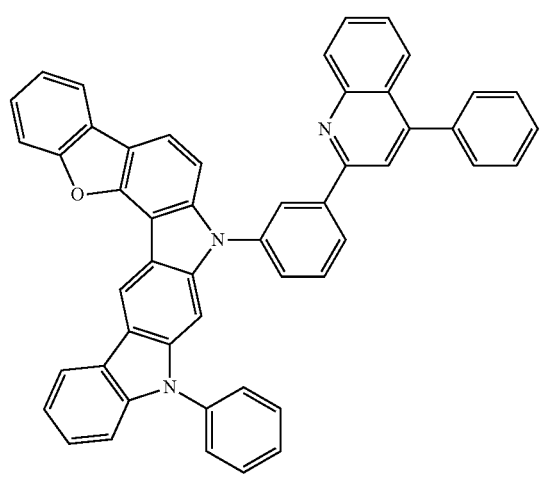
A-47
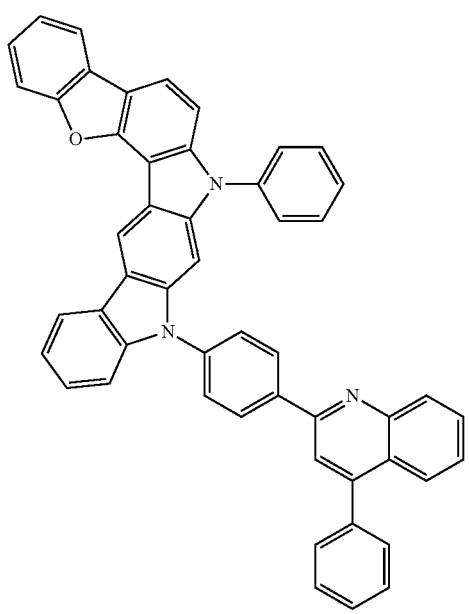
A-48
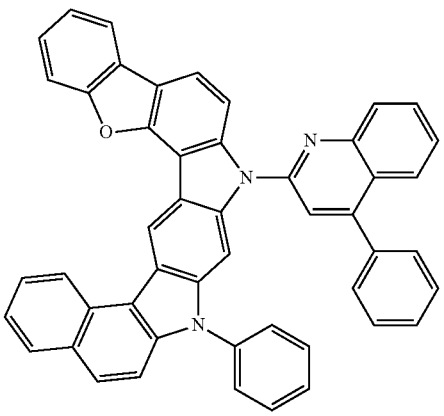
A-49
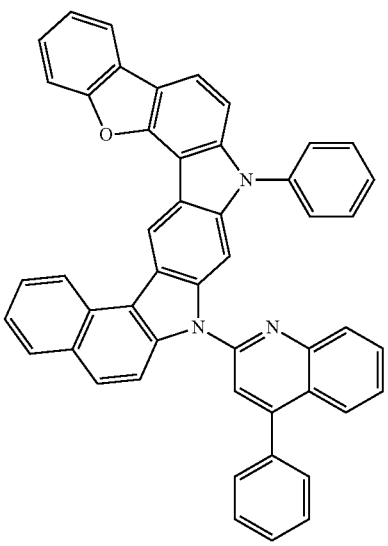
A-50
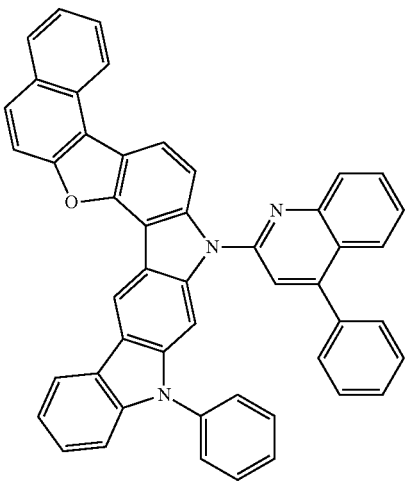

A-51
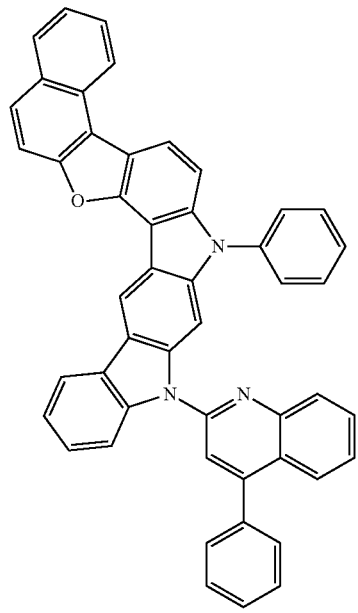
A-52
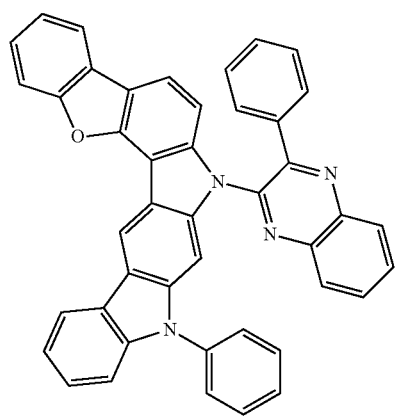
A-53
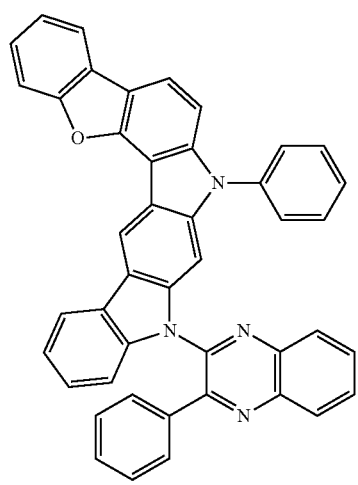
A-54
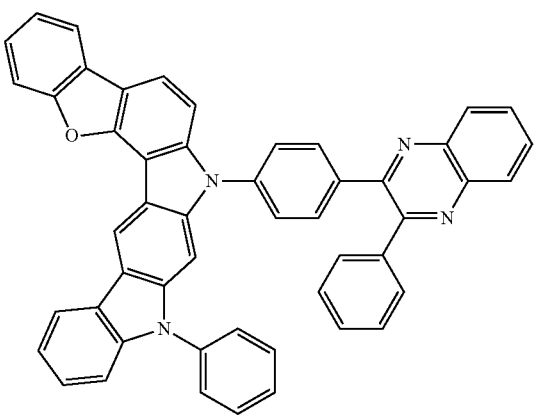
A-55
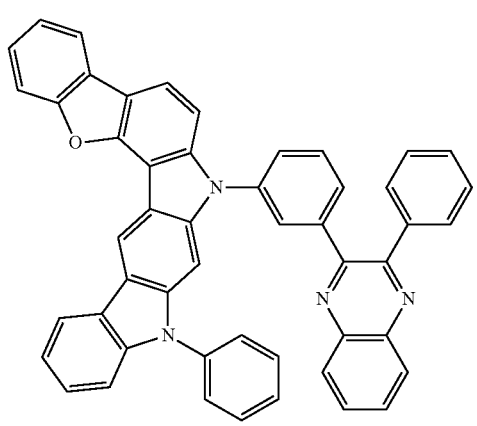
A-56
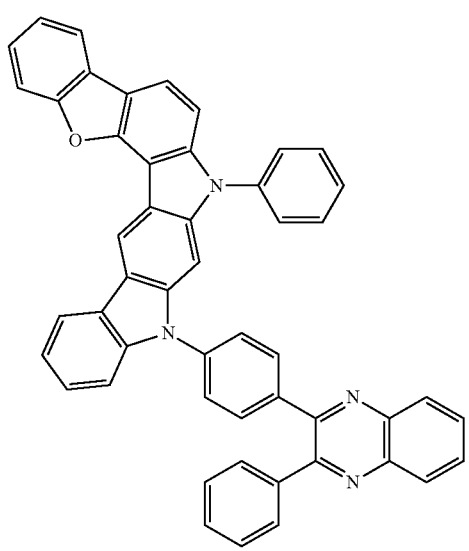

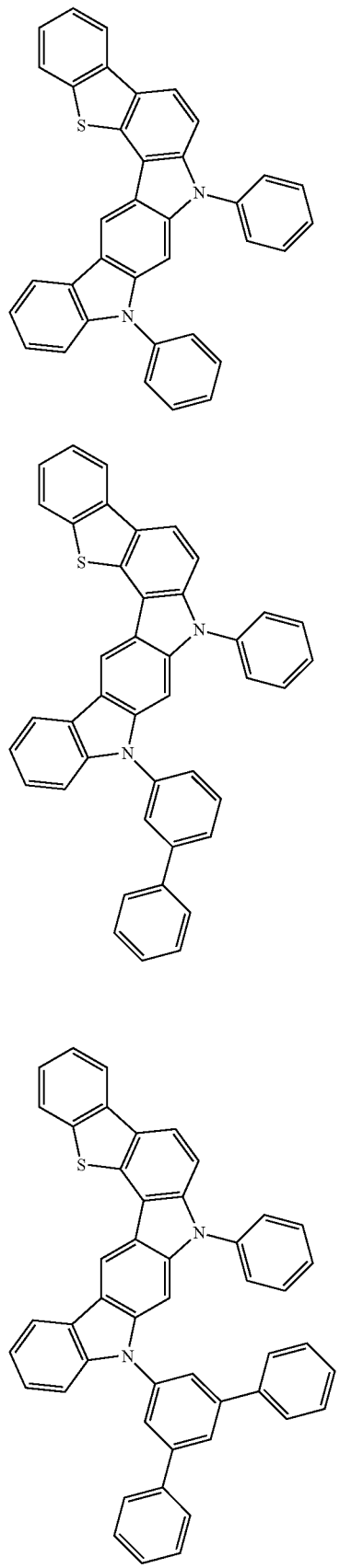
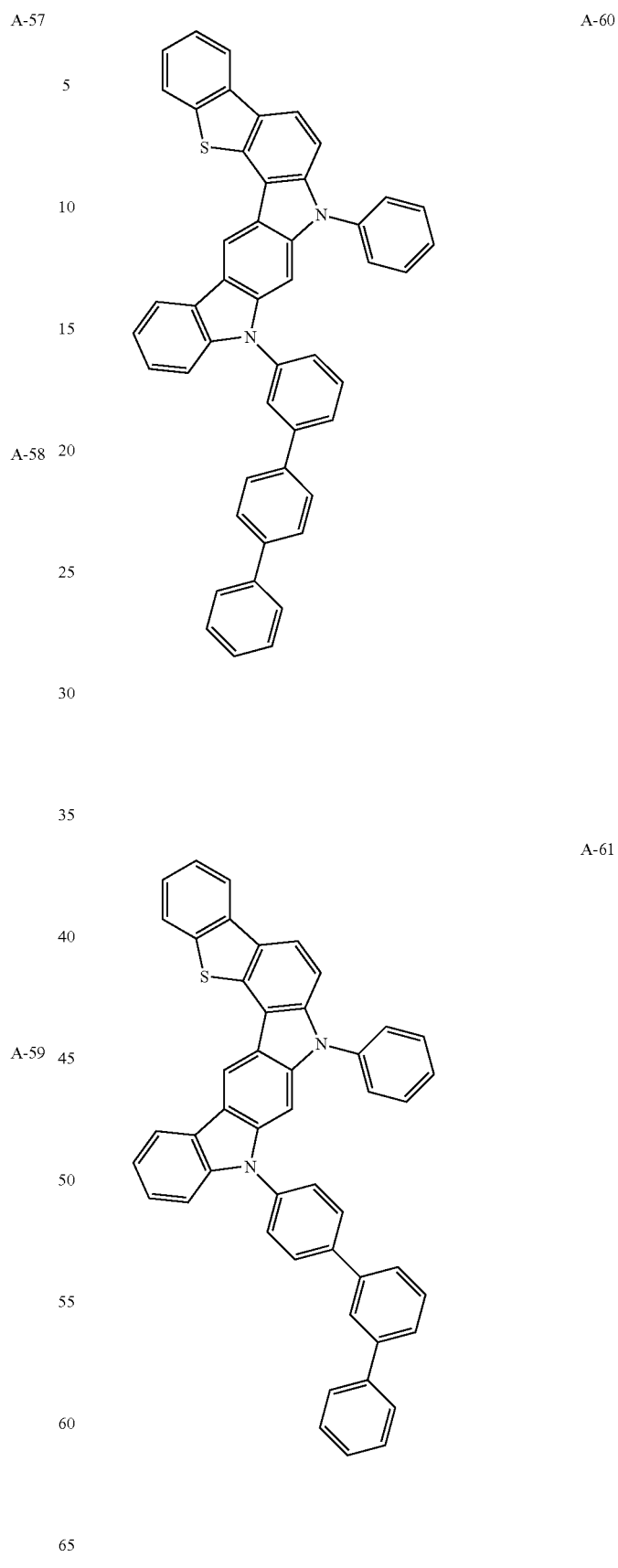

A-62
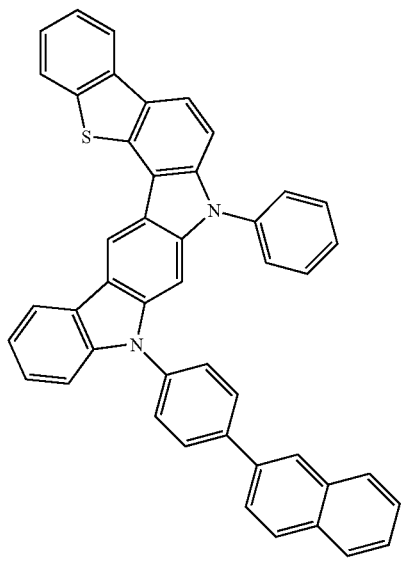
A-63
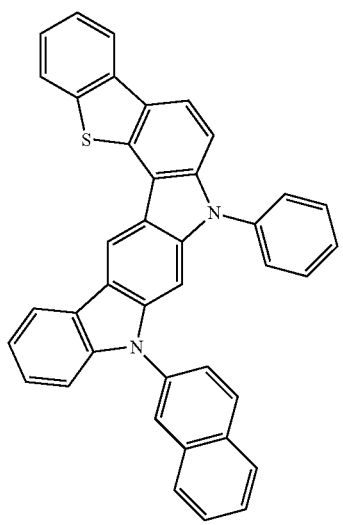
A-64
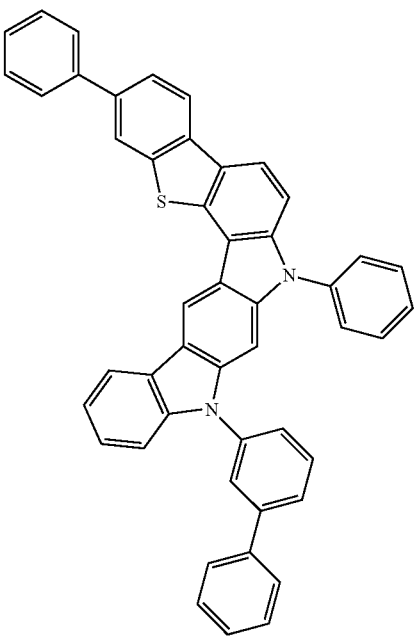
A-65
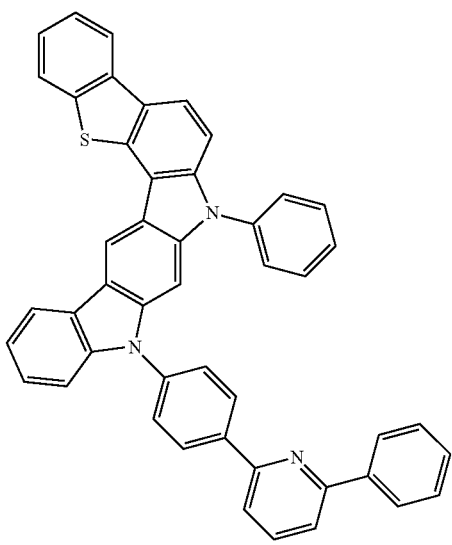

-continued
A-66
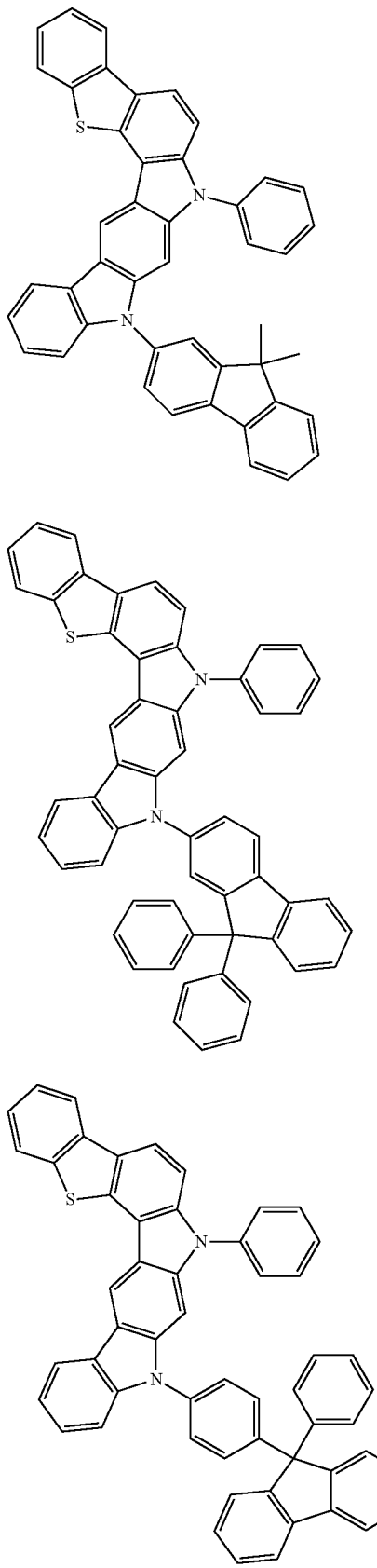
A-67
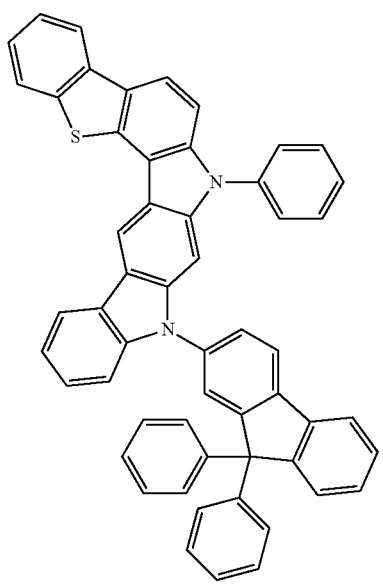
A-68
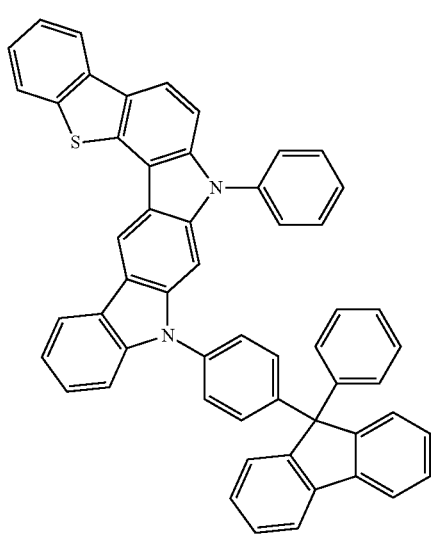
-continued
A-69
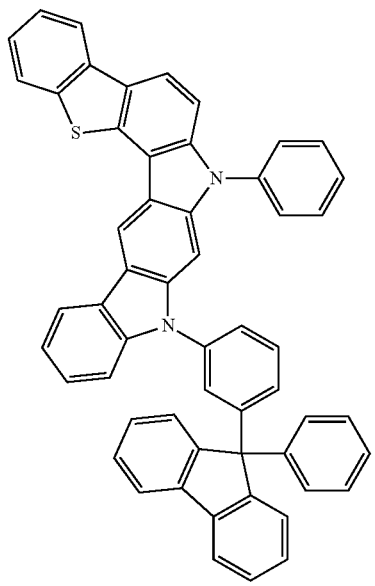
A-70
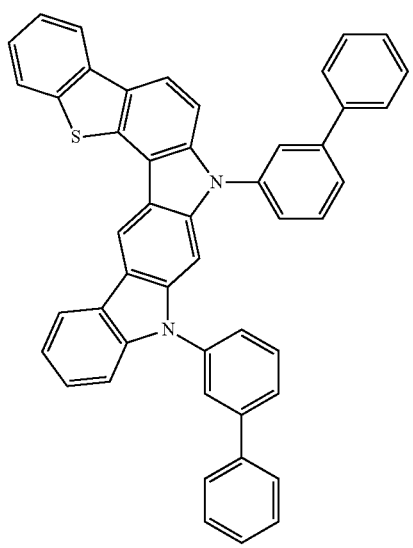
A-71
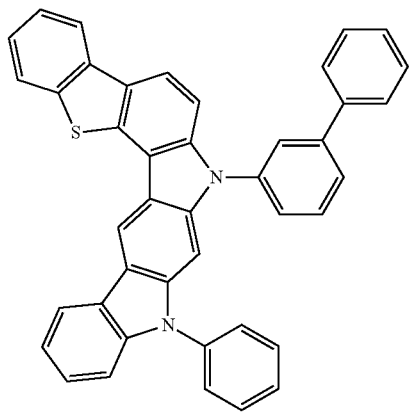

A-72
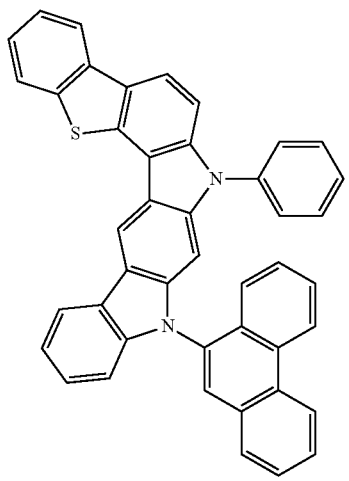
A-75
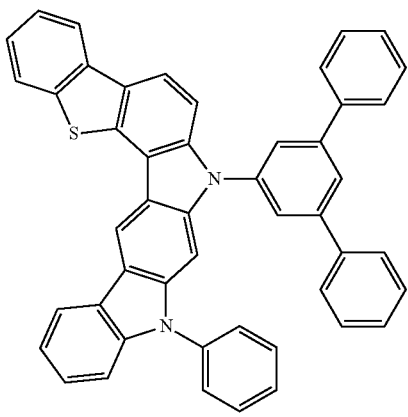
A-73
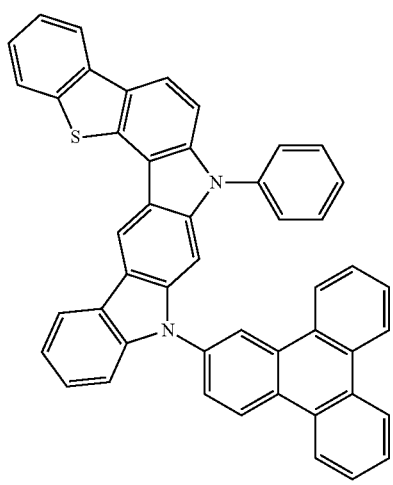
A-76
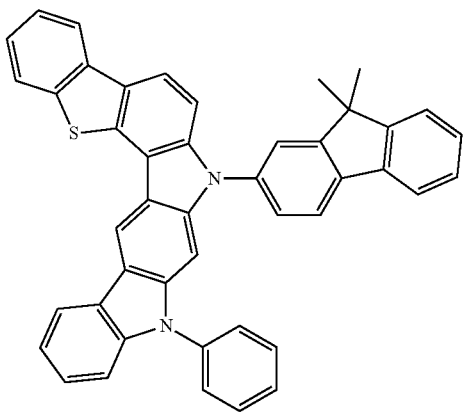
A-74
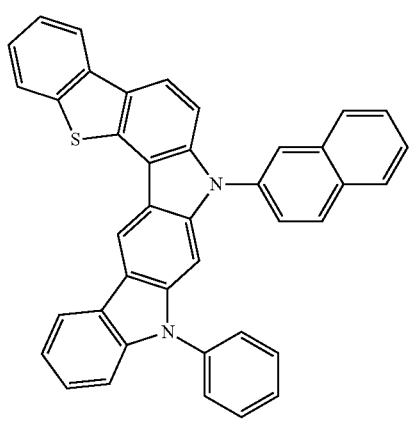
A-77
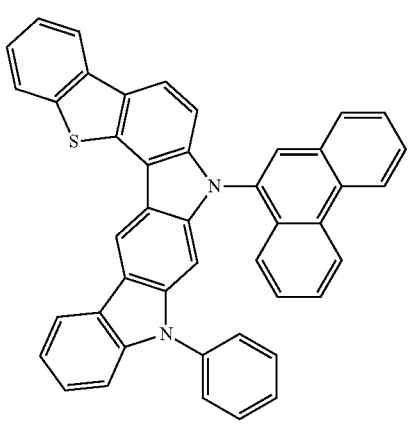

A-78
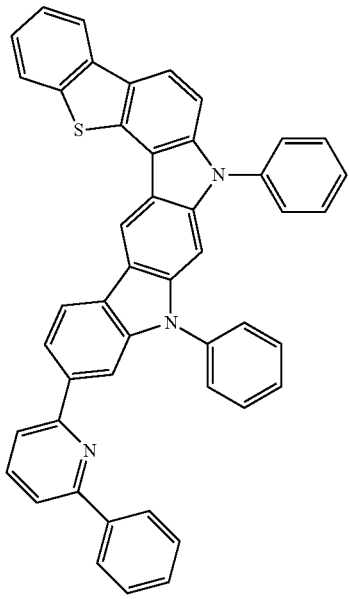
A-79
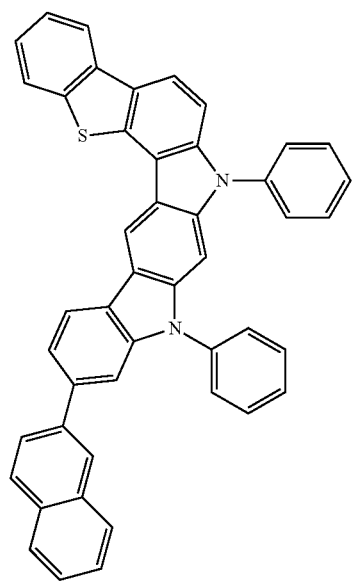
A-80
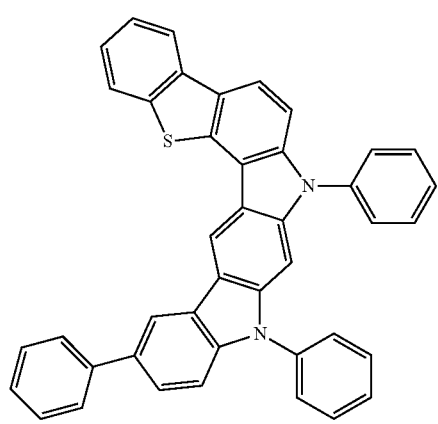
A-81
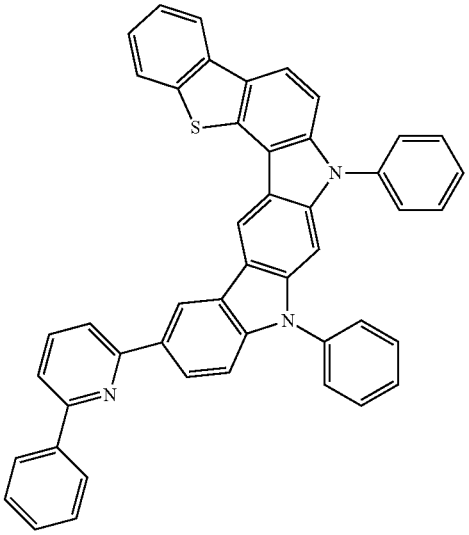
A-82
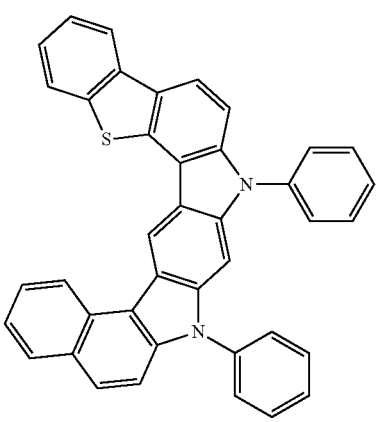
A-83
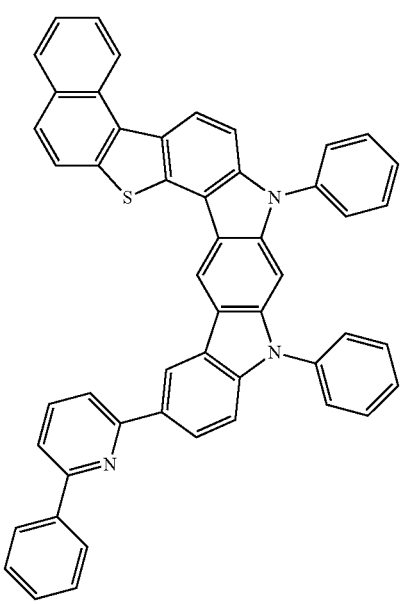

A-84
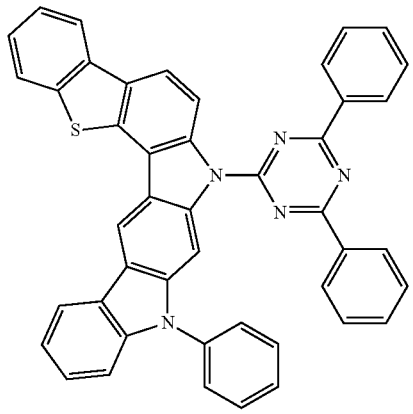
A-85
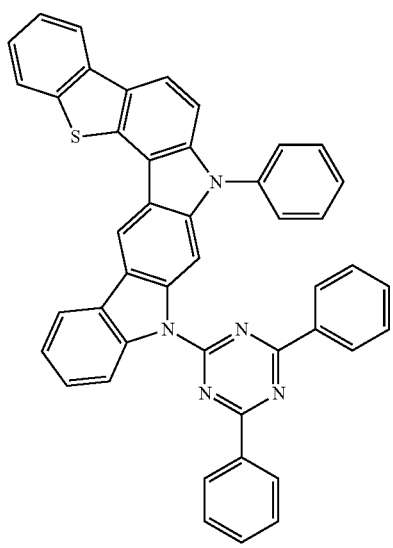
A-86
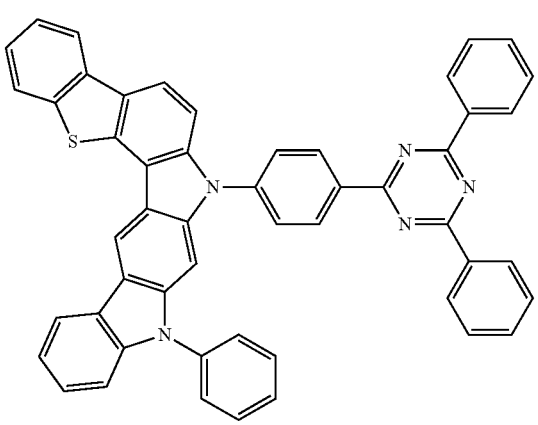
A-87
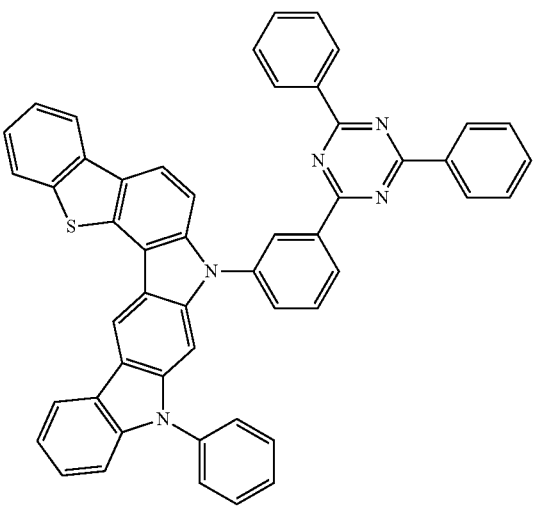
A-88
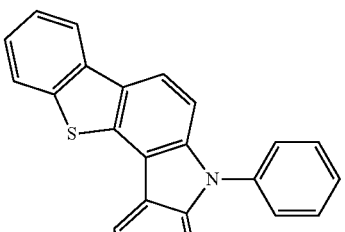
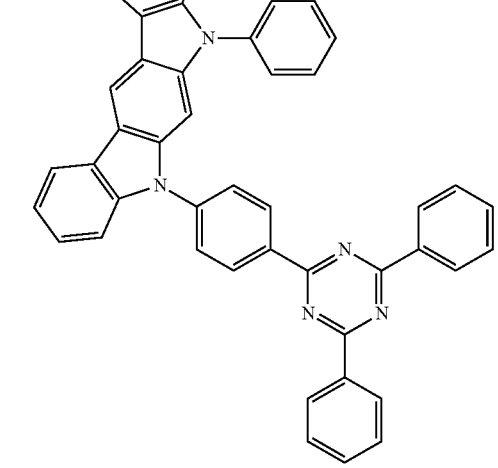

A-89
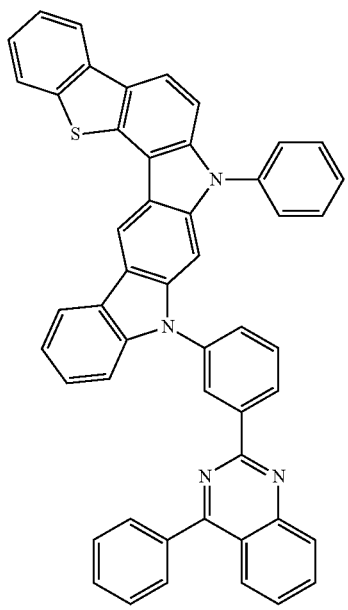
A-90
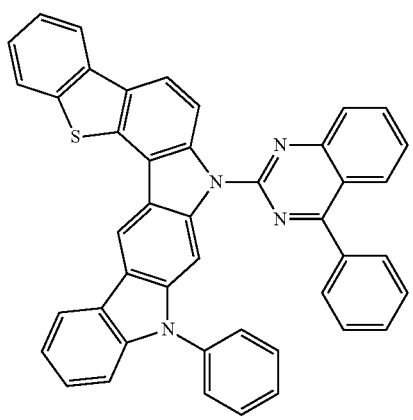
A-91
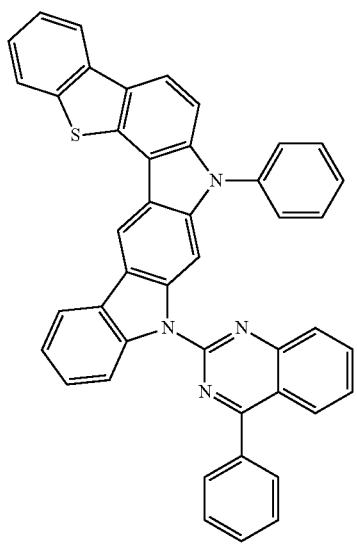
A-92
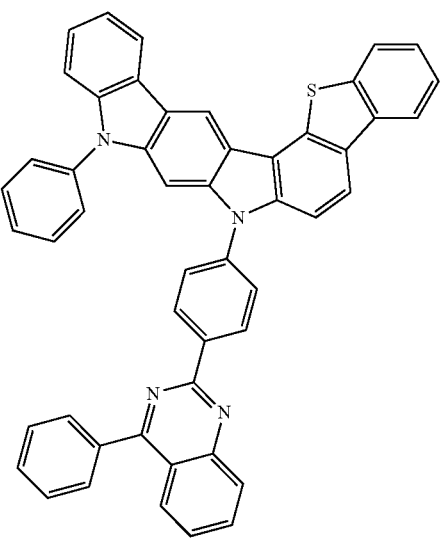
A-93
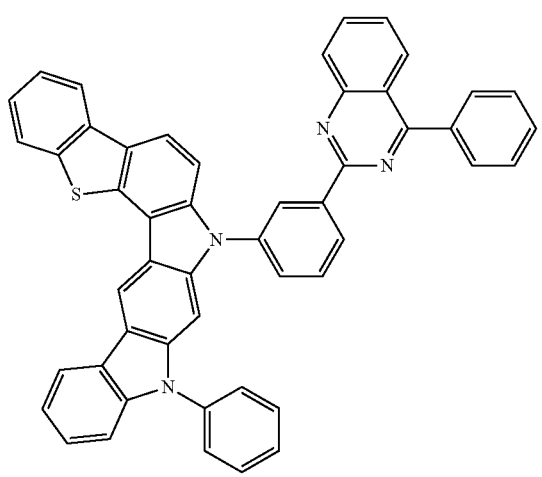
A-94
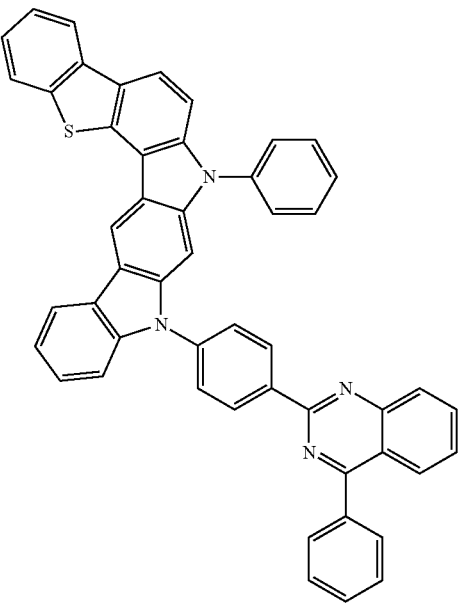

A-95
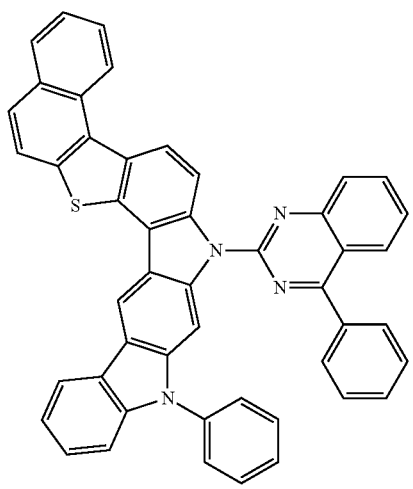
A-96
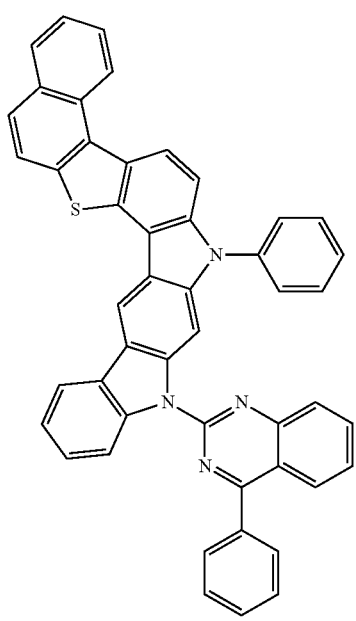
A-97
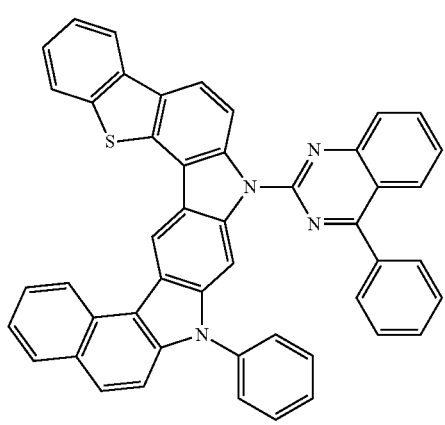
A-98
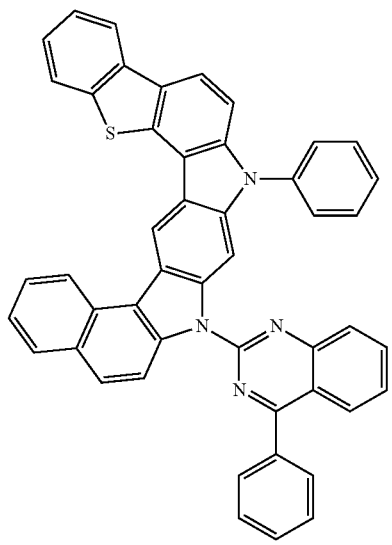
A-99
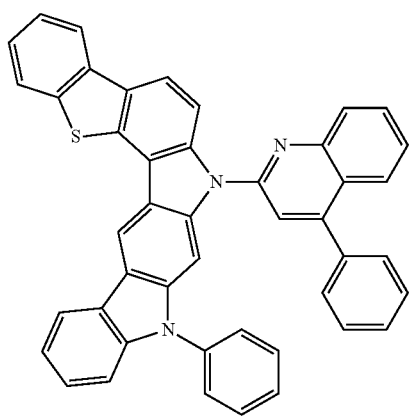
A-100
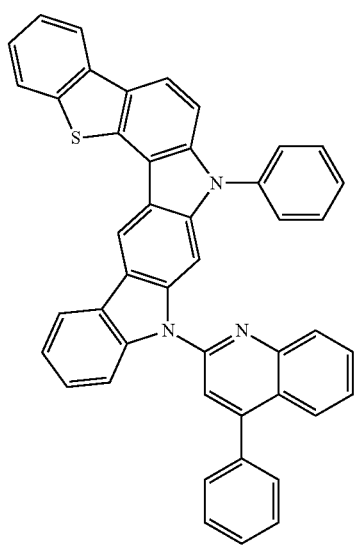

A-101
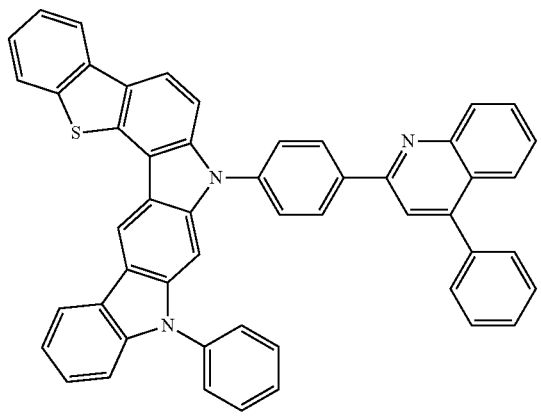
A-102
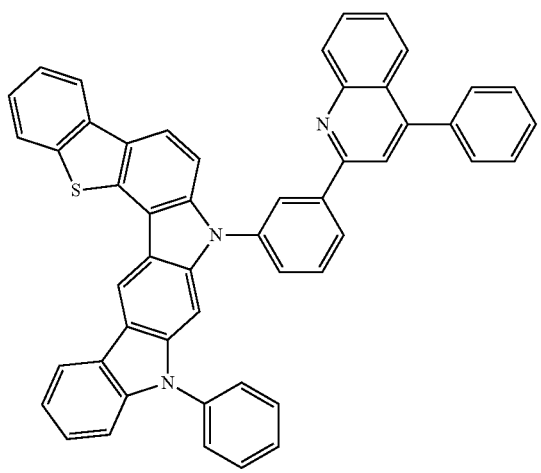
A-103
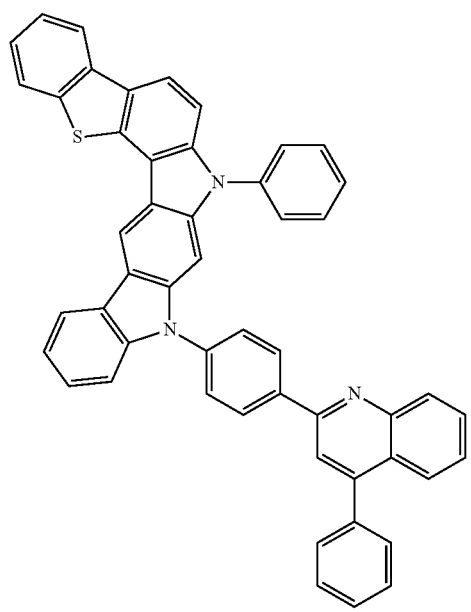
A-104
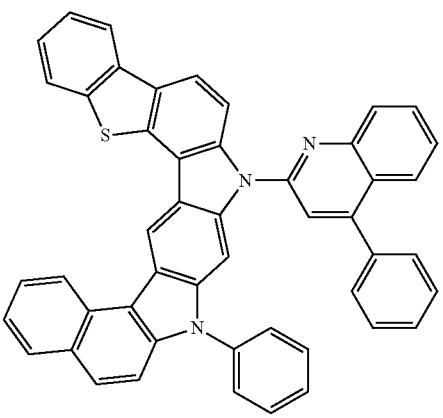
A-105
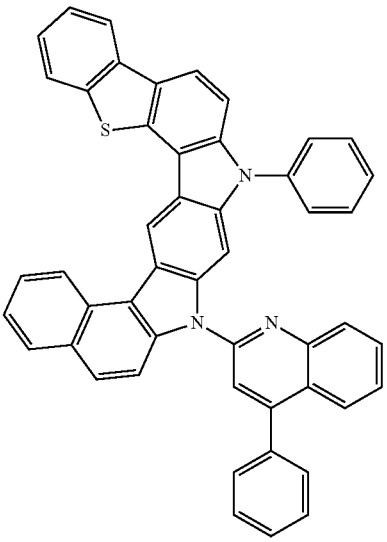
A-106
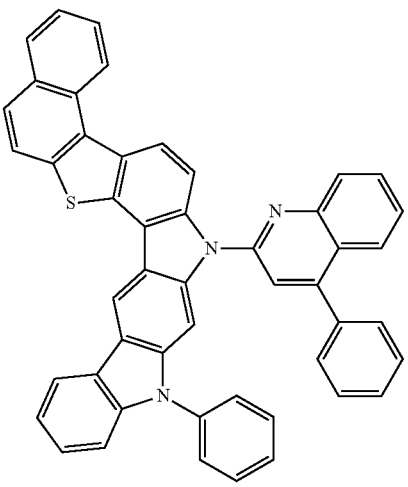

A-107
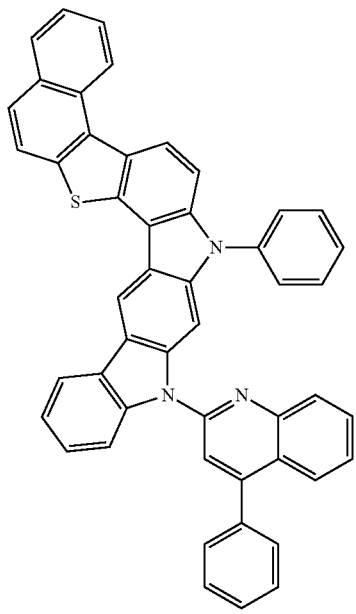
A-108
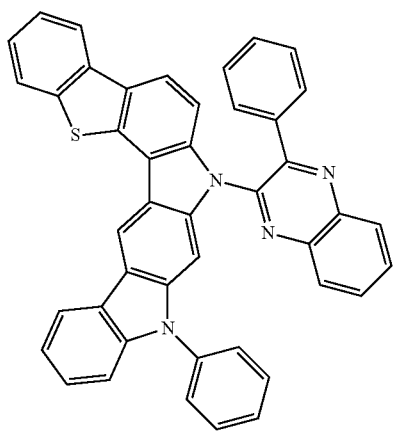
A-109
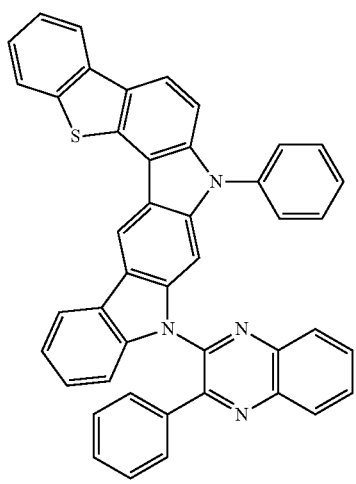
A-110
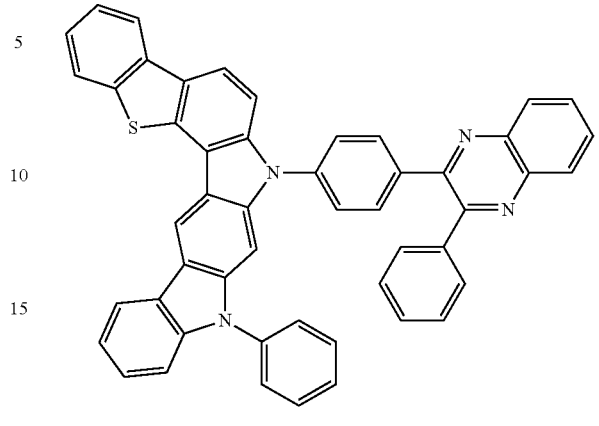
A-111
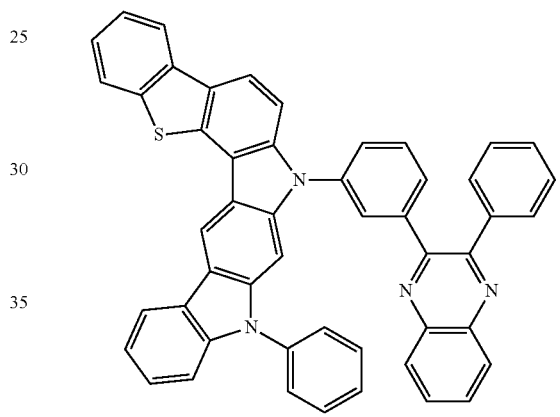
A-112
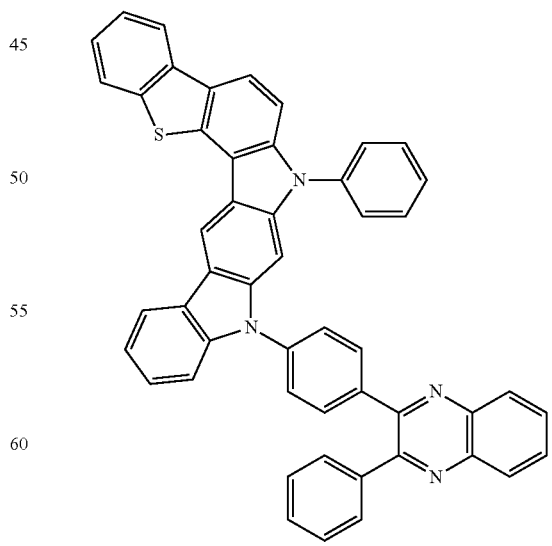

A-113
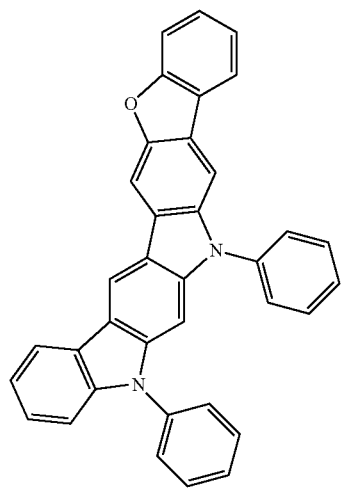
A-114
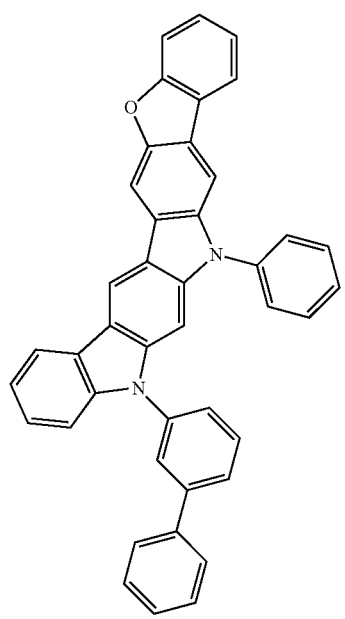
A-115
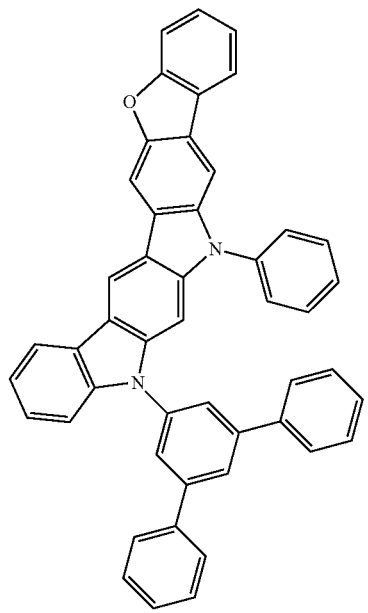
A-116
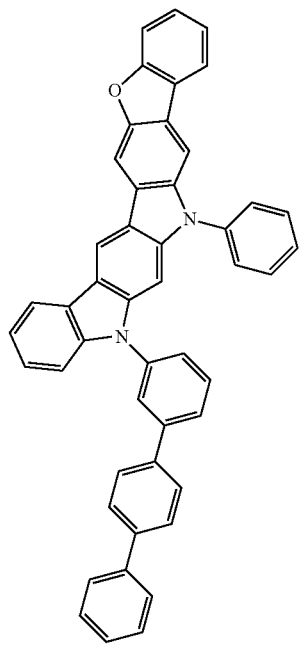

A-117
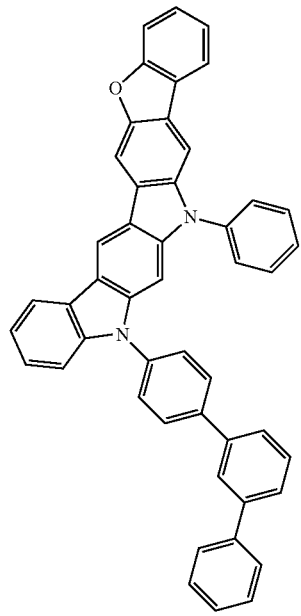
A-118
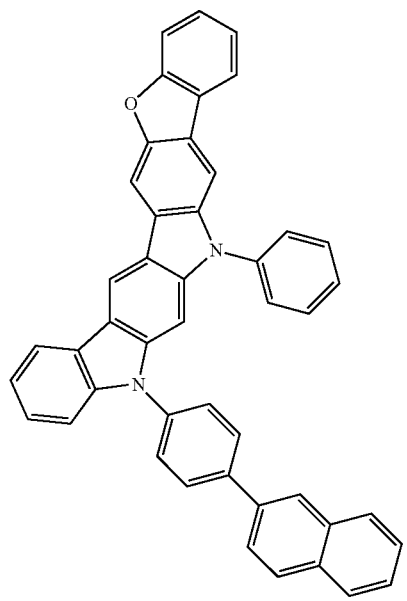
A-119
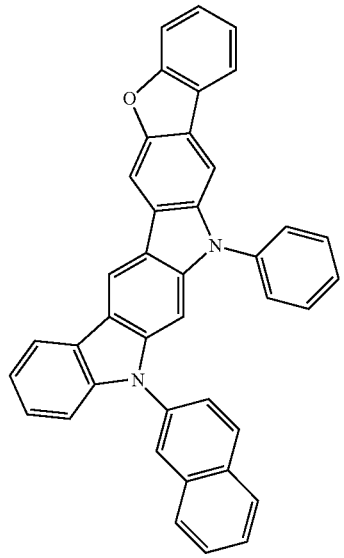
A-120
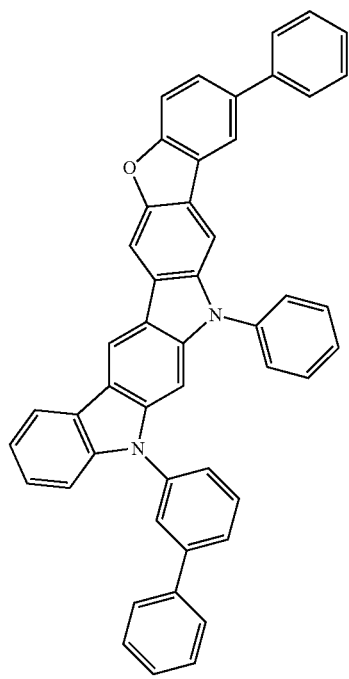

A-121
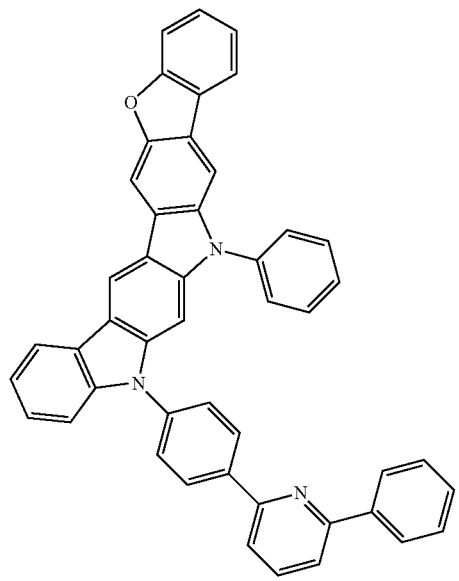
A-122
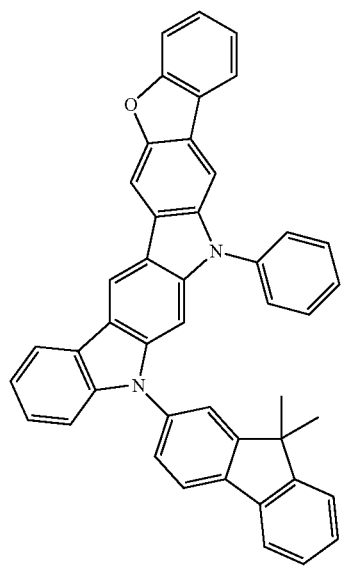
A-123
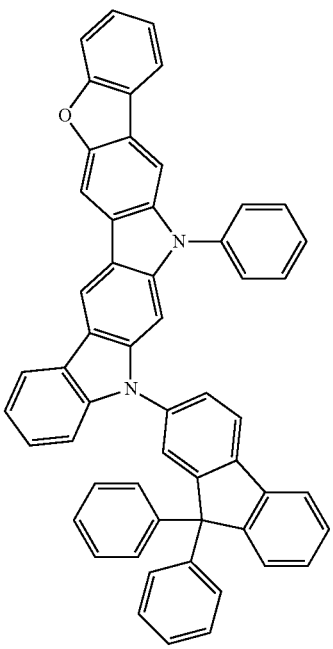
A-124
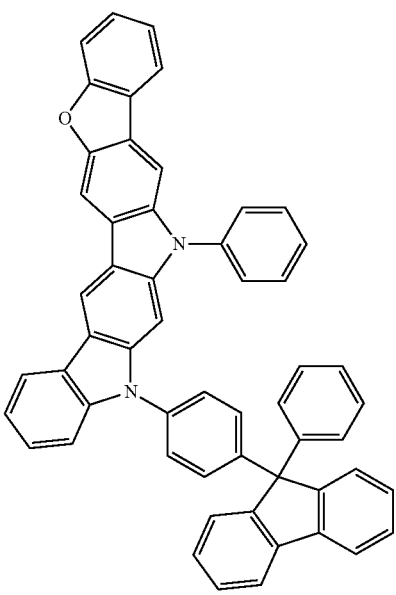

A-125
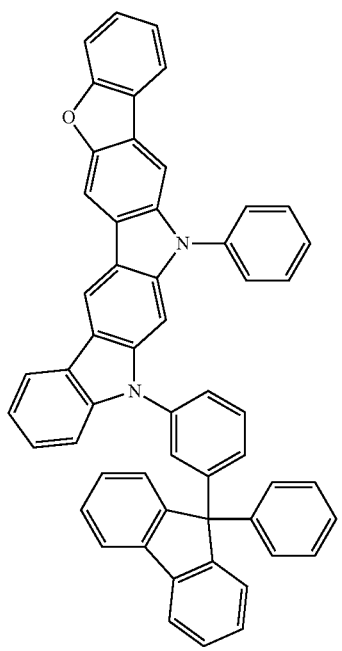
A-126
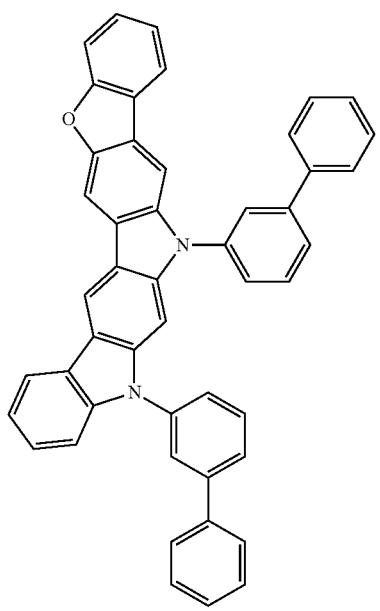
A-127
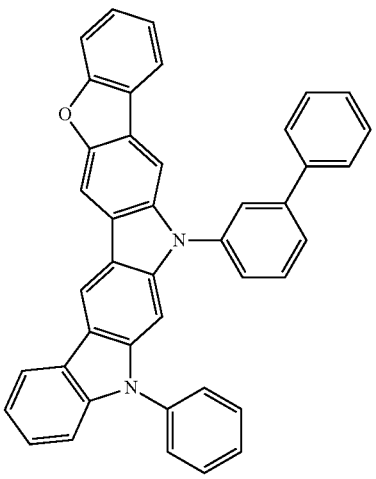
A-128
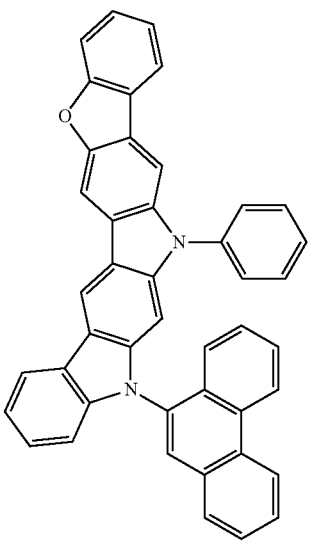
A-129
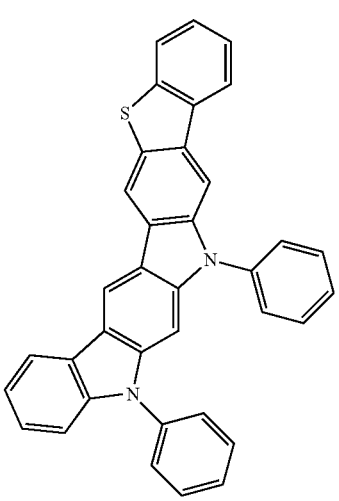

A-130
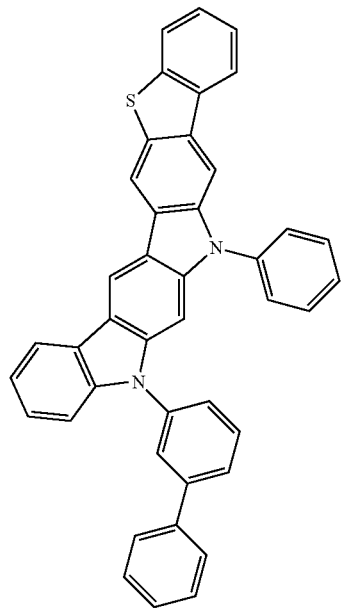
A-131
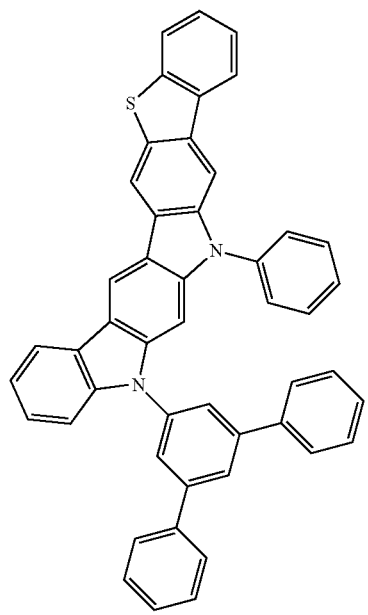
A-132
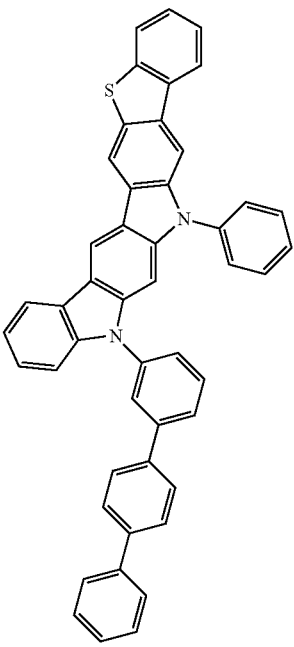
A-133
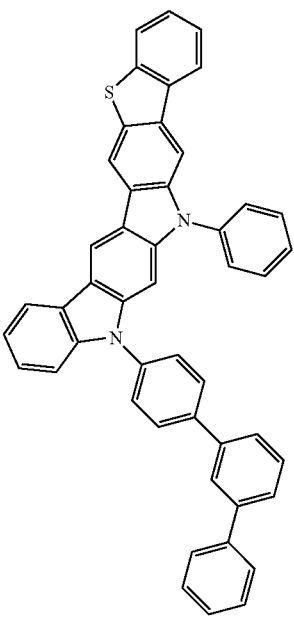

-continued
A-134
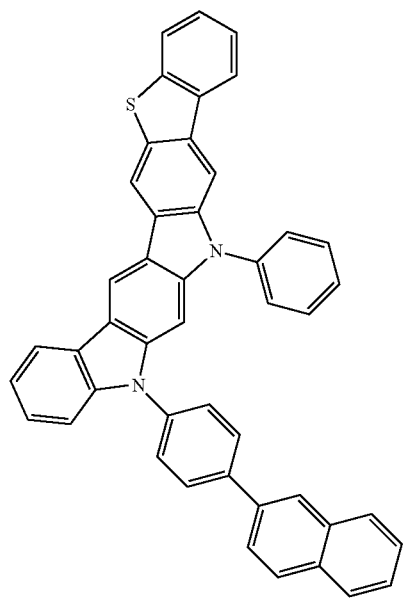
A-135
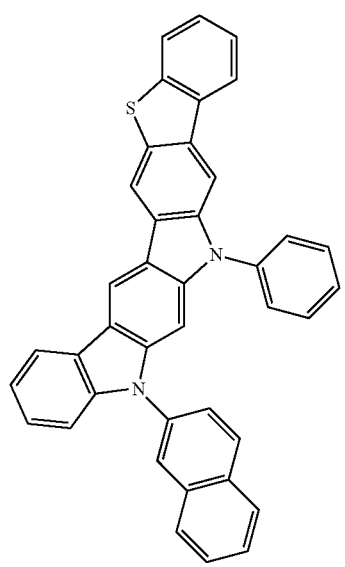
A-136
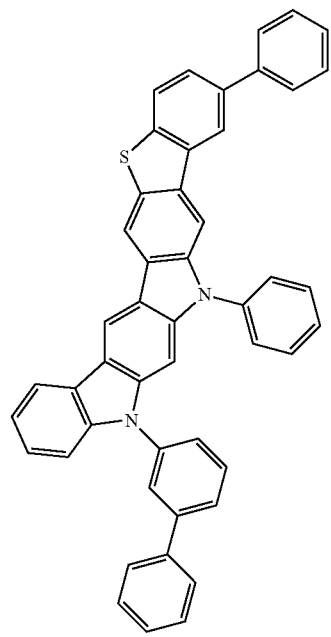
A-137
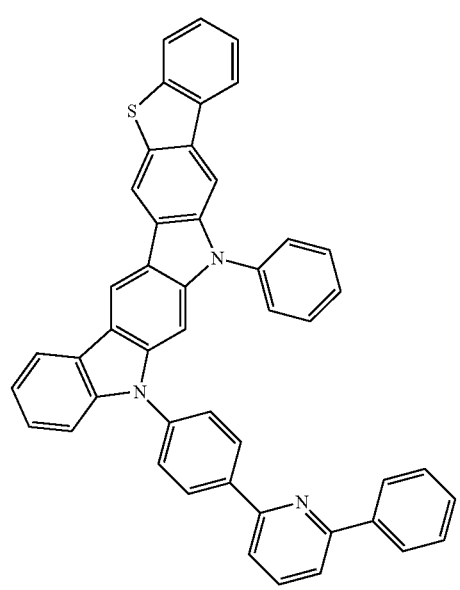

A-138
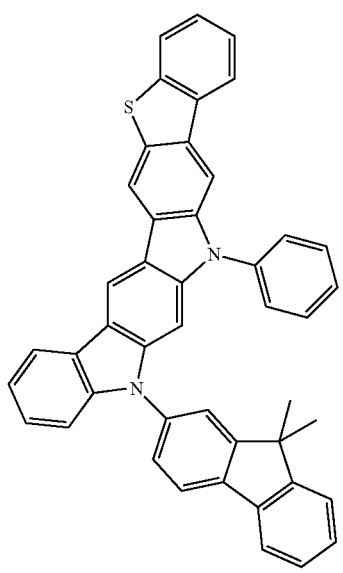
A-139
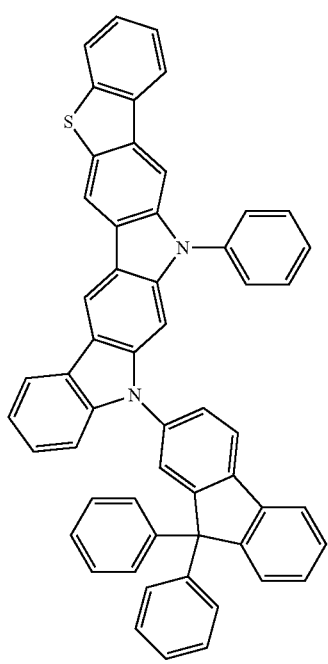
A-140
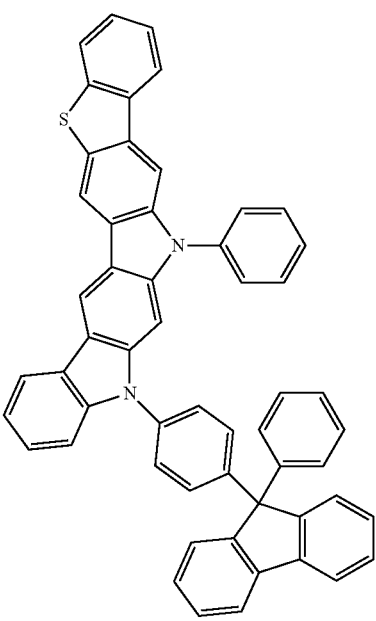
A-141
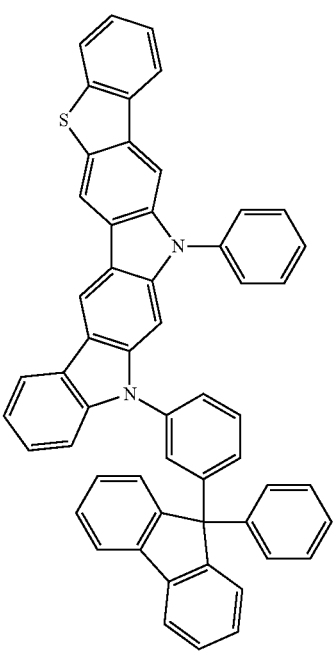

A-142
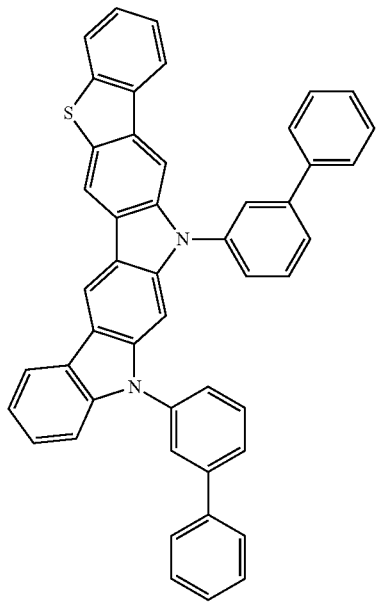
A-143
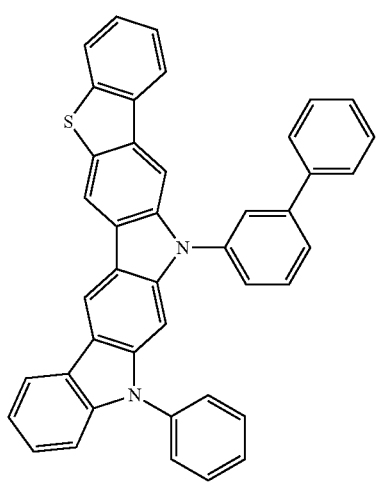
A-144
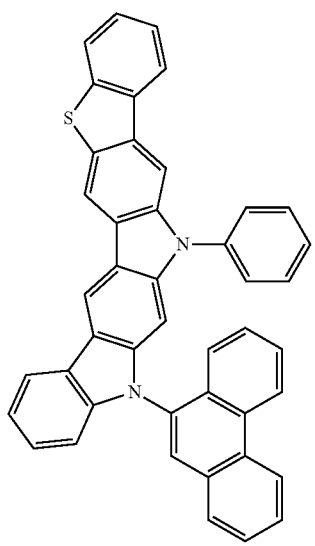
A-145
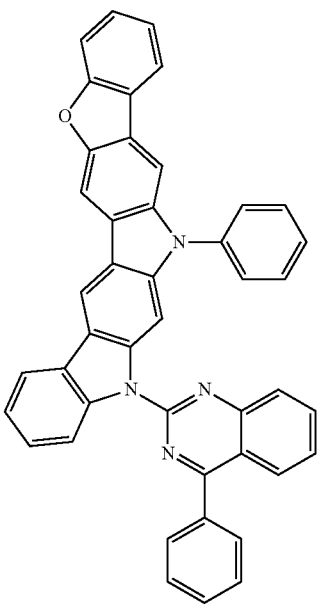
A-146
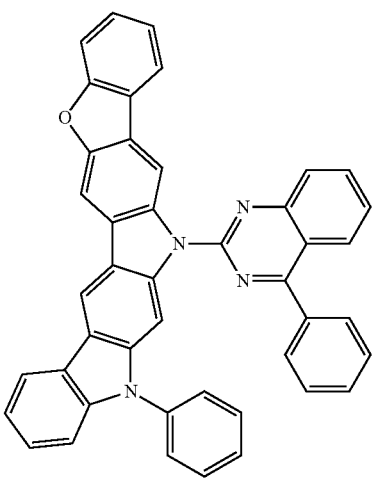

-continued
A-147
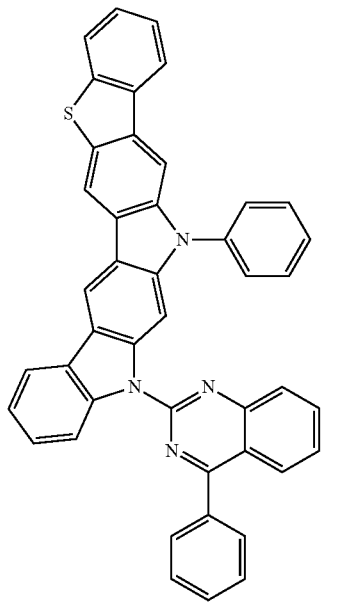
A-148
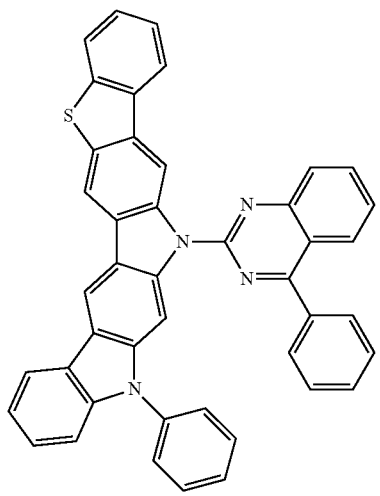
A-149
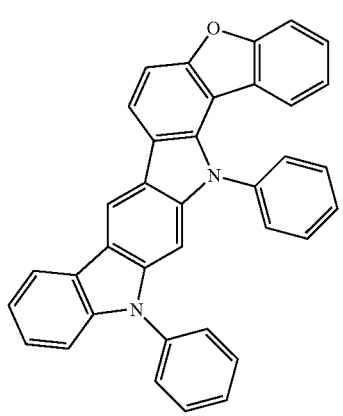
-continued
A-150
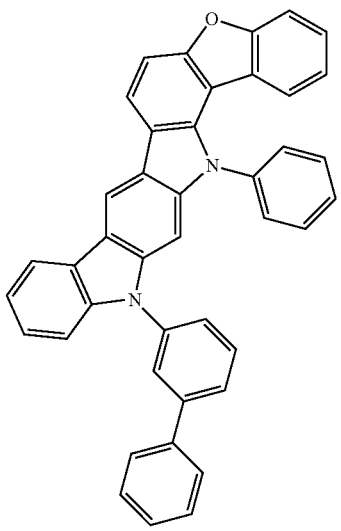
A-151
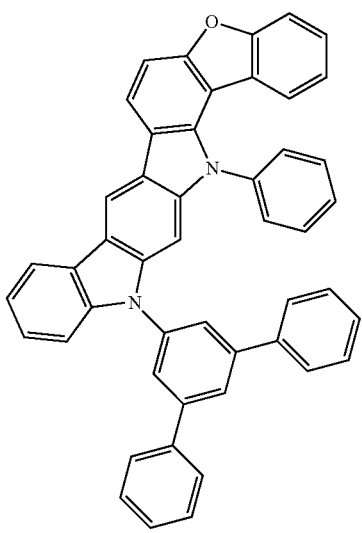
A-152
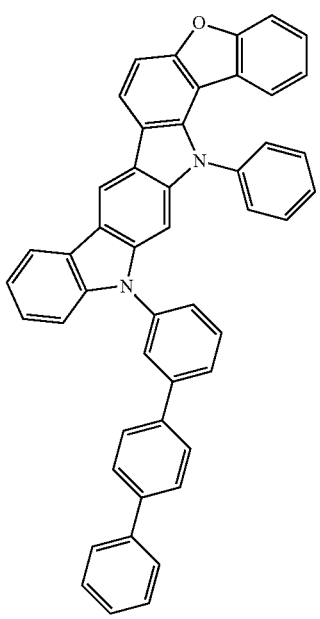

A-153
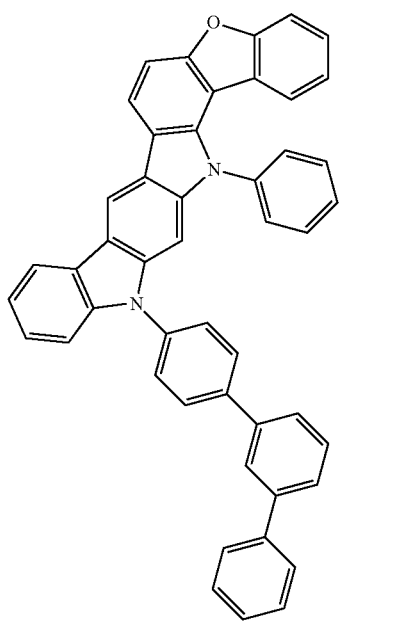
A-154
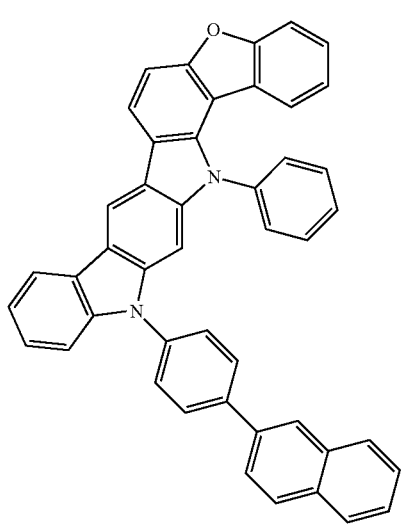
A-155
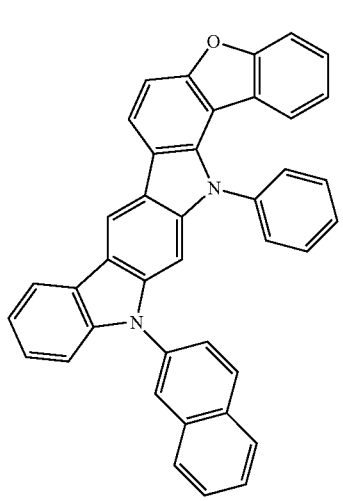
A-156
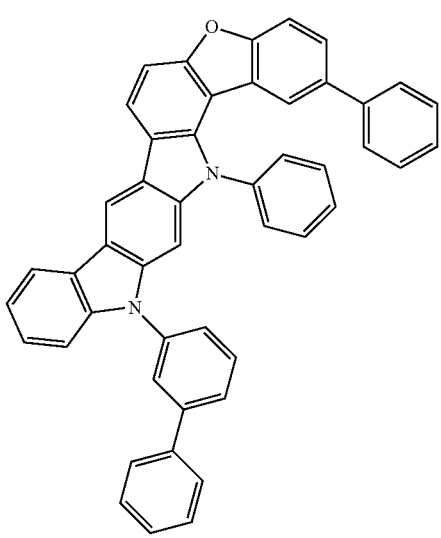
A-157
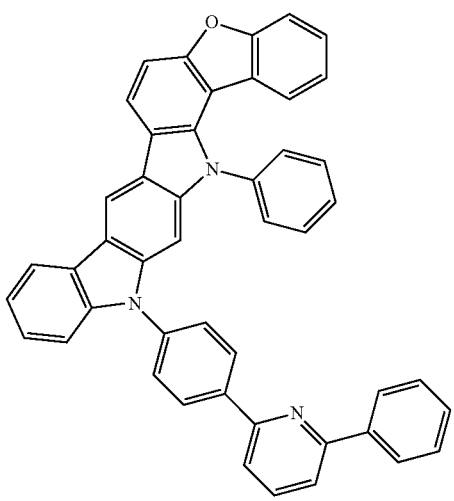
A-158
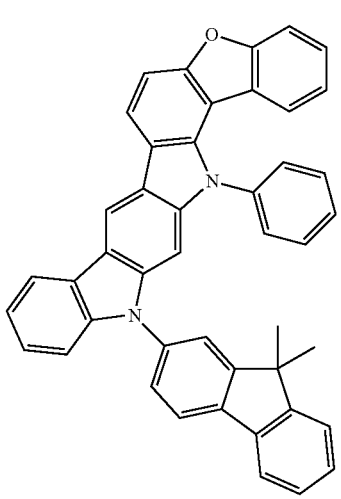

A-159
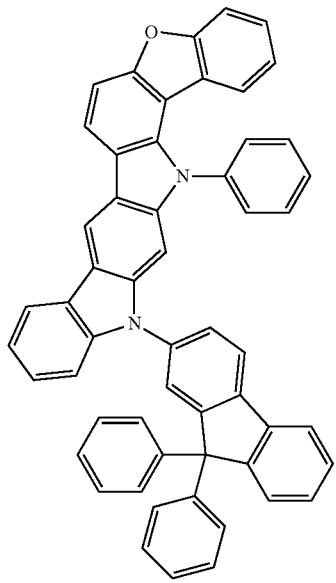
A-160
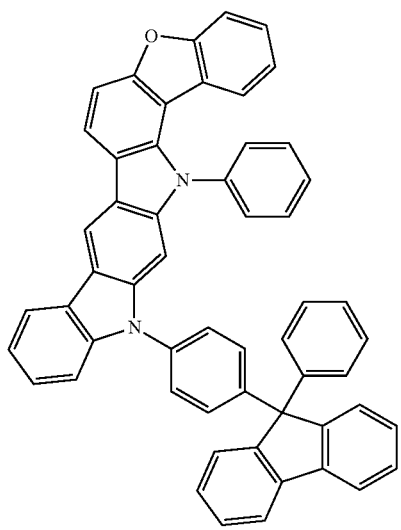
A-161
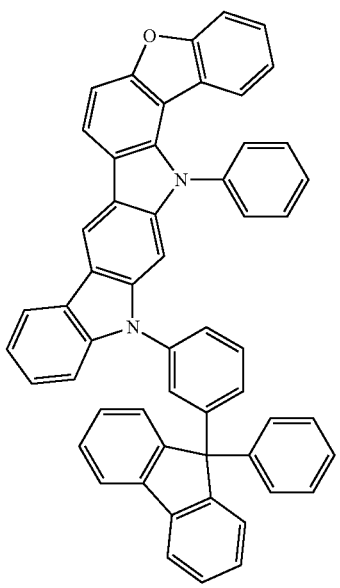
A-162
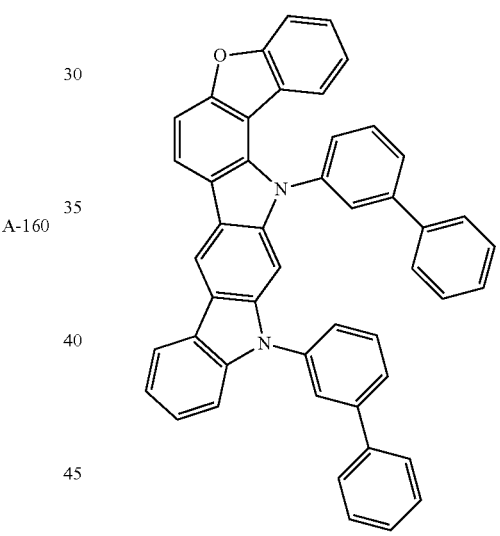
A-163
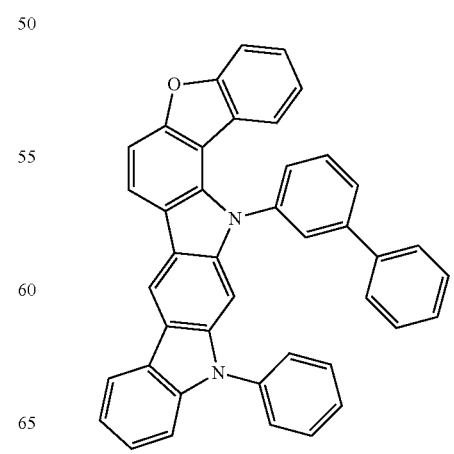

A-164
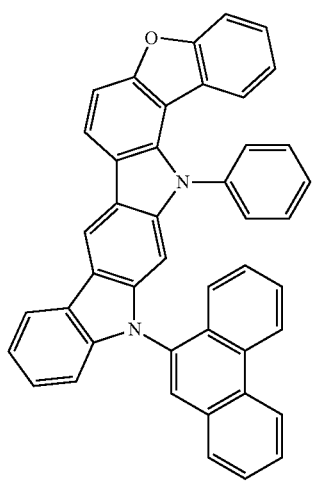
A-165
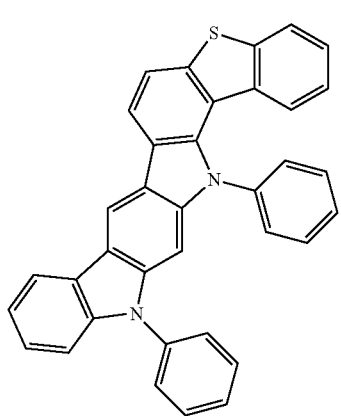
A-166
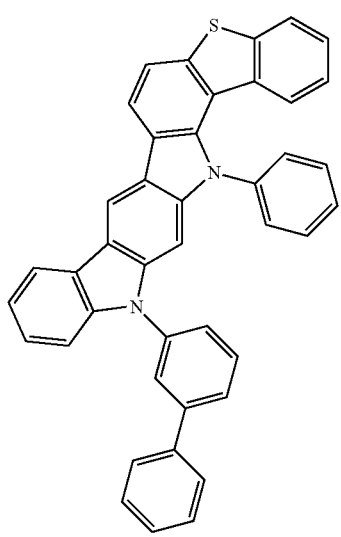
A-167
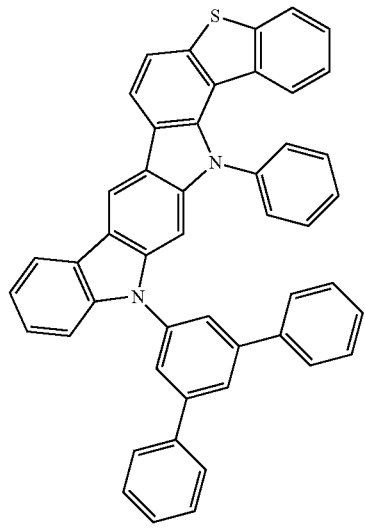
A-168
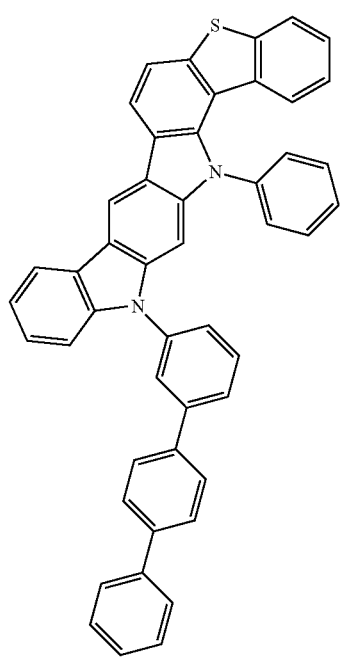

A-169
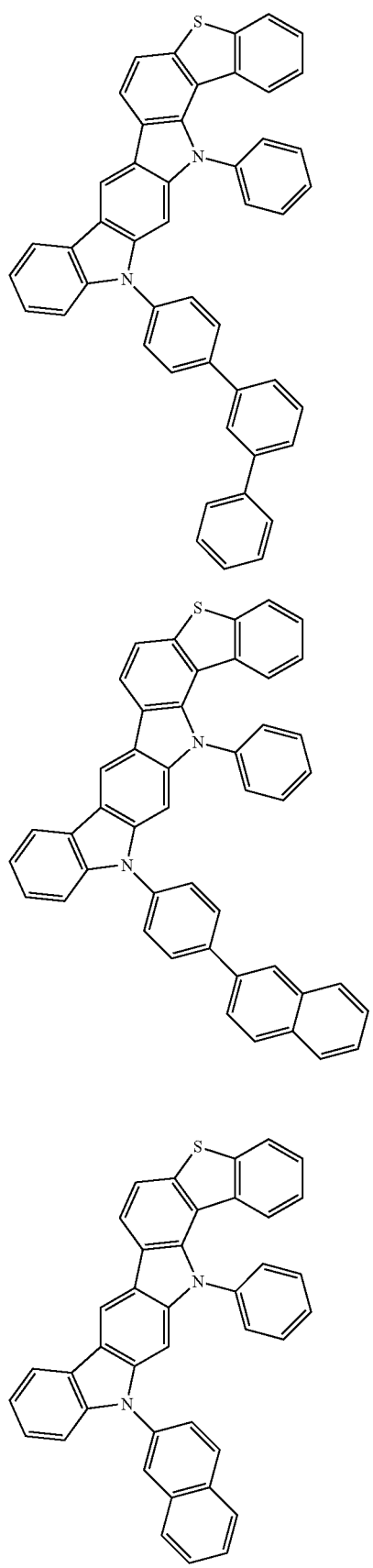
A-170
A-171
A-172
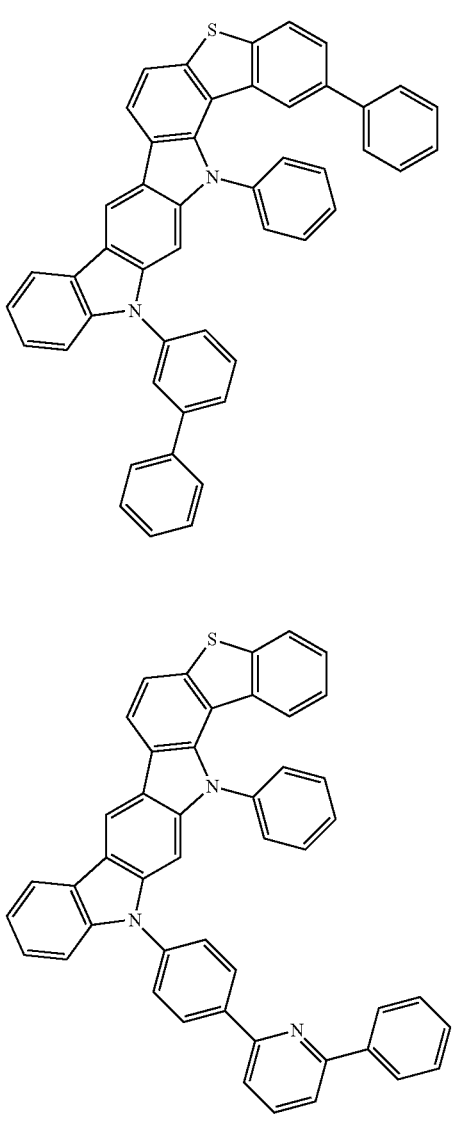
A-173
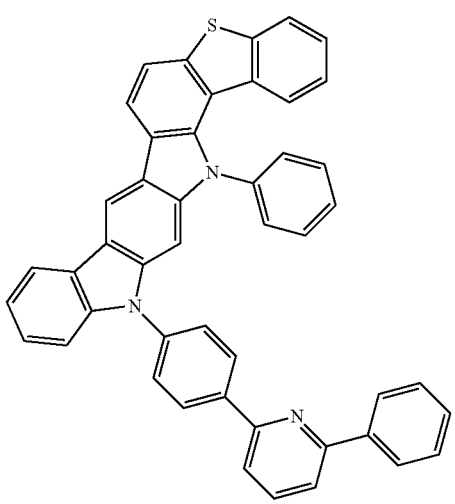
A-174
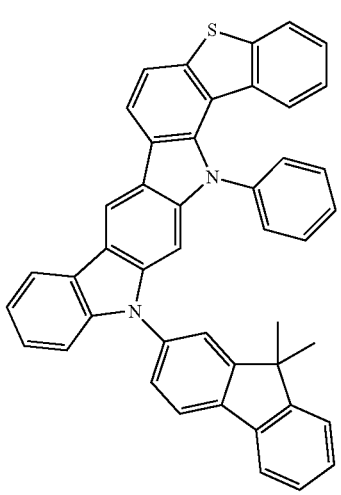

A-175
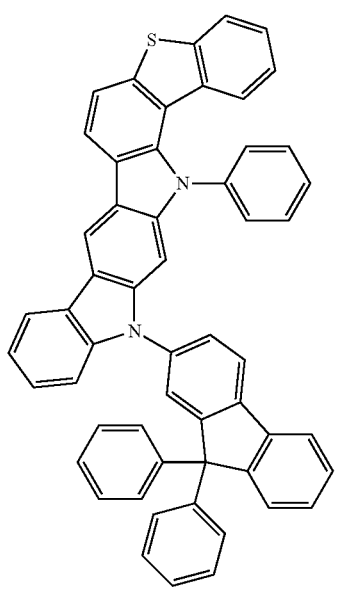
A-176
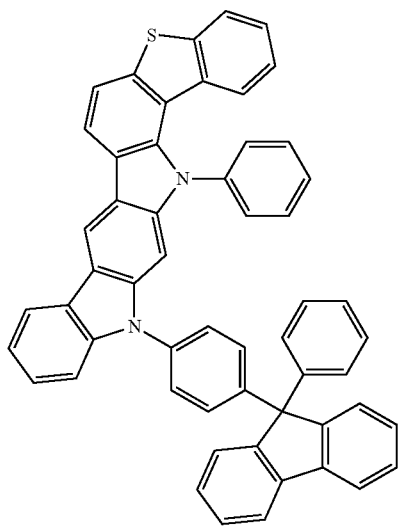
A-177
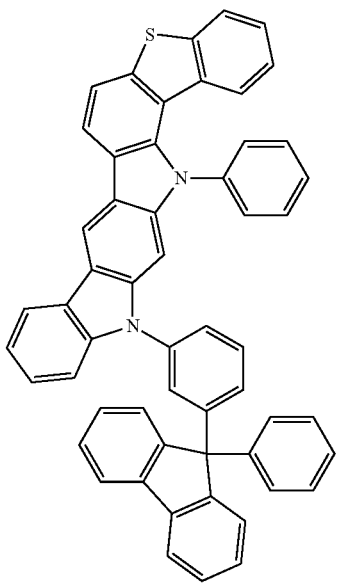
A-178
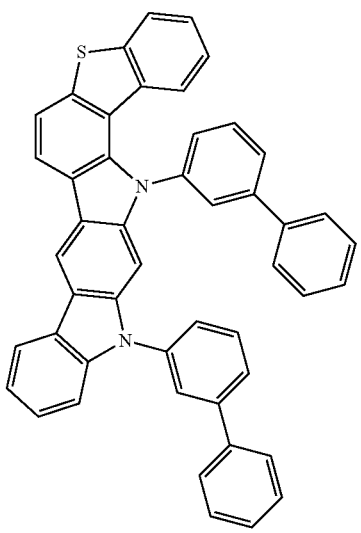
A-179
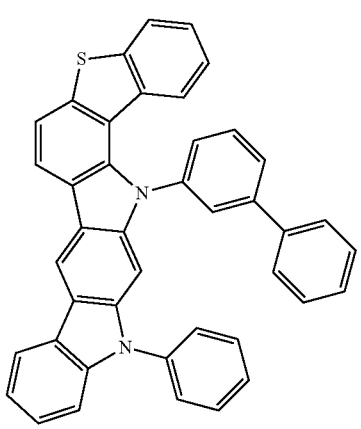

-continued
A-180
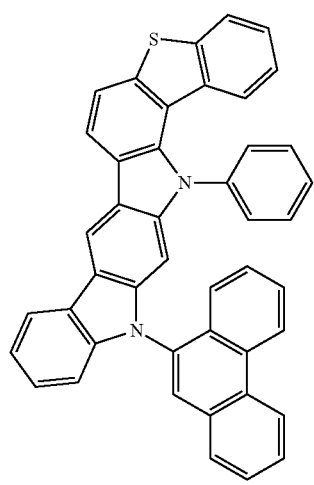
A-181
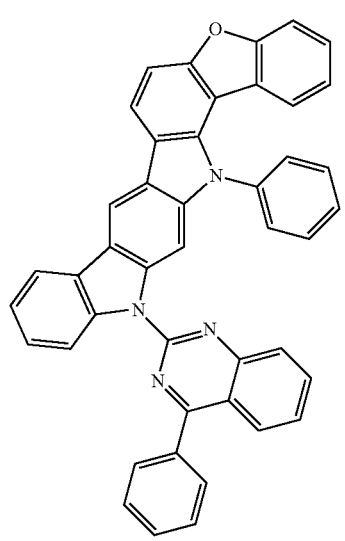
A-182
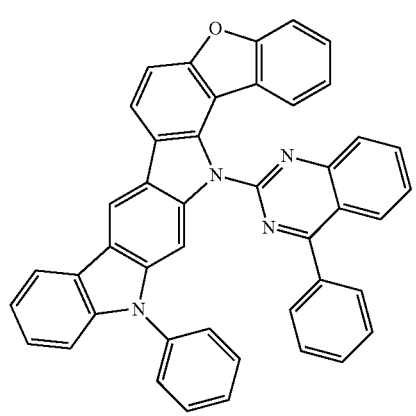
-continued
A-183
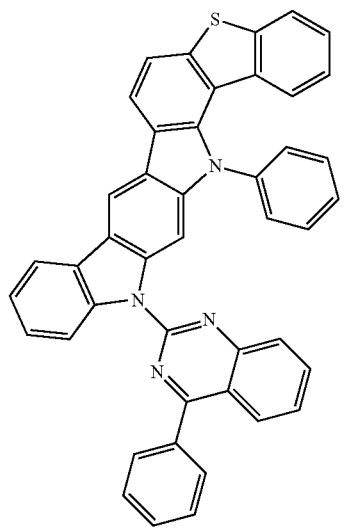
A-184
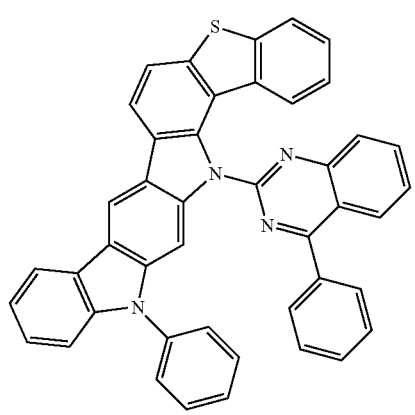
A-185
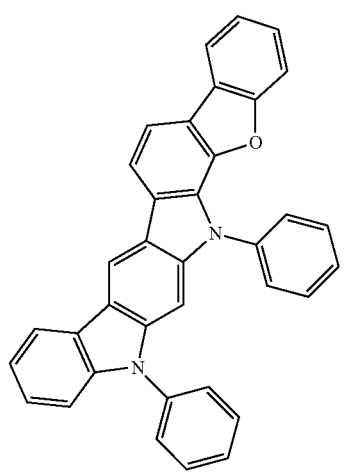

A-186
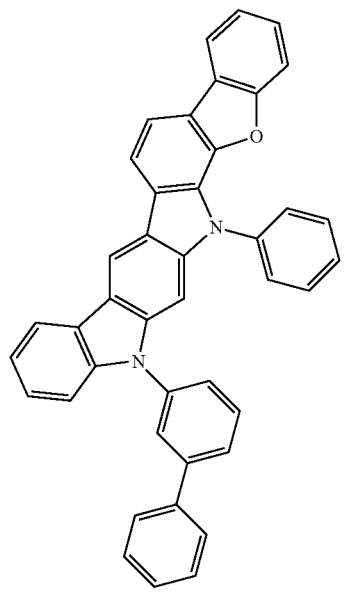
A-187
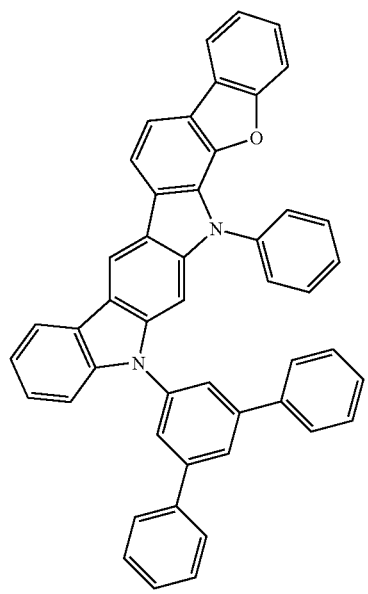
A-188
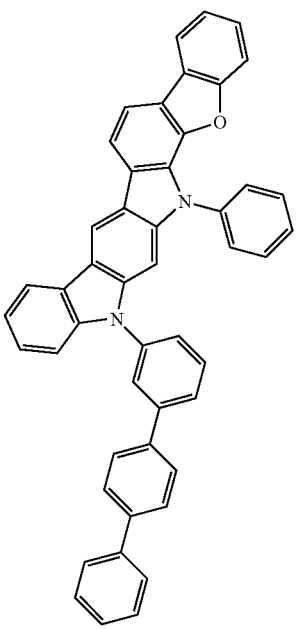
A-189
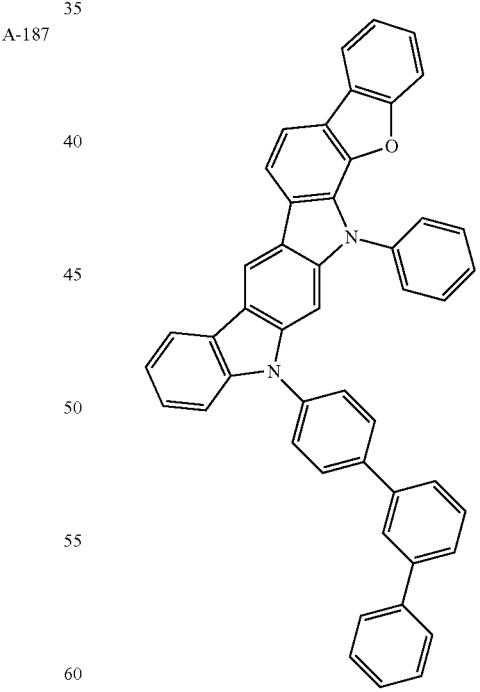

A-190
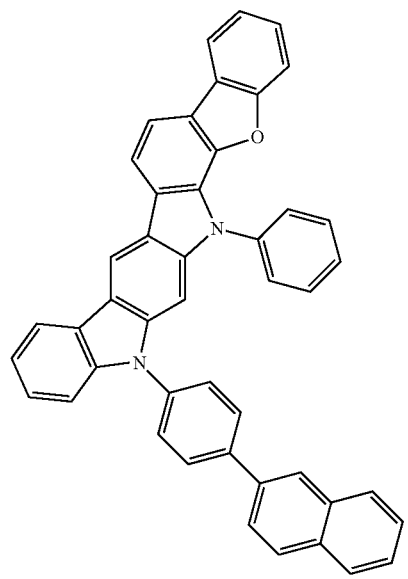
A-192
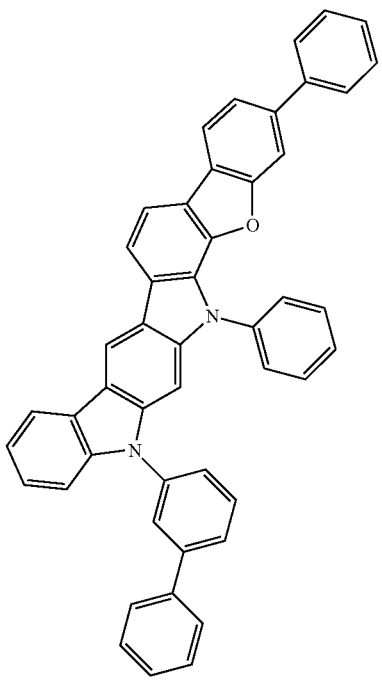
A-191
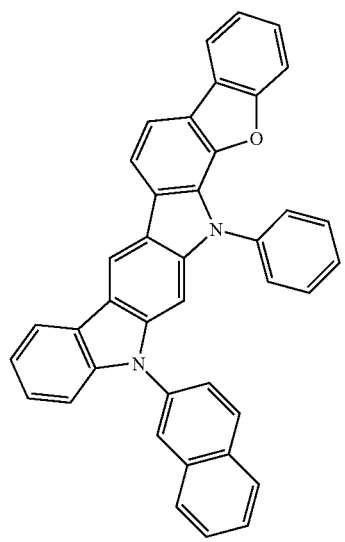
A-193
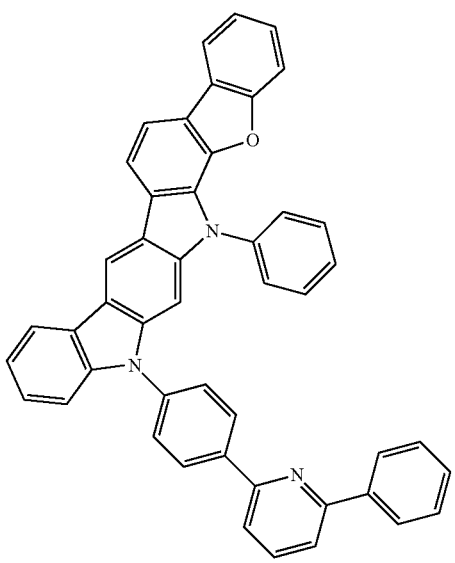

-continued
A-194
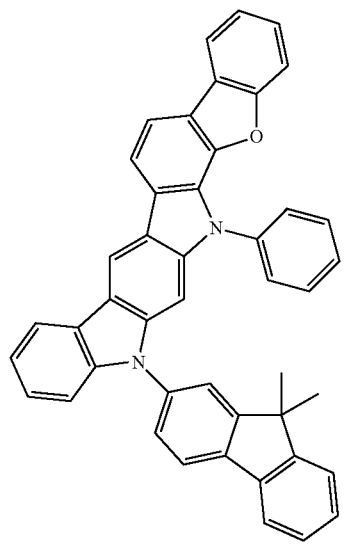
A-195
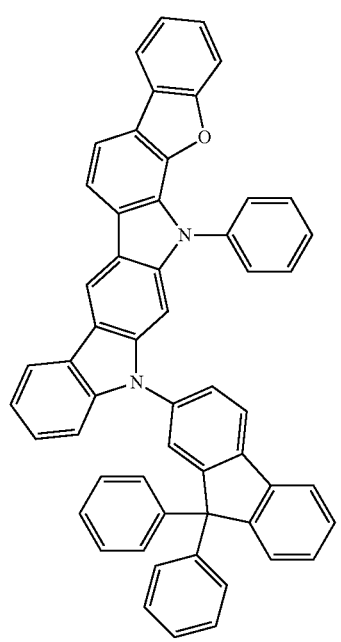
-continued
A-196
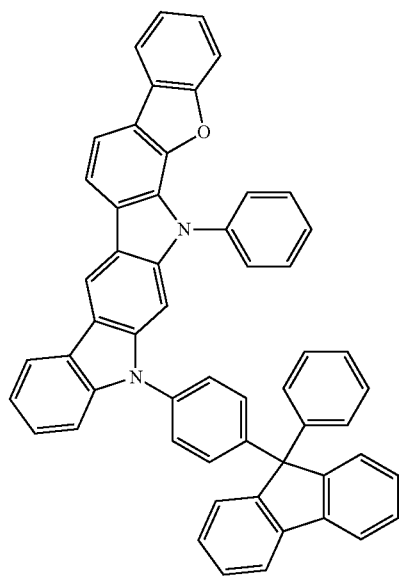
A-197

A-198
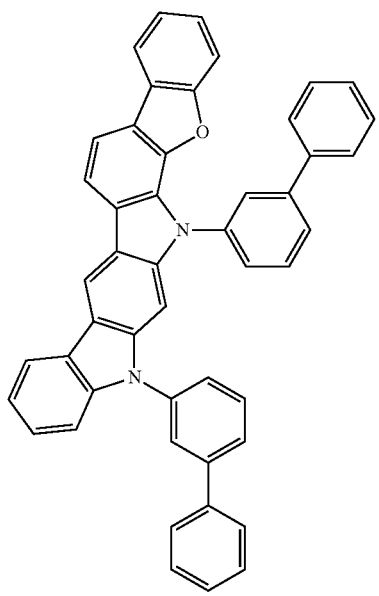
A-199
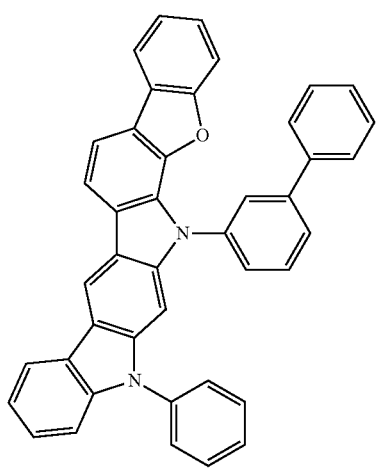
A-200
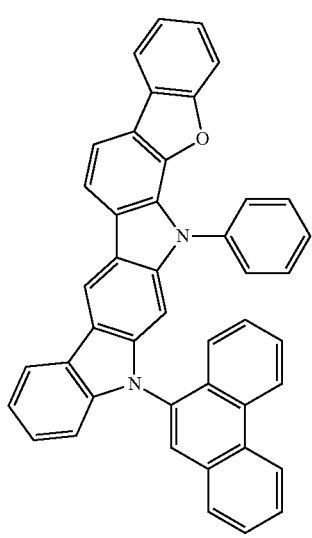
A-201
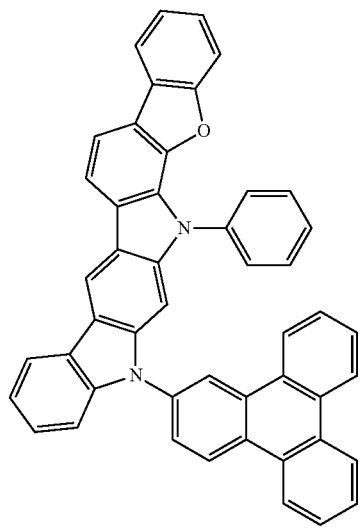
A-202
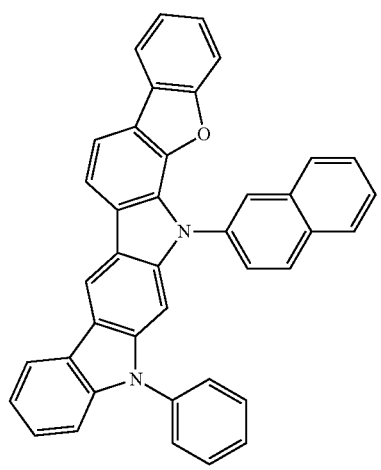
A-203
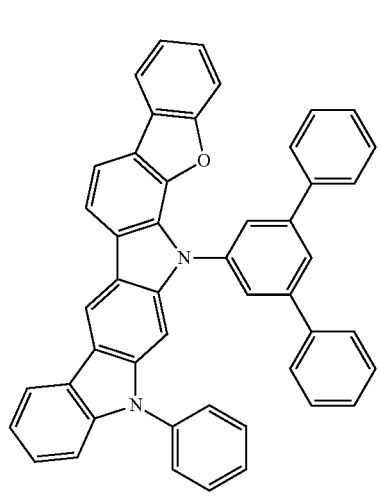

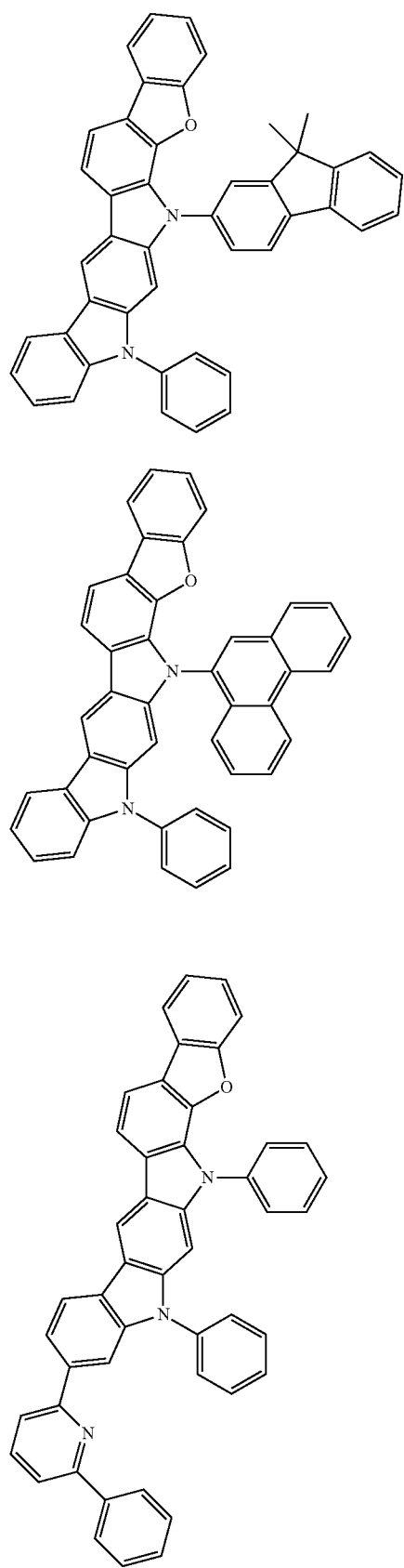
A-204
A-205
A-206
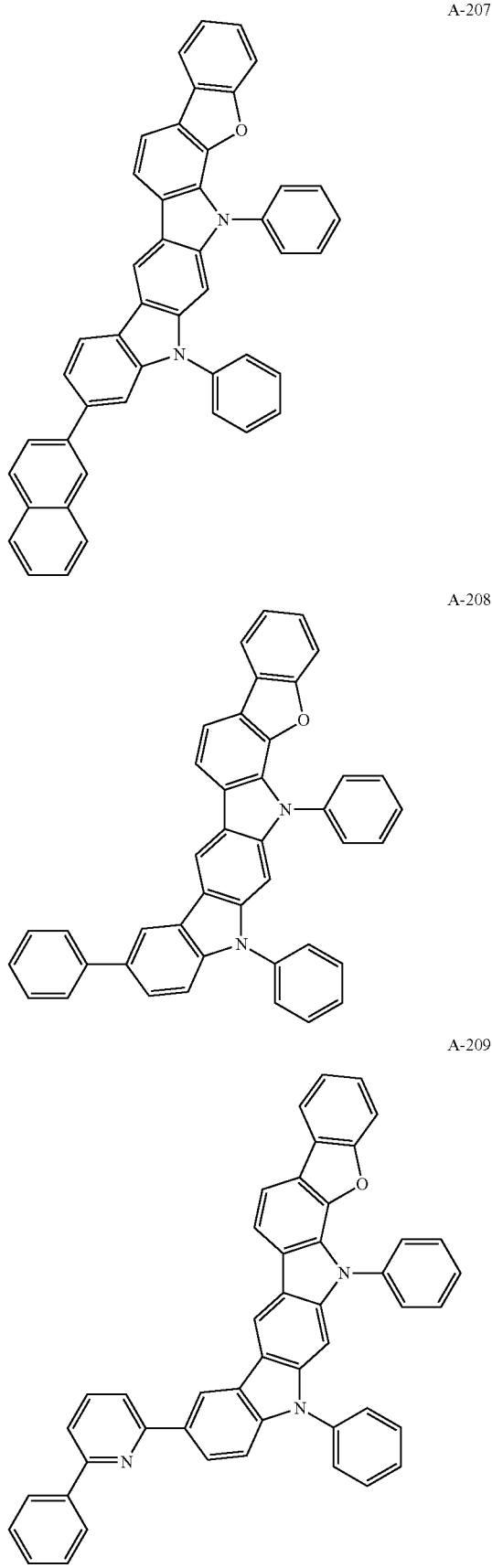 [SMILES: c1ccc(-n2c3cc(-c4ccc5ccccc5c4)ccc3c3cc4c5ccc6c7ccccc7oc6c5n(-c5ccccc5)c4cc32)cc1 ; c1ccc(-c2ccc3c(c2)c2cc4c5ccc6c7ccccc7oc6c5n(-c5ccccc5)c4cc2n3-c2ccccc2)cc1 ; c1ccc(-c2cccc(-c3ccc4c(c3)c3cc5c6ccc7c8ccccc8oc7c6n(-c6ccccc6)c5cc3n4-c3ccccc3)n2)cc1]
A-207
A-208
A-209

A-210
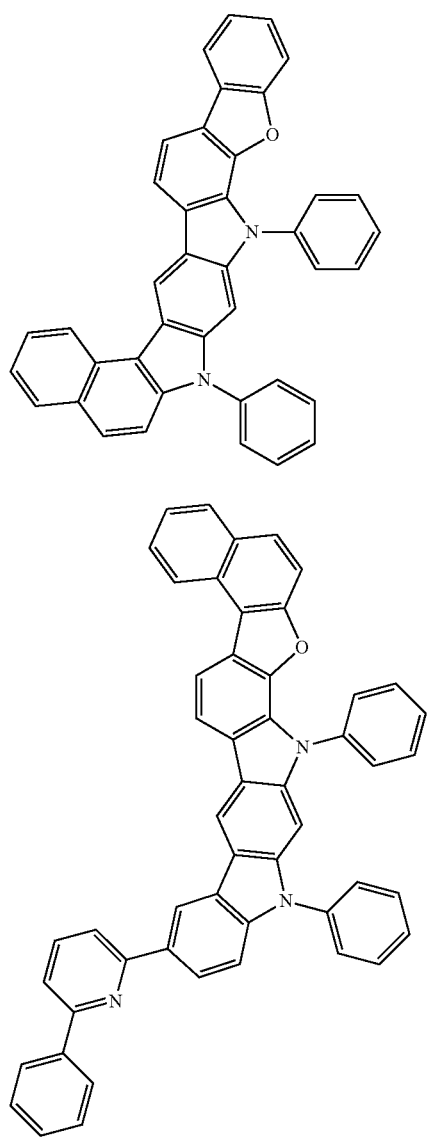
A-211
A-212
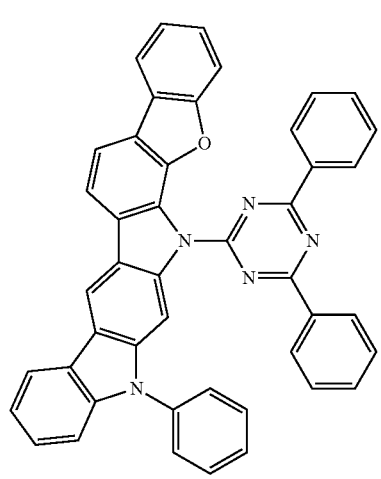
A-213
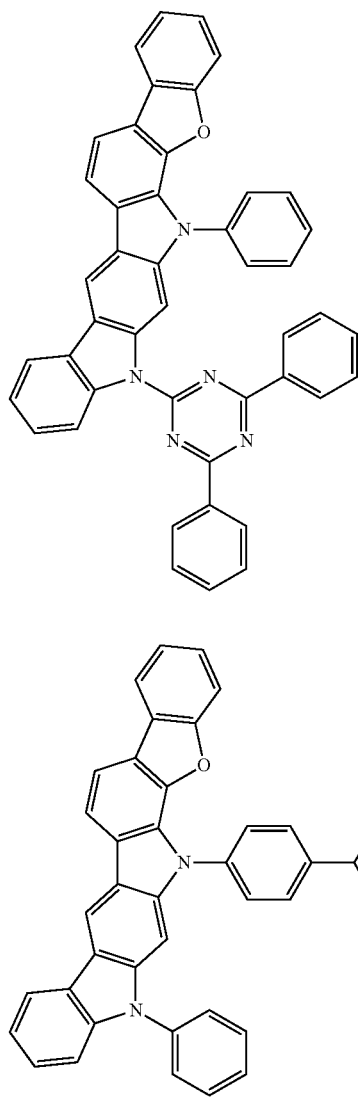
A-214
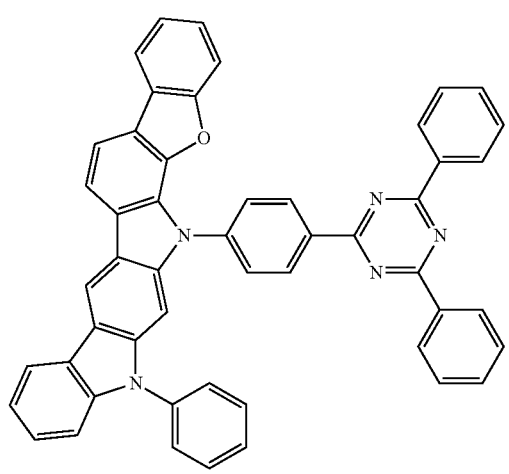
A-215
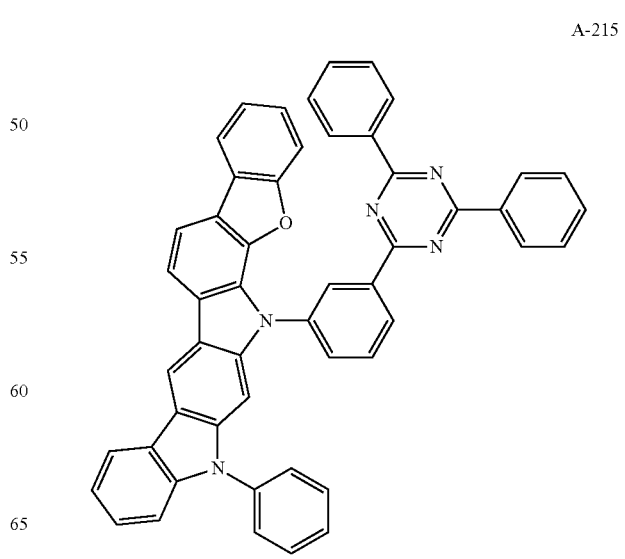

A-216
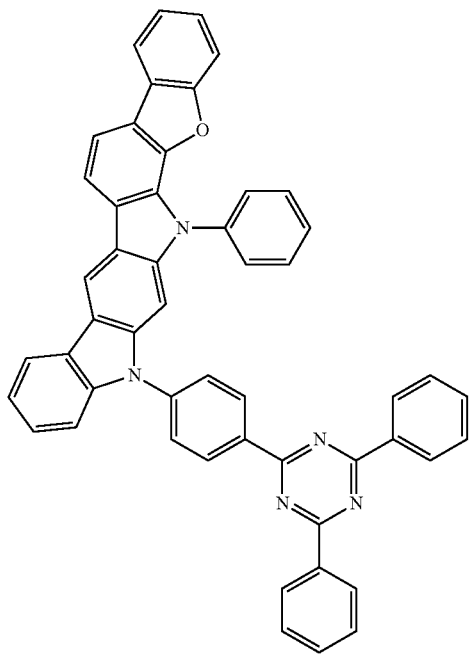
A-217
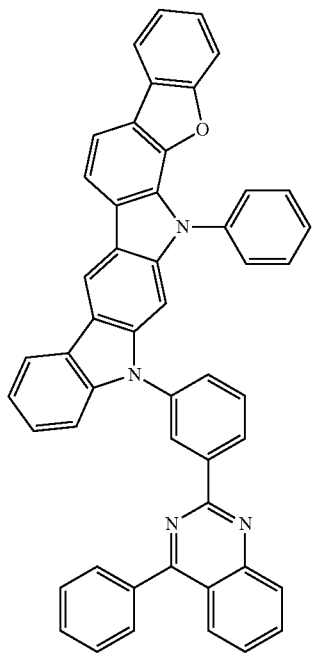
A-218
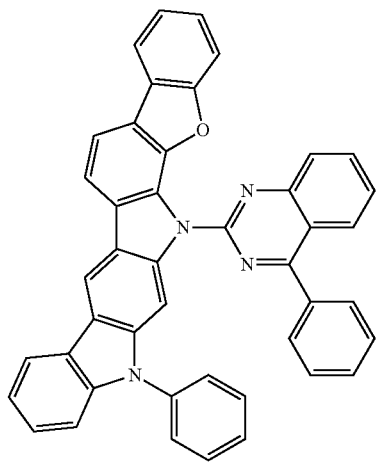
A-219
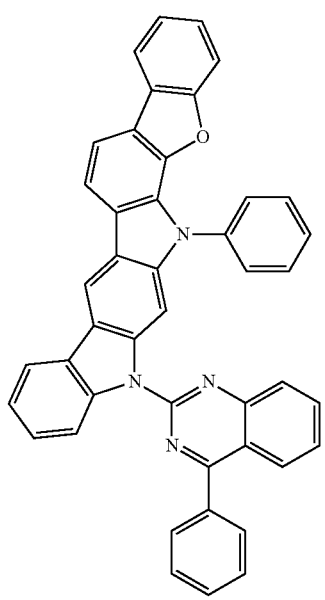
A-220
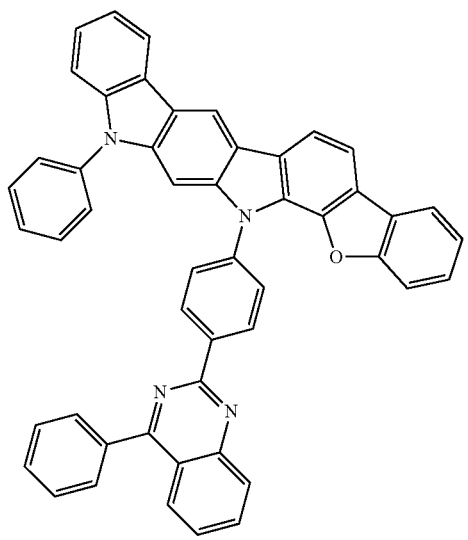

A-221
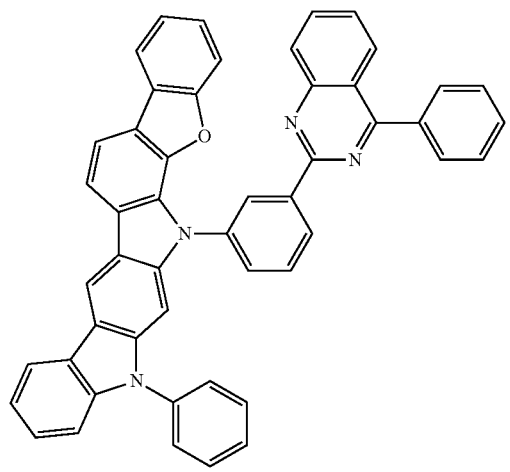
A-223
A-225
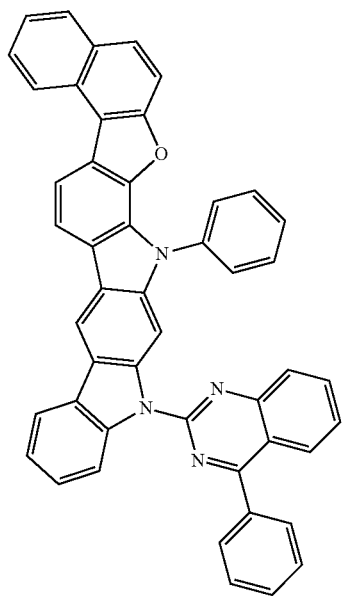
A-226
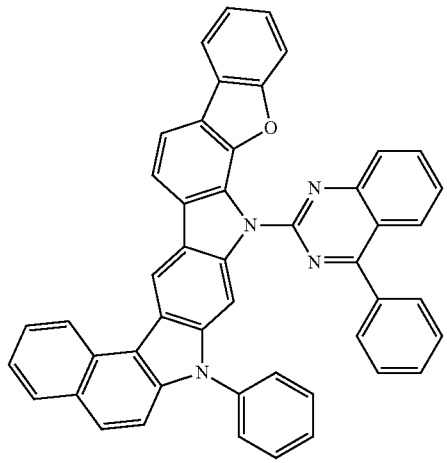
A-224
A-227
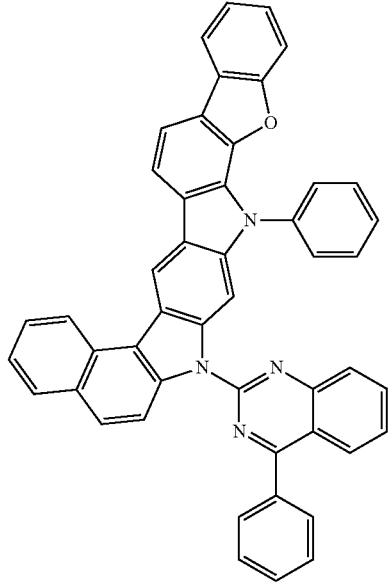

A-228
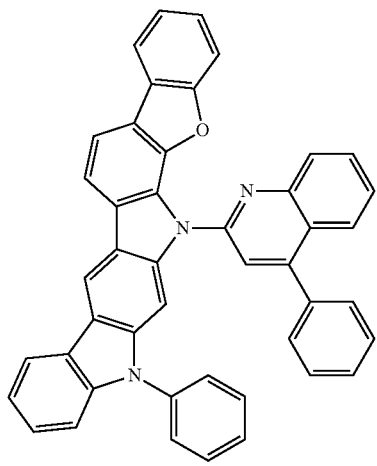
A-231
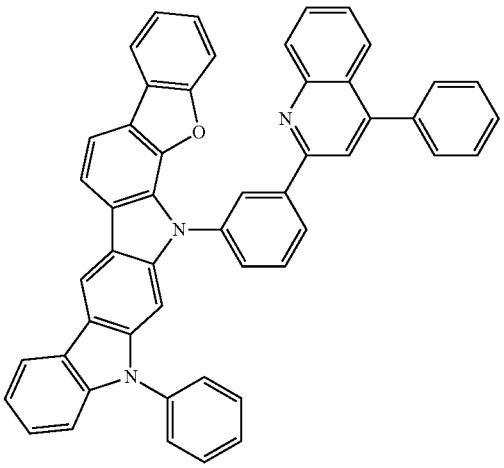
A-229
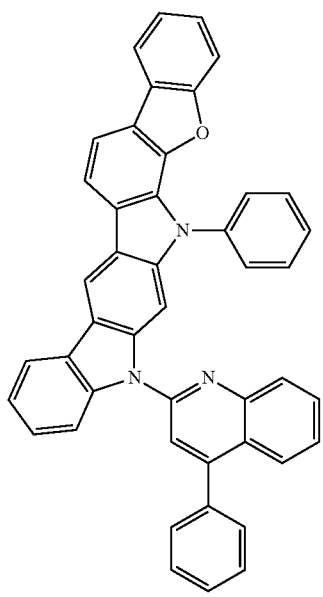
A-232
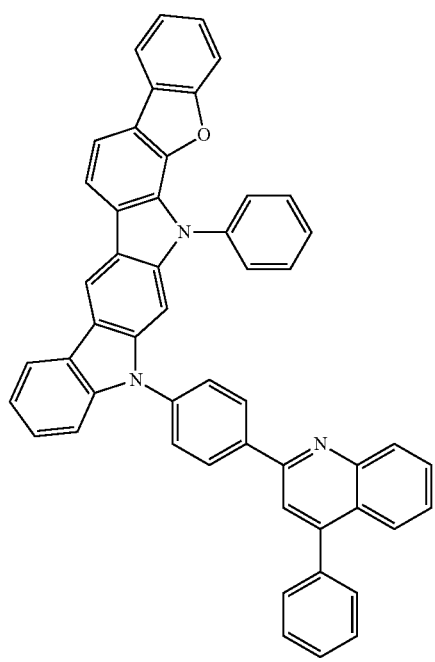
A-230
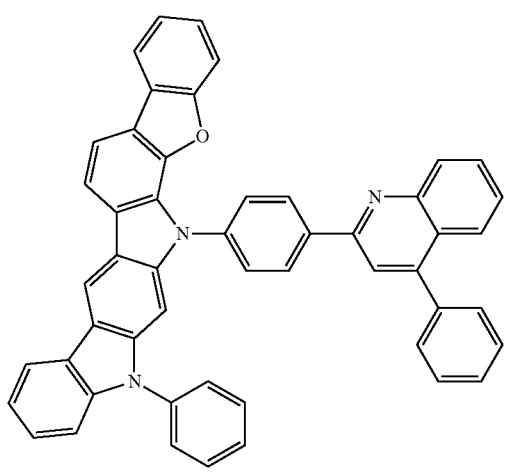
A-233
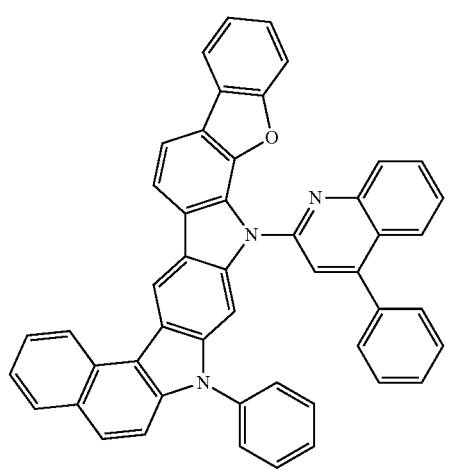

A-234
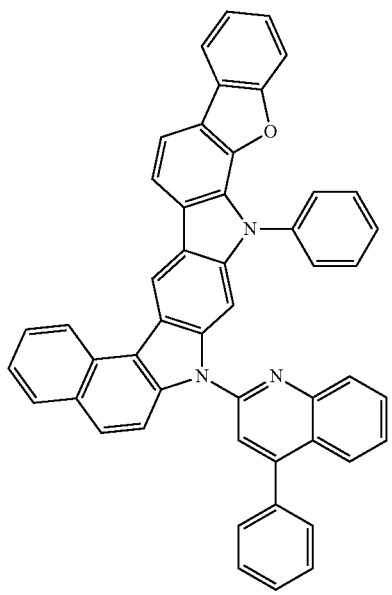
A-235
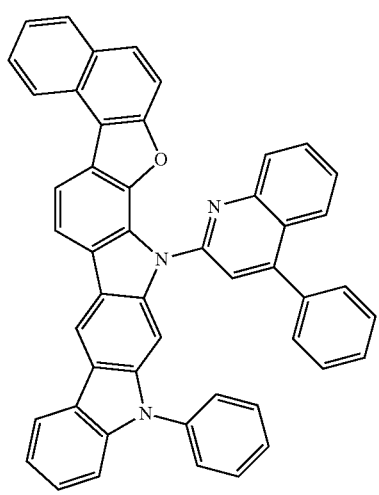
A-236
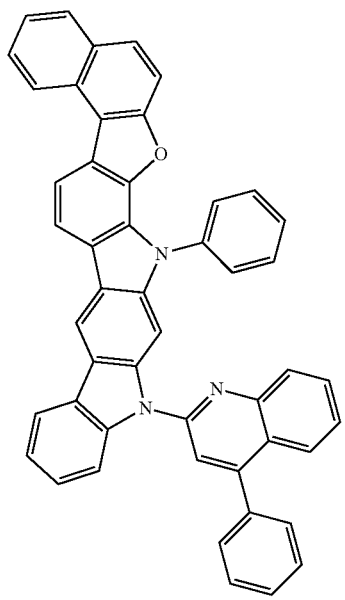
A-237
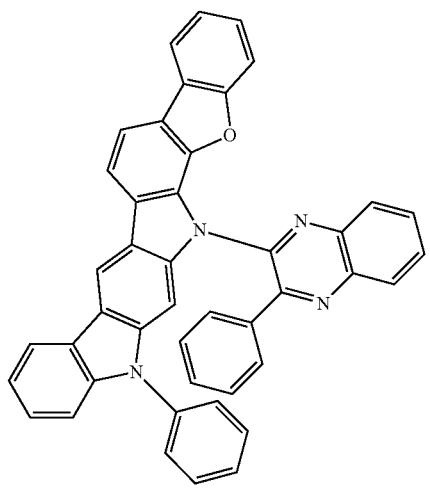
A-238
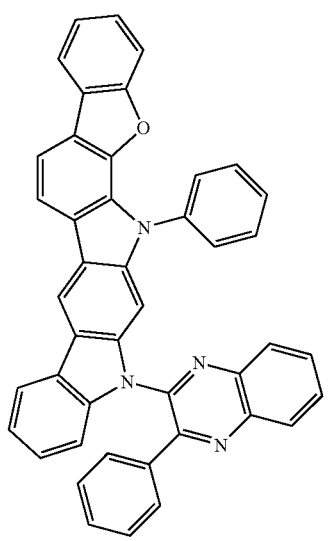
A-239
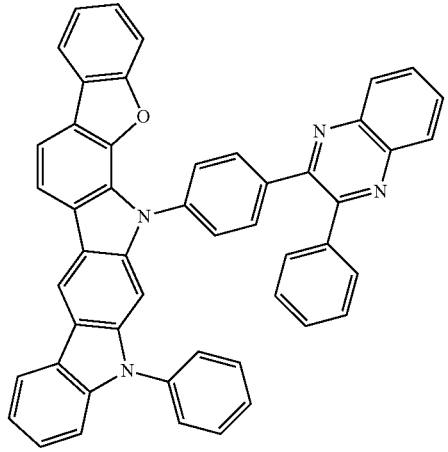

A-240
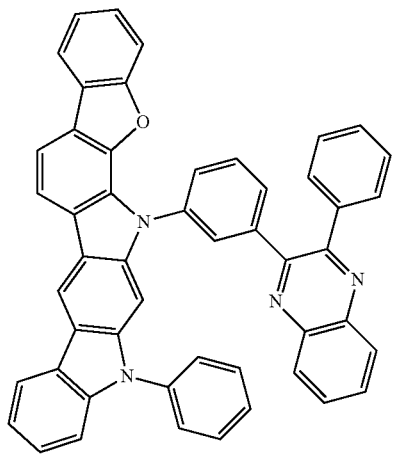
A-241
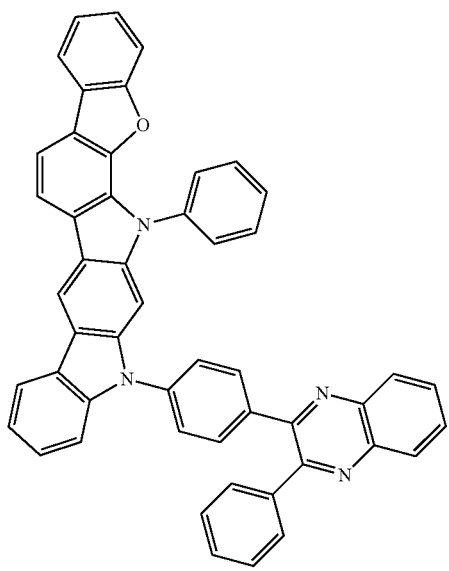
A-242
A-243
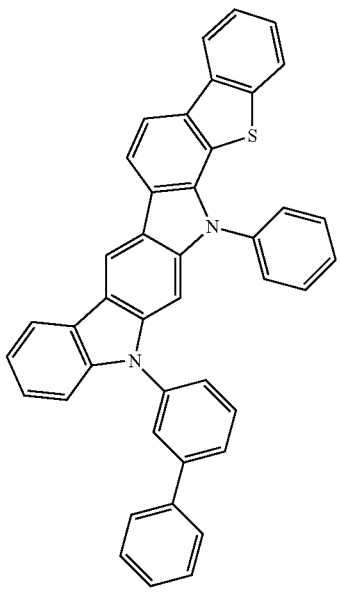
A-244
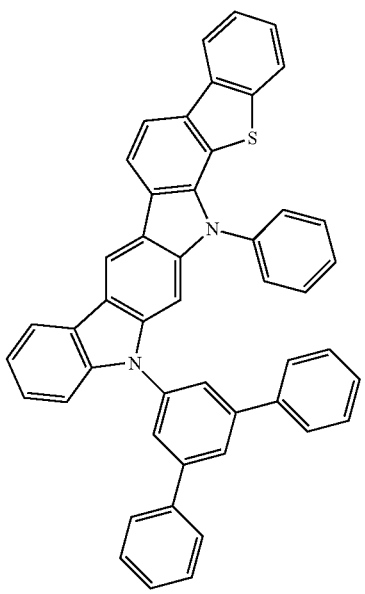

A-245
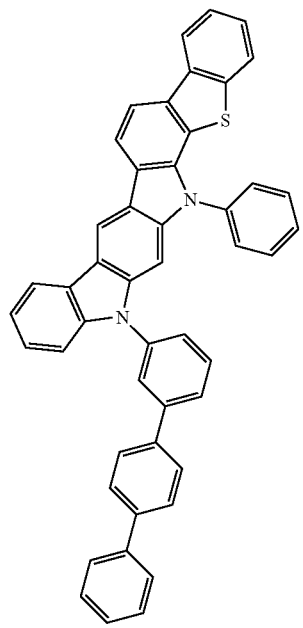
A-246
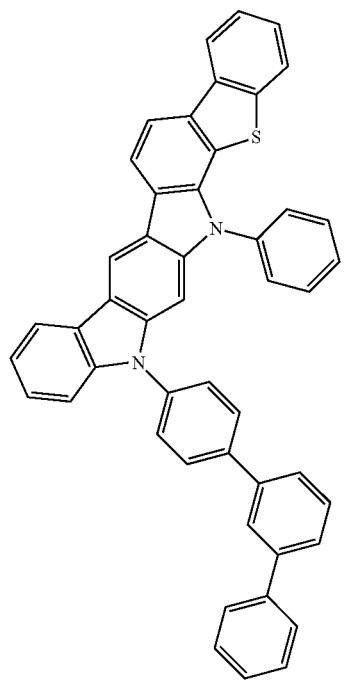
A-247
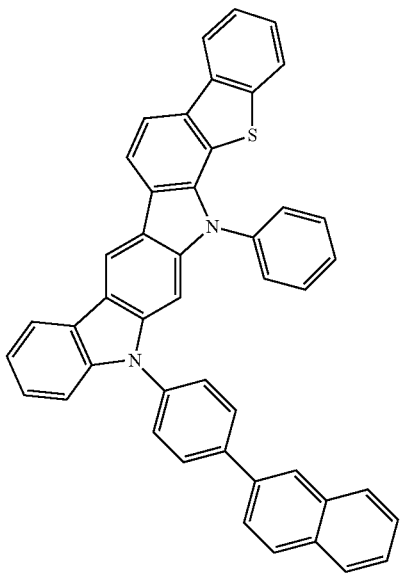
A-248
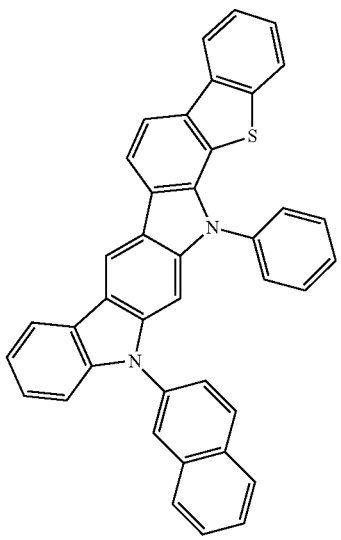

-continued
A-249
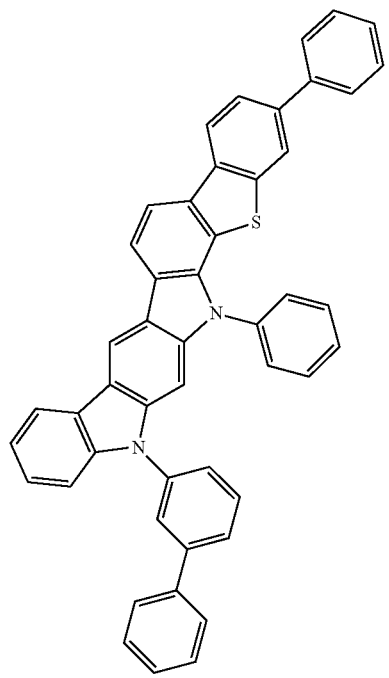
A-250
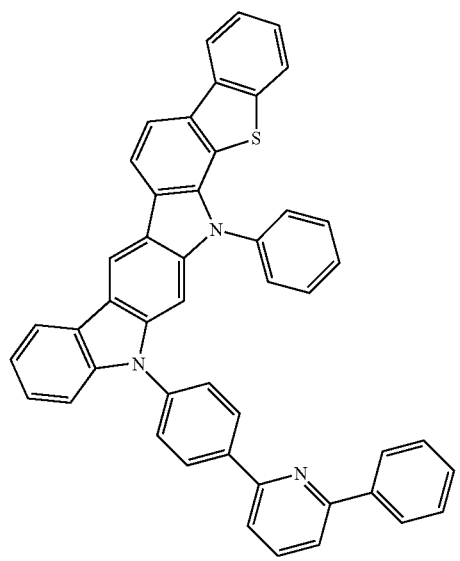
-continued
A-251
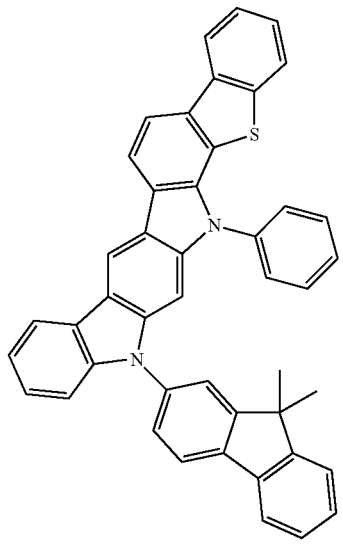
A-252
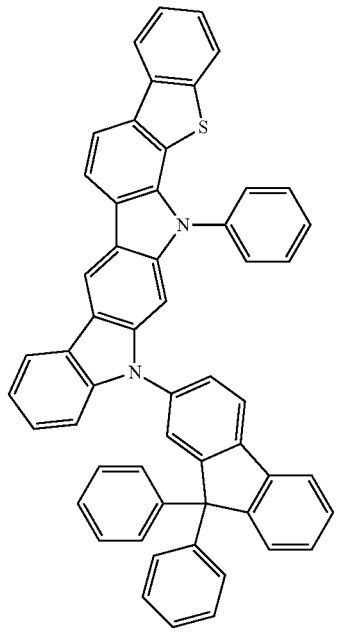

A-253
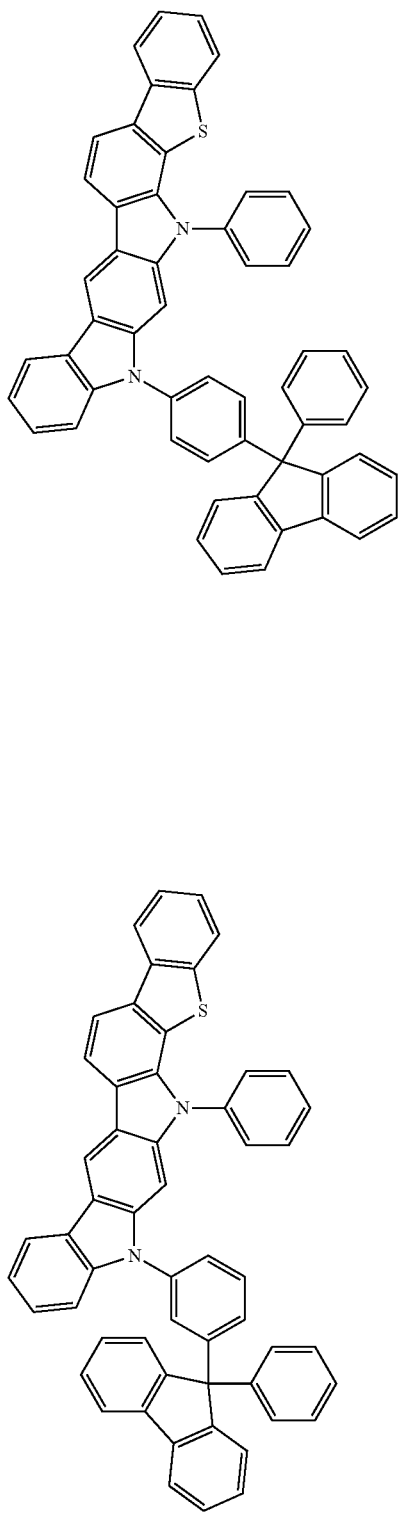
A-254
A-255
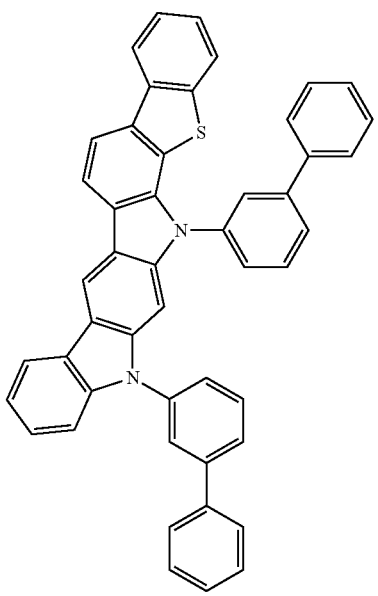
A-256
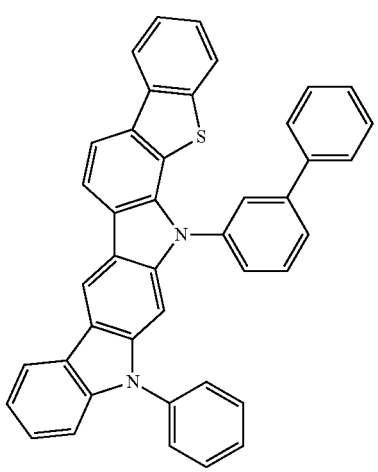
A-257
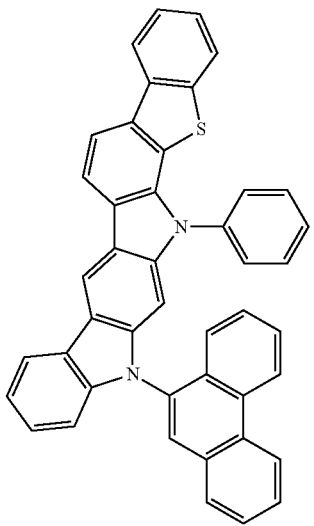

A-258
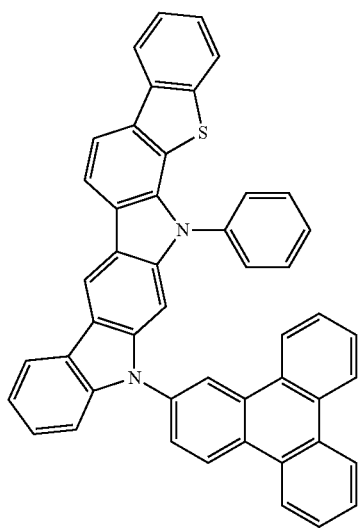
A-259
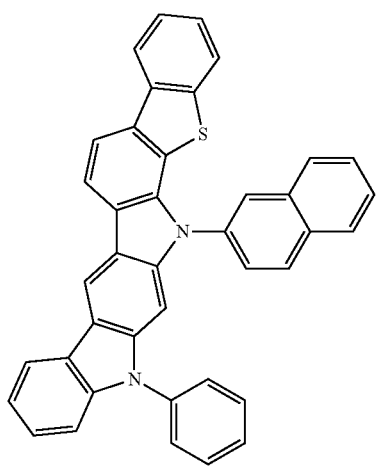
A-260
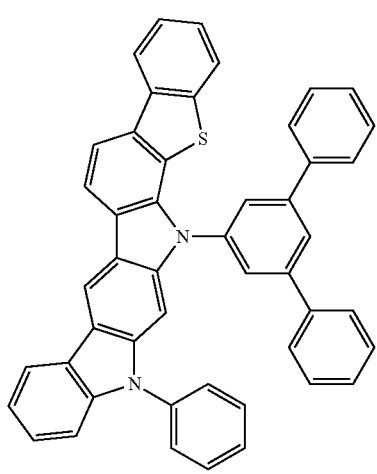
A-261
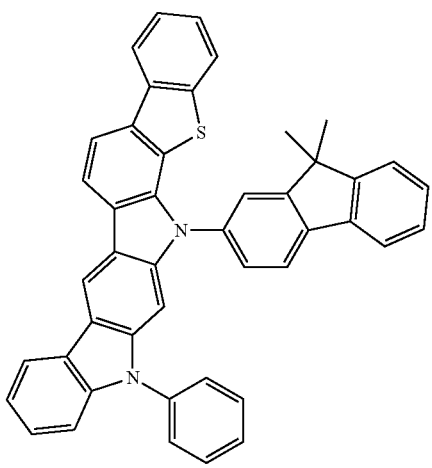
A-262
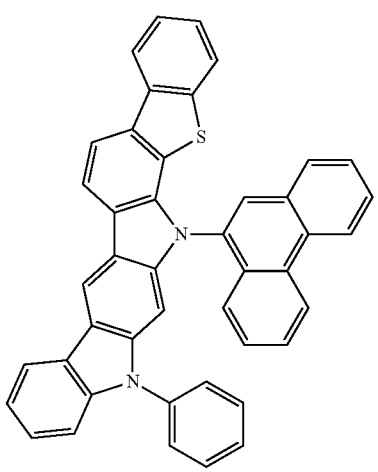
A-263
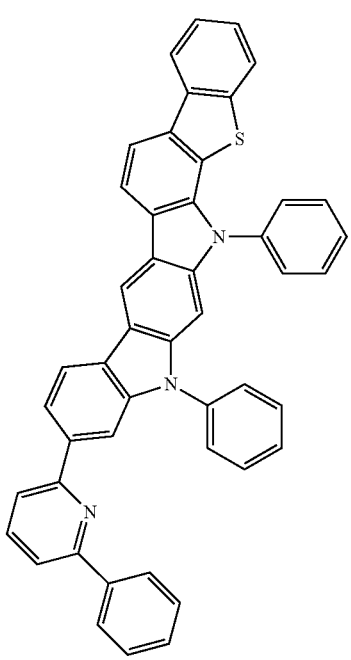

A-264
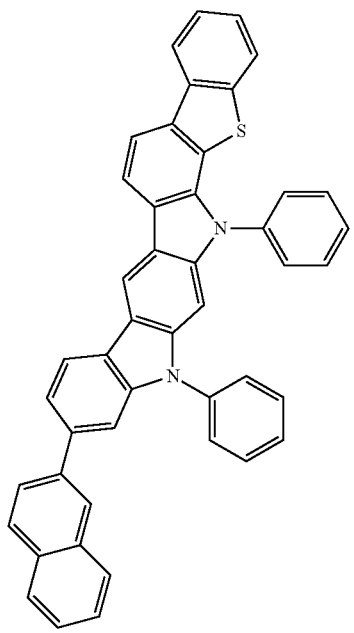
A-267
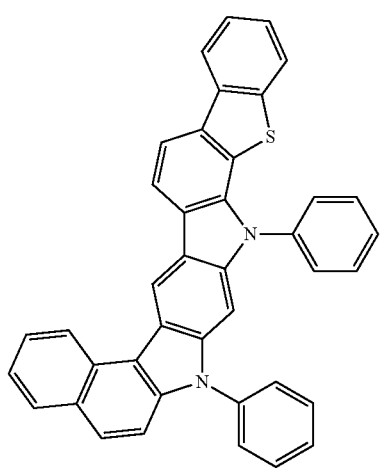
A-265
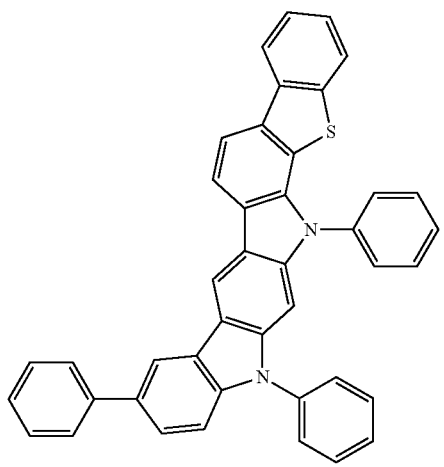
A-268
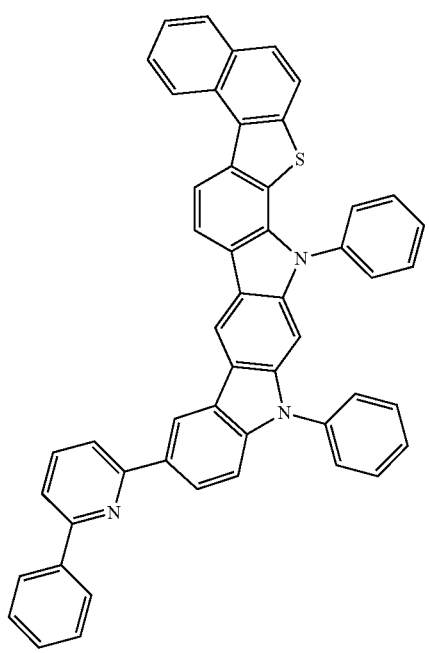
A-266
A-269
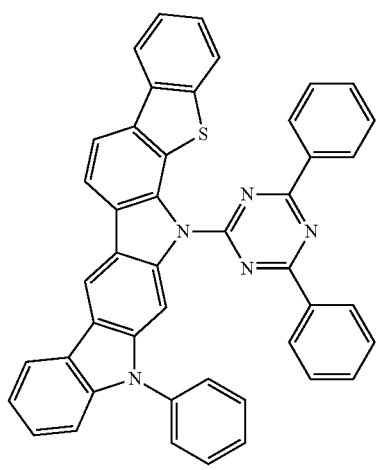

A-270
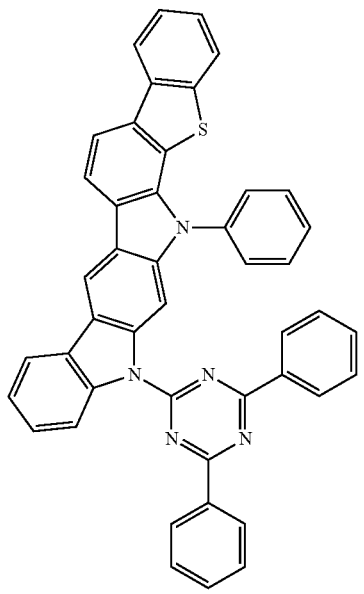
A-271
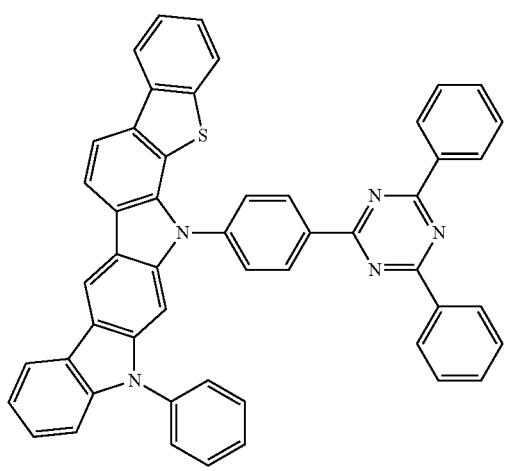
A-272
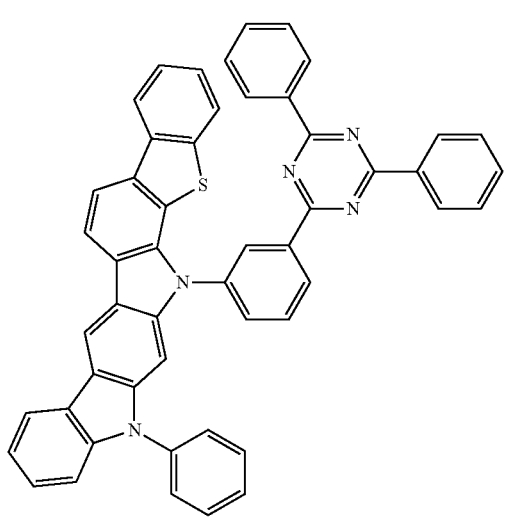
A-273
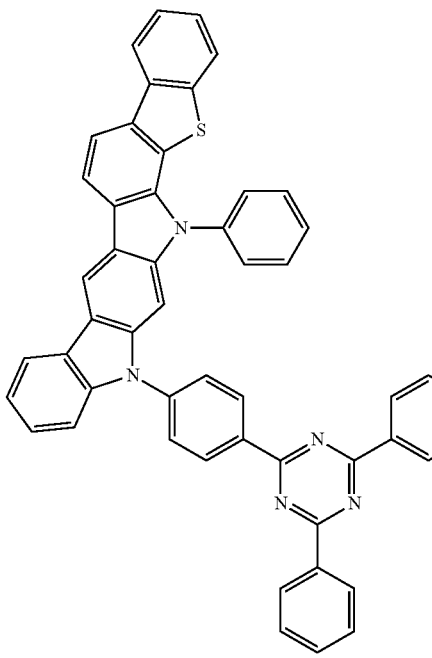
A-274
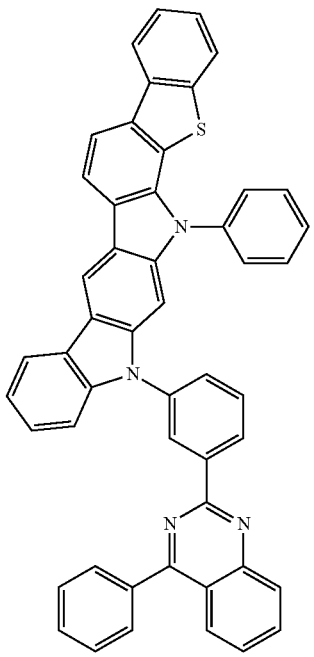

A-275
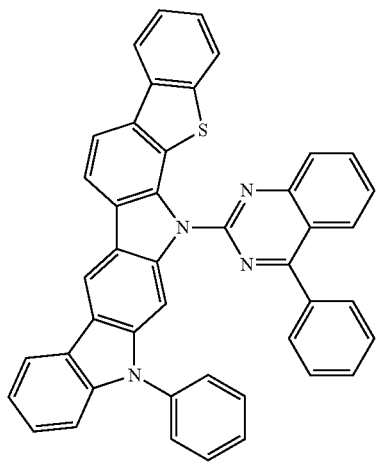
A-276
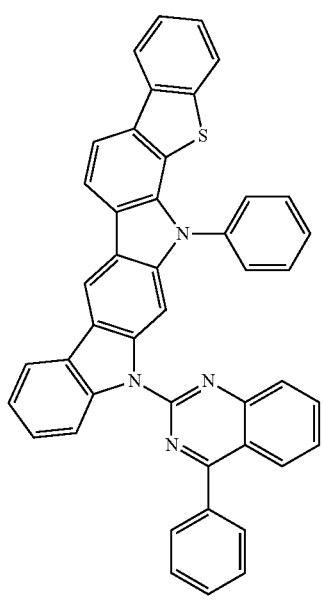
A-277
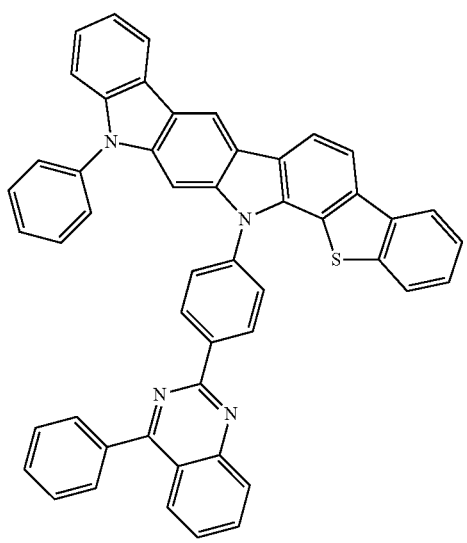
A-278
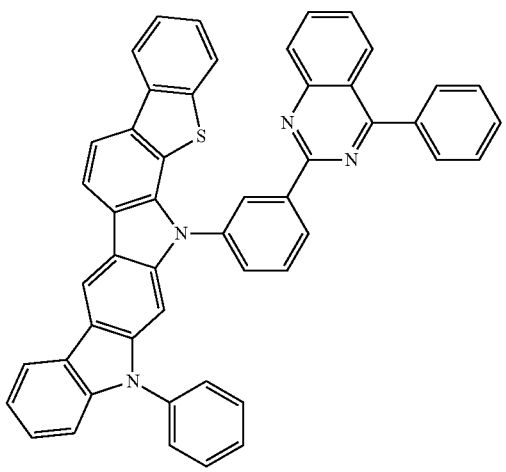
A-279
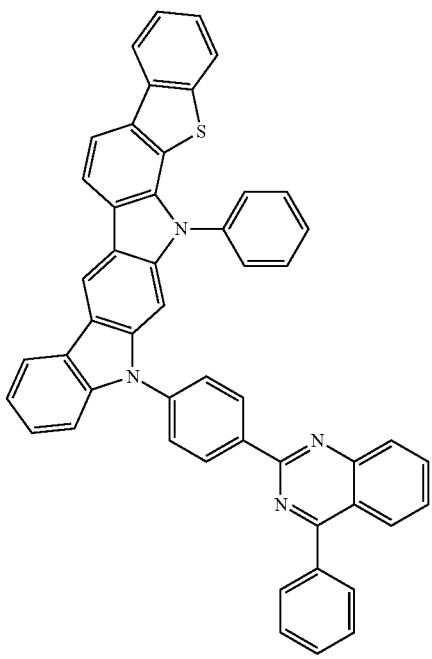
A-280
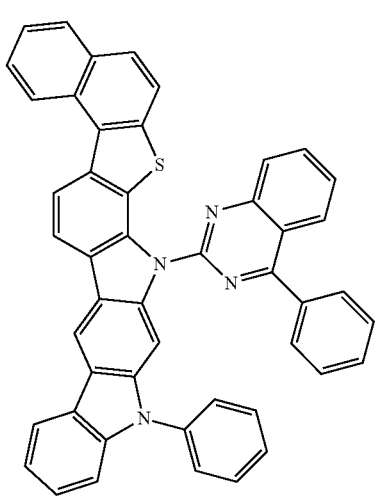

A-281
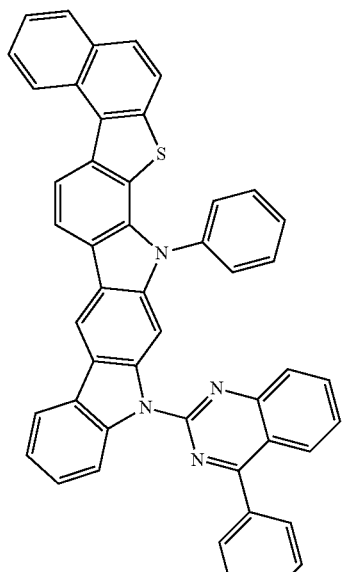
A-282
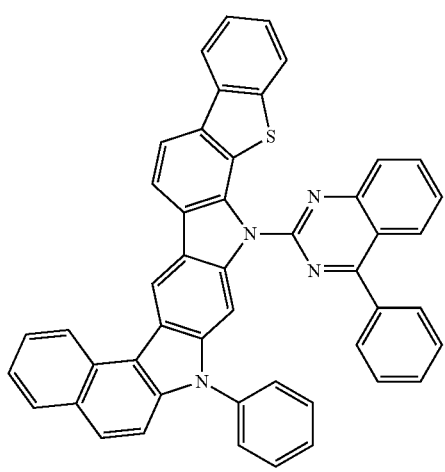
A-283
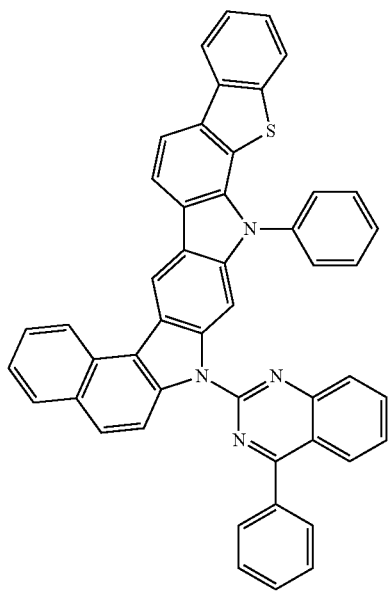
A-284
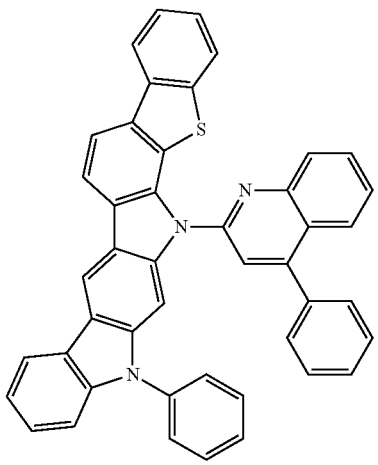
A-285
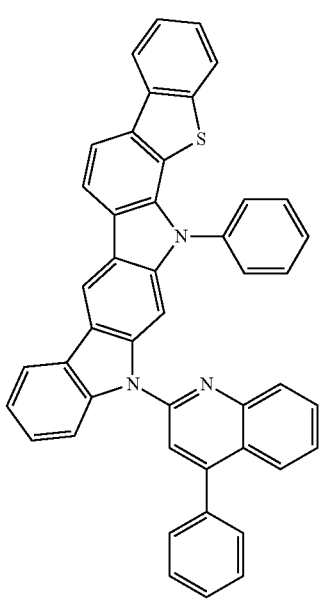
A-286
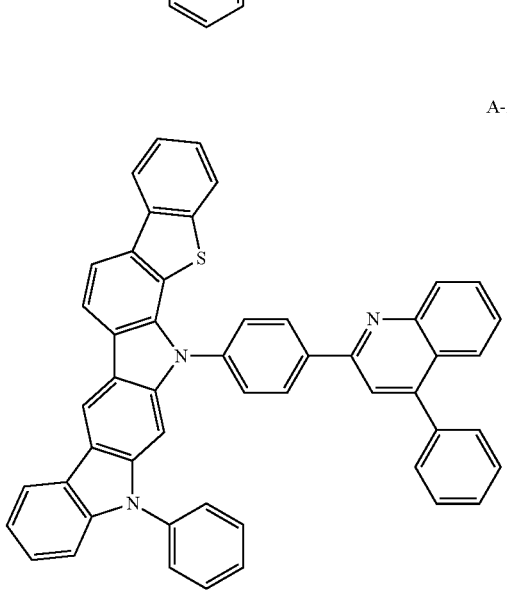

A-287
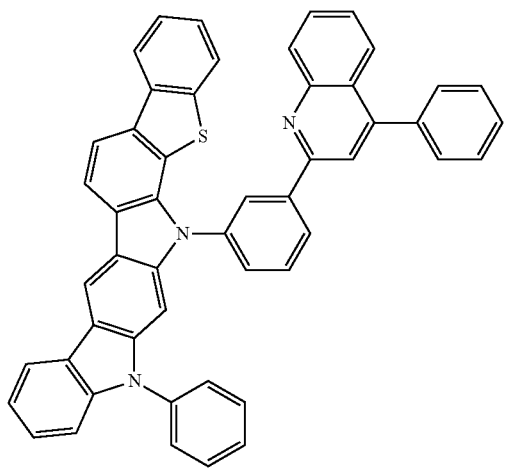
A-288
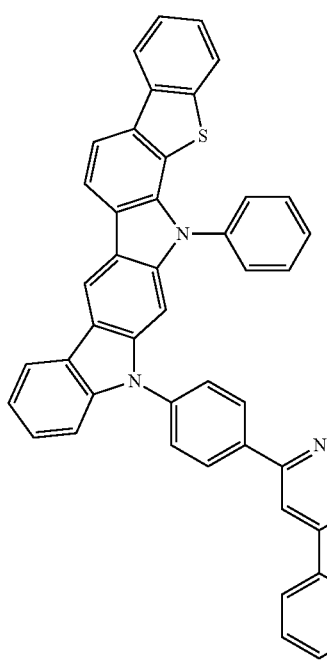
A-289
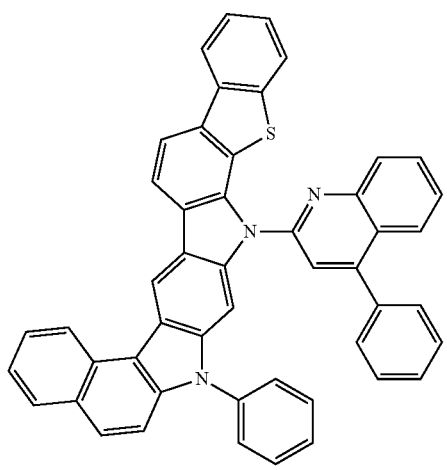
A-290
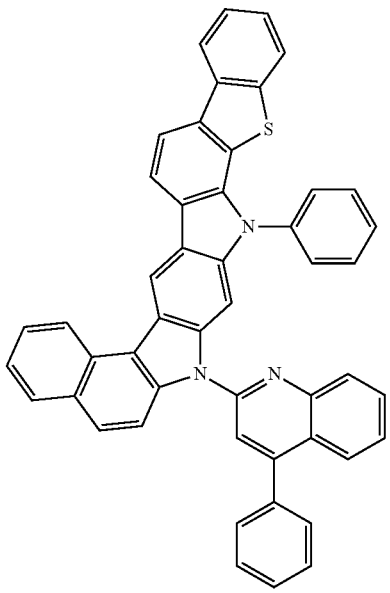
A-291
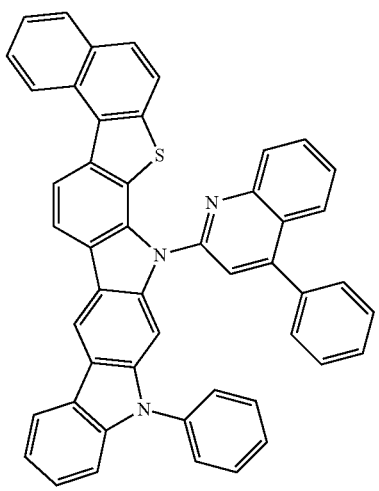
A-292
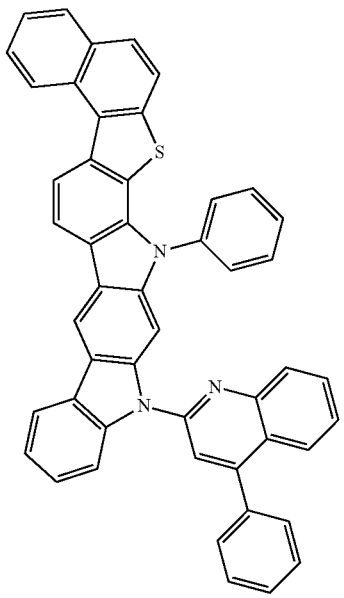

A-293
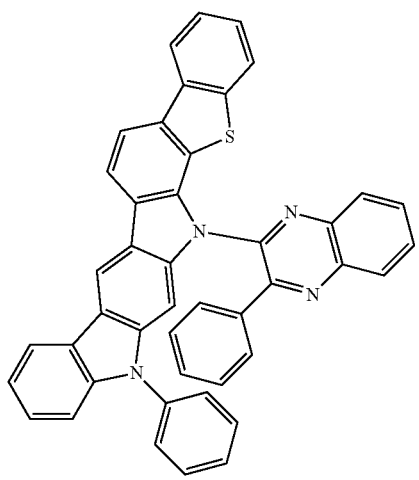
A-294
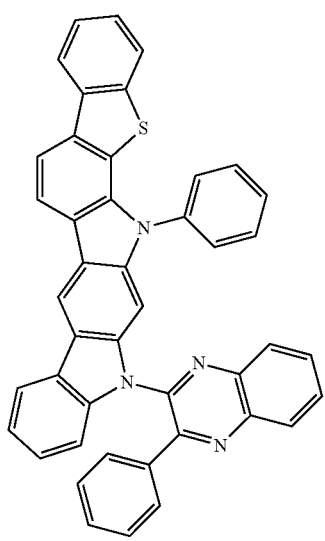
A-295
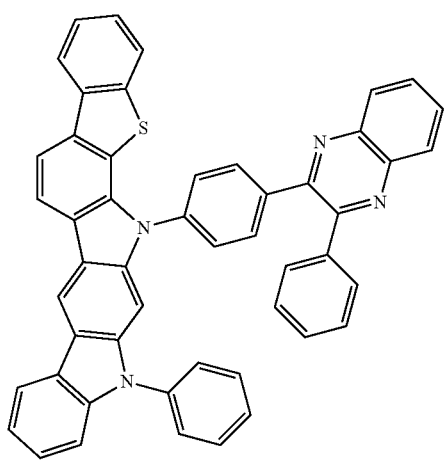
A-296
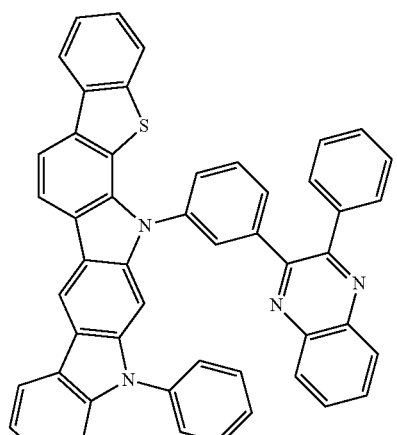
A-297
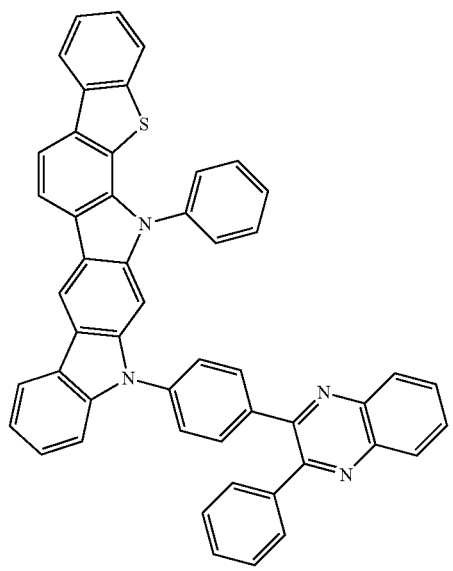
A-298
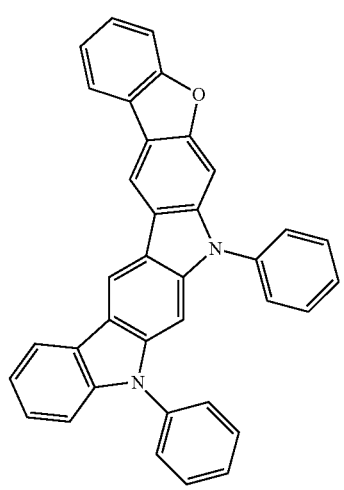

A-299
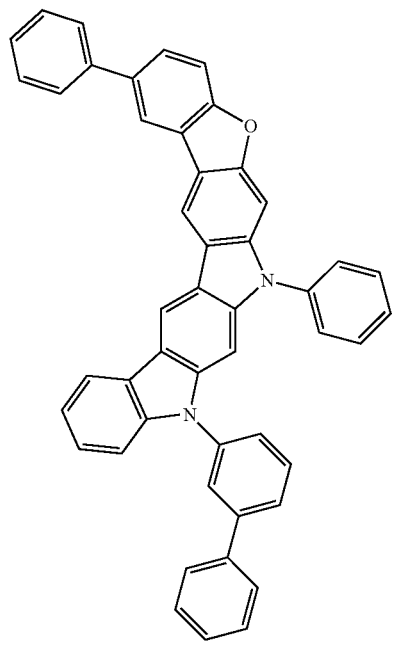
A-300
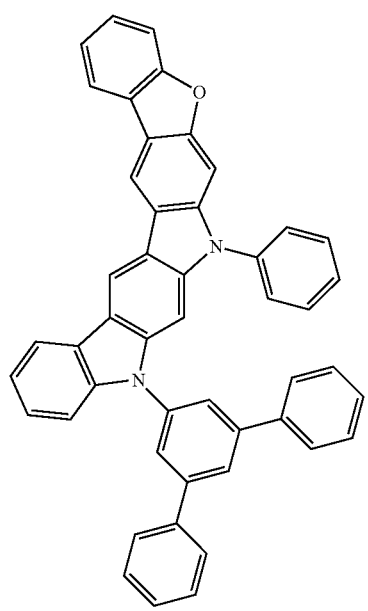
A-301
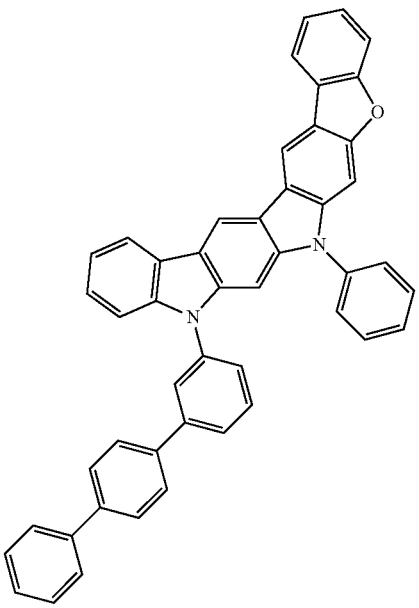
A-302
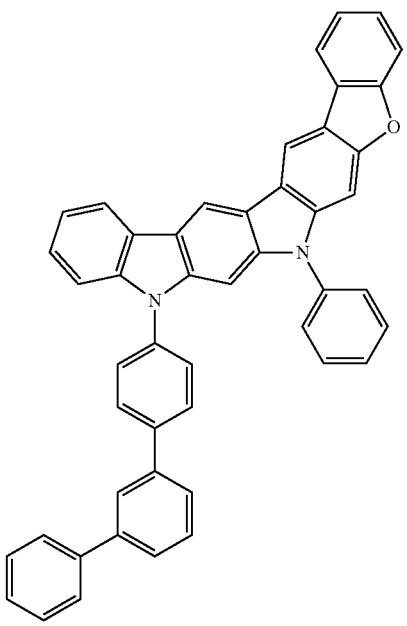

A-303
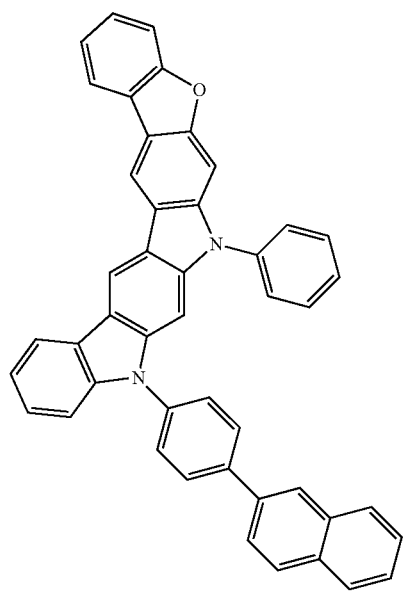
A-304
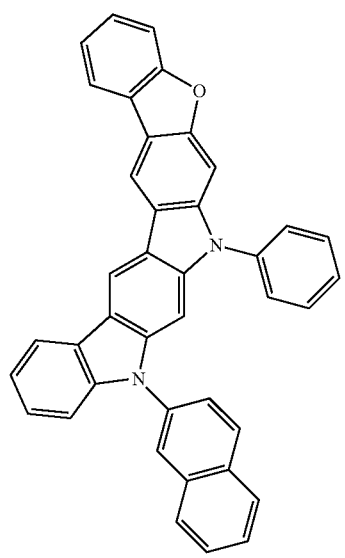
A-305
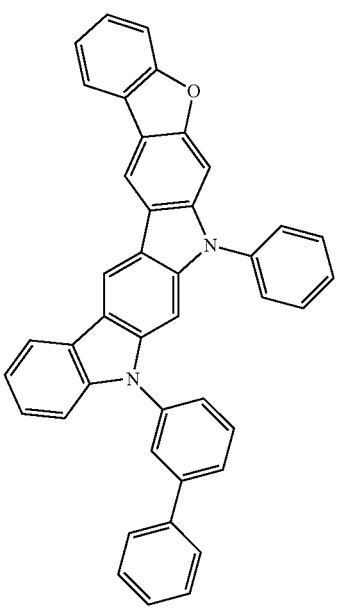
A-306
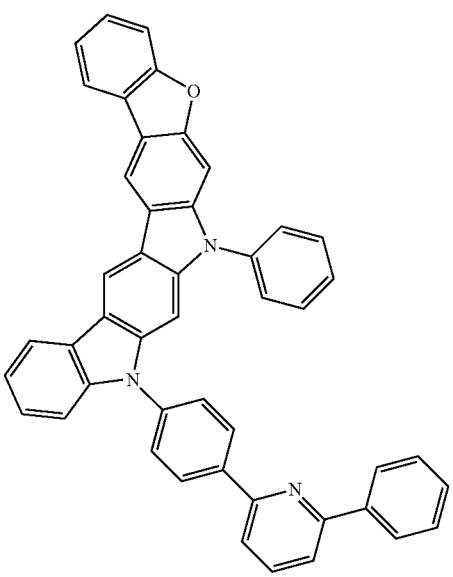

A-307
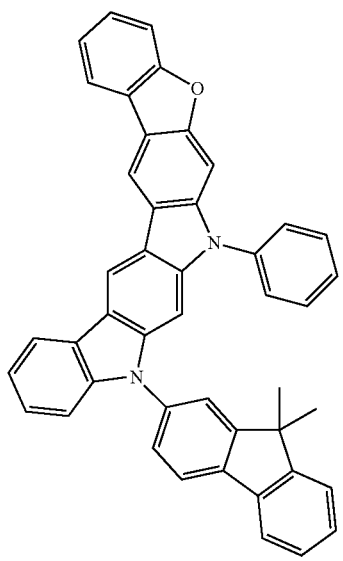
A-308
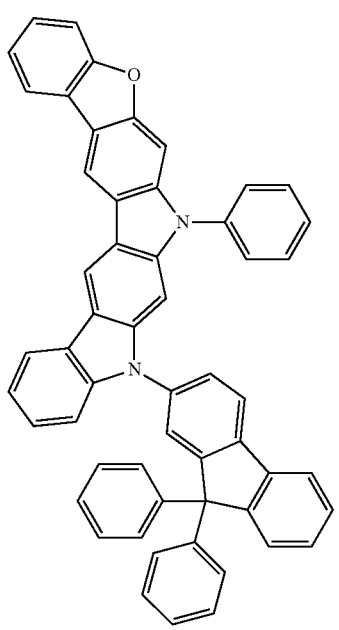
A-309
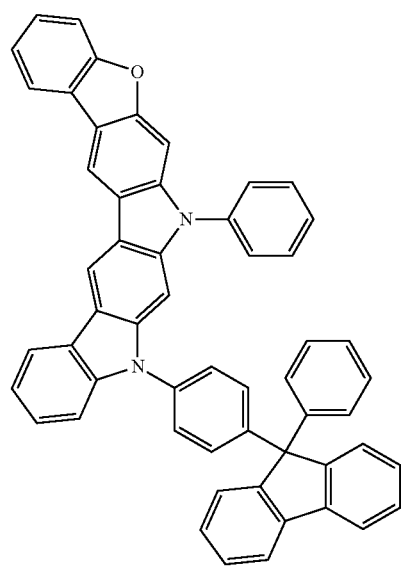
A-310
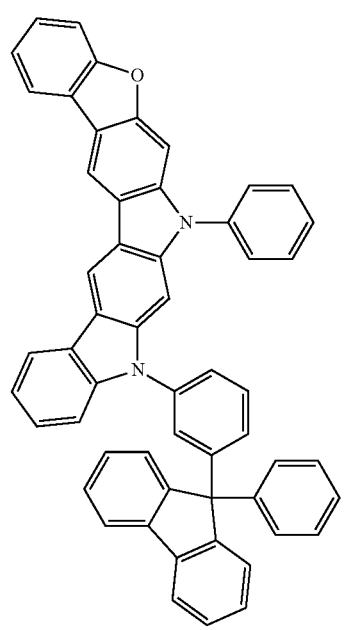

A-311
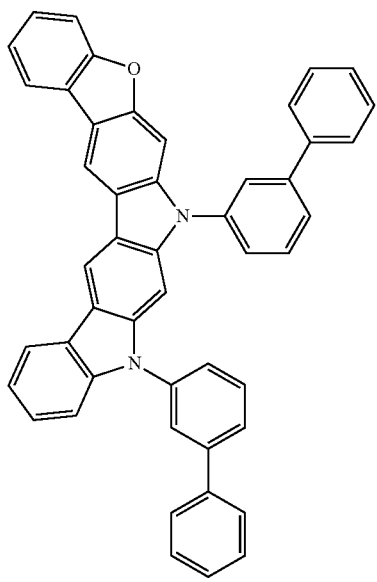
A-312
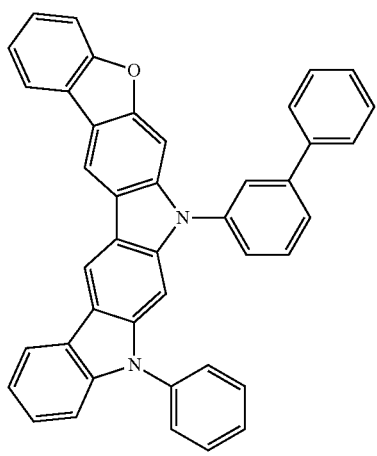
A-313
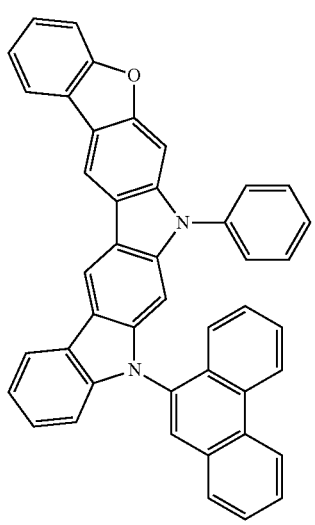
A-314
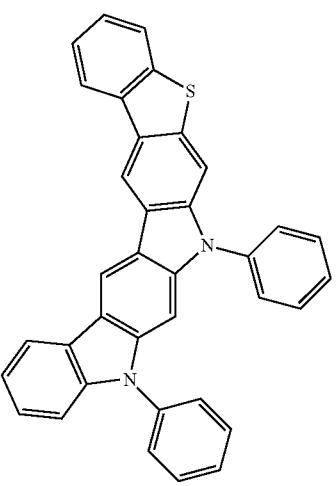
A-315
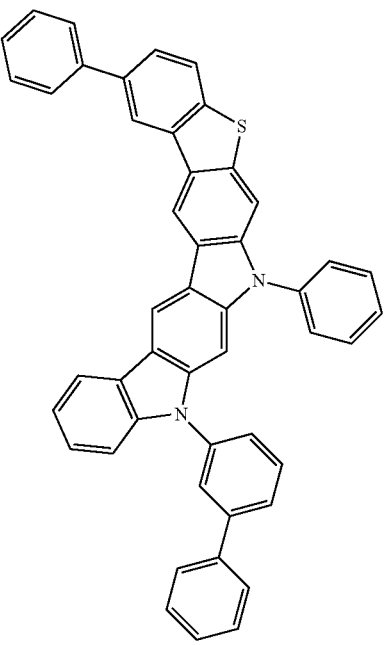

A-316
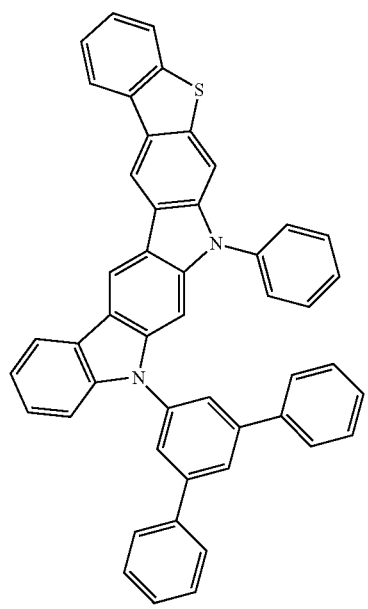
A-317
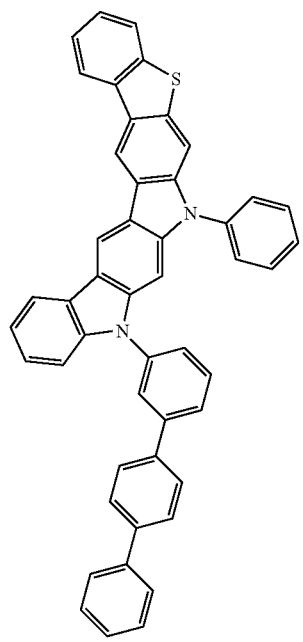
A-318
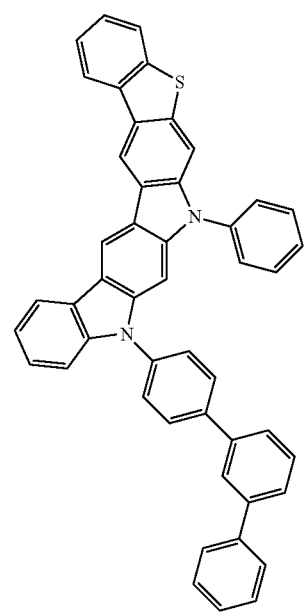
A-319
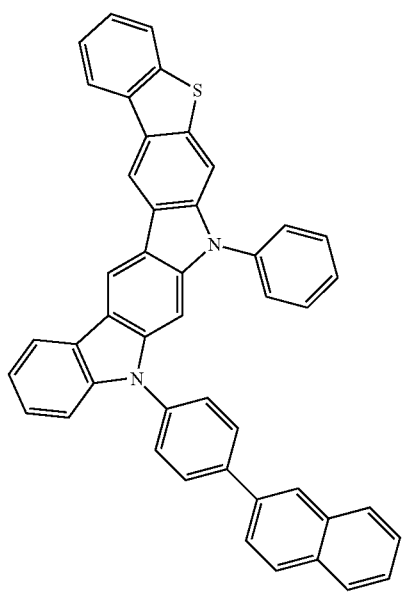

A-320
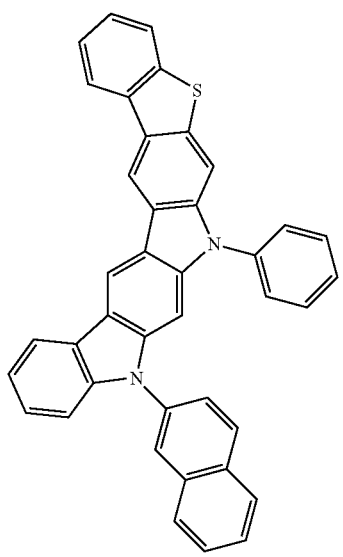
A-322
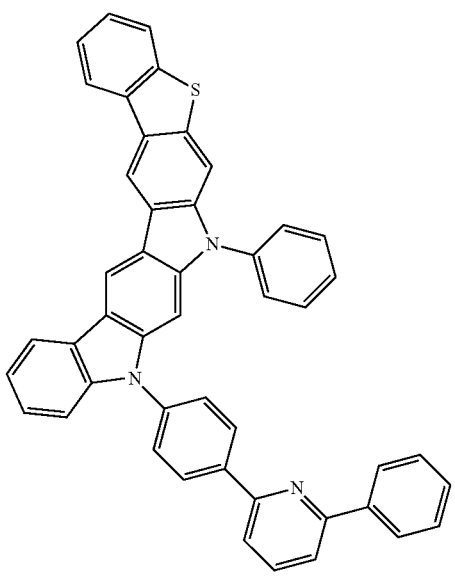
A-321
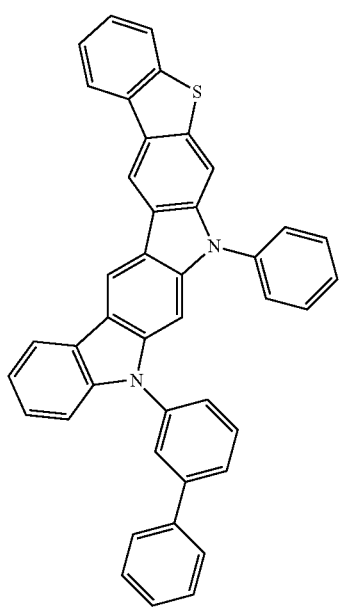
A-323
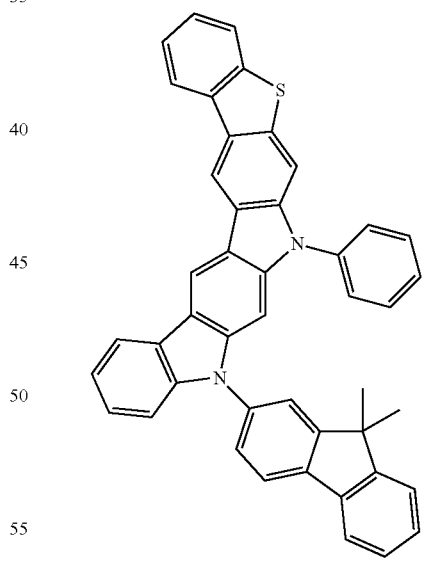

A-324
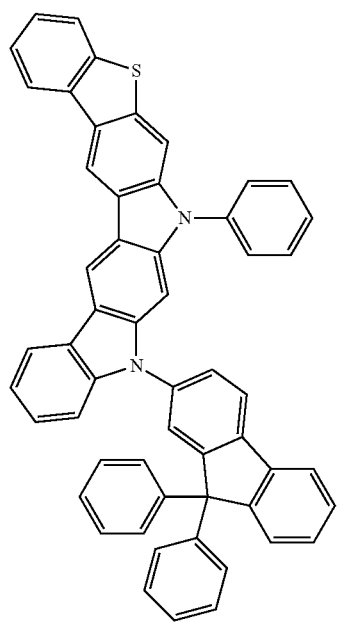
A-325
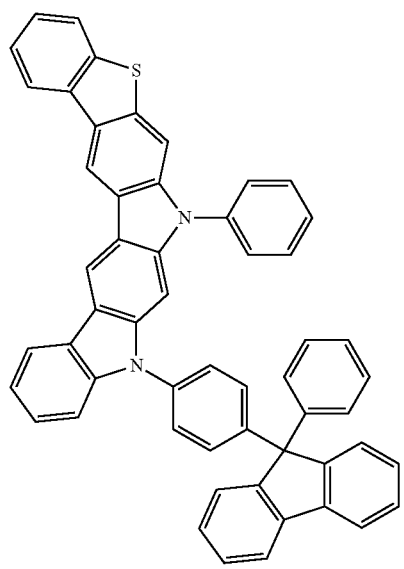
A-326
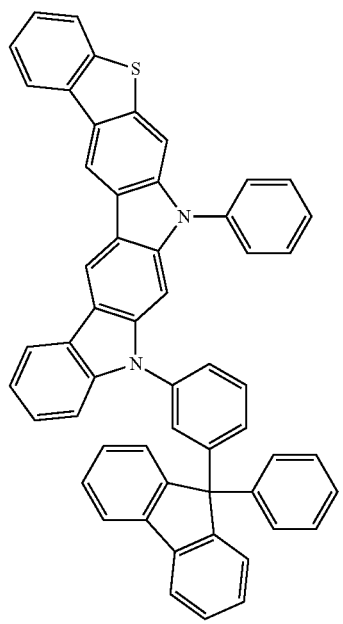
A-327
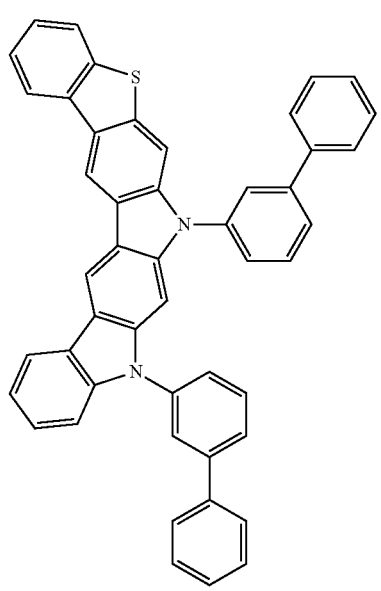
A-328
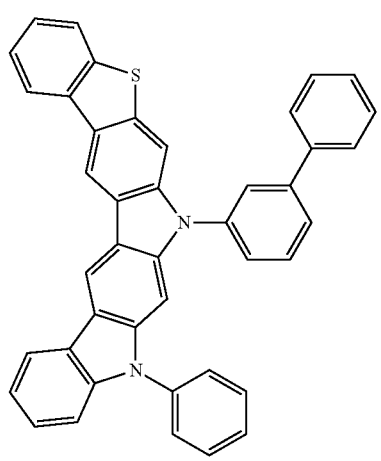

A-329
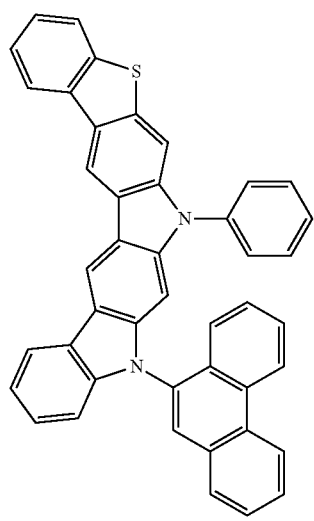
A-330
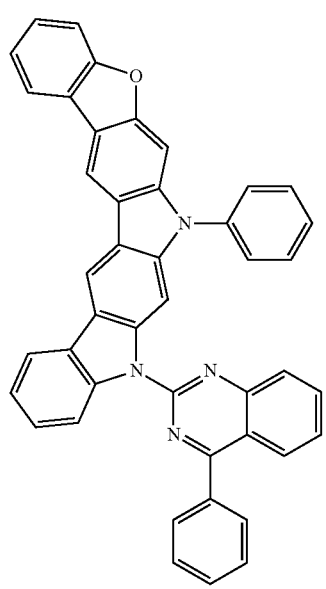
A-331
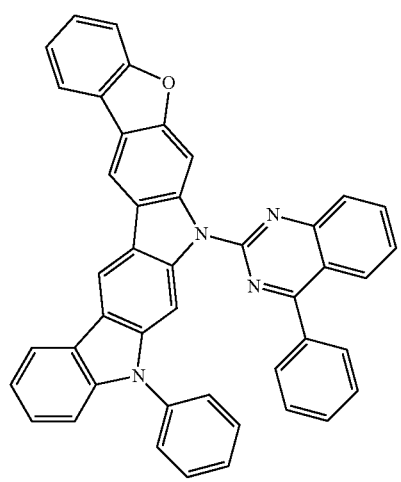
A-332
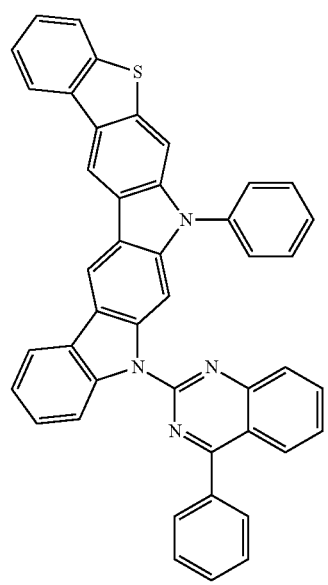
A-333
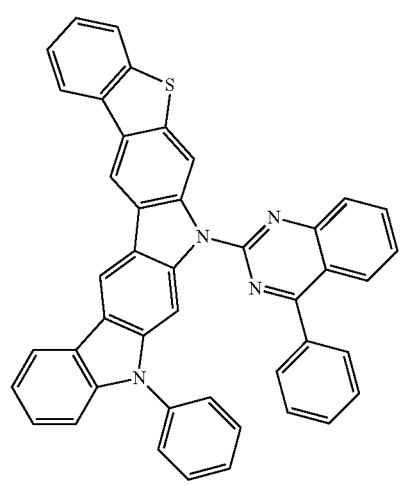
A-334
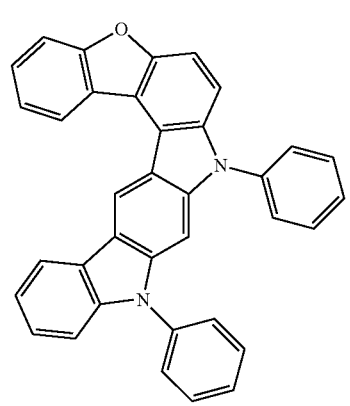

A-335
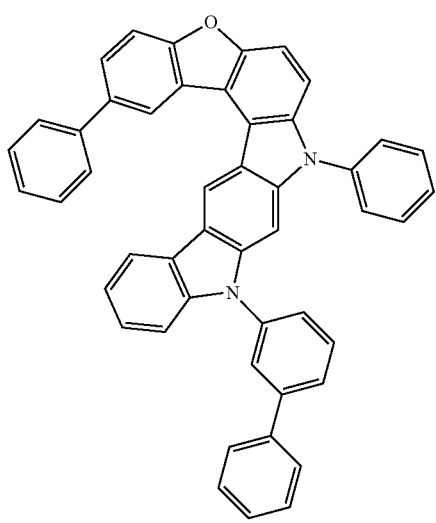
A-336
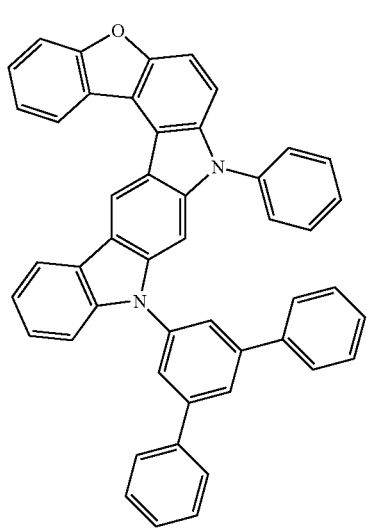
A-337
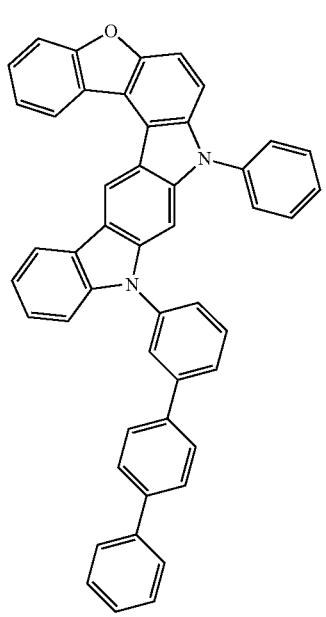
A-338
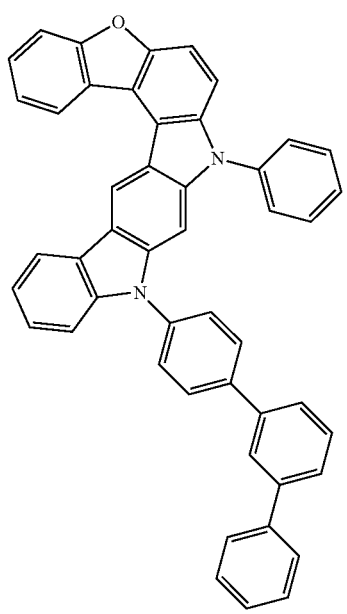
A-339
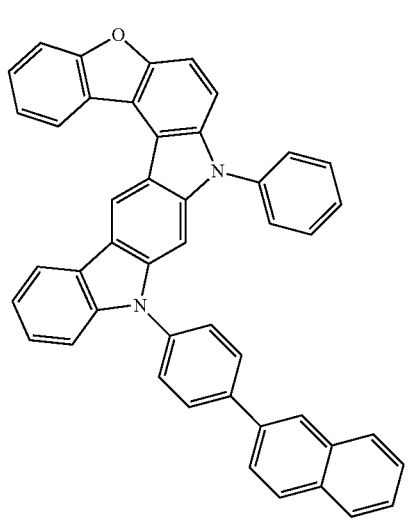
A-340
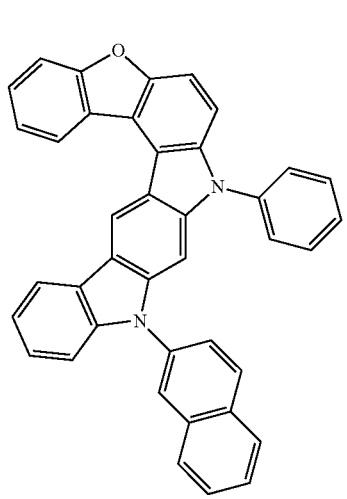

A-341
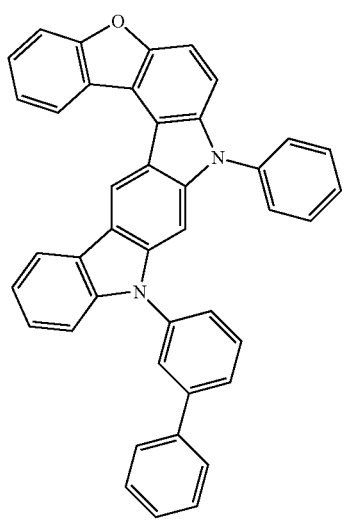
A-344
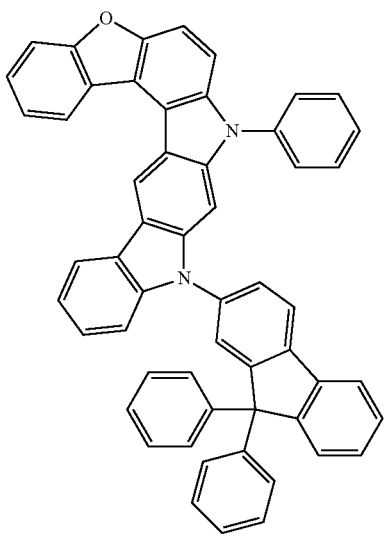
A-342
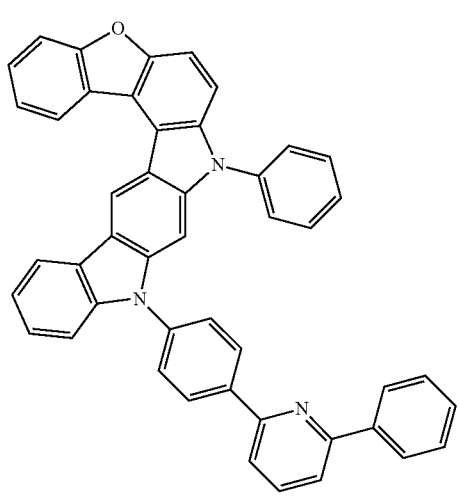
A-345
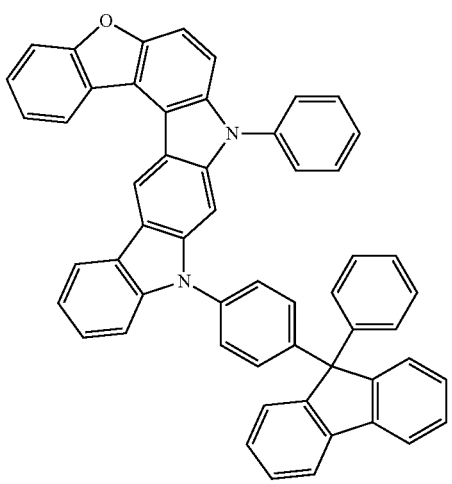
A-343
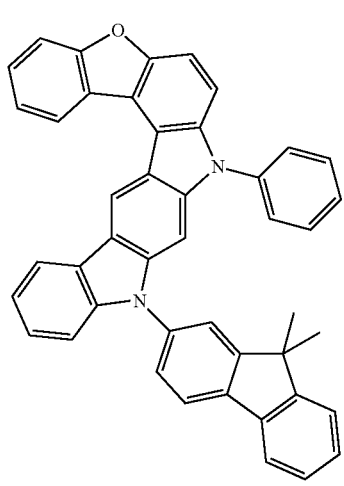
A-346
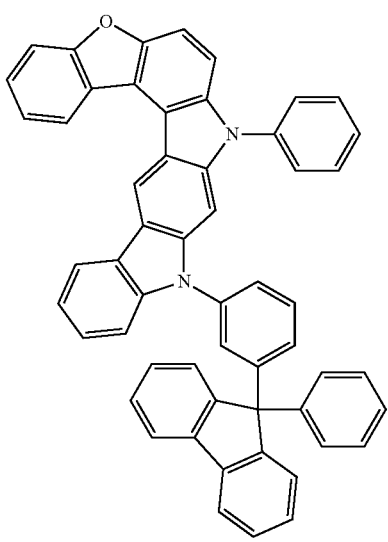

A-347
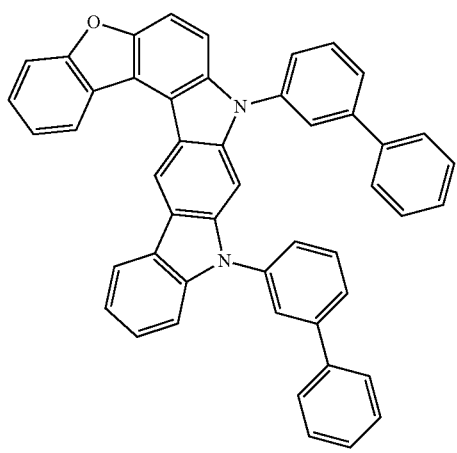
A-348
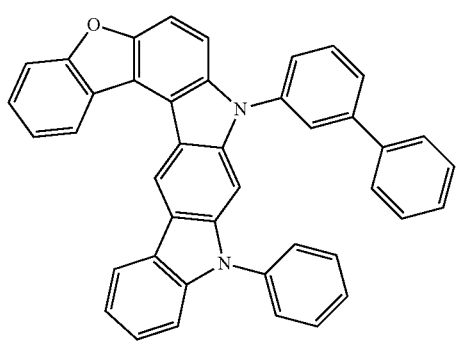
A-349
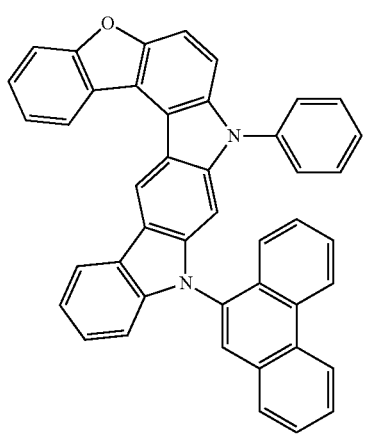
A-350
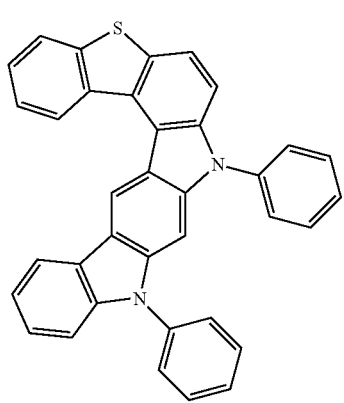
A-351
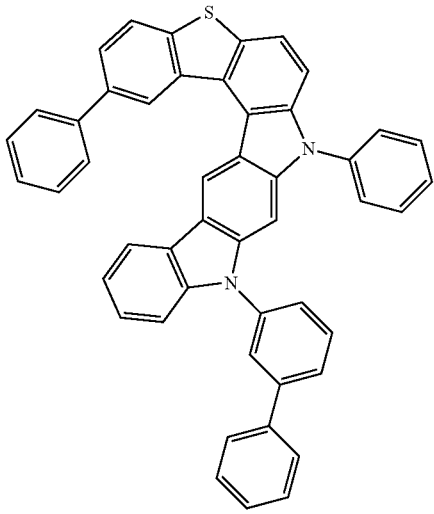
A-352
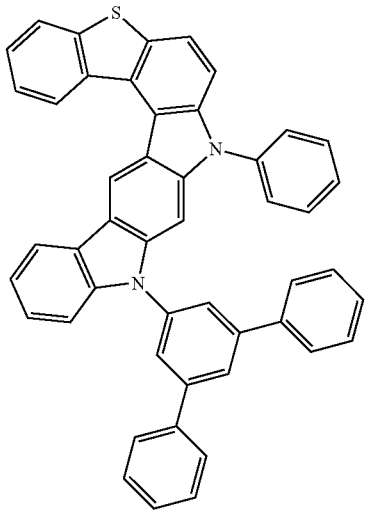
A-353
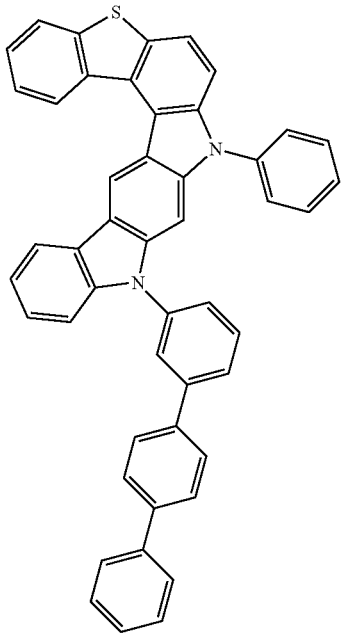

A-354
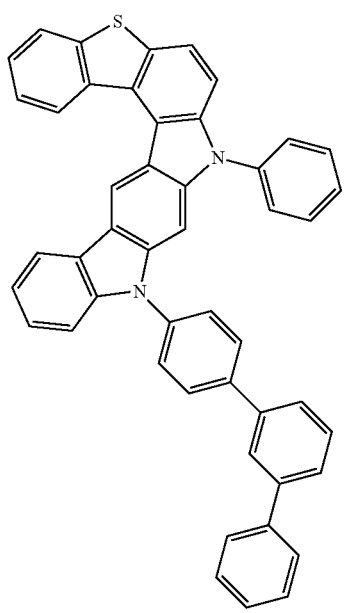
A-357
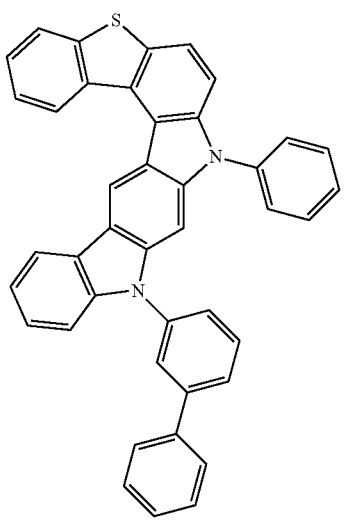
A-355
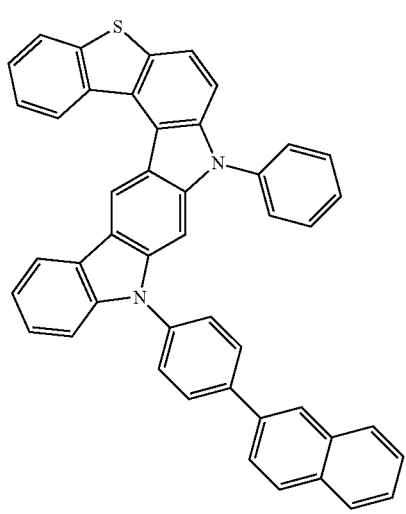
A-358
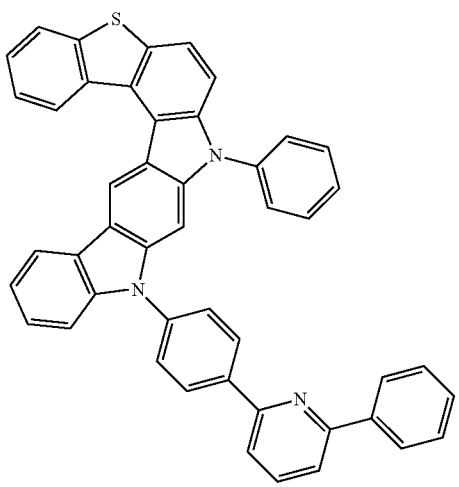
A-356
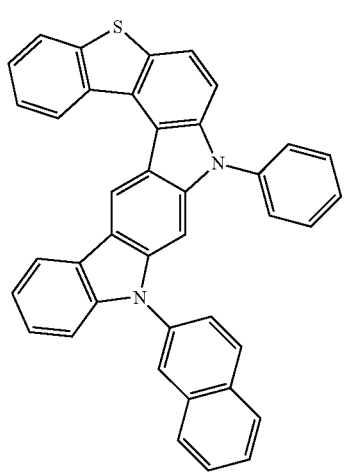
A-359
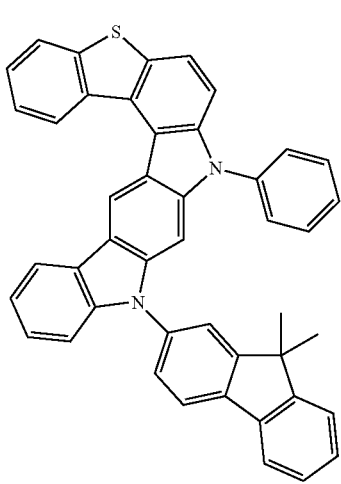

A-360
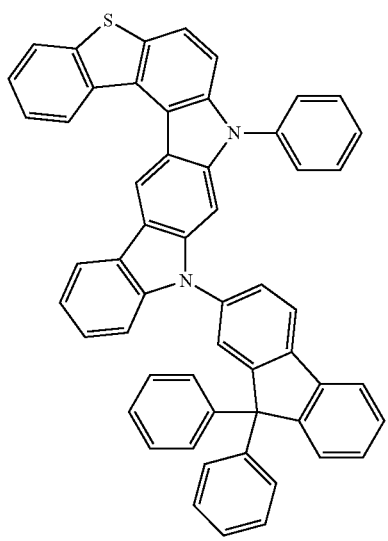
A-361
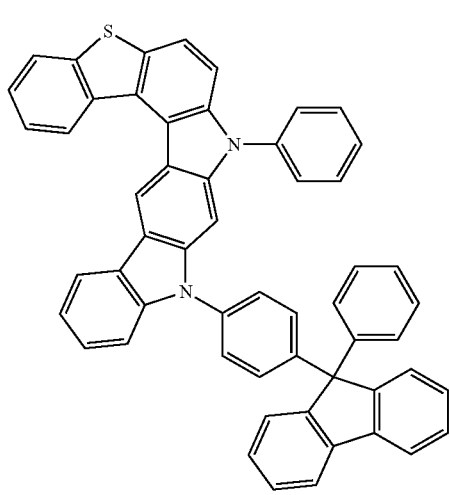
A-362
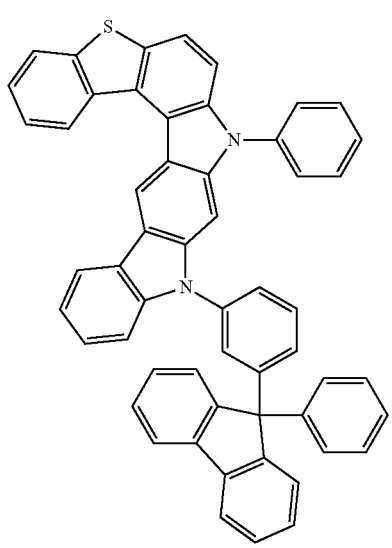
A-363
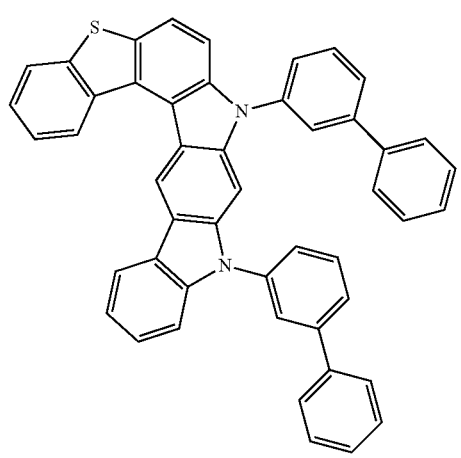
A-364
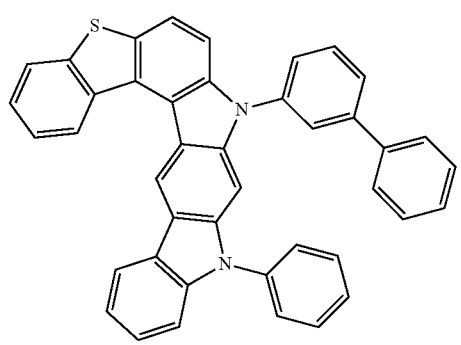
A-365
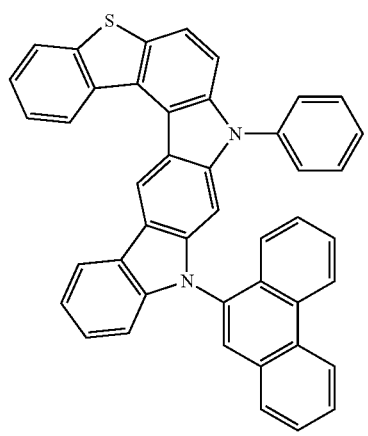

A-366
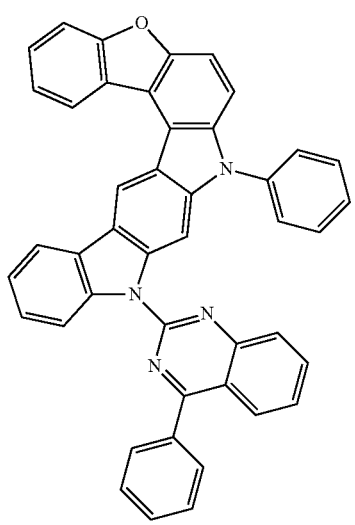
A-367
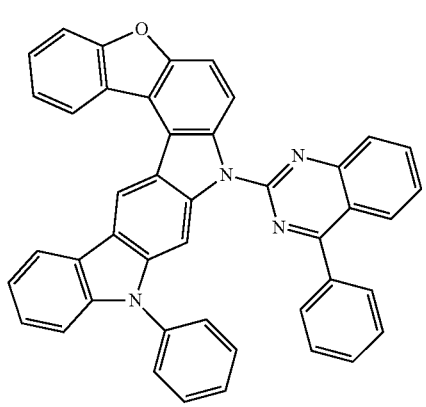
A-368
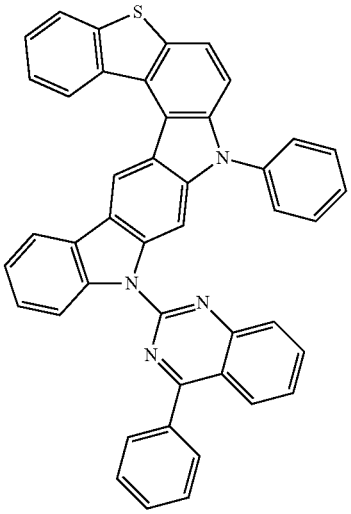
A-369
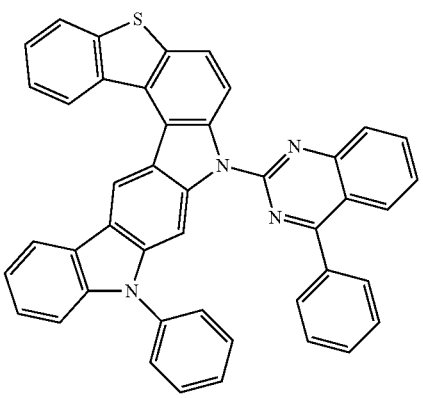
The organic electroluminescent compound of the present disclosure can be prepared by a synthetic method known to one skilled in the art. For example, it can be prepared according to the following reaction scheme 1.
[Reaction Scheme 1]
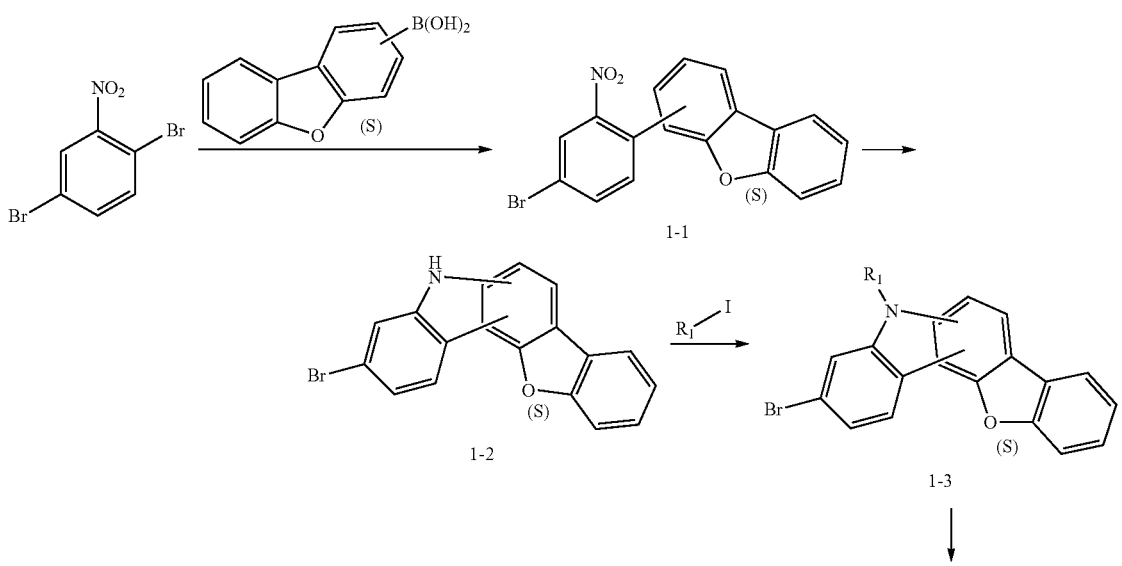

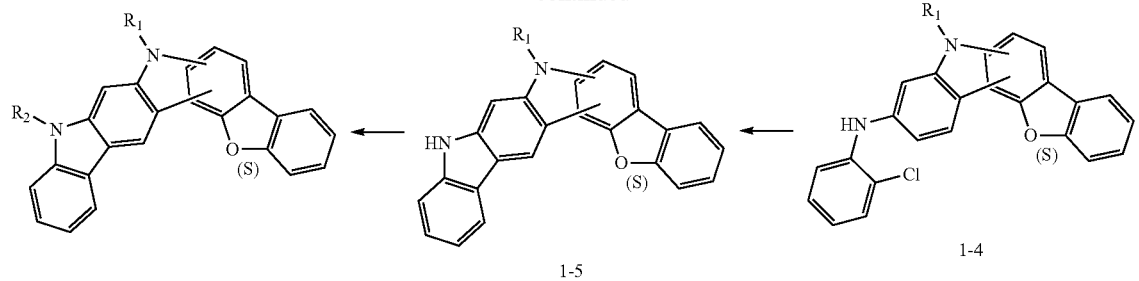

1-5 ← 1-4

Furthermore, the present disclosure provides an organic electroluminescent material comprising the organic electroluminescent compound of formula 1, and an organic electroluminescent device comprising the material.

The material may consist of the organic electroluminescent compound of the present disclosure. Otherwise, the material may further comprise a conventional compound(s) which has been comprised for an organic electroluminescent material.

The organic electroluminescent material may be preferably, a host material, or a hole transport material. The host material may be a fluorescent host material or a phosphorescent host material, and specifically a phosphorescent host material. Where the organic electroluminescent material is used as a host material, it may further comprise, in addition to the compound of formula 1, a second host material mentioned below.

The organic electroluminescent device of the present disclosure may comprise a first electrode, a second electrode, and at least one organic layer disposed between the first and second electrodes. The organic layer may comprise at least one compound of formula 1.

One of the first and second electrodes may be an anode, and the other may be a cathode. The organic layer may comprise a light-emitting layer, and may further comprise at least one layer selected from a hole injection layer, a hole transport layer, an electron transport layer, an electron injection layer, an interlayer, a hole blocking layer, an electron blocking layer, and an electron buffer layer.

The organic electroluminescent compound of the present disclosure may be comprised in at least one of the light-emitting layer and the hole transport layer. When used in the hole transport layer, the organic electroluminescent compound of the present disclosure may be comprised as a hole transport material. When the compound of the present disclosure is used in the hole transport layer, the light-emitting layer may comprise a fluorescent host material or phosphorescent host material as a host material, wherein the host material may be selected from the well-known materials, and may be identical with or different from the material used in the hole transport layer. When used in the light-emitting layer, the compound of the present disclosure may be comprised as a host material, and specifically as a phosphorescent host material. Preferably, the light-emitting layer may further comprise at least one or more dopants, and, if necessary, a second host material other than the compound of formula 1 of the present disclosure. It is preferable that a doping amount of the dopant compound is less than 20 wt % based on the total amount of the host compound and the dopant compound in a light-emitting layer. The weight ratio in the light-emitting layer between the first host material and the second host material is in the range of 1:99 to 99:1, and specifically 30:70 to 70:30 in view of driving voltage, luminous efficiency, and lifespan.

The second host material may be from any of the known phosphorescent host materials. The material selected from the group consisting of the compounds of formulae 10 to 14 below is preferable as the second host material in view of luminous efficiency.

(10)

(11)

(12)

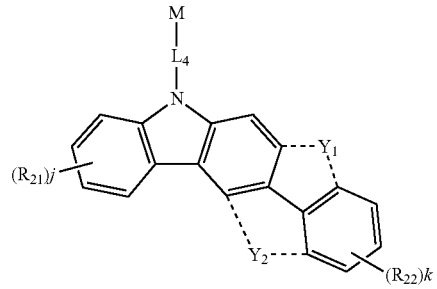

(13)

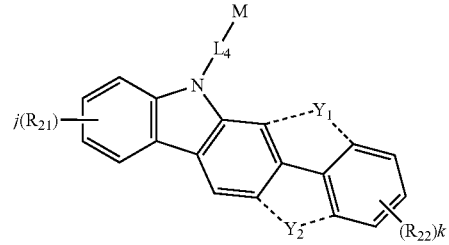

(14)

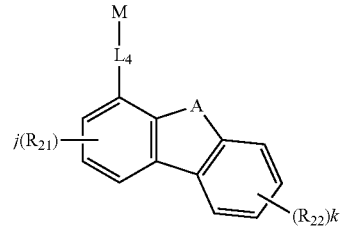

Wherein, Cz represents the following structure:

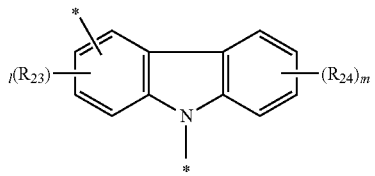

A represents —O— or —S—; $R_{21}$ to $R_{24}$, each independently, represent hydrogen, deuterium, a halogen, a substituted or unsubstituted (C1-C30)alkyl, a substituted or unsubstituted (C6-C30)aryl, a substituted or unsubstituted 5- to 30-membered heteroaryl or $R_{25}R_{26}R_{27}Si$—; $R_{25}$ to $R_{27}$, each independently, represent a substituted or unsubstituted (C1-C30)alkyl, or a substituted or unsubstituted (C6-C30)aryl; $L_4$ represents a single bond, a substituted or unsubstituted (C6-C30)arylene, or a substituted or unsubstituted 5- to 30-membered heteroarylene; M represents a substituted or unsubstituted (C6-C30)aryl, or a substituted or unsubstituted 5- to 30-membered heteroaryl; $Y_1$ and $Y_2$, each independently, represent —O—, —S—, —N($R_{31}$)—, or —C($R_{32}$)($R_{33}$)—, and $Y_1$ and $Y_2$ are not present simultaneously; $R_{31}$ to $R_{33}$, each independently, represent a substituted or unsubstituted (C1-C30)alkyl, a substituted or unsubstituted (C6-C30)aryl, or a substituted or unsubstituted 5- to 30-membered heteroaryl, $R_{32}$ and $R_{33}$ may be the same or different; h and i, each independently, represent an integer of 1 to 3; j, k, l and m each independently, represent an integer of 0 to 4; and where h, i, j, k, l or m is an integer of 2 or more, each of (Cz-$L_4$), (Cz), $R_{21}$, $R_{22}$, $R_{23}$, or $R_{24}$ may be the same or different.

Specifically, the preferable examples of the second host material include the following:

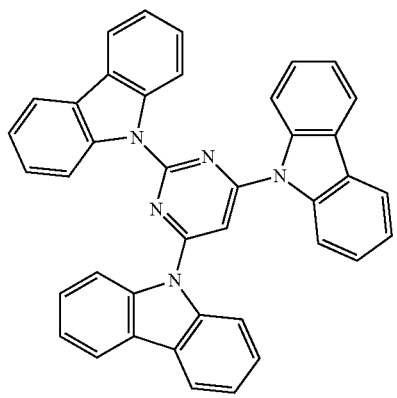

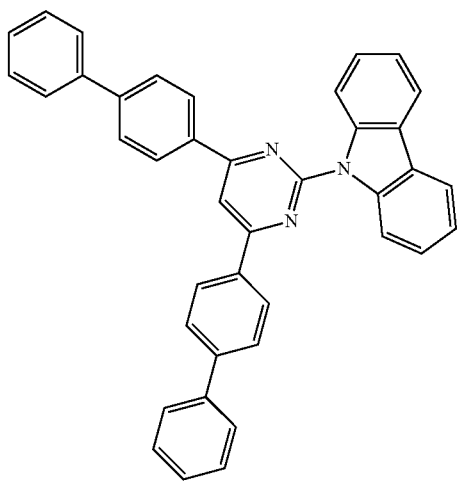

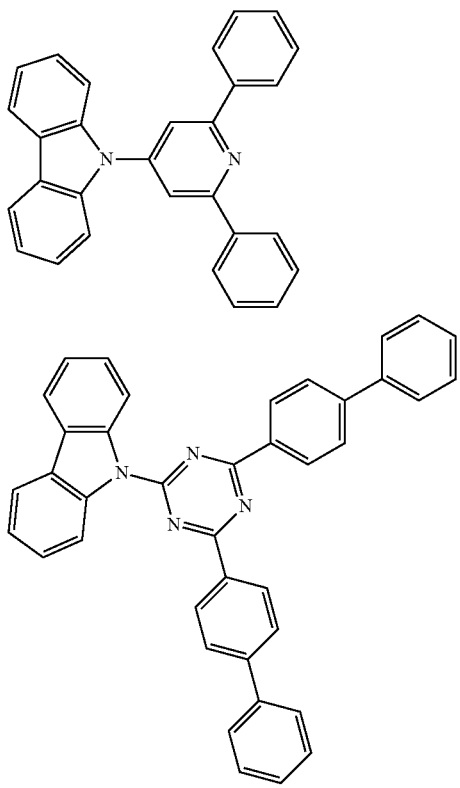

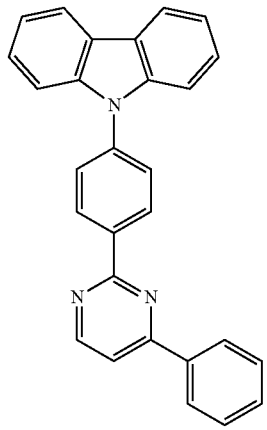

153
-continued
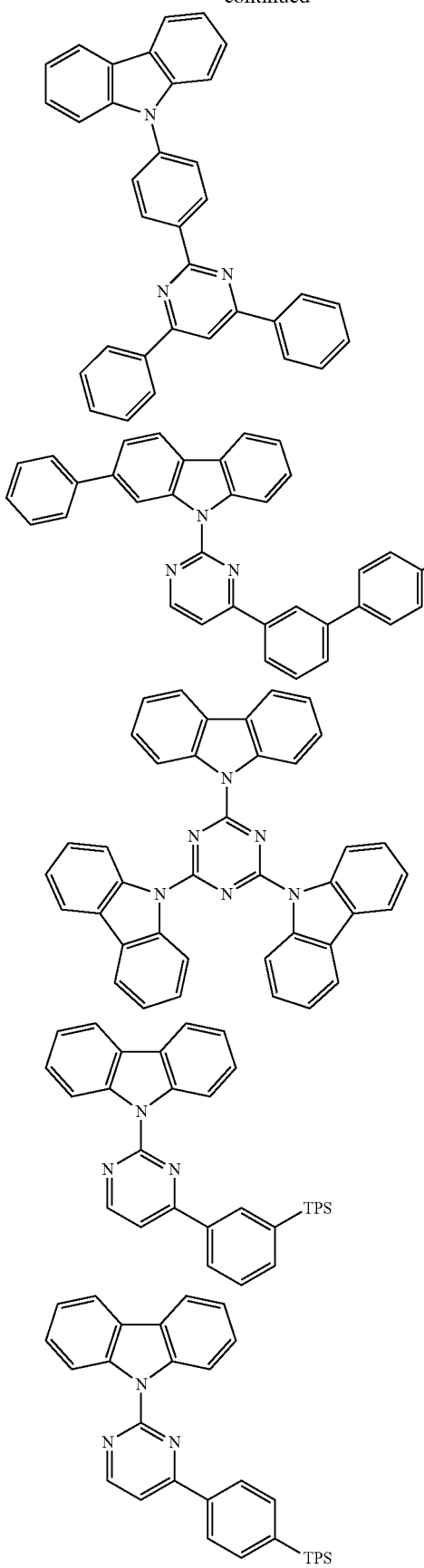
154
-continued
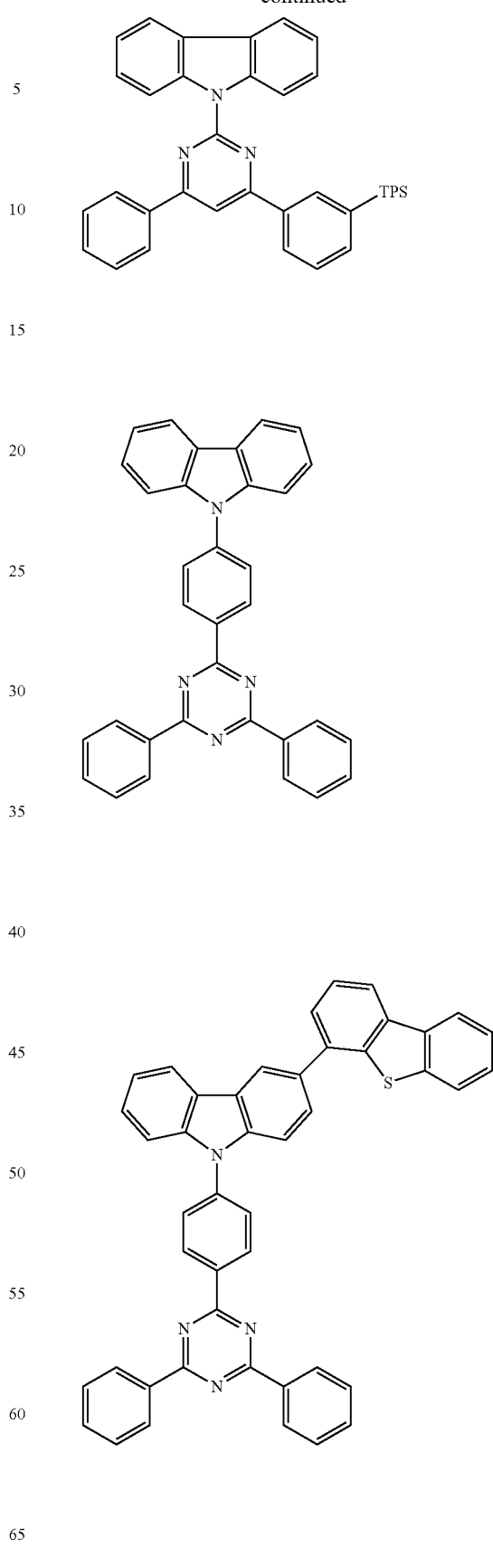

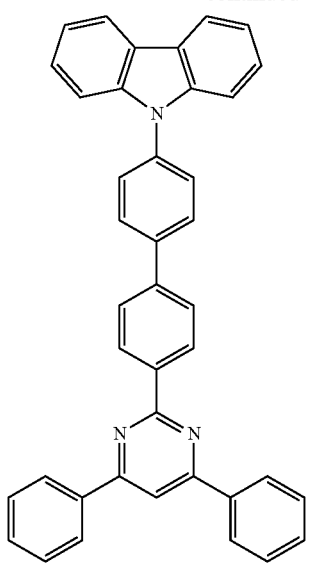
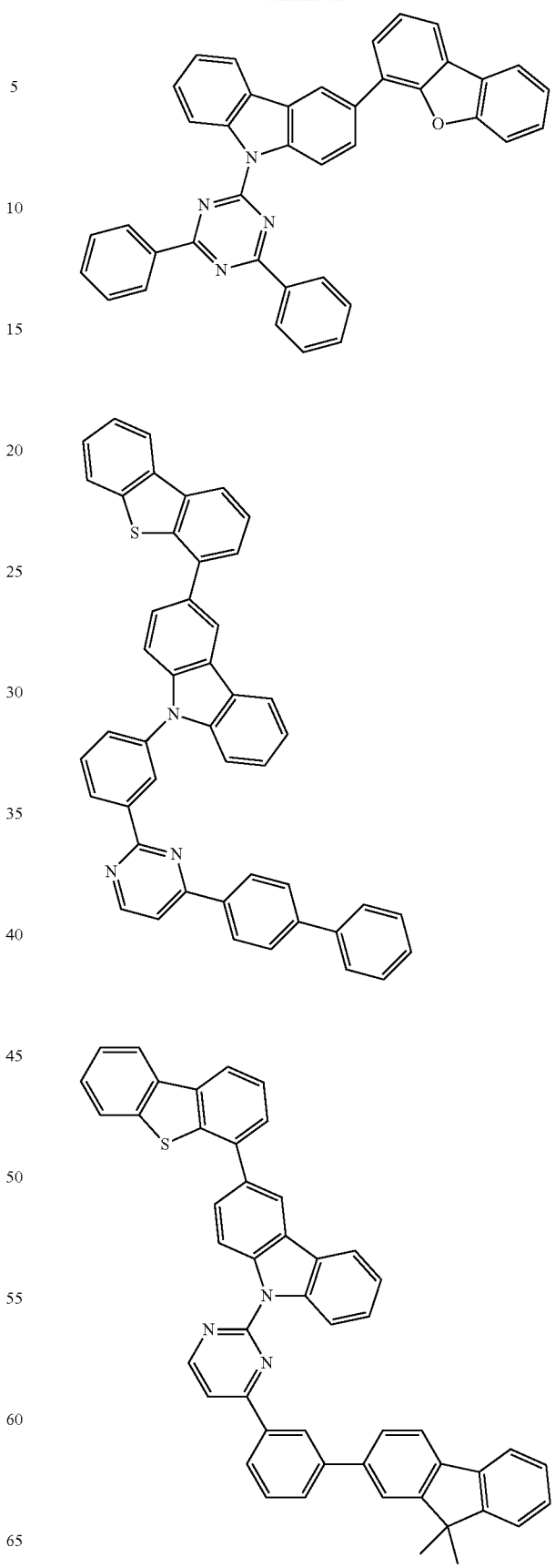

157
-continued
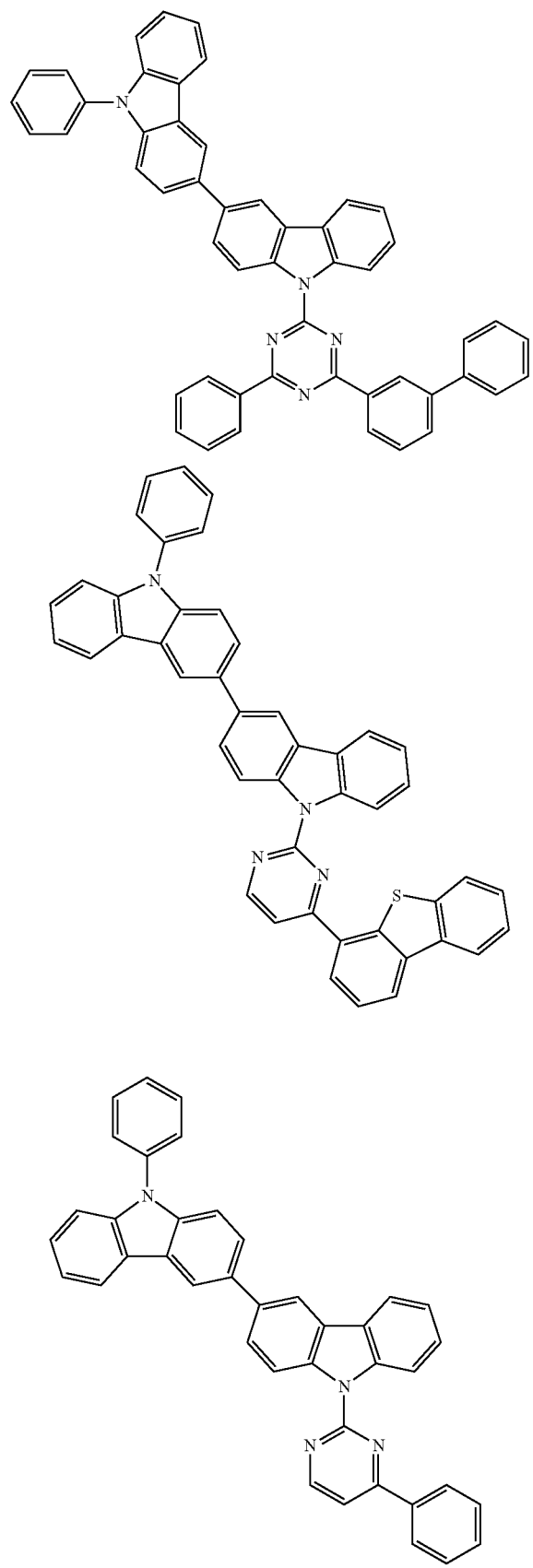
158
-continued
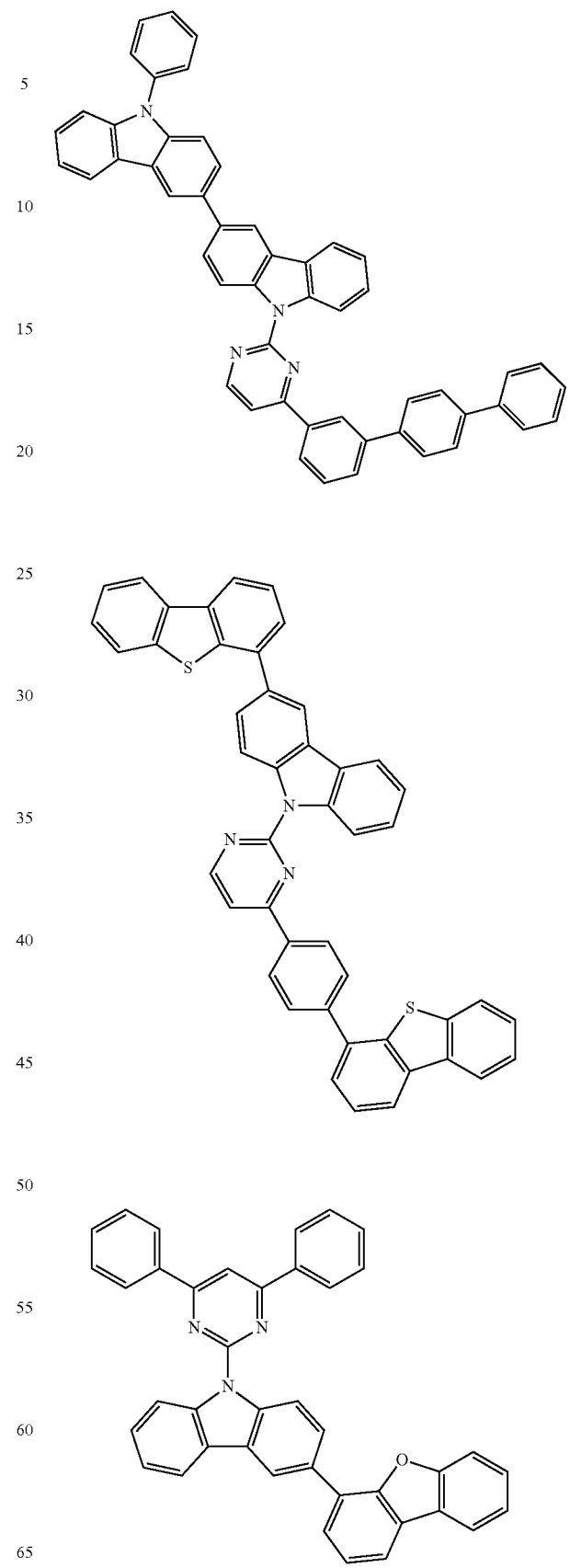

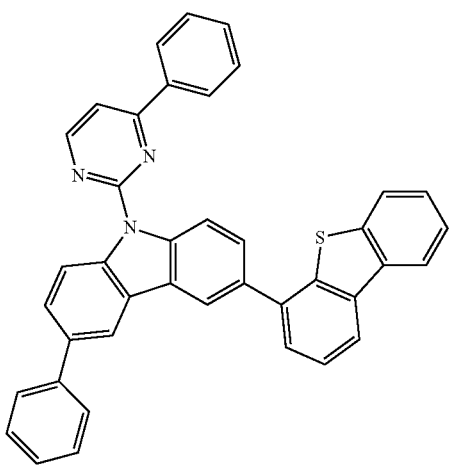
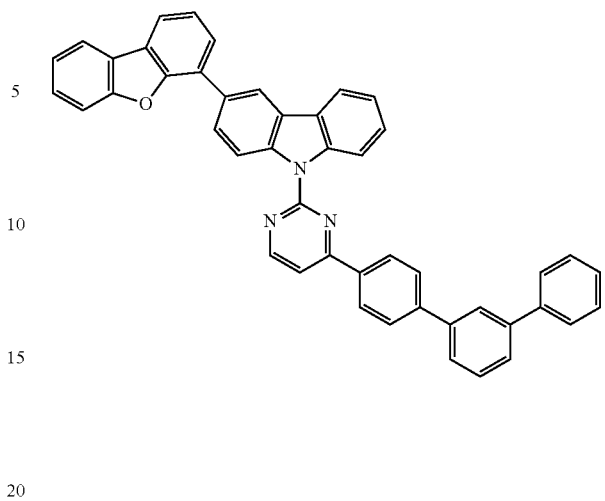
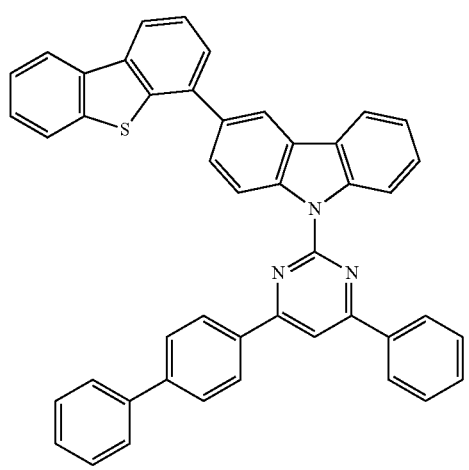
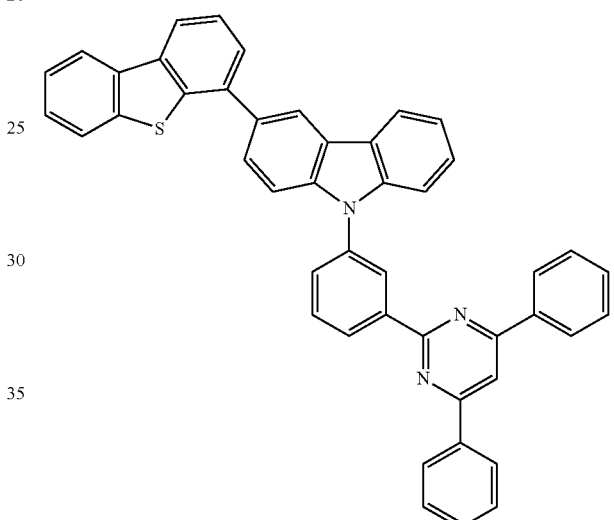
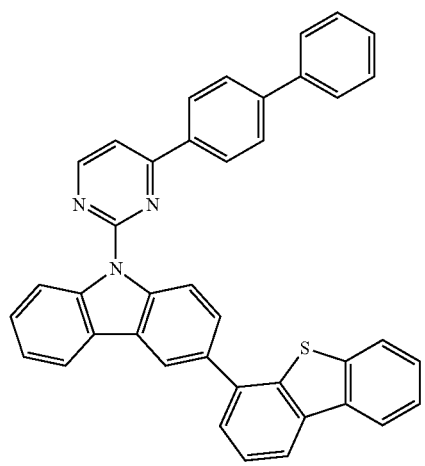
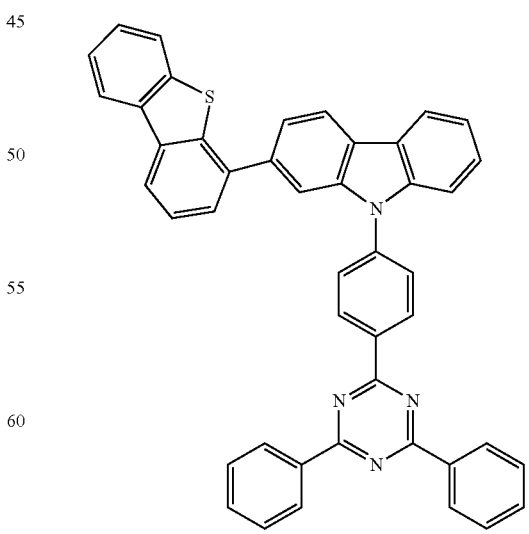

161
-continued
162
-continued
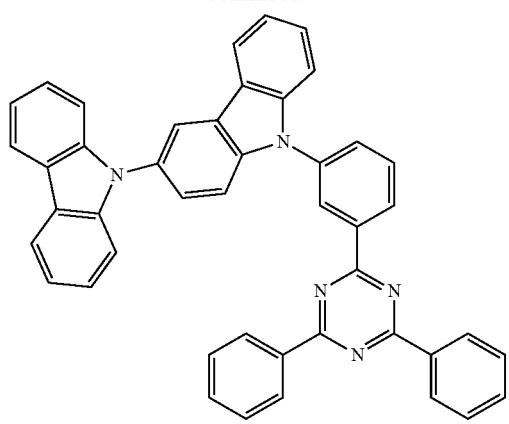
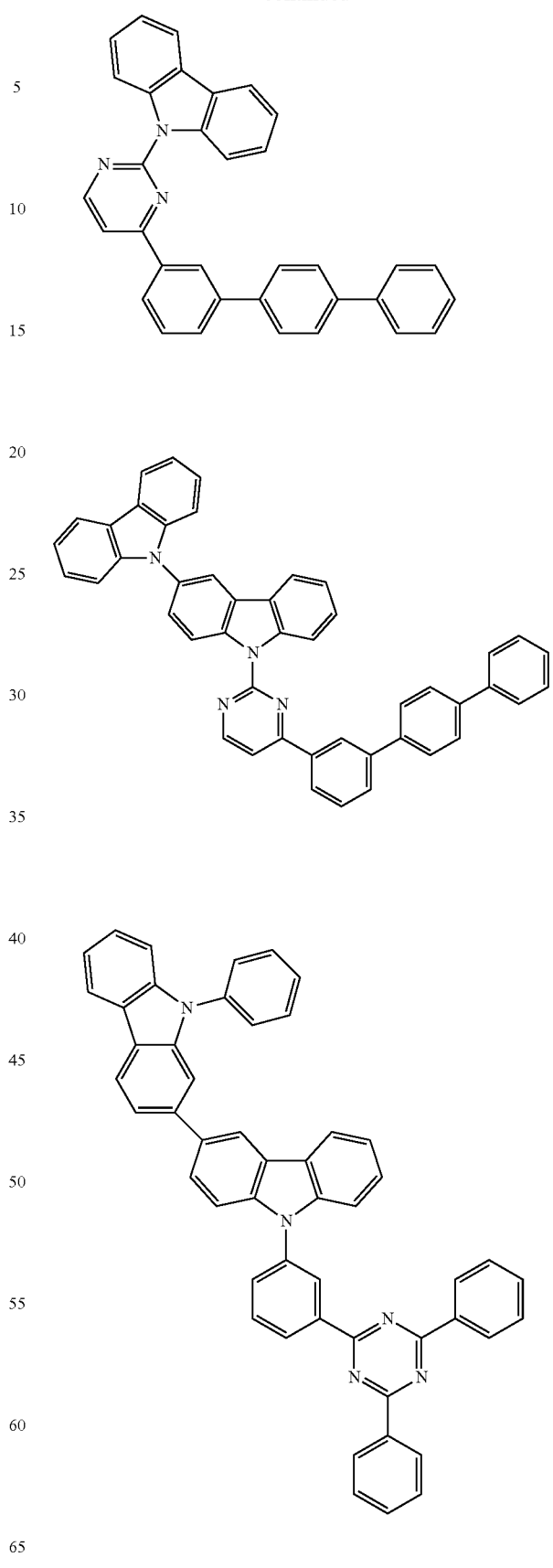

-continued
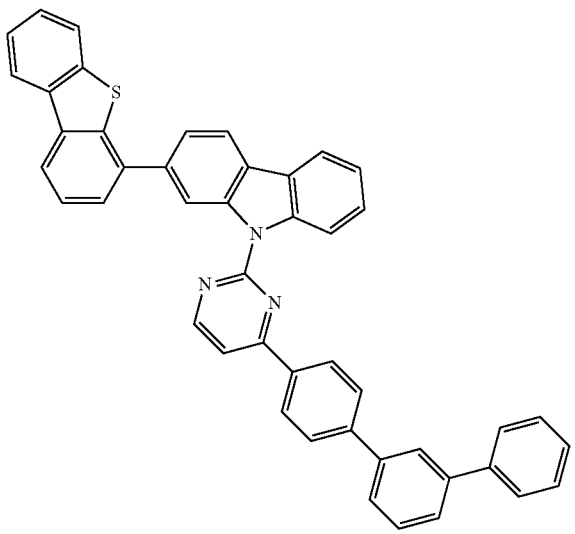
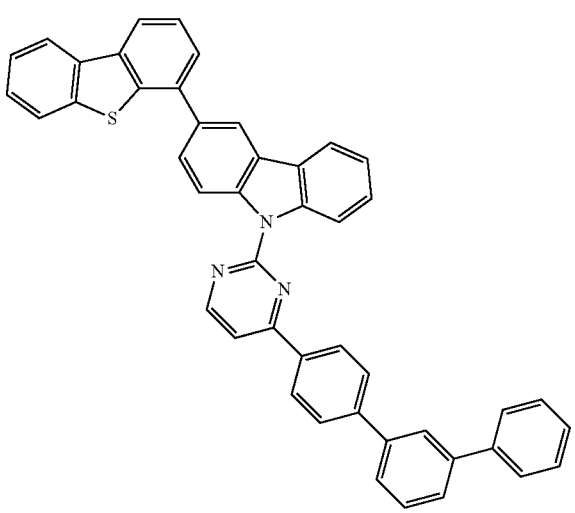
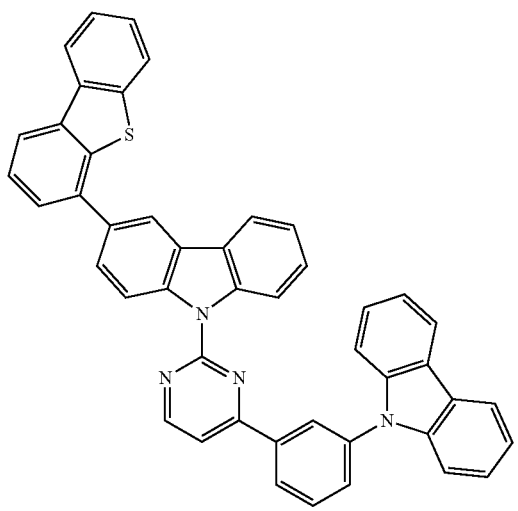
-continued
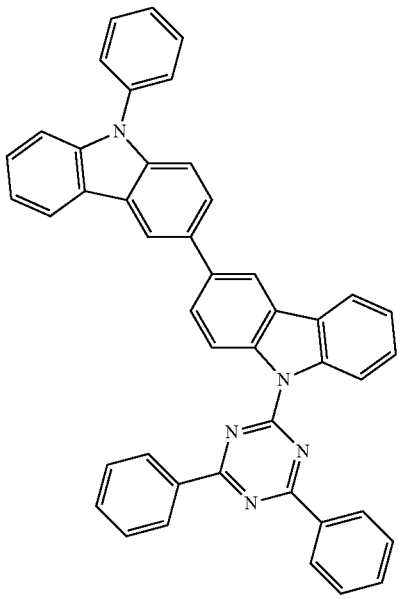
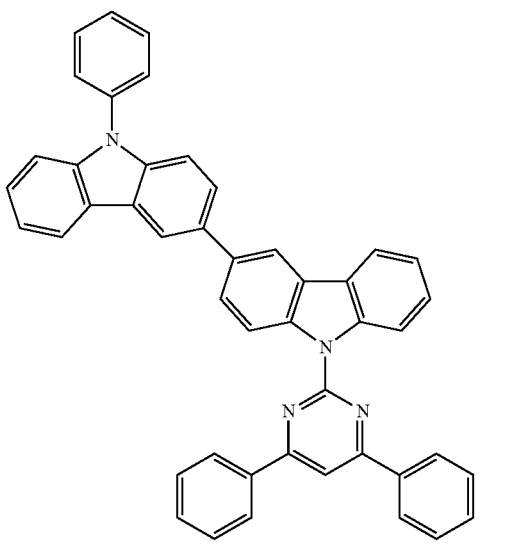

165
-continued
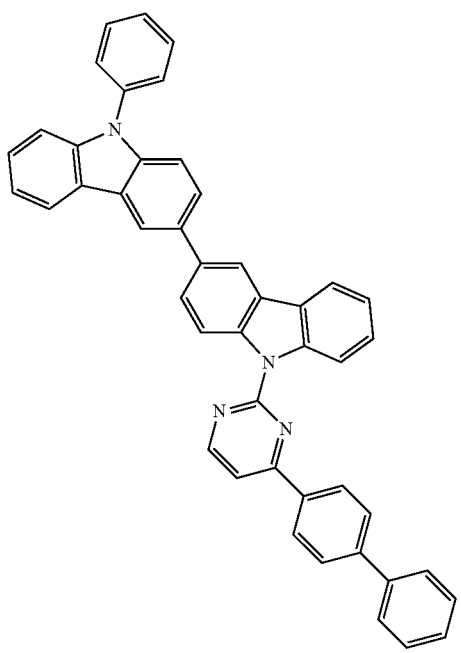
166
-continued
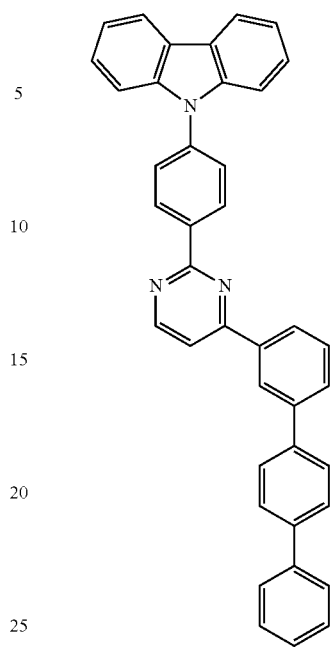
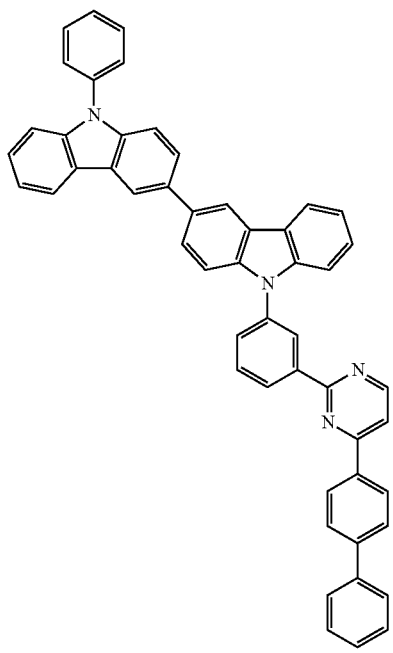
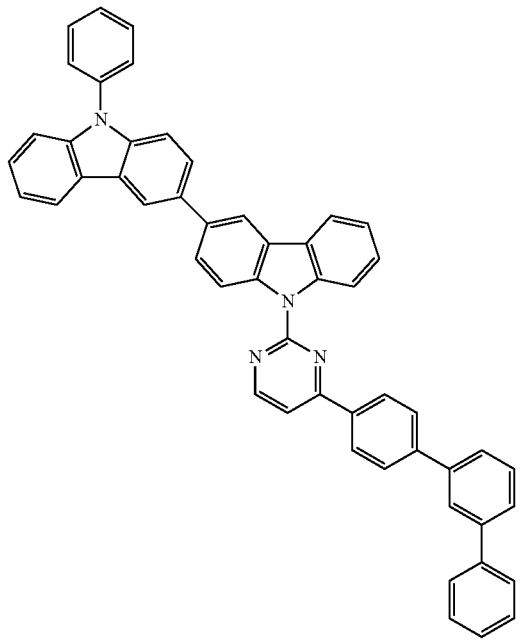

167
-continued
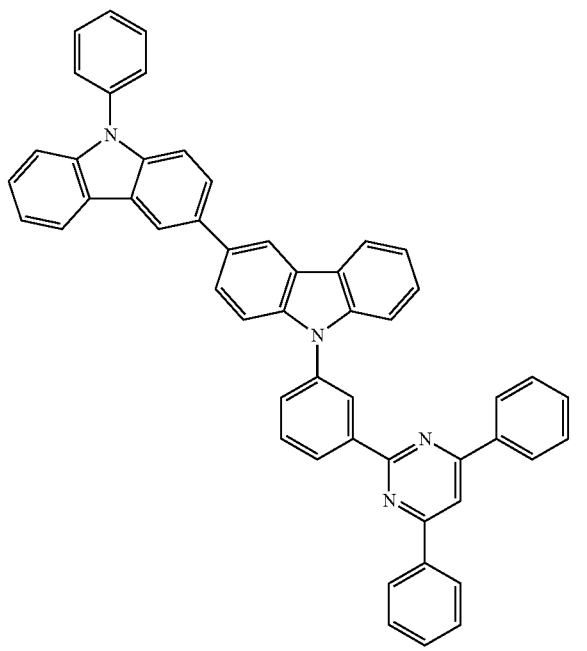
168
-continued
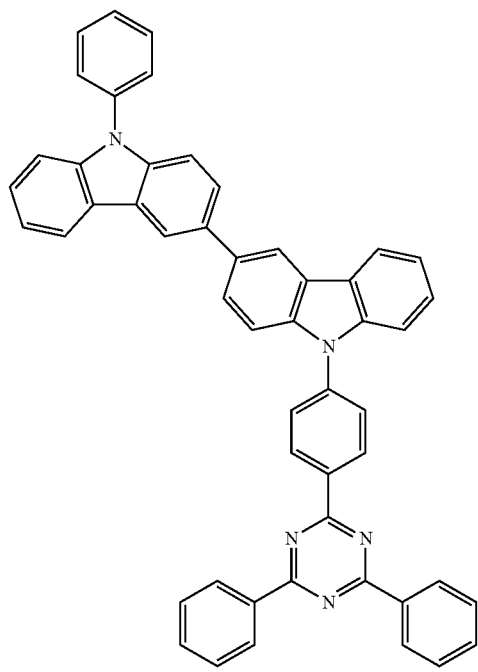
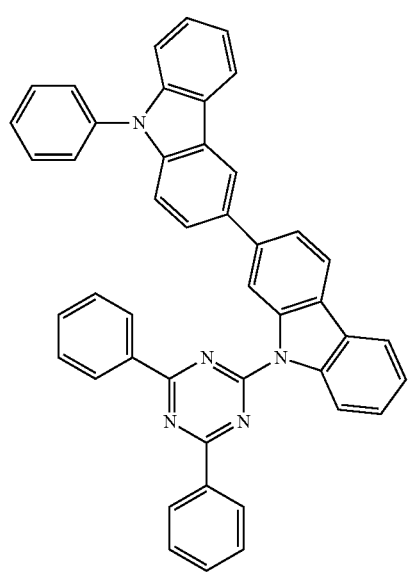
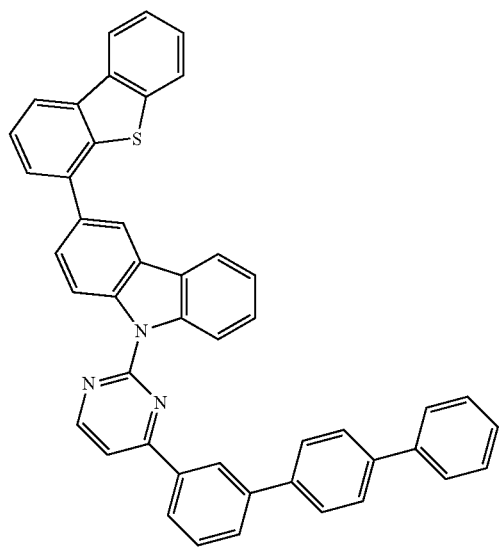

169
-continued
170
-continued
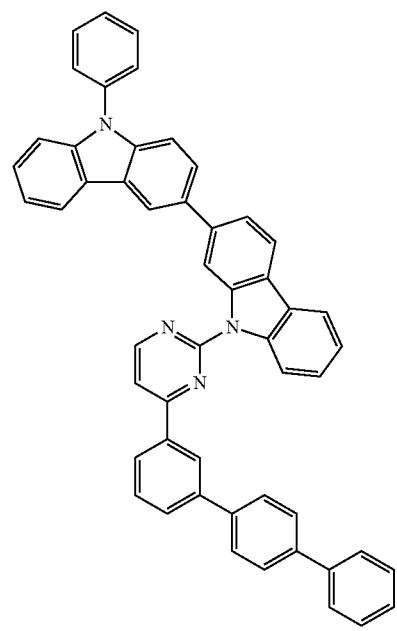
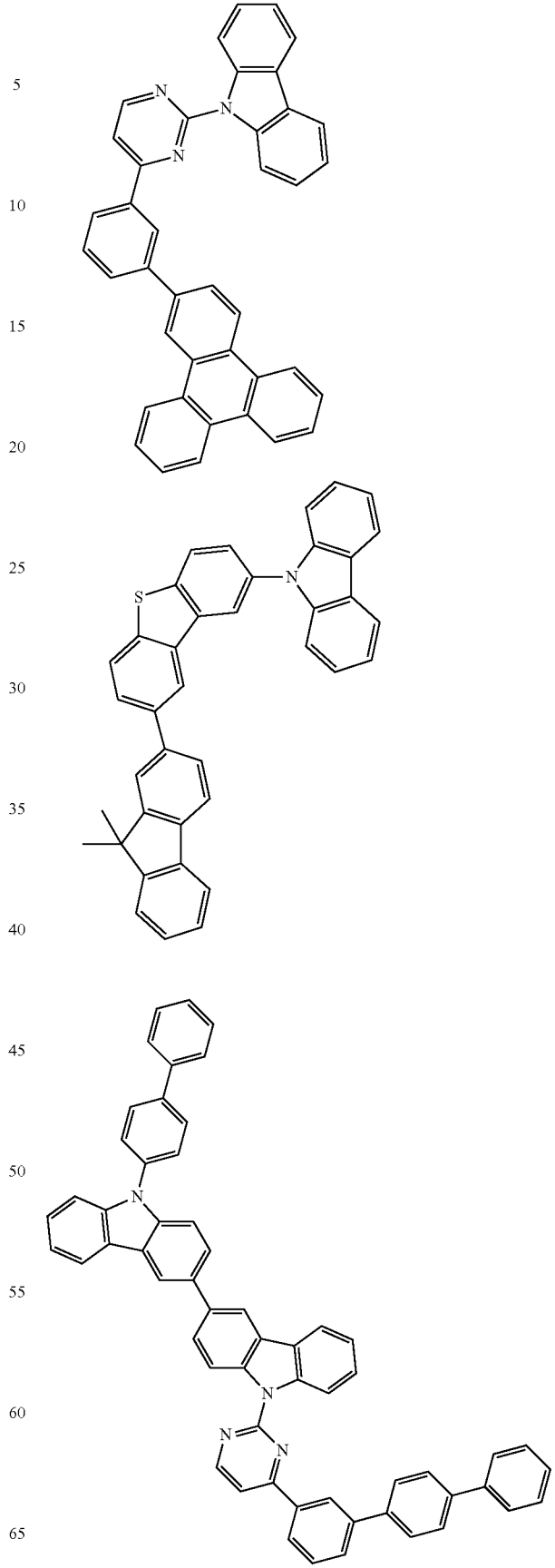

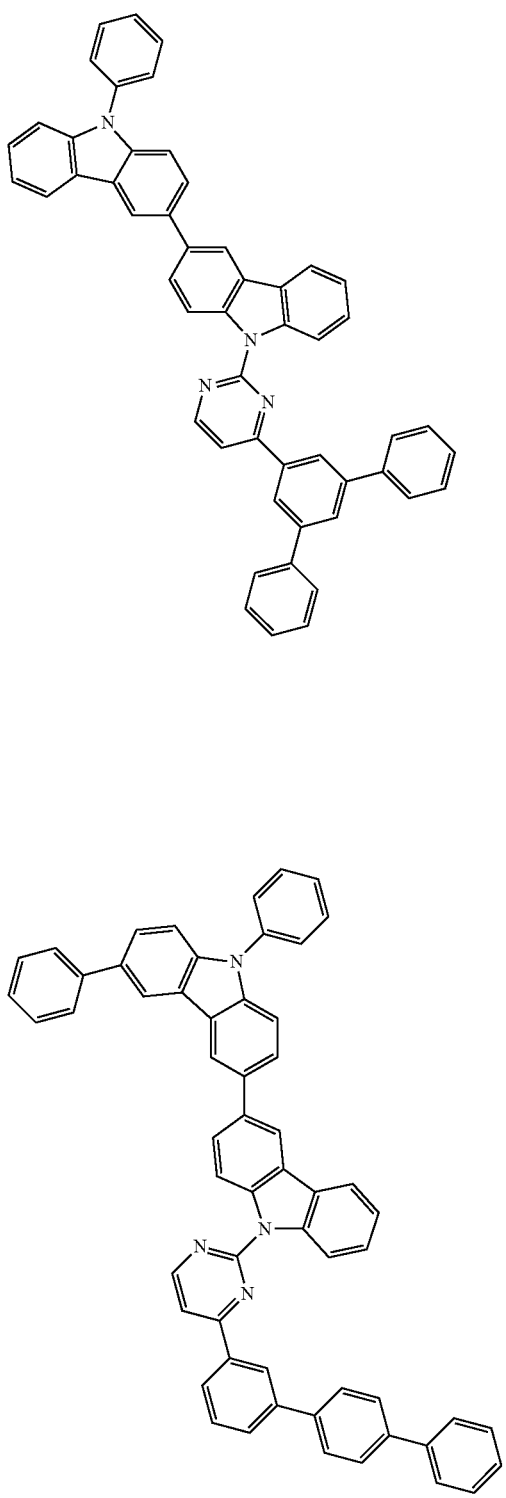

173
-continued
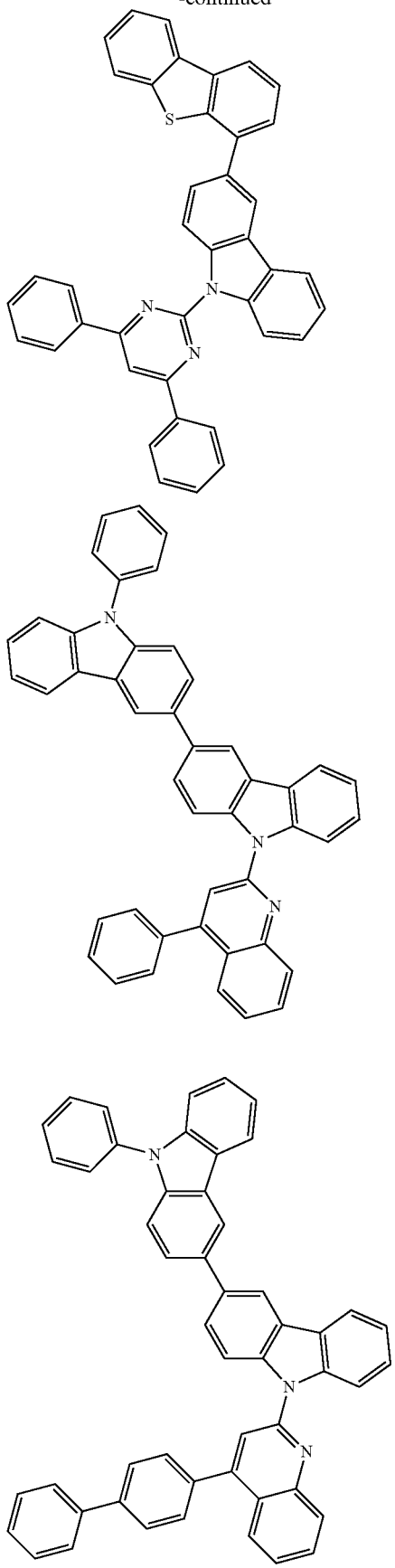
174
-continued
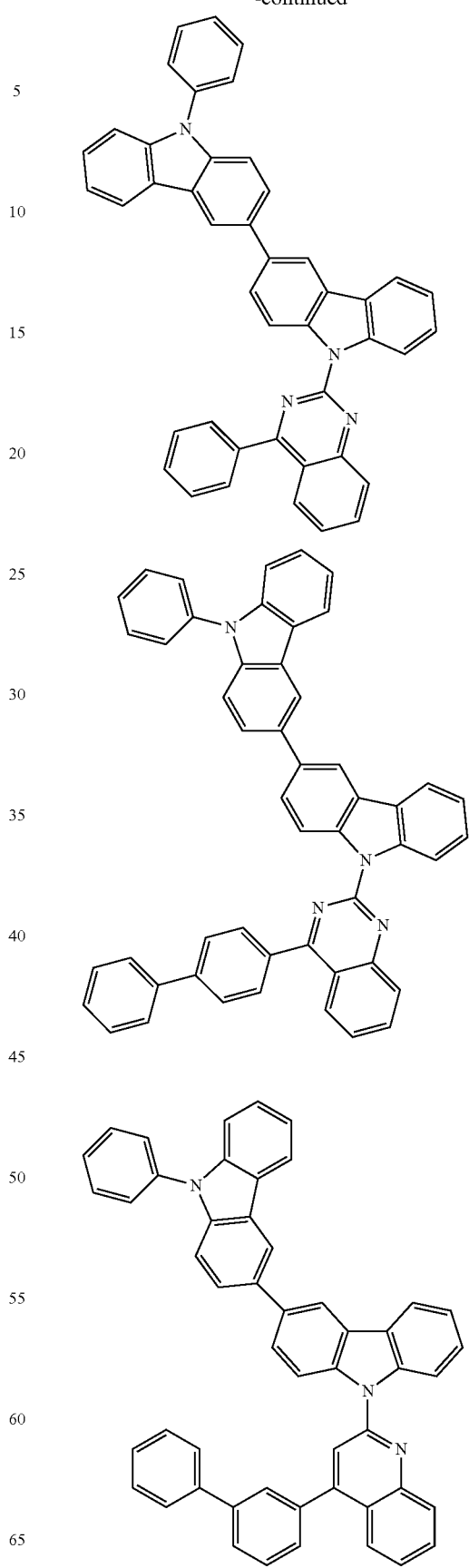

175
-continued
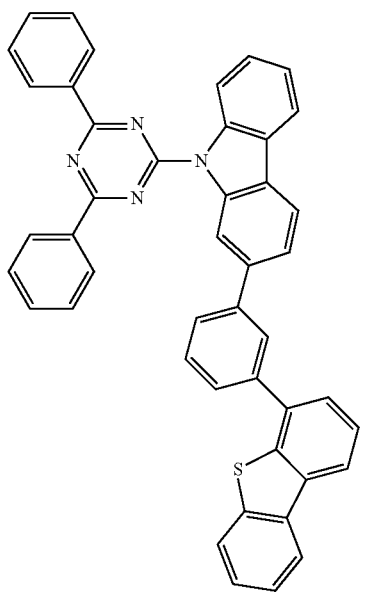
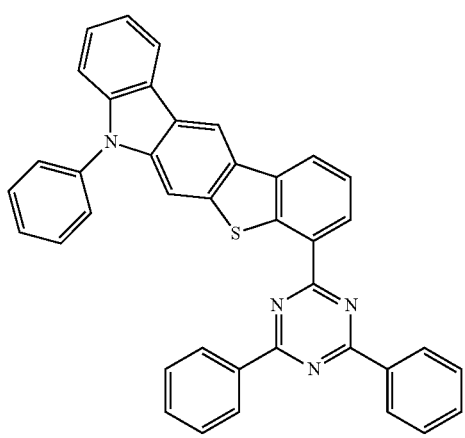
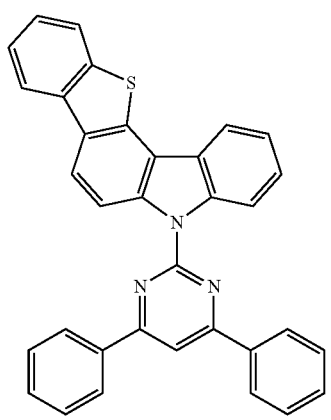
176
-continued
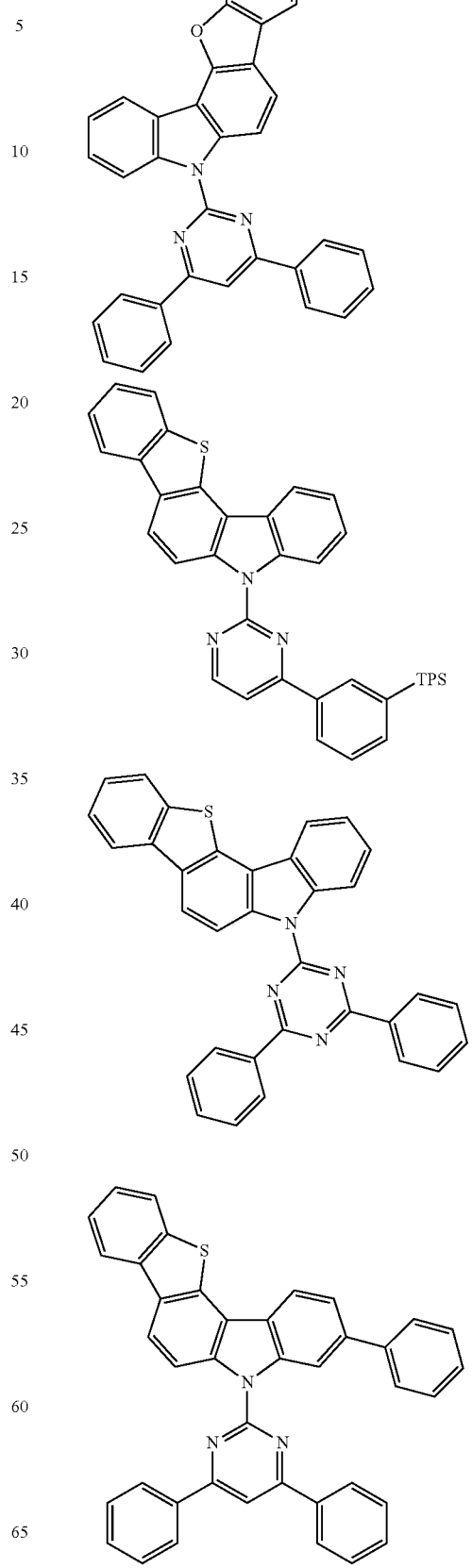

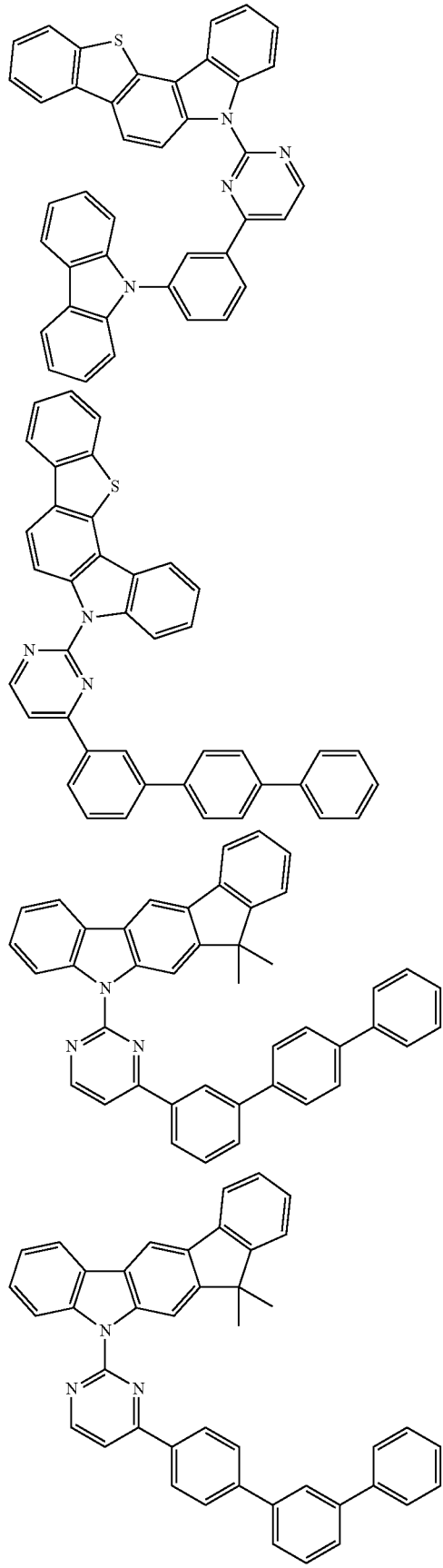
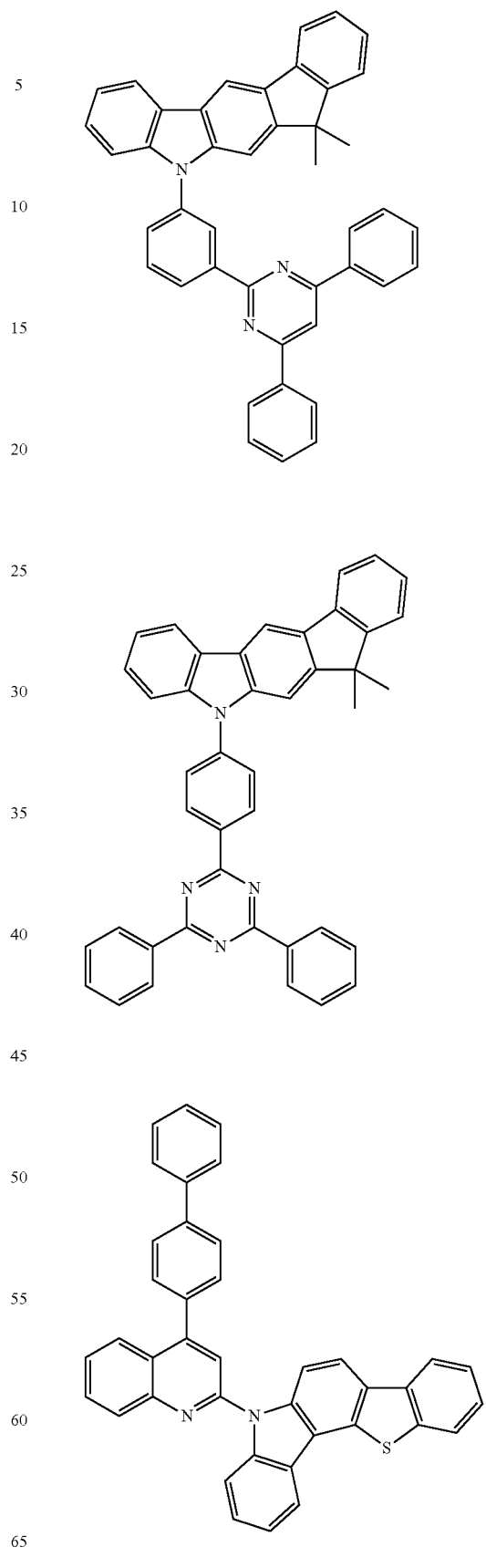

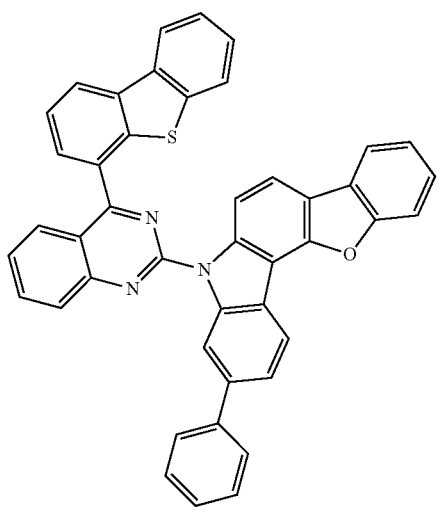
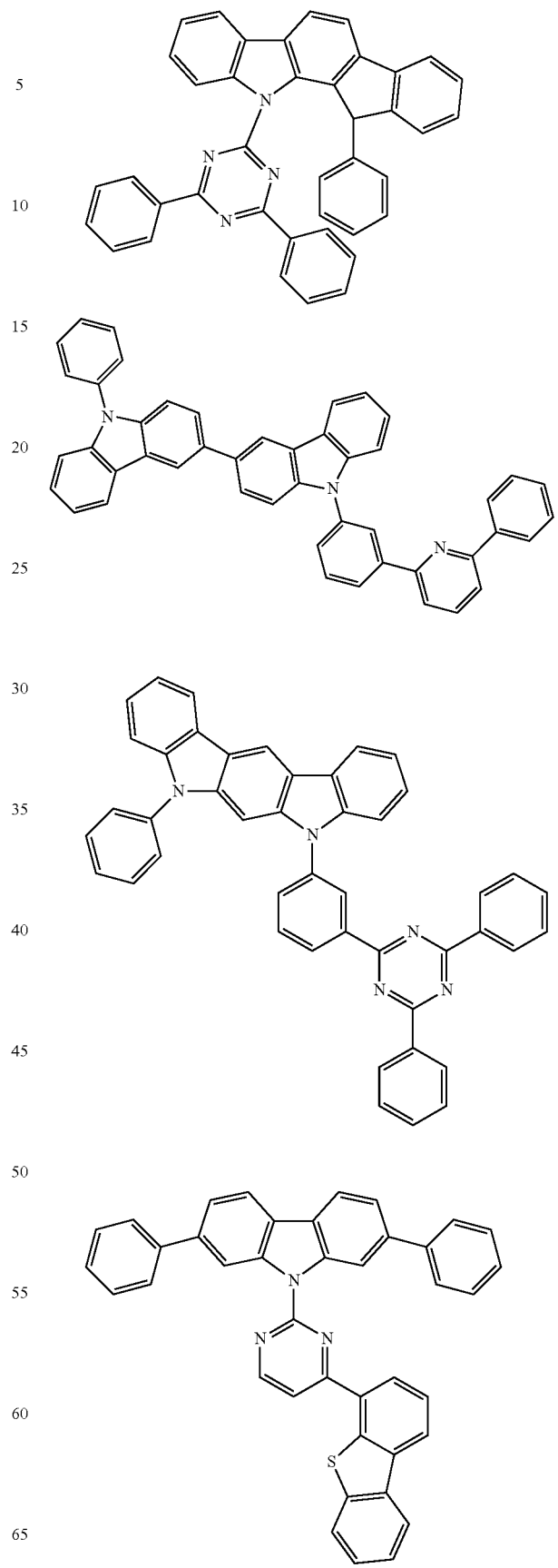

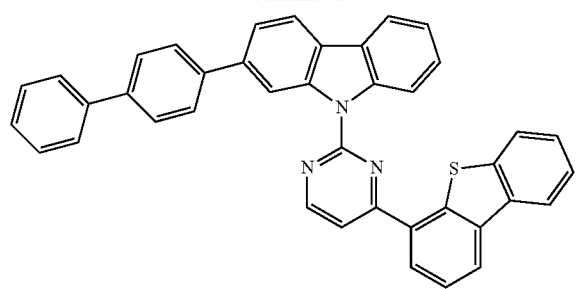
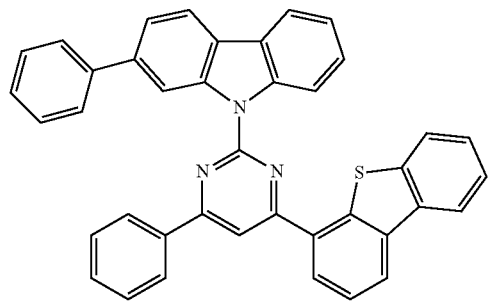
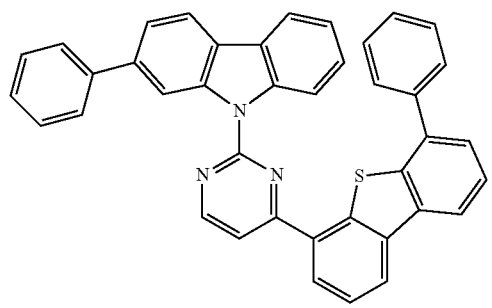
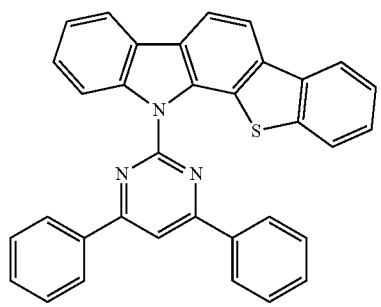
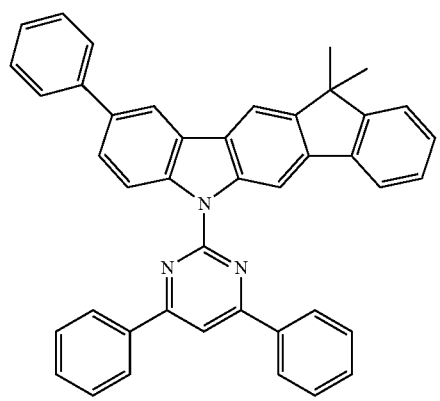
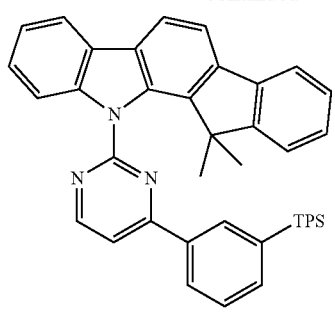
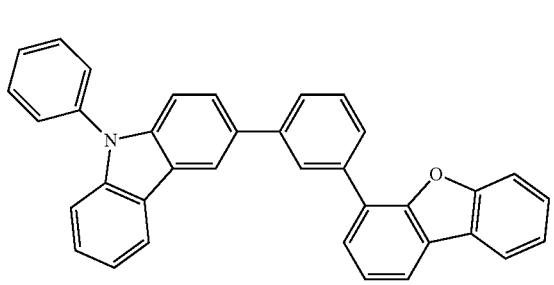
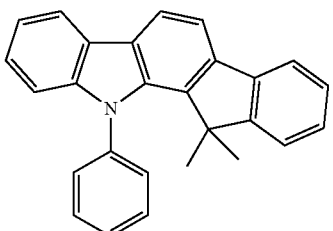
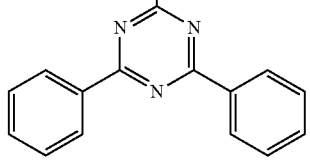
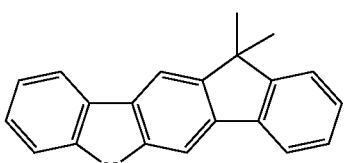
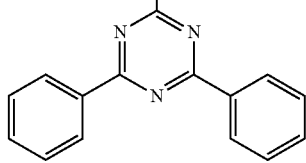

-continued

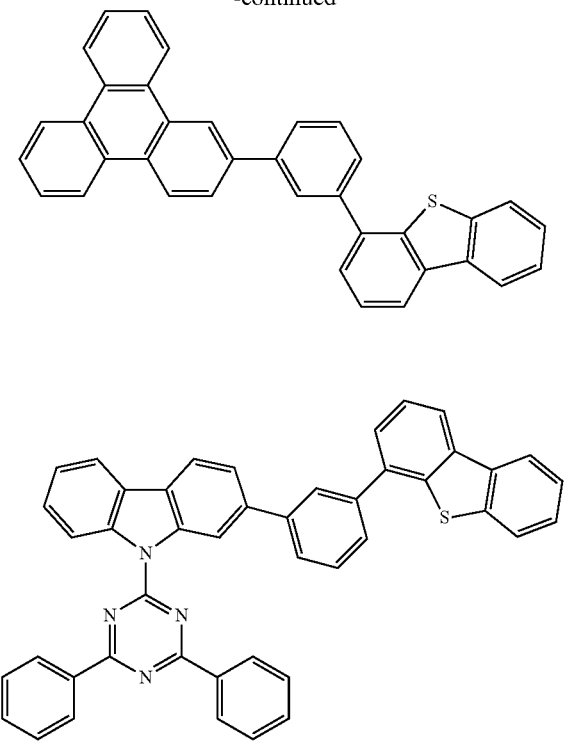

(wherein, TPS represents triphenylsilyl.)

The dopant is preferably at least one phosphorescent dopant. The phosphorescent dopant material for the organic electroluminescent device of the present disclosure is not limited, but may be preferably selected from metallated complex compounds of iridium (Ir), osmium (Os), copper (Cu) or platinum (Pt), more preferably selected from ortho-metallated complex compounds of iridium (Ir), osmium (Os), copper (Cu) or platinum (Pt), and even more preferably ortho-metallated iridium complex compounds.

The dopant to be comprised in the organic electroluminescent device of the present disclosure may be selected from the group consisting of compounds represented by the following formulae 15 to 17.

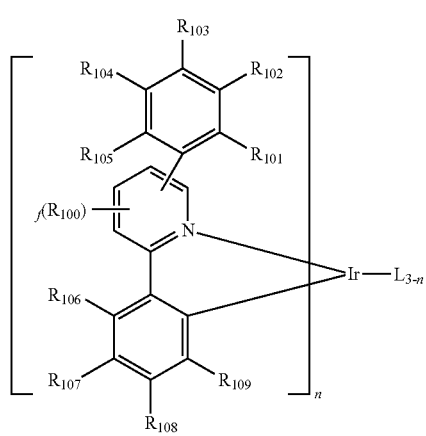

-continued

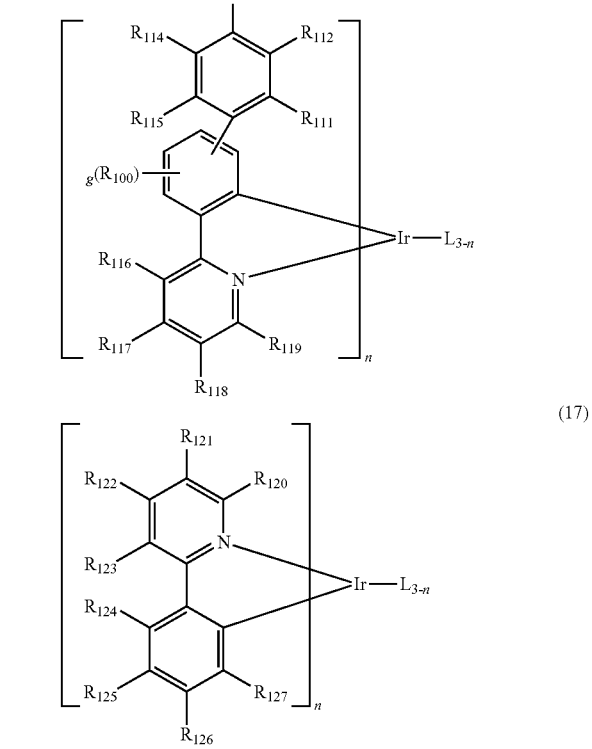

wherein L is selected from the following structures:

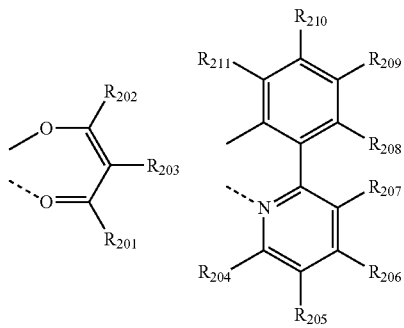

$R_{100}$ represents hydrogen, a substituted or unsubstituted (C1-C30)alkyl, or a substituted or unsubstituted (C3-C30) cycloalkyl; $R_{101}$ to $R_{103}$ and $R_{111}$ to $R_{123}$, each independently, represent hydrogen, deuterium, a halogen, a (C1-C30)alkyl unsubstituted or substituted with a halogen, a substituted or unsubstituted (C3-C30)cycloalkyl, a cyano, or a substituted or unsubstituted (C1-C30)alkoxy; $R_{106}$ to $R_{103}$ may be linked to an adjacent substituent(s) to form a substituted or unsubstituted fused ring, for example, a substituted or unsubstituted fluorene, a substituted or unsubstituted dibenzothiophene, or a substituted or unsubstituted dibenzofuran; $R_{120}$ to $R_{123}$ may be linked to an adjacent substituent(s) to form a substituted or unsubstituted fused ring, for example, a substituted or unsubstituted quinoline; $R_{124}$ to $R_{127}$, each independently, represent hydrogen, deuterium, a halogen, a substituted or unsubstituted (C1-C30) alkyl, or a substituted or unsubstituted (C1-C30)aryl; where any of $R_{124}$ to $R_{127}$ is aryl, it may be linked to an adjacent substituent(s) to form a substituted or unsubstituted fused ring, for example, a substituted or unsubstituted fluorene, a substituted or unsubstituted dibenzofuran, or a substituted or unsubstituted dibenzothiophene; $R_{201}$ to $R_{211}$, each independently, represent hydrogen, deuterium, a halogen, a (C1-C30)alkyl unsubstituted or substituted with a halogen, a substituted or unsubstituted (C3-C30)cycloalkyl, or a substituted or unsubstituted (C6-C30)aryl; any of $R_{208}$ to $R_{211}$ may be linked to an adjacent substituent(s) to form a substituted or unsubstituted fused ring, for example, a substituted or unsubstituted fluorene, a substituted or unsubstituted dibenzothiophene, or a substituted or unsubstituted dibenzofuran; f and g, each independently, represent an integer of 1 to 3; where f or g is an integer of 2 or more, each of $R_{100}$ may be the same or different; and n represents an integer of 1 to 3.

Specifically, the dopant material includes the following:

D-1
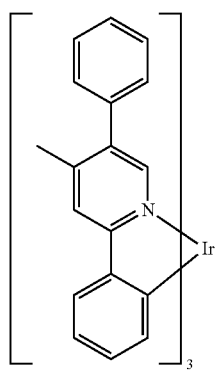

D-2
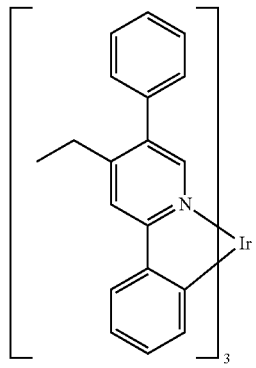

D-3
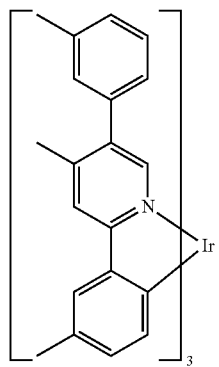

D-4
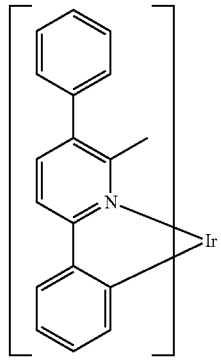

D-5
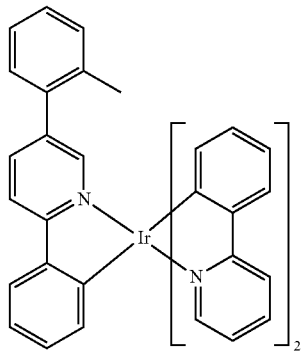

D-6
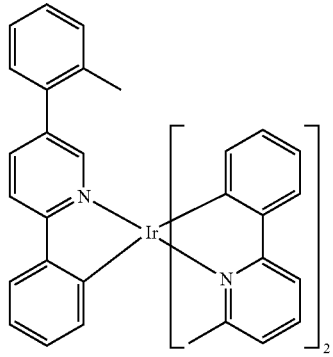

D-7

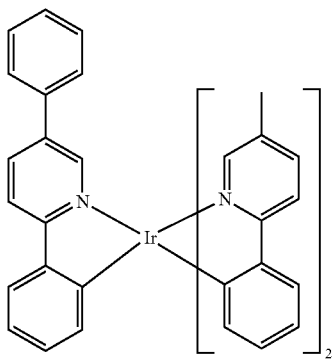
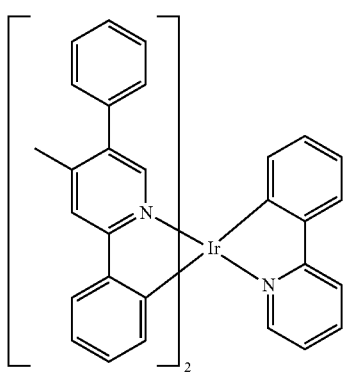
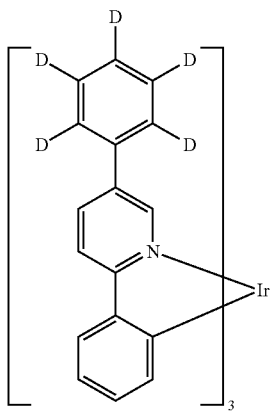
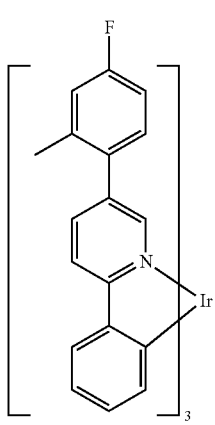
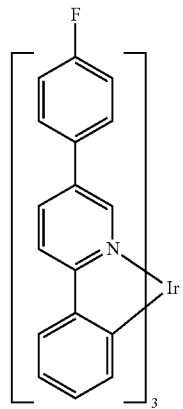
D-8
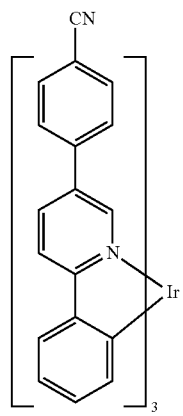
D-9
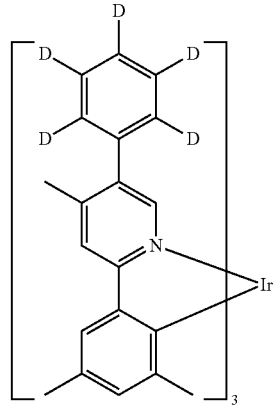
D-10
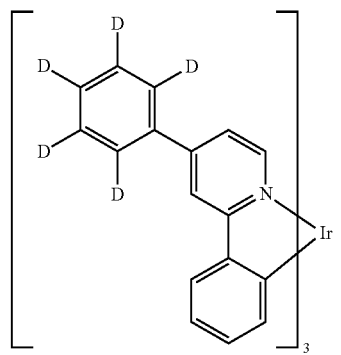
D-11
D-12
D-13
D-14
D-15

-continued
D-16
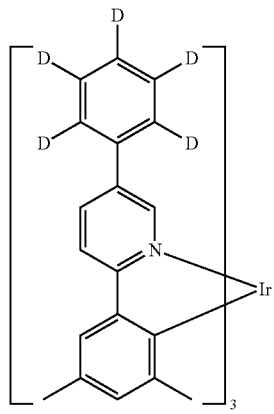
D-17
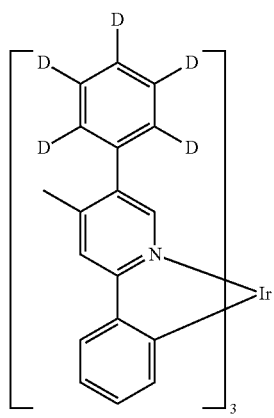
D-18
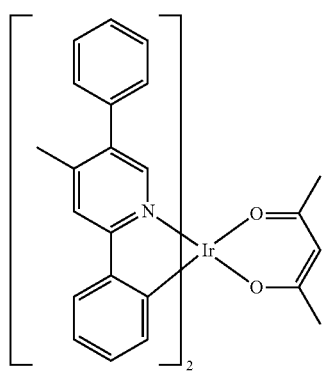
D-19
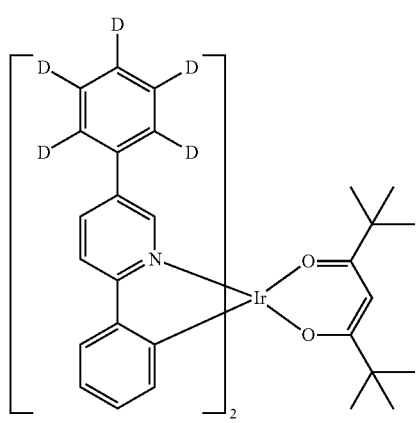
-continued
D-20
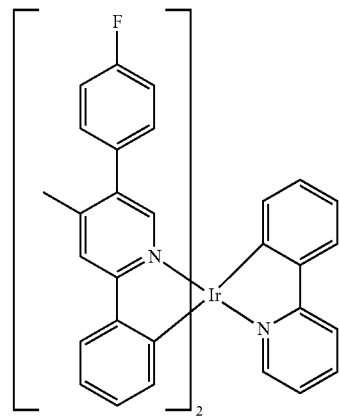
D-21
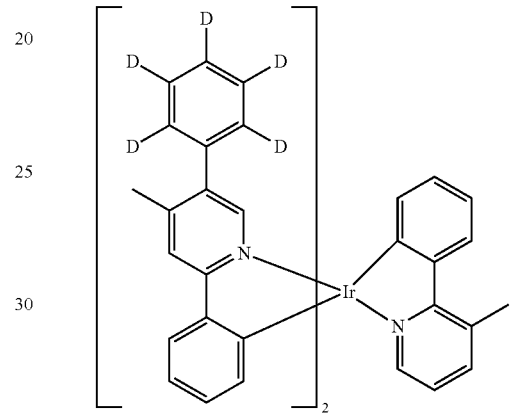
D-22
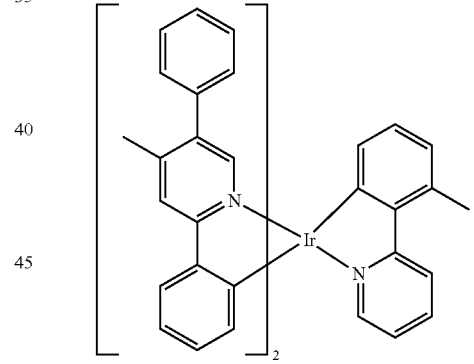
D-23
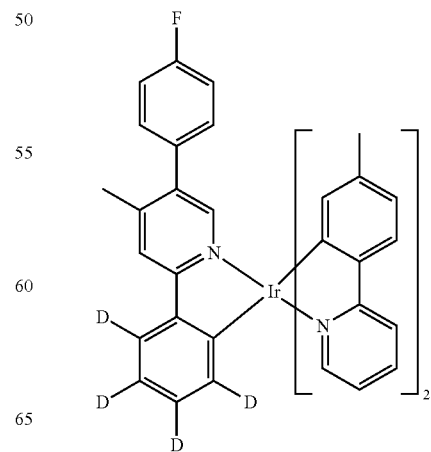

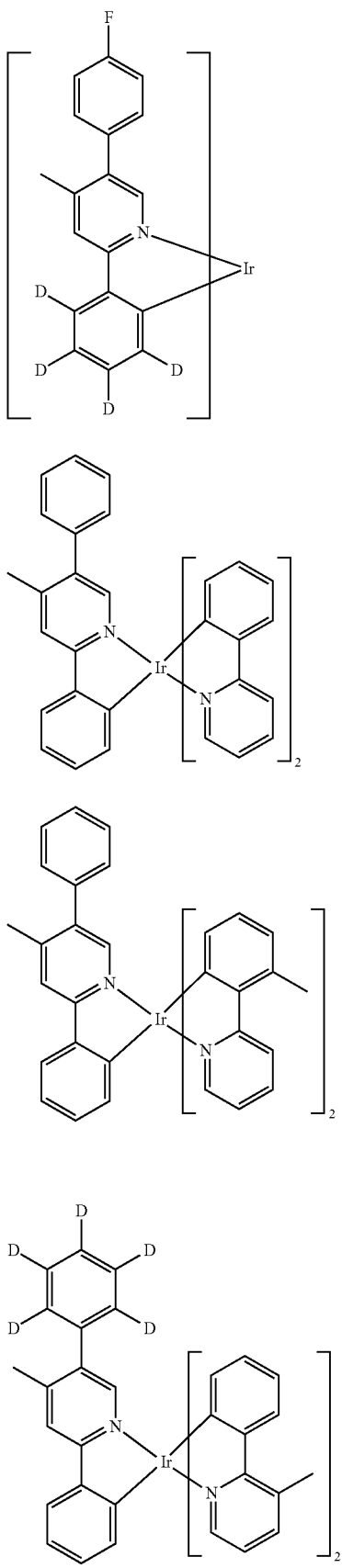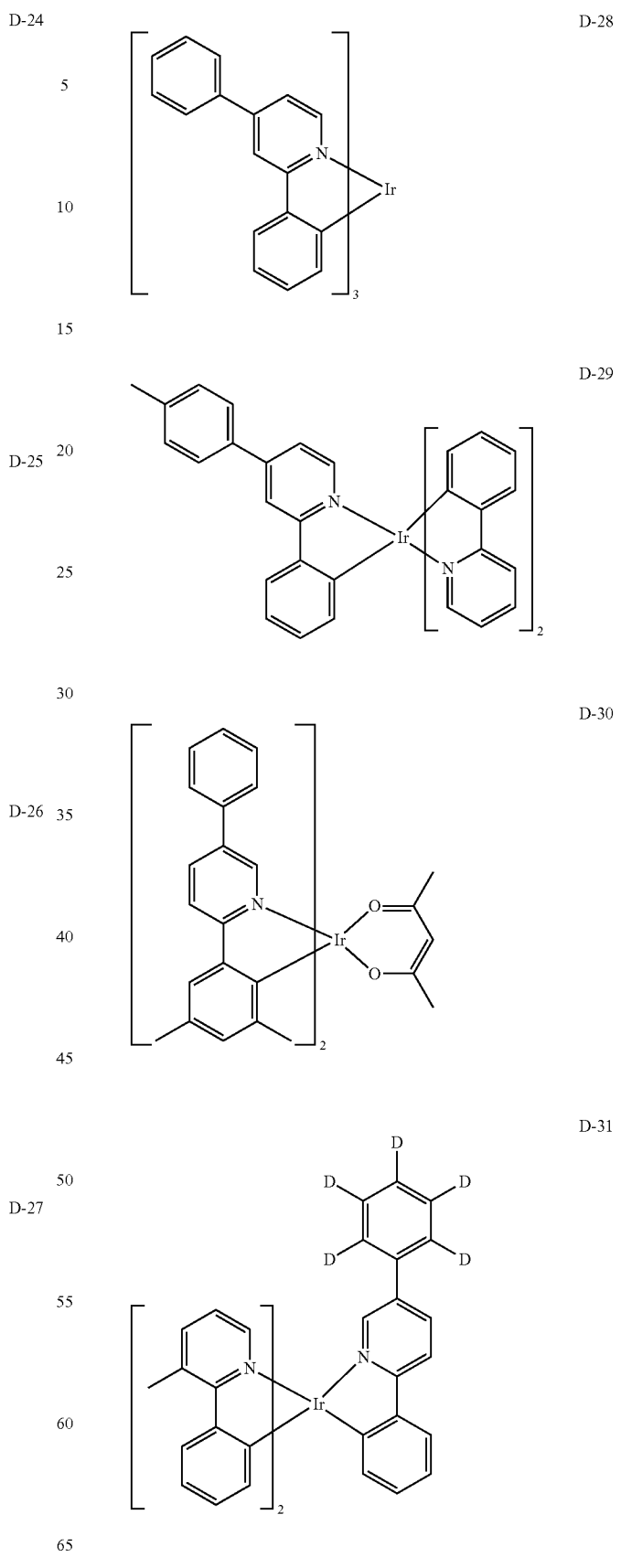

D-32 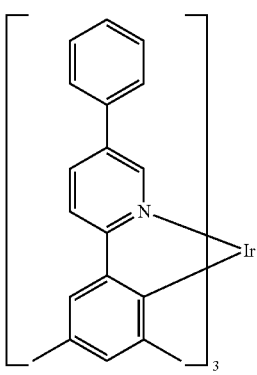
D-33 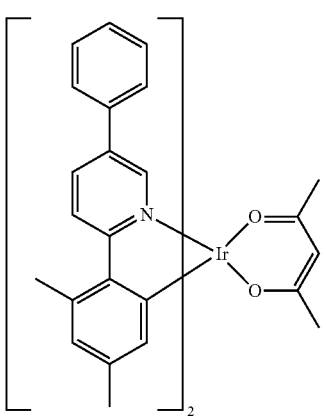
D-34 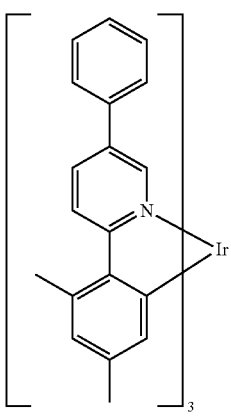
D-35 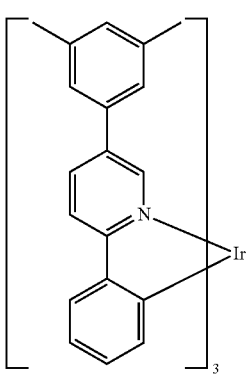
D-36 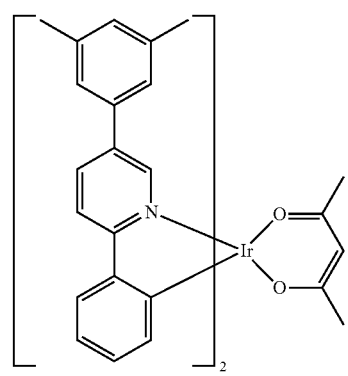
D-37 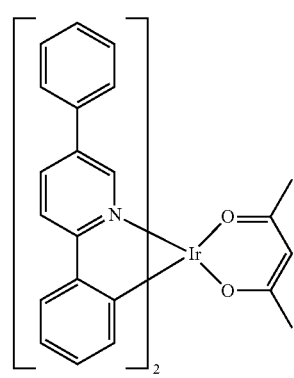
D-38 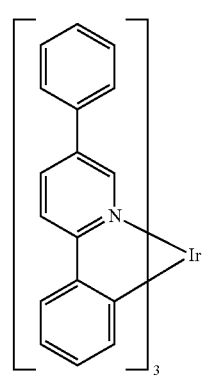
D-39 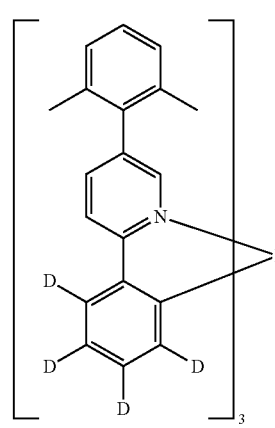

D-40 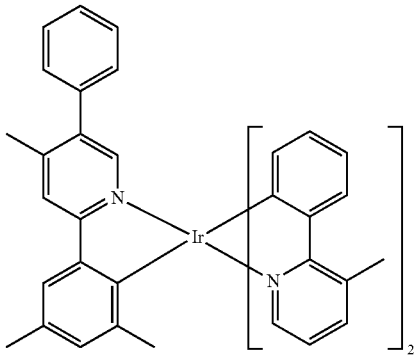
D-41 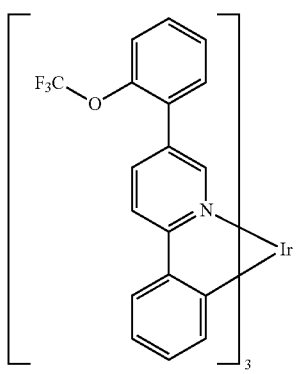
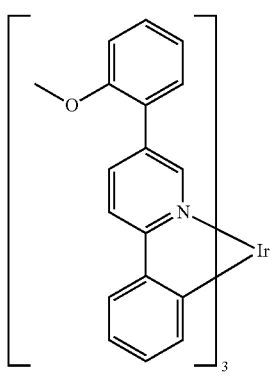
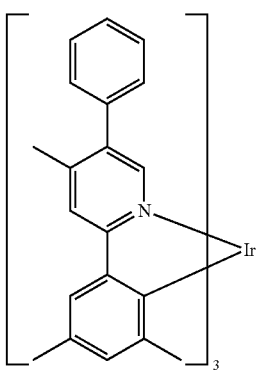
D-42 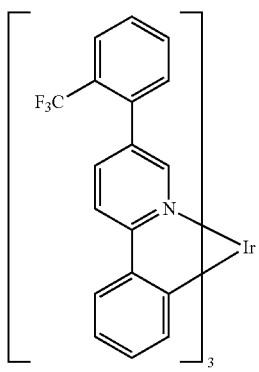
D-44
D-45
D-46 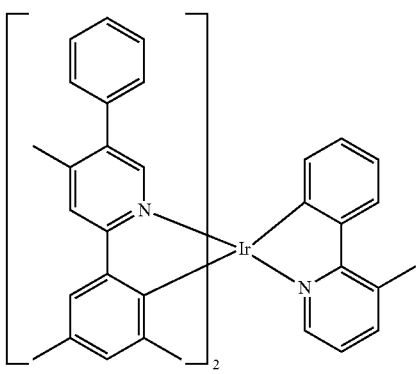
D-43 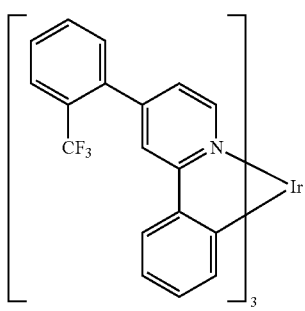
D-47 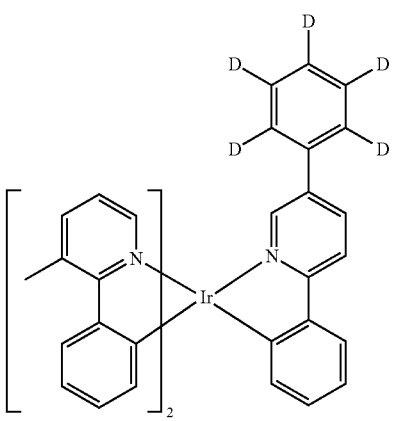

D-48
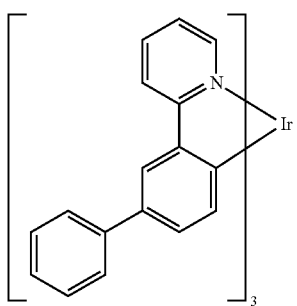
D-49
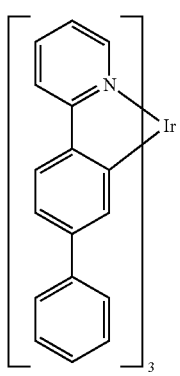
D-50
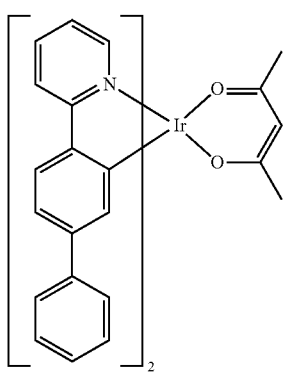
D-51
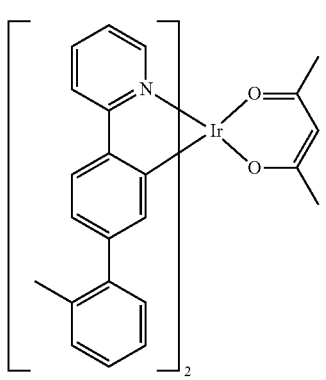
D-52
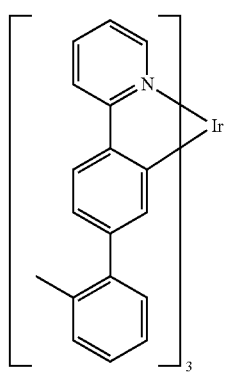
D-53
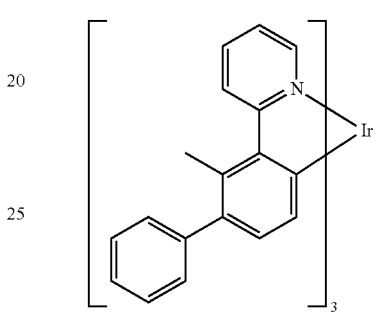
D-54
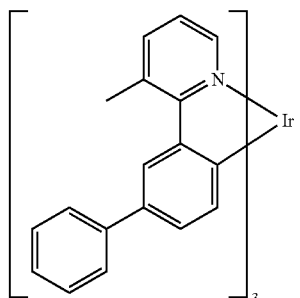
D-55
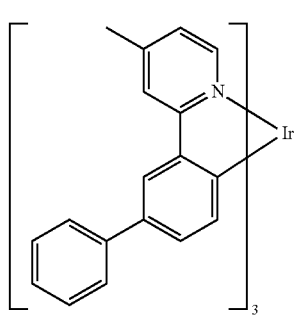
D-56
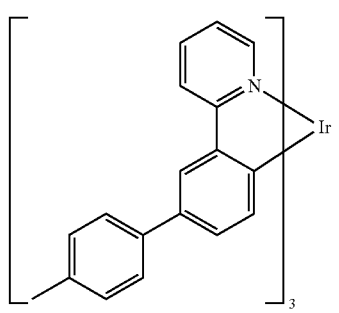

D-57 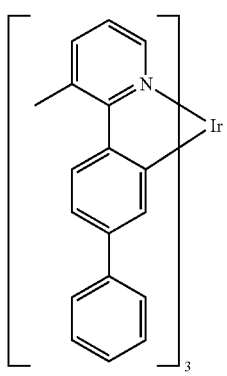
D-58 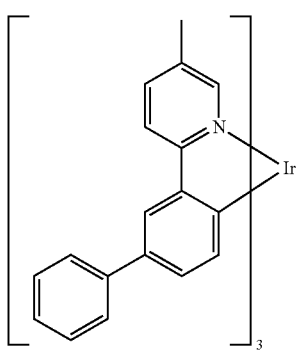
D-59 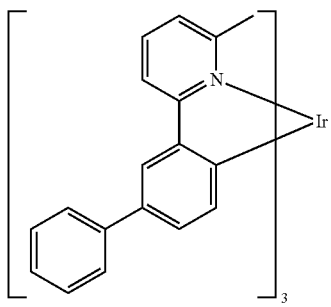
D-60 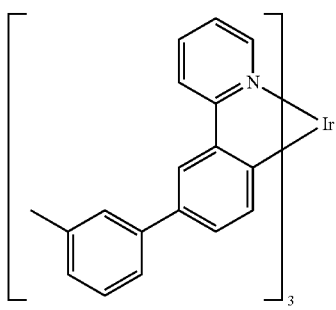
D-61 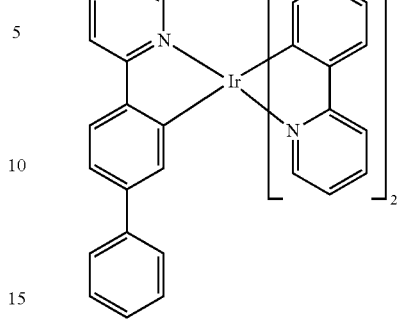
D-62 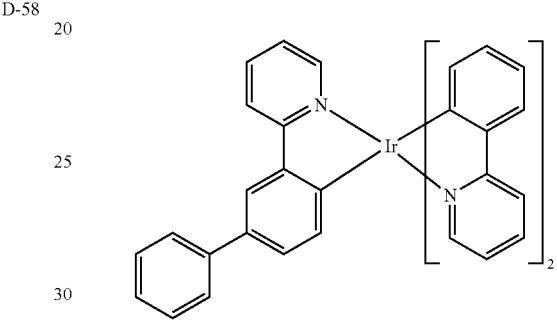
D-63 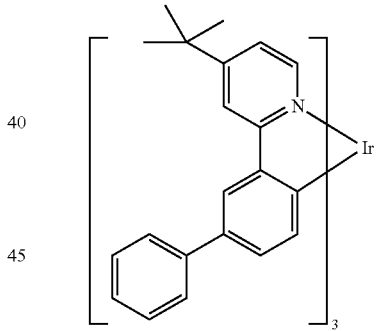
D-64 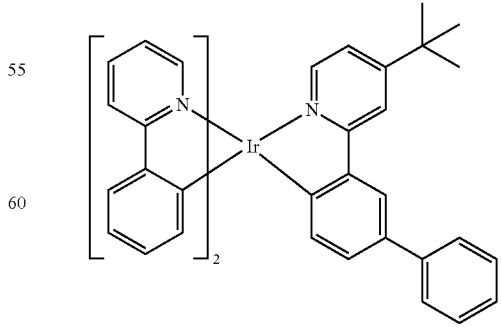

-continued
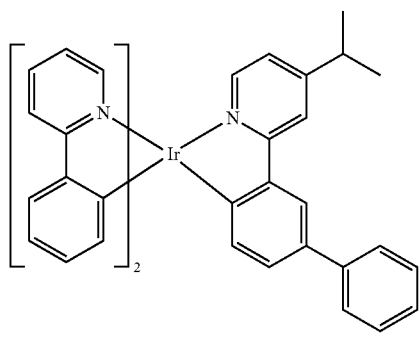
D-65
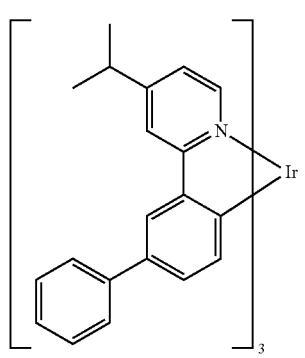
D-66
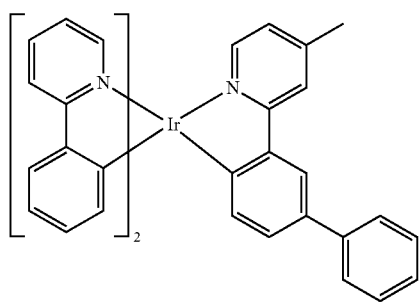
D-67
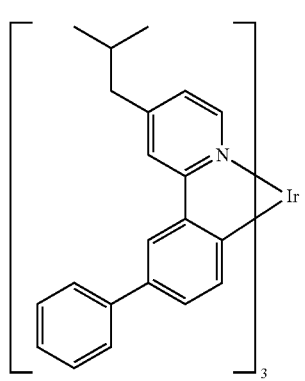
D-68
-continued
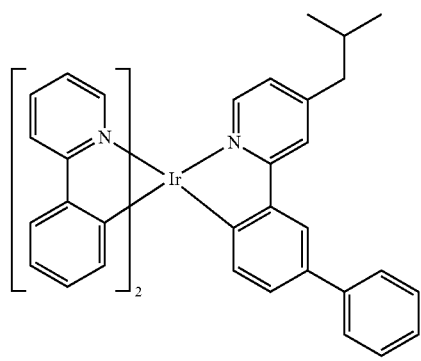
D-69
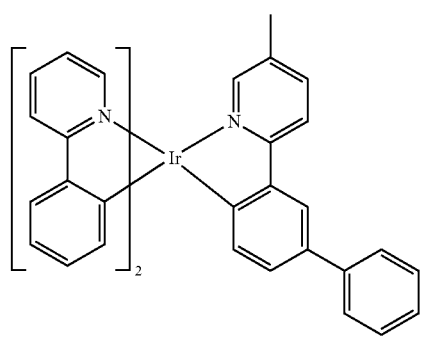
D-70
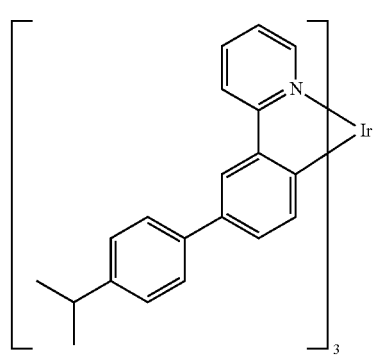
D-71
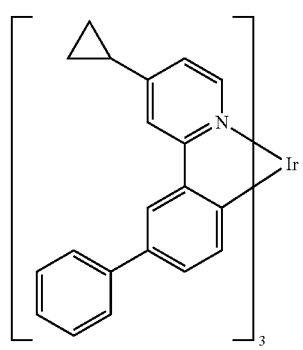
D-72

D-73 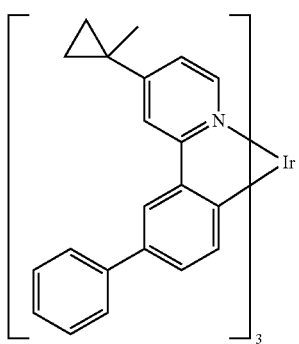
D-74 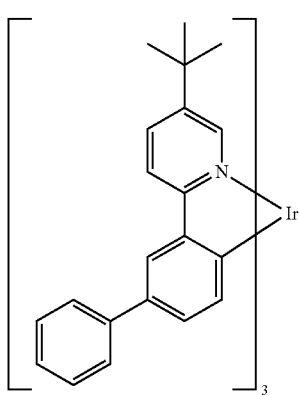
D-75 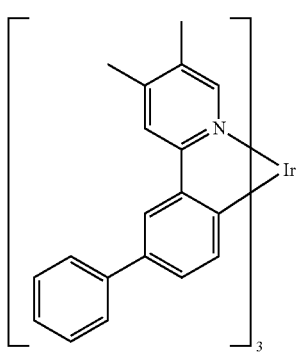
D-76 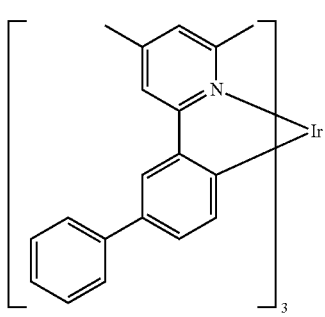
D-77 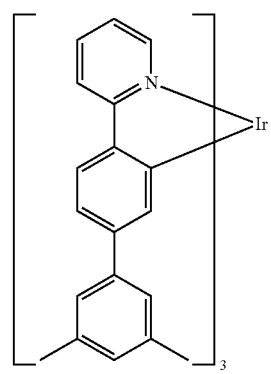
D-78 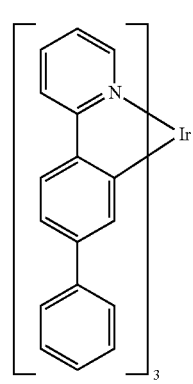
D-79 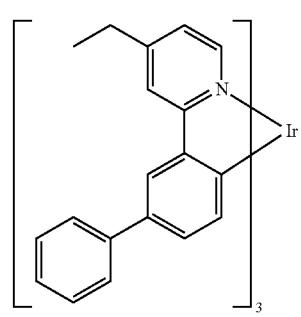
D-80 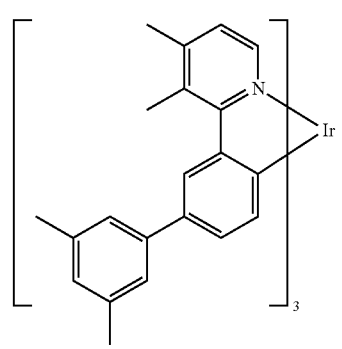

D-81
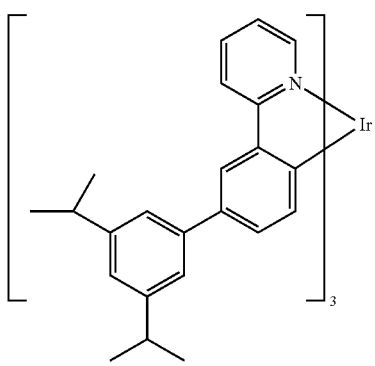
D-82
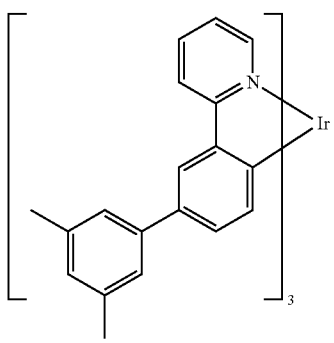
D-83
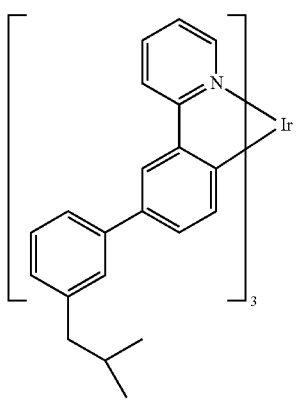
D-84
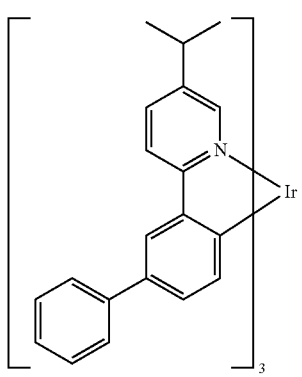
D-85
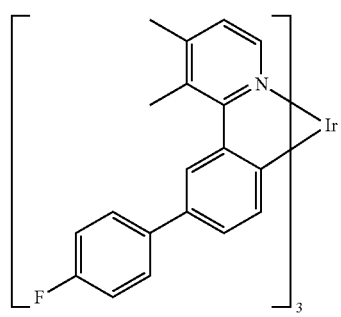
D-86
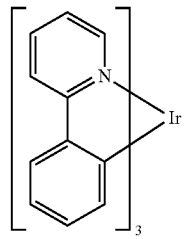
D-87
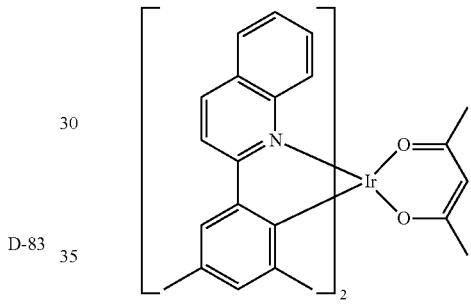
D-88
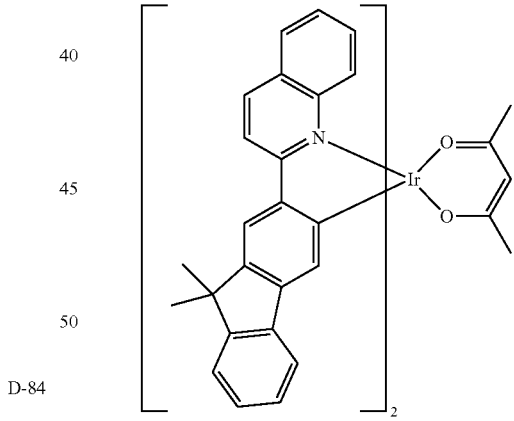
D-89
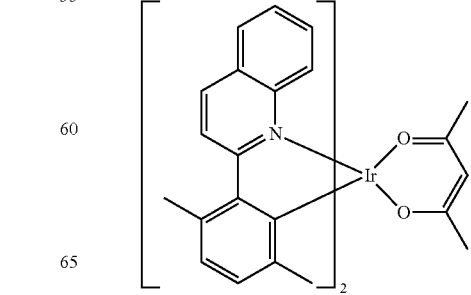

D-90
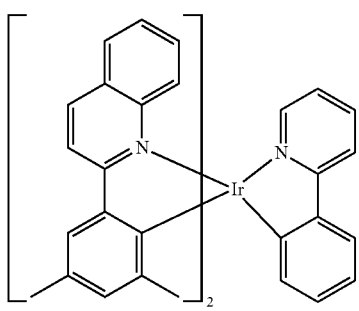
D-91
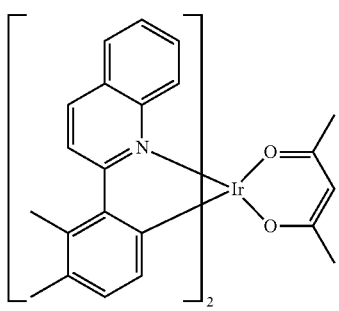
D-92
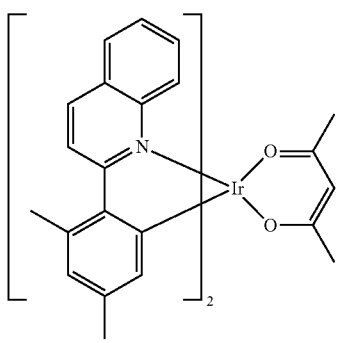
D-93
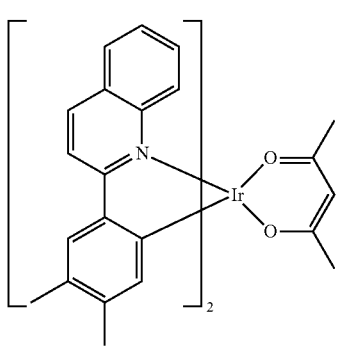
D-94
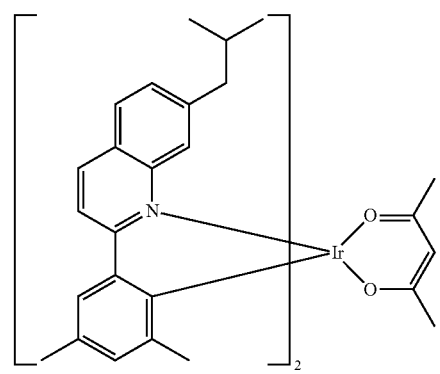
D-95
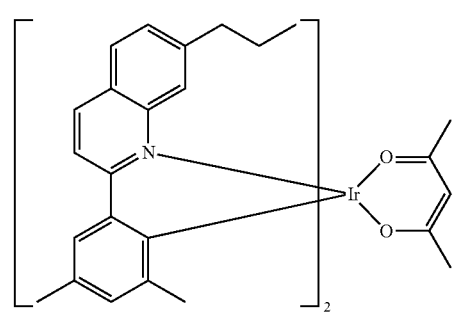
D-96
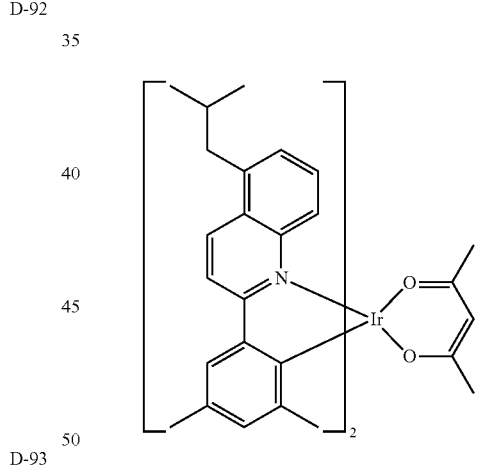
D-97
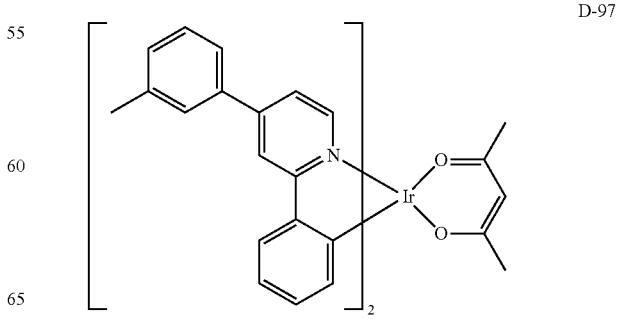

-continued
D-98
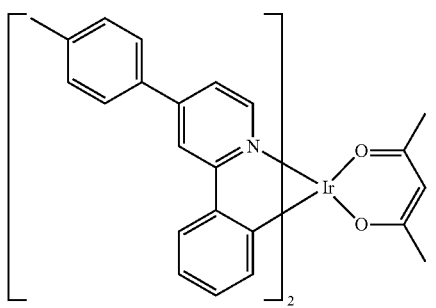
D-99
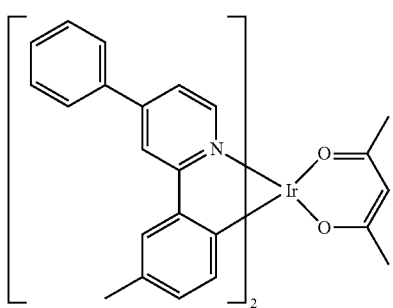
D-100
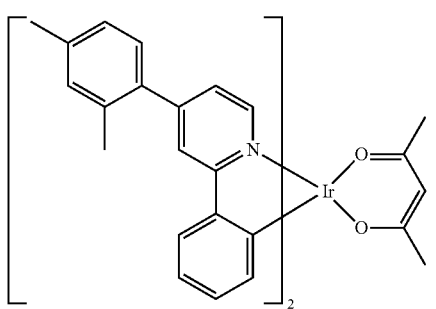
D-101
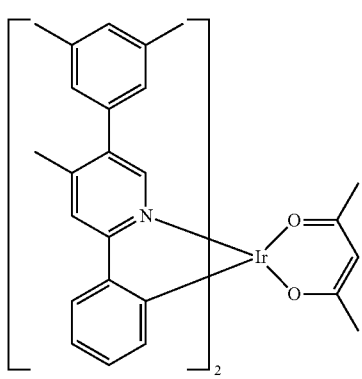
D-102
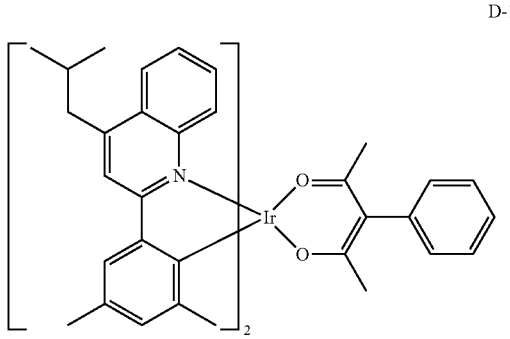
-continued
D-103
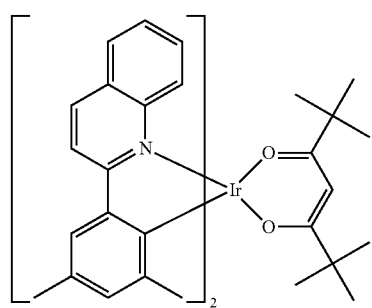
D-104
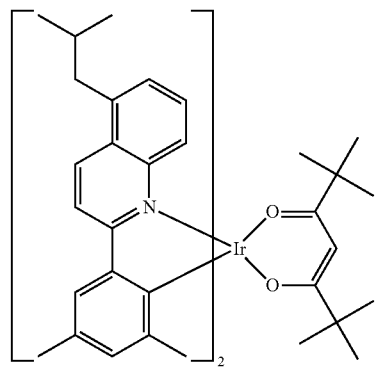
D-105
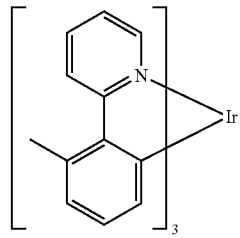
D-106
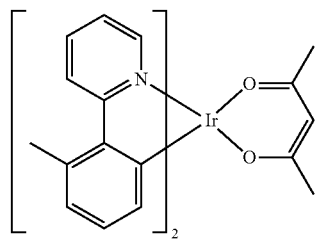
D-107
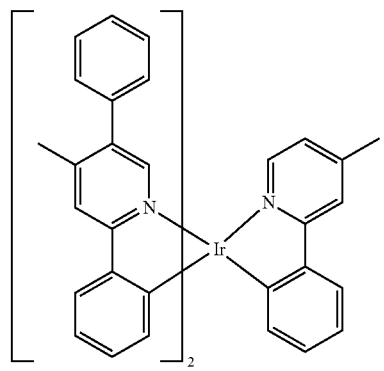

D-108 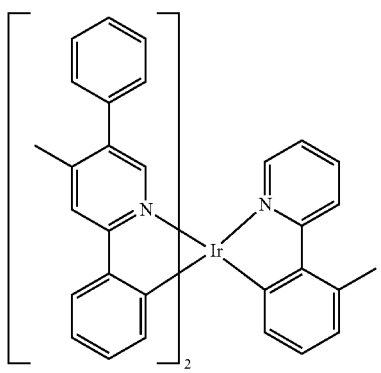
D-109 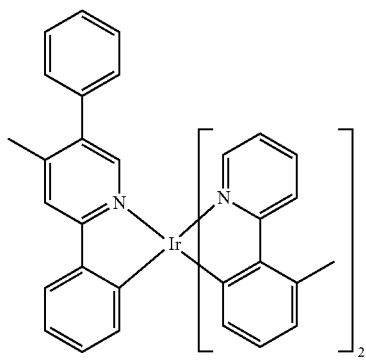
D-110 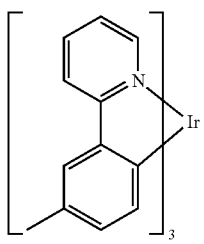
D-111 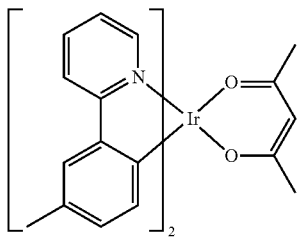
D-112 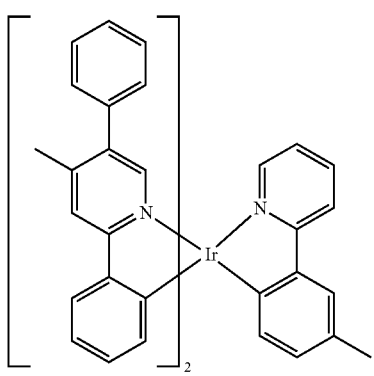
D-113 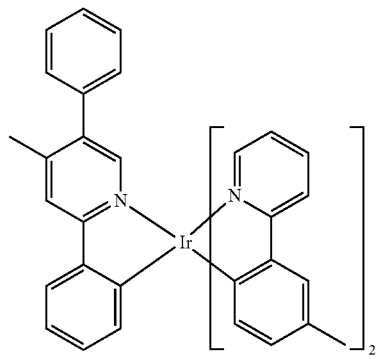
D-114 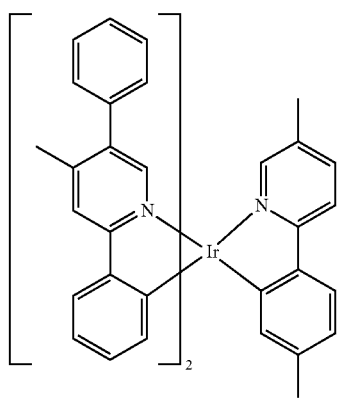
D-115 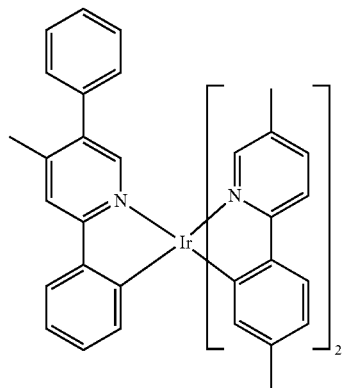
D-116 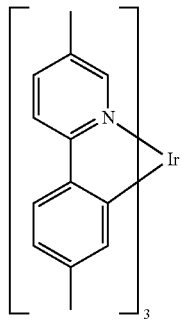

D-117
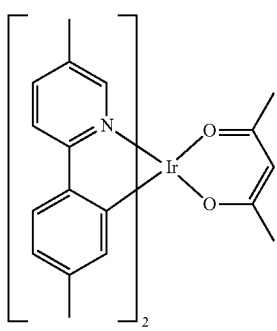
D-118
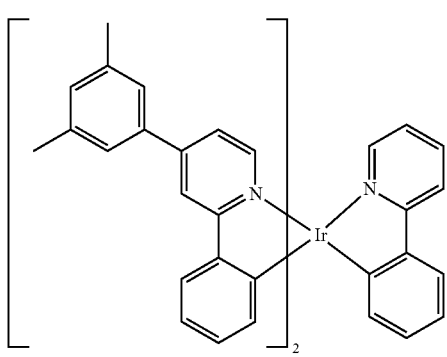
D-119
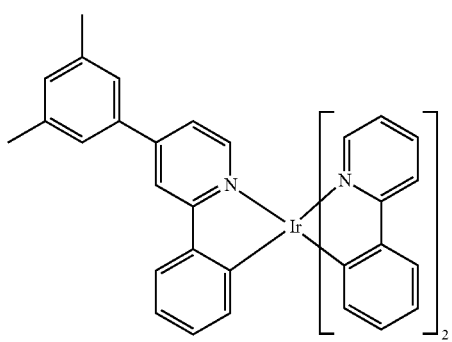
D-120
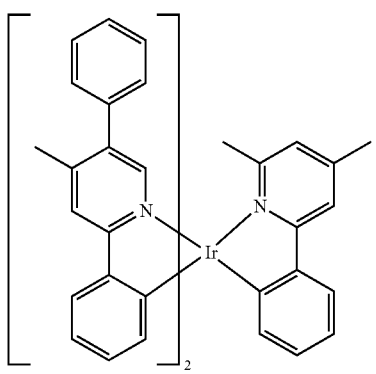
D-121
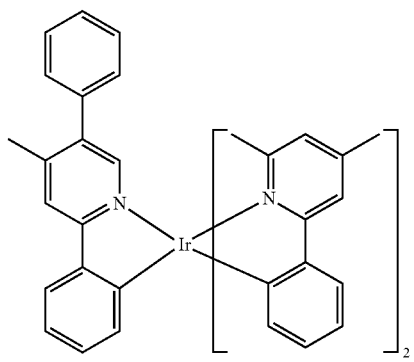
D-122
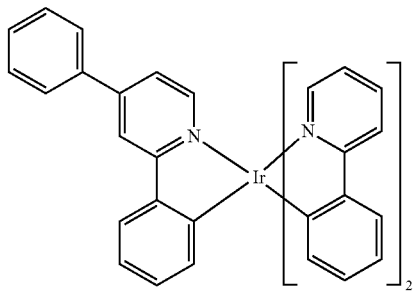
D-123
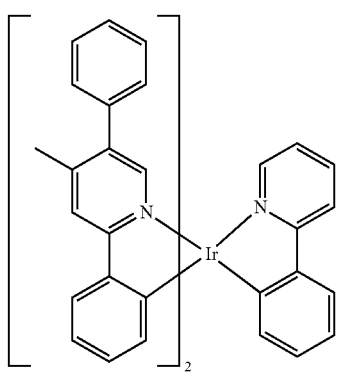
D-124
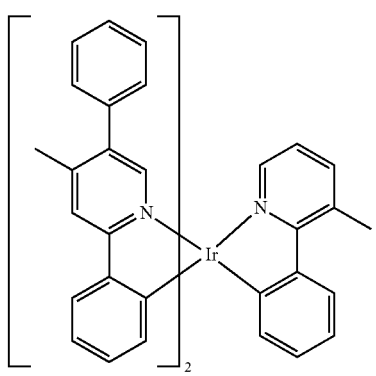

D-125 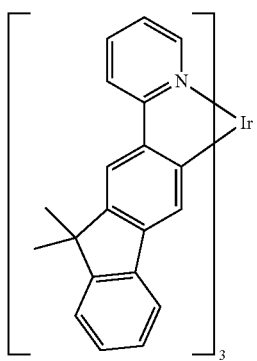
D-126 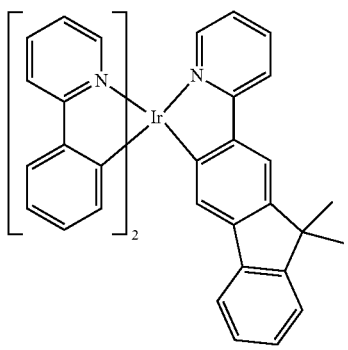
D-127 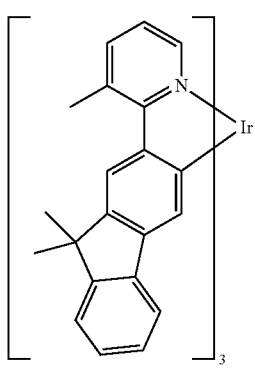
D-128 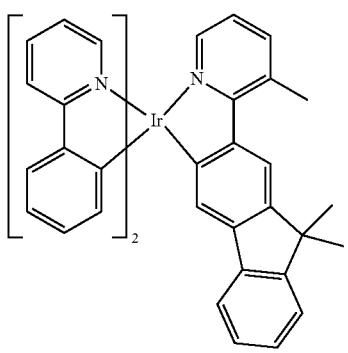
D-129 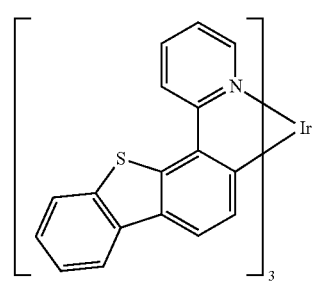
D-130 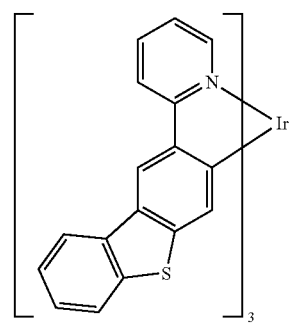
D-131 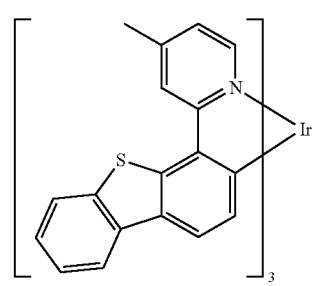
D-132 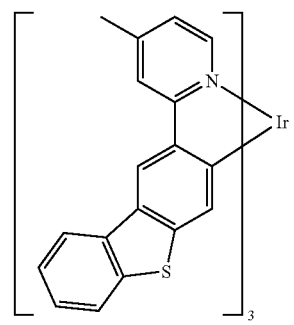
D-133 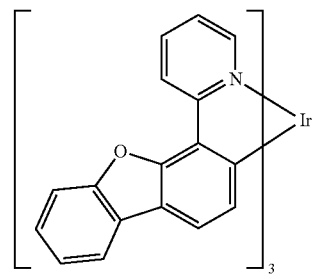

D-134
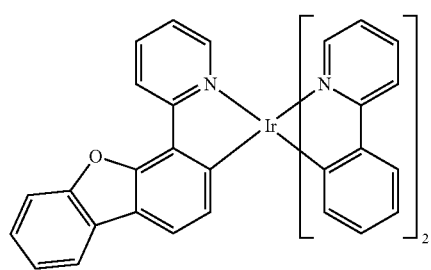
D-135
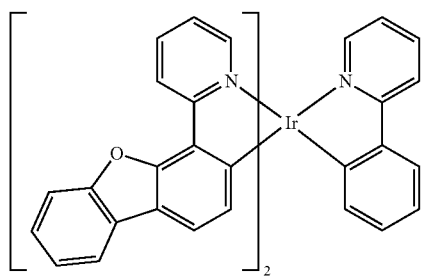
D-136
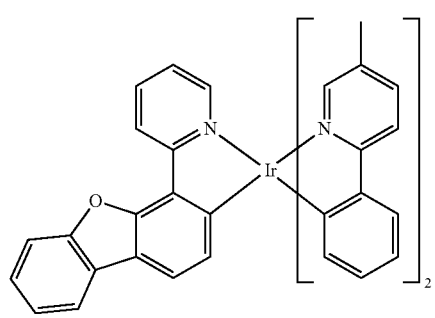
D-137
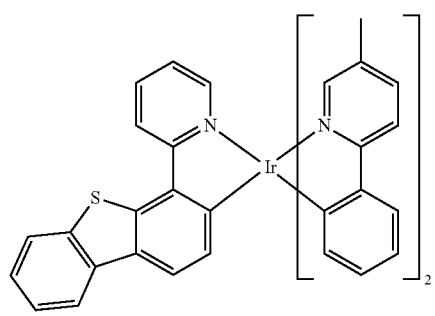
D-138
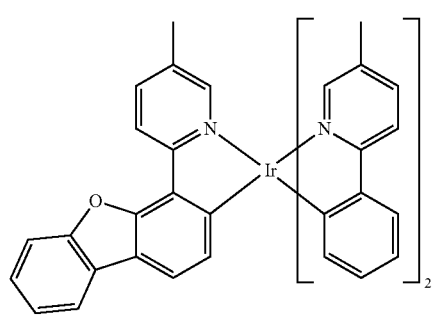
D-139
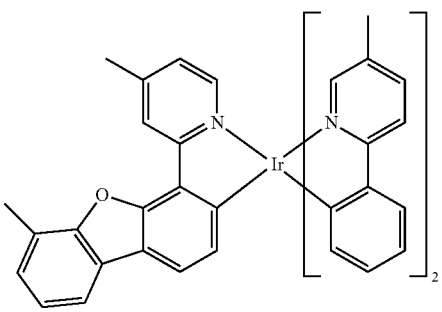
D-140
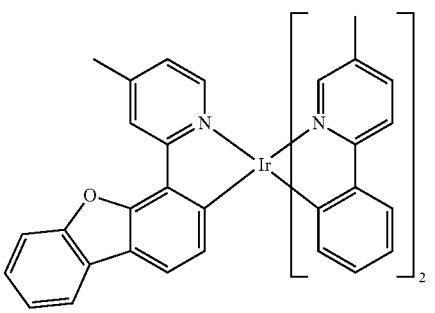
D-141
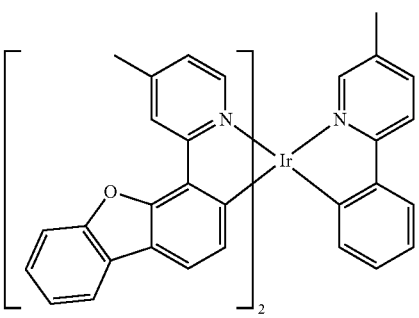
D-142
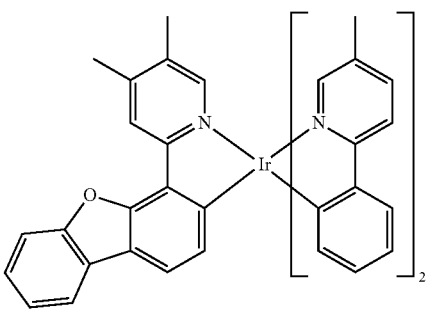
D-143
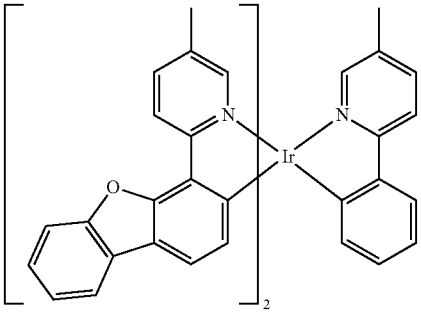

D-144
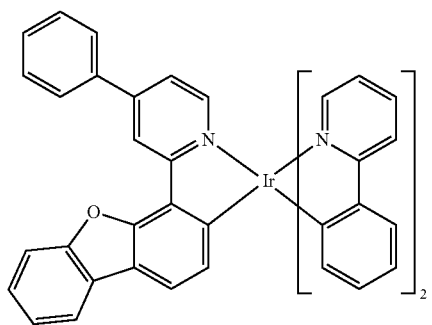
D-145
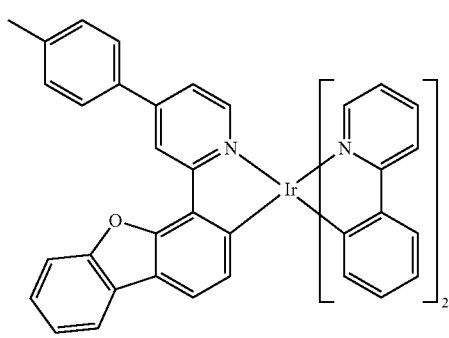
D-146
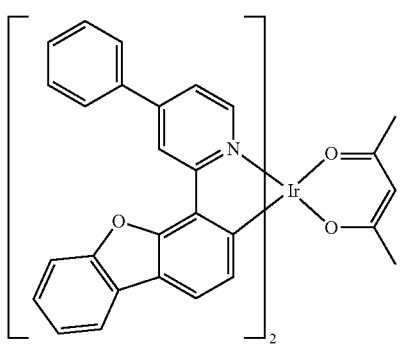
D-147
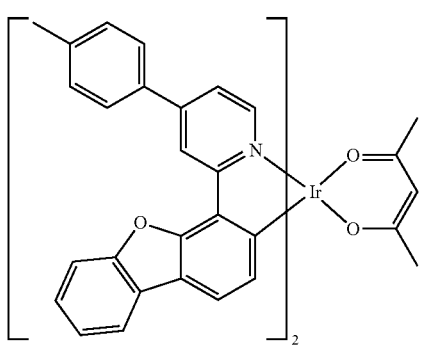
D-148
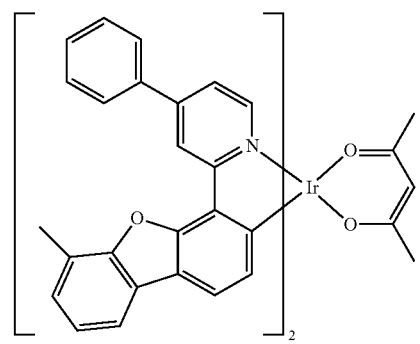
D-149
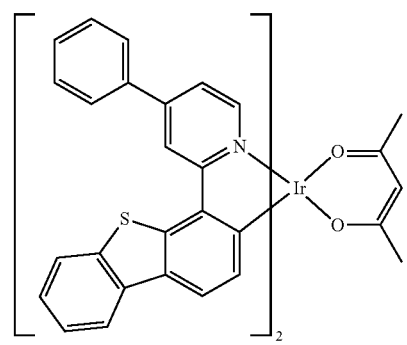
D-150
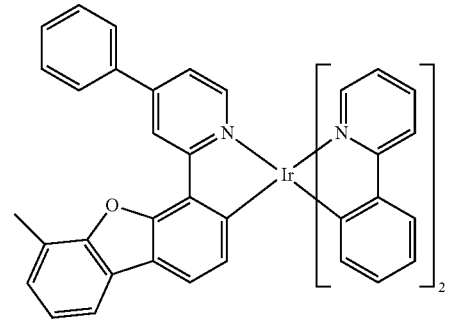
D-151
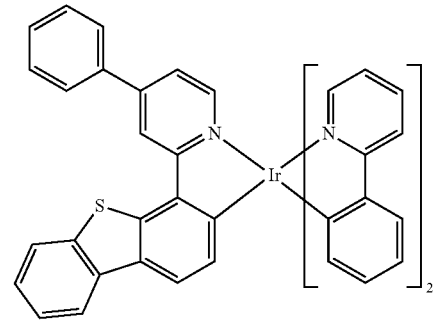
D-152
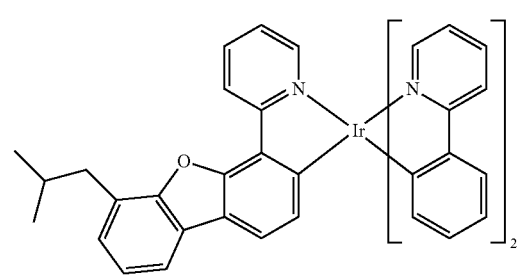

D-153
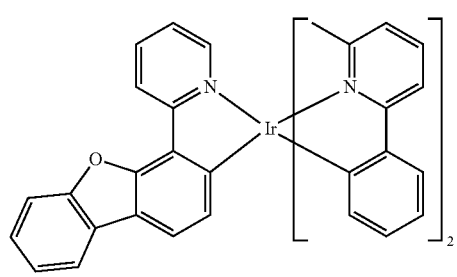
D-154
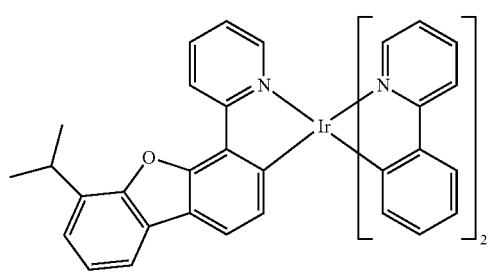
D-155
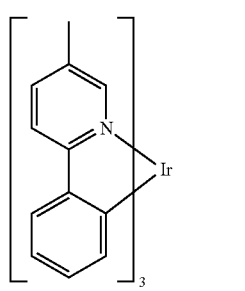
D-156
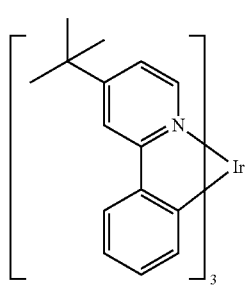
D-157
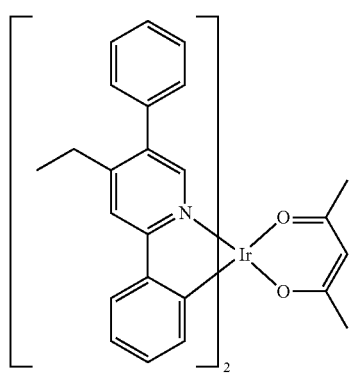
D-158
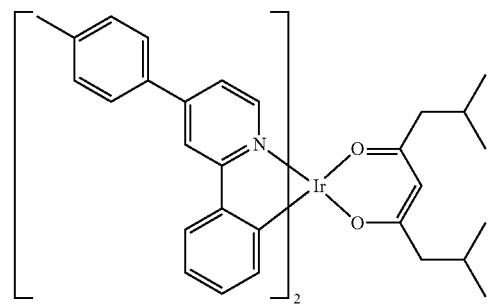
D-159
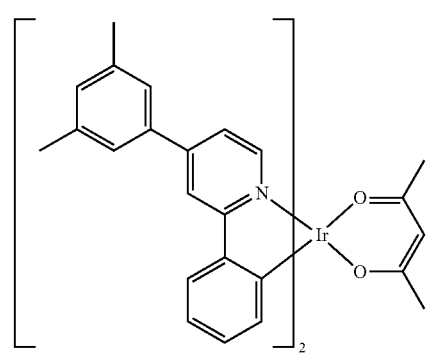
D-160
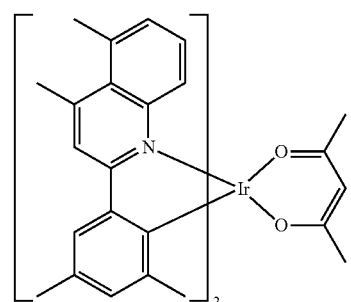
D-161
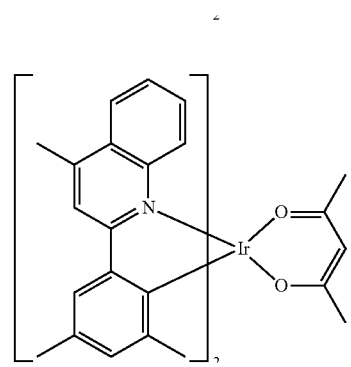

-continued
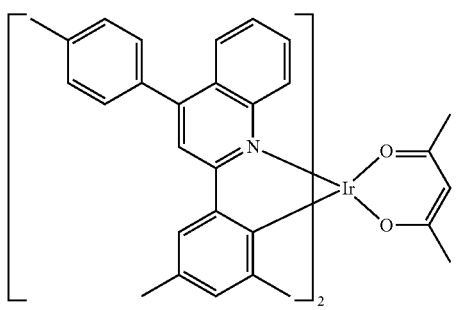
D-162
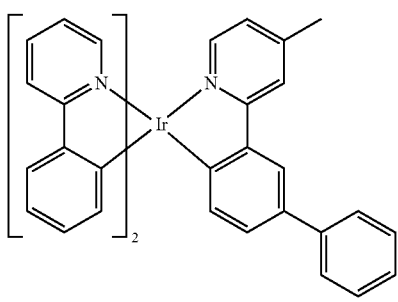
D-163
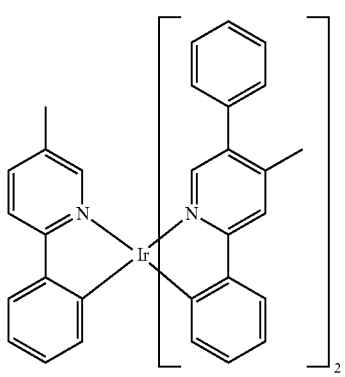
D-164
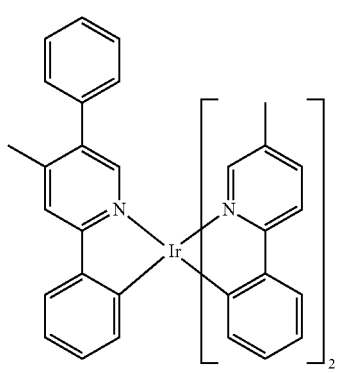
D-165
-continued
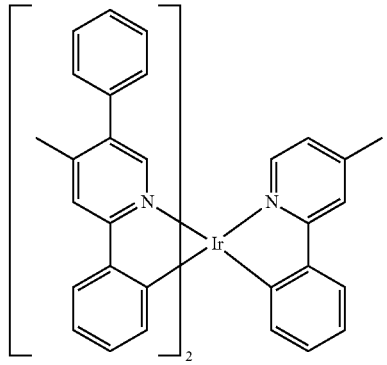
D-166
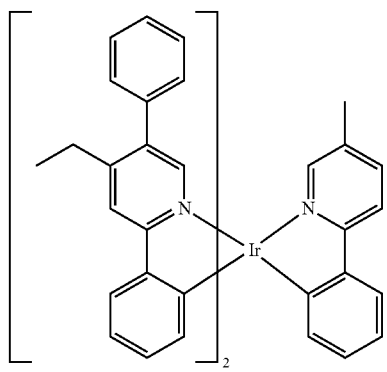
D-167
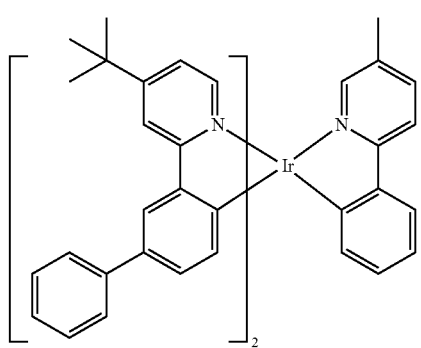
D-168
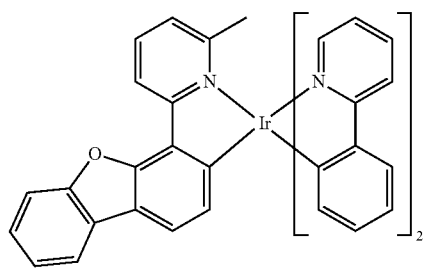
D-169
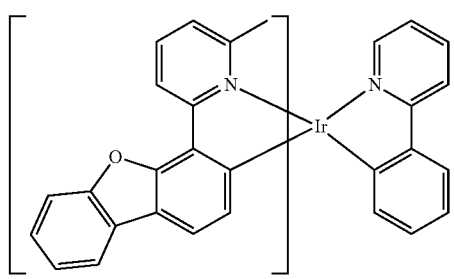
D-170

D-171
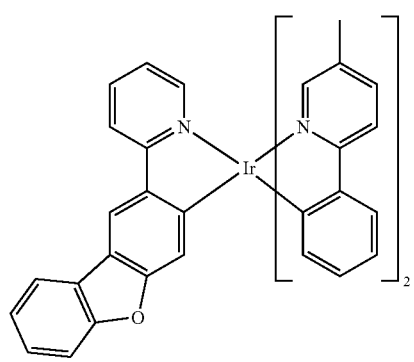
D-175
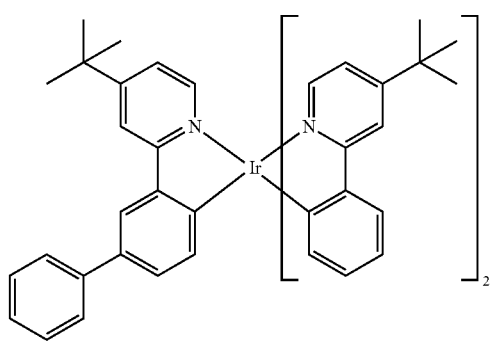
D-172
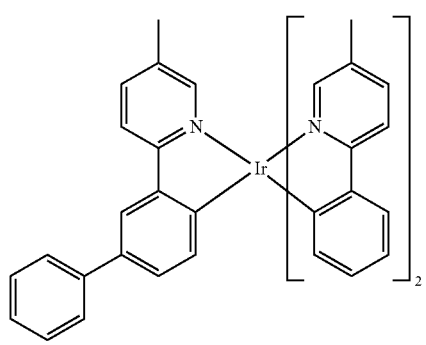
D-176
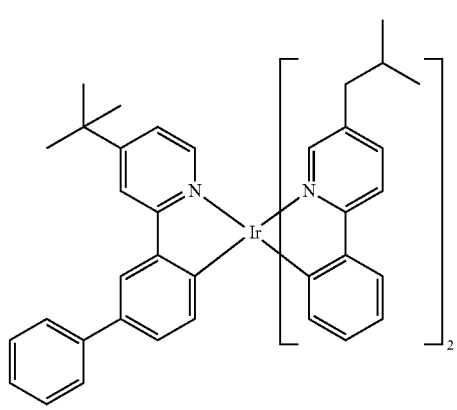
D-173
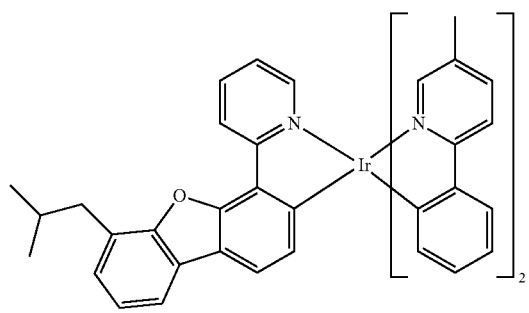
D-177
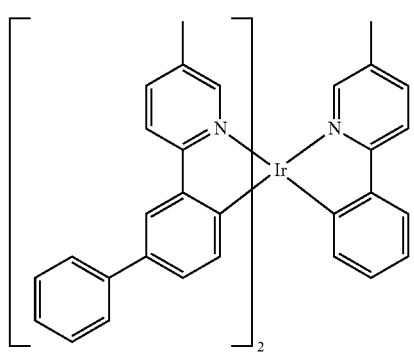
D-174
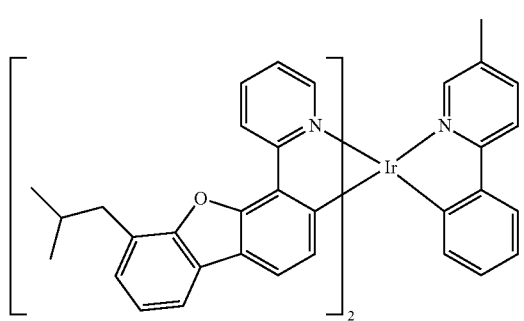
D-178
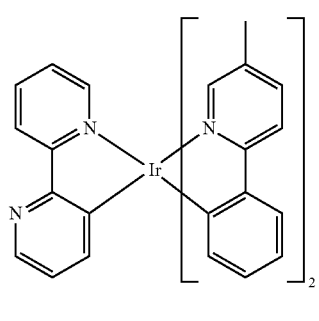

D-179 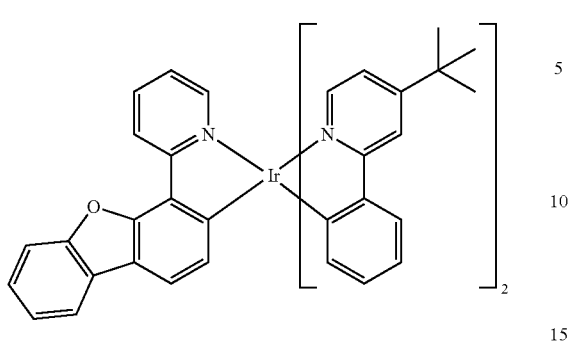
D-180 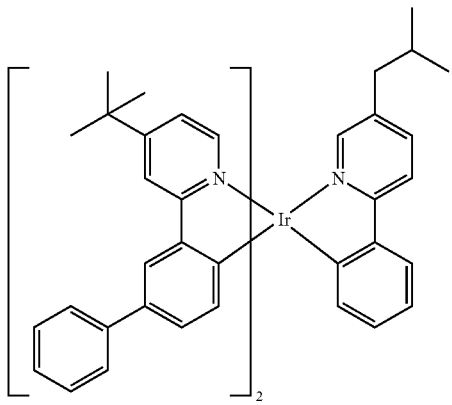
D-181 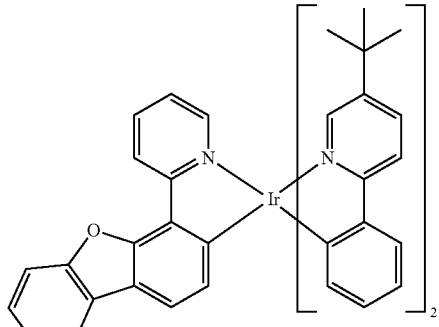
D-182 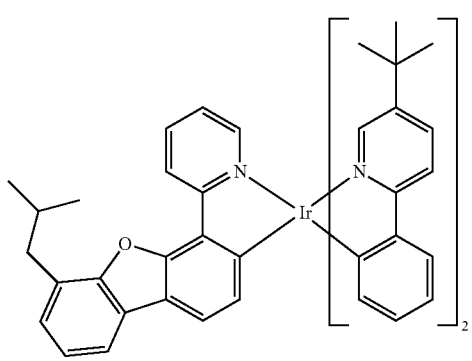
D-183 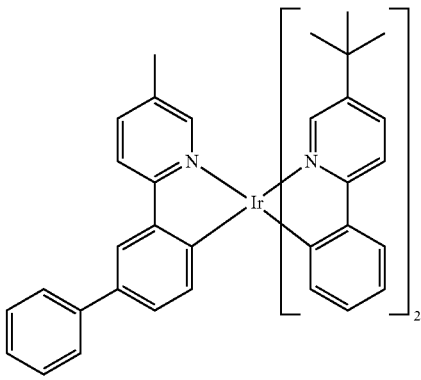
D-184 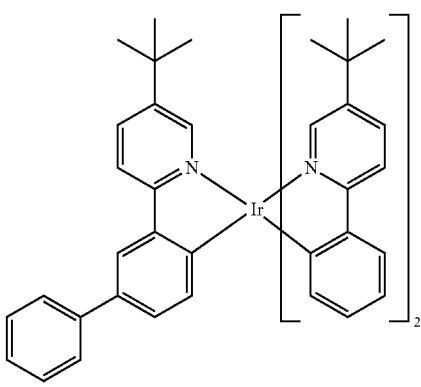
D-185 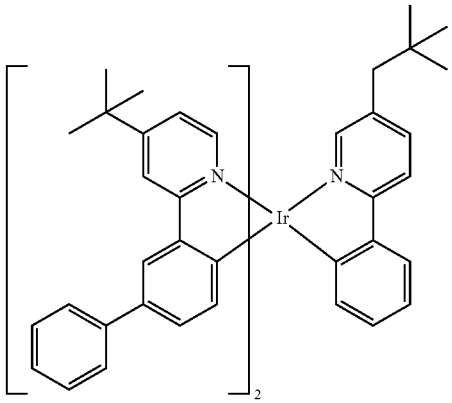
D-186 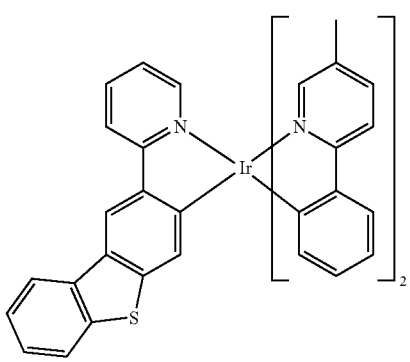

D-187 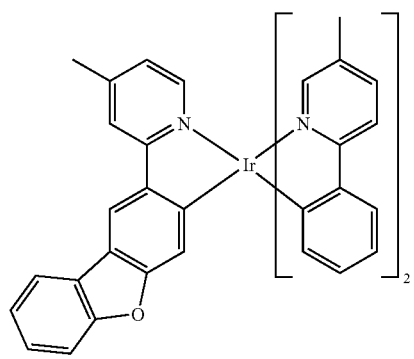
D-188 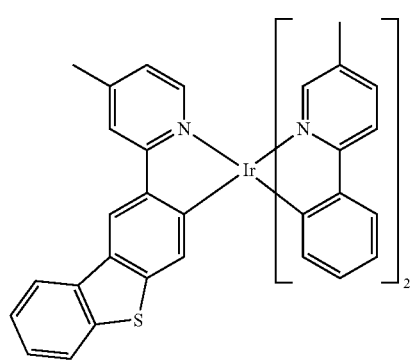
D-189 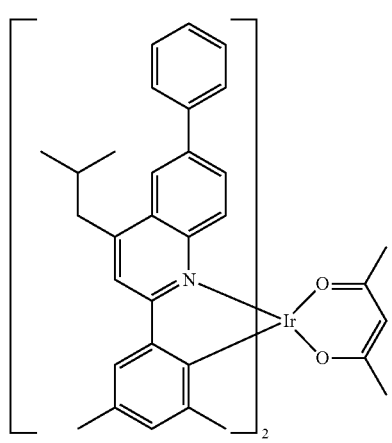
D-190 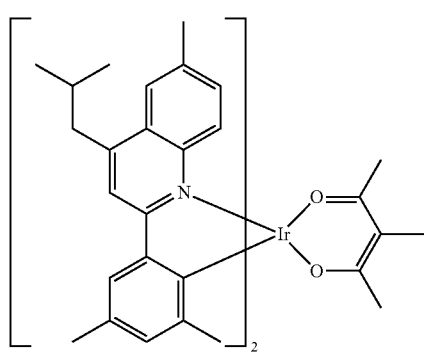
D-191 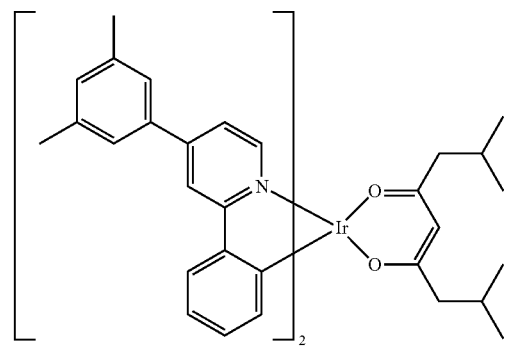
D-192 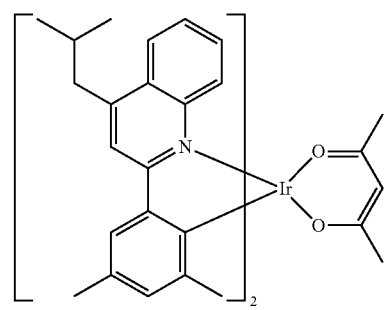
D-193 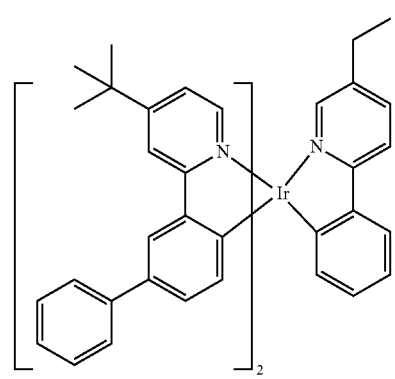
D-194 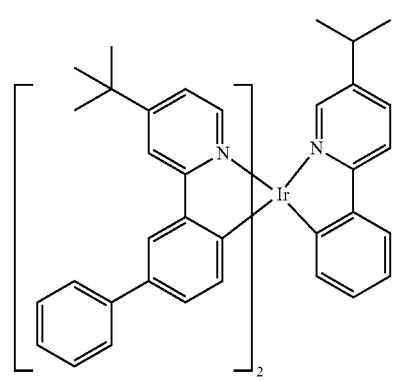

-continued
D-195
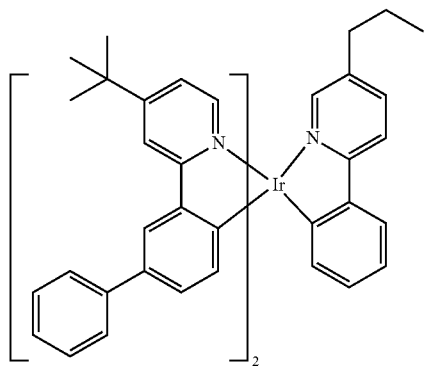
D-199
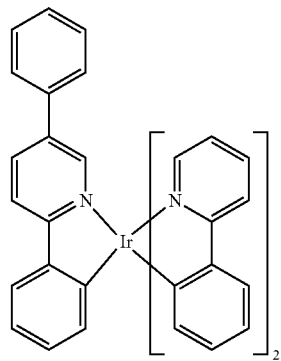
D-196
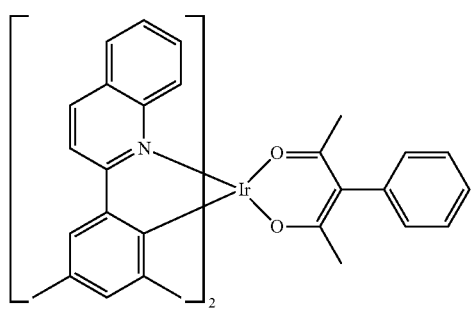
D-200
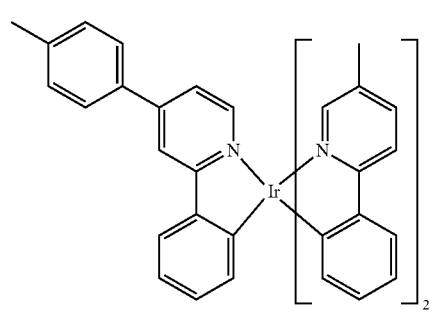
D-197
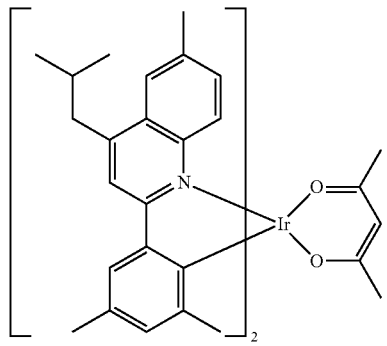
D-201
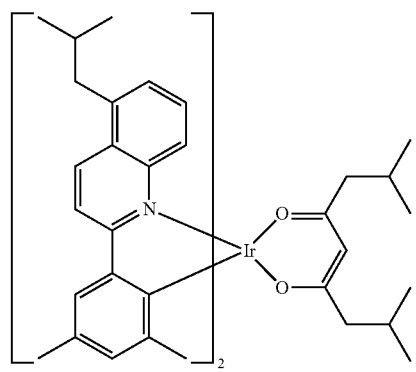
D-198
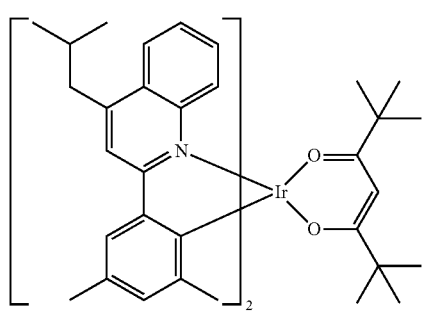
D-202
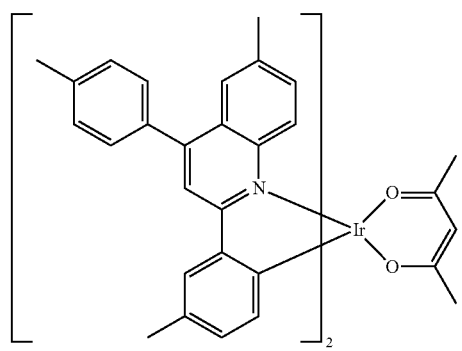

D-203
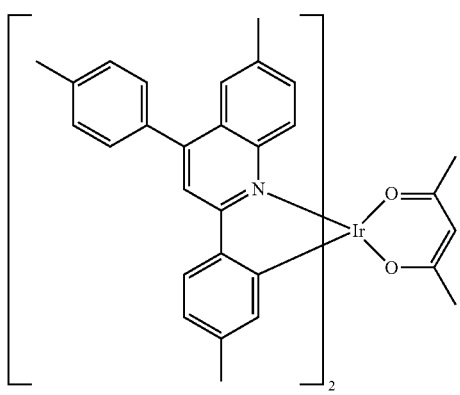
D-204
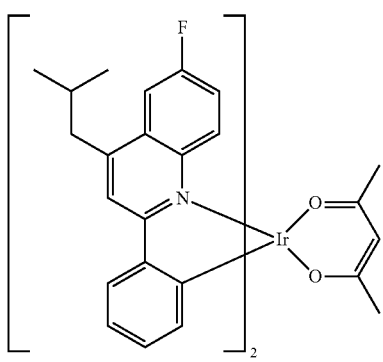
D-205
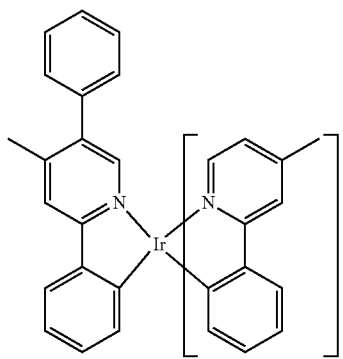
D-206
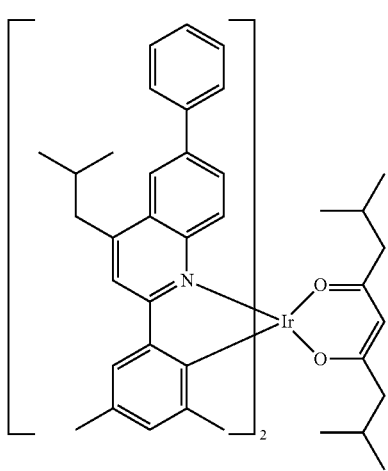
D-207
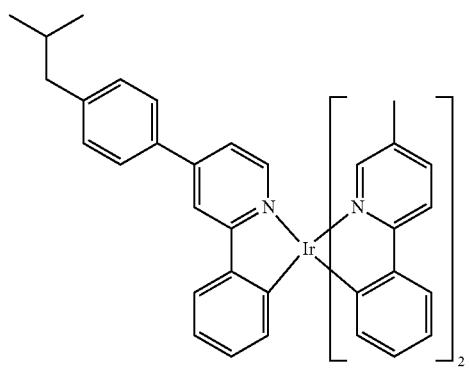
D-208
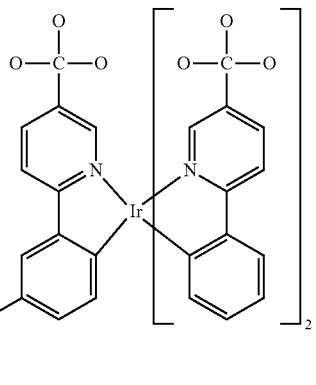
D-209
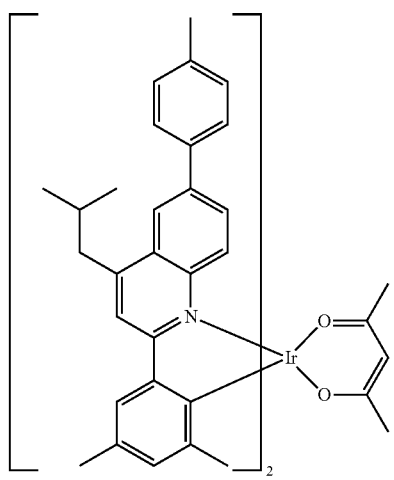

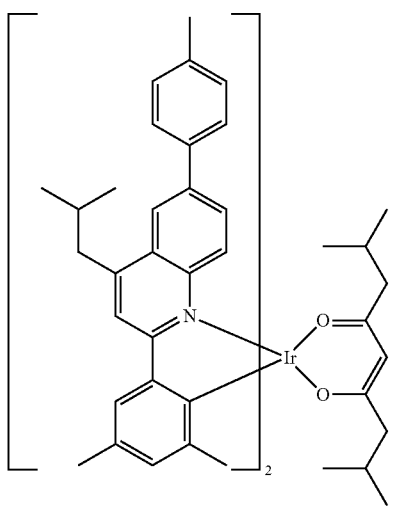

D-210

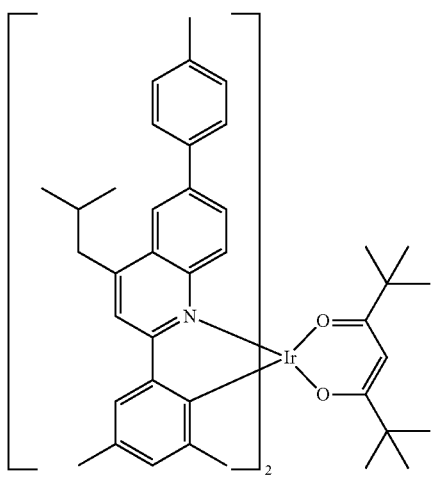

D-211

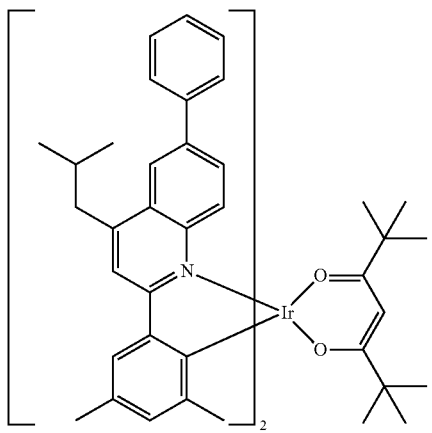

D-212

According to an additional aspect of the present disclosure, a mixture or composition for preparing an organic electroluminescent device is provided. The mixture or composition comprises the compound of the present disclosure. The mixture or composition may be used for preparing a light-emitting layer or hole transport layer of the organic electroluminescent device. The mixture or composition may be used for preparing a phosphorescent or fluorescent light-emitting layer, and specifically a red-emitting phosphorescent light-emitting layer of the organic electroluminescent device. When comprised in the mixture or composition for preparing a hole transport layer of the organic electroluminescent device, the compound of the present disclosure may be comprised as a hole transport material. When comprised in the mixture or composition for preparing a light-emitting layer of the organic electroluminescent device, the compound of the present disclosure may be comprised as a host material. When comprised as a host material, the mixture or composition may further comprise a second host material. The weight ratio between the first host material and the second host material is in the range of 1:99 to 99:1.

The organic electroluminescent device of the present disclosure may comprise a first electrode, a second electrode, and at least one organic layer disposed between the first and second electrodes, wherein the organic layer may comprise the mixture or composition for preparing an organic electroluminescent device of the present disclosure.

The organic electroluminescent device of the present disclosure may further comprise, in addition to the compound of formula 1, at least one compound selected from the group consisting of arylamine-based compounds and styrylarylamine-based compounds.

In the organic electroluminescent device of the present disclosure, the organic layer may further comprise, in addition to the compound of formula 1, at least one metal selected from the group consisting of metals of Group 1, metals of Group 2, transition metals of the $4^{th}$ period, transition metals of the $5^{th}$ period, lanthanides and organic metals of the d-transition elements of the Periodic Table, or at least one complex compound comprising the metal. The organic layer may further comprise a light-emitting layer and a charge generating layer.

In addition, the organic electroluminescent device of the present disclosure may emit white light by further comprising at least one light-emitting layer, which comprises a blue electroluminescent compound, a red electroluminescent compound or a green electroluminescent compound known in the art, besides the compound of the present disclosure.

In the organic electroluminescent device of the present disclosure, preferably, at least one layer (hereinafter, "a surface layer") may be placed on an inner surface(s) of one or both electrode(s), selected from a chalcogenide layer, a metal halide layer and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x(1 \leq X \leq 2)$, $AlO_x(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma and ion plating methods, or wet film-forming methods such as spin coating, dip coating, and flow coating methods can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the organic electroluminescent compound of the present disclosure, the preparation method of the compound, and the luminescent properties of the device will be explained in detail with reference to the following examples.

Example 1: Preparation of Compound A-53

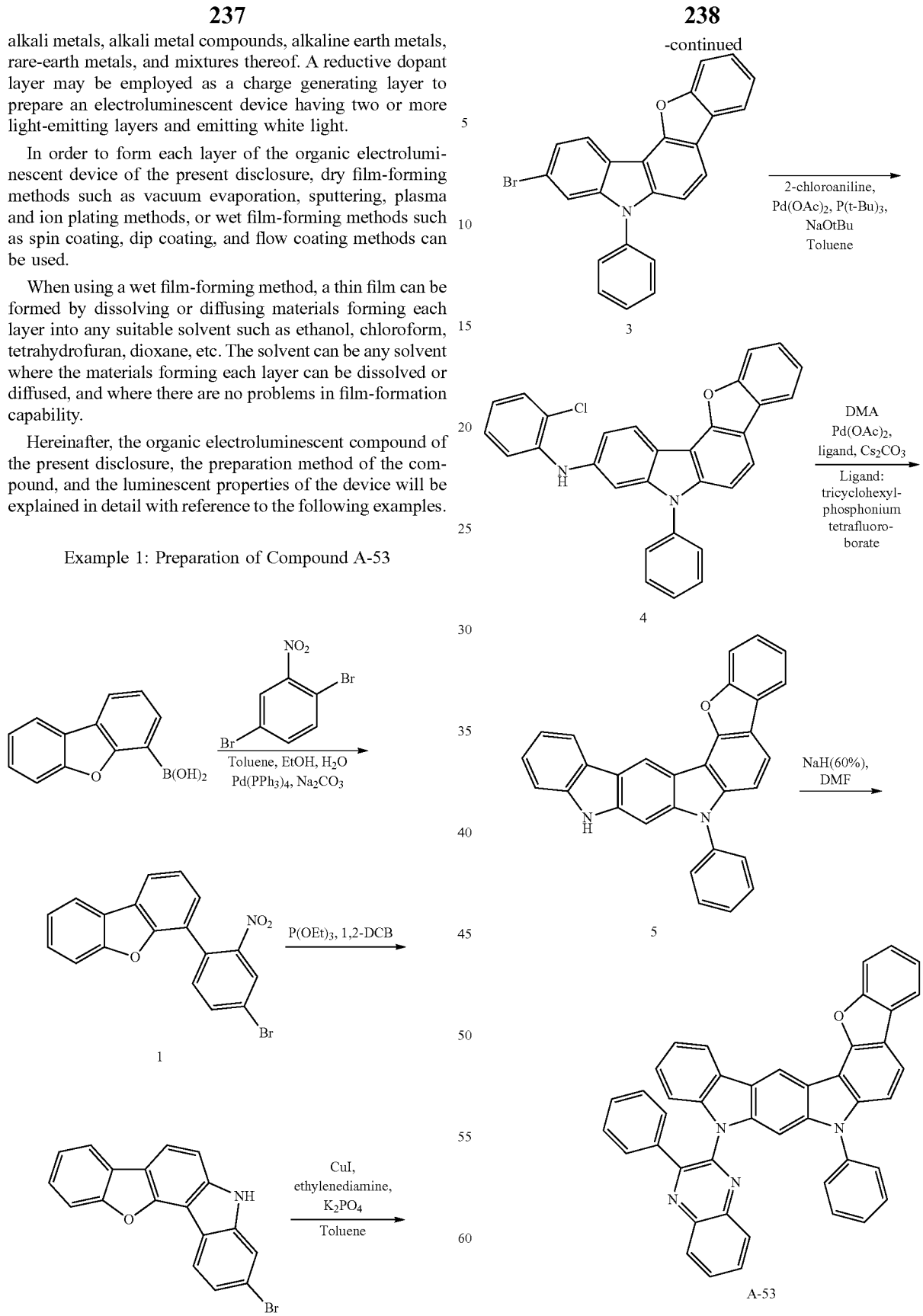

1) Preparation of Compound 1

After introducing dibenzofuran-4-boronic acid (35 g, 165 mmol), 2,5-dibromo-nitrobenzene (55.6 g, 198 mmol), tetrakis(triphenylphosphine)palladium (Pd(PPh$_3$)$_4$) (7.6 g, 6.6 mmol), Na$_2$CO$_3$ (43.7 g, 413 mmol), toluene (800 mL), ethanol (100 mL), and water (200 mL) into a 2 L round-bottom flask, the mixture was stirred at 120° C. for 3.5 hours. A work-up of the reaction mixture was performed with ethyl acetate (EA)/H$_2$O. The resultant was dried with MgSO$_4$, and distilled under reduced pressure. The crude product was subjected to column chromatography with methylene chloride (MC):Hexane to obtain yellow liquid of compound 1 (41 g, yield 67%).

2) Preparation of Compound 2

After introducing 4-(4-bromo-2-nitrophenyl)dibenzo[b,d]furan (41 g, 111 mmol), triethylphosphite (370 mL), and 1,2-dichlorobenzene (1,2-DCB) (370 mL) into a 2 L round-bottom flask, the mixture was stirred at 150° C. for 4 hours. The reaction mixture was distilled under reduced pressure to obtain solids. The crude product was subjected to column chromatography with MC:Hexane to obtain white solids of compound 2 (27.3 g, yield 73%).

3) Preparation of Compound 3

After introducing 3-bromo-5H-benzofuro[3,2-c]carbazole (27.3 g, 81 mmol), iodobenzene (22.7 mL, 203 mmol), CuI (23.2 g), ethylene diamine (16.4 mL), K$_3$PO$_4$ (34.5 g), and toluene (400 mL) into 1 L round-bottom flask, the mixture was stirred at 120° C. for 2.5 hours. A work-up of the reaction mixture was performed with EA/H$_2$O. The resultant was dried with MgSO$_4$, and then distilled under reduced pressure. The crude product was subjected to column chromatography with MC:Hexane to obtain white solids of compound 3 (20.6 g, yield 61%).

4) Preparation of Compound 4

After dissolving 3-bromo-5-phenyl-5H-benzofuro[3,2-c]carbazole (20.6 g, 50 mmol), 2-chloroaniline (8 mL, 75 mmol), palladium(II) acetate (Pd(OAc)$_2$) (449 mg, 2 mmol), tri-tert-butylphosphine (P(t-Bu)$_3$) (2 mL, 4 mmol), and sodium t-butoxide (NaOtBu) (12 g, 125 mmol) into toluene (250 mL) in a 1 L round-bottom flask, the mixture was stirred at 130° C. for 2.5 hours. A work-up of the reaction mixture was performed with EA/H$_2$O. The resultant was dried with MgSO$_4$, and then distilled under reduced pressure. The crude product was subjected to column chromatography with MC:Hexane to obtain white solids of compound 4 (18 g, yield 78%).

5) Preparation of Compound 5

After introducing N-(2-chlorophenyl)-5-phenyl-5H-benzofuro[3,2-c]carbazole-3-amine (18 g, 39 mmol), palladium (II) acetate (Pd(OAc)$_2$) (440 mg, 1.96 mmol), ligand (1.4 g, 3.9 mmol), Cs$_2$CO$_3$ (38 g, 117 mmol), and dimethylacetylamide (DMA) (200 mL) into a 1 L round-bottom flask, the mixture was stirred at 190° C. overnight. The reaction mixture was added dropwise back to water to obtain solids. The crude products were subjected to column chromatography with MC:Hexane to obtain white solids of compound 5 (7 g, yield 42%).

6) Preparation of Compound A-53

After introducing 7-phenyl-7,9-dihydrobenzofuro[2,3-g]indolo[2,3-b]carbazole (6 g, 14.2 mmol), 2-chloro-3-phenylquinoxaline (3.1 g, 12.9 mmol), NaH (60% in a dispersion oil) (771 mg, 19.3 mmol), and dimethylformamide (DMF) (70 mL) into a 500 mL round-bottom flask, the mixture was stirred at 50° C. for 5 hours. The reaction mixture was added dropwise back to water to obtain solids. The crude products were subjected to column chromatography with MC:Hexane to obtain yellow solids of compound A-53 (1.8 g, yield 22%).

| | Molecular weight (MW) | UV | PL | Melting point (M.P) |
|---|---|---|---|---|
| A-53 | 627 | 344 nm | 519 nm | 298° C. |

Example 2: Preparation of Compound A-35

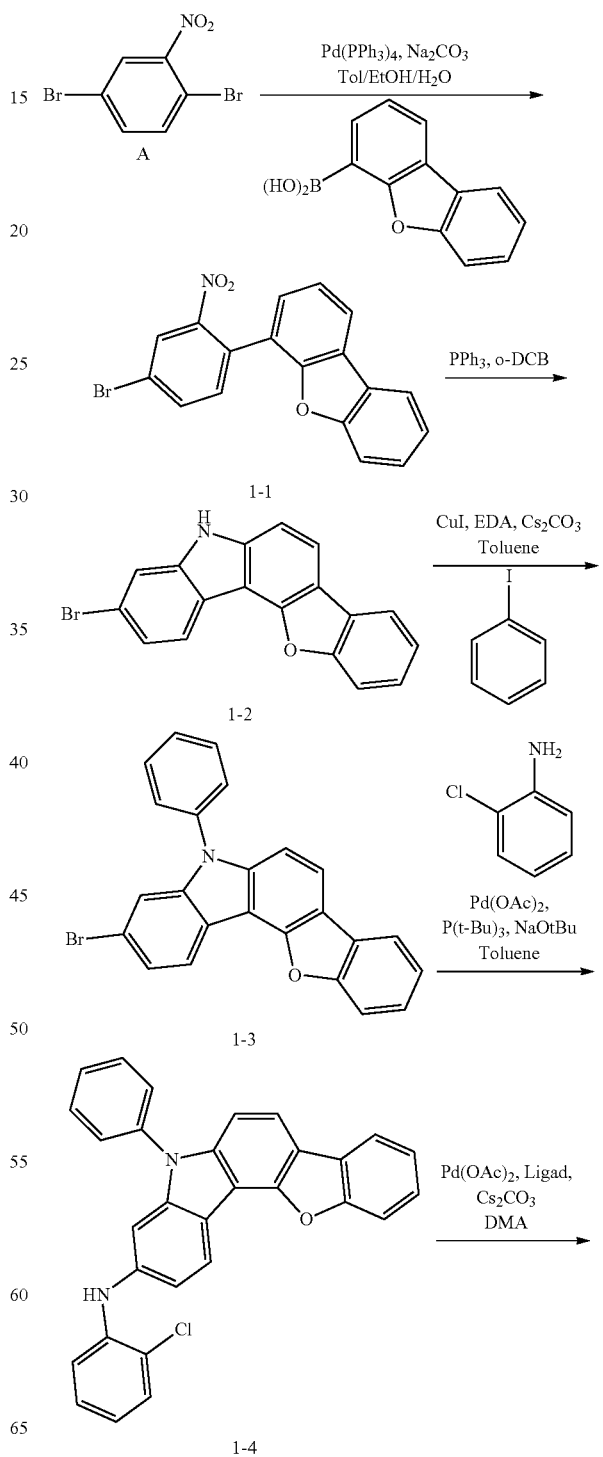

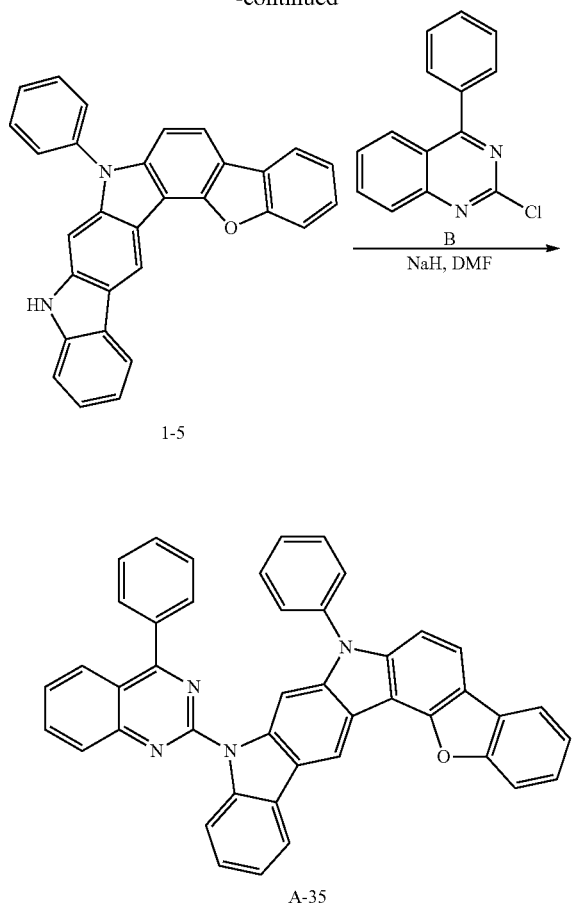

1) Preparation of Compound 1-1

After introducing compound A (80 g, 284.7 mmol), dibenzo[b,d]furan-4-yl boronic acid (51 g, 342 mmol), Pd(PPh₃)₄ (9.8 g, 8.54 mmol), 2M Na₂CO₃ (5000 mL), toluene (1000 mL), purified water (500 mL), and ethanol (500 mL) into a flask, the mixture was stirred under reflux for 5 hours. After completion of the reaction, the mixture was extracted with ethyl acetate. The obtained organic layer was dried with magnesium sulfate to remove the remaining moisture, and then subjected to column chromatography to obtain compound 1-1 (70 g, yield 67%).

2) Preparation of Compound 1-2

After dissolving compound 1-1 (70 g, 190 mmol), and triphenylphosphine (125 g, 475 mmol) into dichlorobenzene (1 L) of a flask, the mixture was under reflux at 150° C. for 6 hours. After completion of the reaction, the mixture was distilled and subjected to trituration with methanol (MeOH) to obtain compound 1-2 (41 g, yield 64%).

3) Preparation of Compound 1-3

After dissolving compound 1-2 (41 g, 120.77 mmol), iodobenzene (27 mL, 241.54 mmol), CuI (12 g, 60.38 mmol), Cs₂CO₃ (118 g, 362 mmol), and ethylene diamine (EDA) (4 mL, 60.38 mmol) into toluene (600 mL) in a flask, the mixture was under reflux at 120° C. for 5 hours. After completion of the reaction, the mixture was extracted with ethyl acetate and the obtained organic layer was dried with magnesium sulfate to remove the remaining moisture. The resultant was subjected to column chromatography to obtain compound 1-3 (34 g, yield 67%).

4) Preparation of Compound 1-4

After dissolving compound 1-3 (34 g, 82.42 mmol), 2-chloroaniline (13 mL, 123.70 mmol), Pd(OAc)₂ (0.7 g, 3.29 mmol), NaOtBu (19 g, 206 mmol), and P(t-Bu)₃ (3 mL, 6.59 mmol) into toluene (500 mL) in a flask, the mixture was under reflux at 120° C. for 5 hours. After completion of the reaction, the mixture was extracted with ethyl acetate and the obtained organic layer was dried with magnesium sulfate to remove the remaining moisture. The resultant was subjected to column chromatography to obtain compound 1-4 (16.3 g, yield 47%).

5) Preparation of Compound 1-5

After dissolving compound 1-4 (15.3 g, 33.34 mmol), Pd(OAc)₂ (0.3 g, 1.677 mmol), Cs₂CO₃ (32 g, 100.02 mmol), and ligand (tricyclohexylphosphine tetrafluoroborate) (PCy₃HBF₄) (1.2 g, 3.34 mmol) in N,N-dimethylacetylamide (170 mL) in a flask, the mixture was under reflux at 120° C. for 5 hours. After completion of the reaction, the mixture was extracted with ethyl acetate and dried with magnesium sulfate to remove the remaining moisture. The resultant was dried, and subjected to column chromatography to obtain compound 1-5 (6 g, yield 43%).

6) Preparation of Compound A-35

After dissolving compound 1-5 (6 g, 14 mmol), and compound B (4 g, 17 mmol) into DMF (100 mL), NaH (0.8 g, 21 mmol, 60% in a mineral oil) was added thereto. The mixture was stirred at room temperature for 12 hours. Methanol and distilled water were added to the mixture. The mixture was filtered under reduced pressure, and the obtained solids were subjected to column chromatography to obtain compound A-35 (4.5 g, yield 56%).

|      | MW     | UV     | PL     | M.P    |
|------|--------|--------|--------|--------|
| A-35 | 626.70 | 356 nm | 521 nm | 274° C.|

Example 3: Preparation of Compound A-6

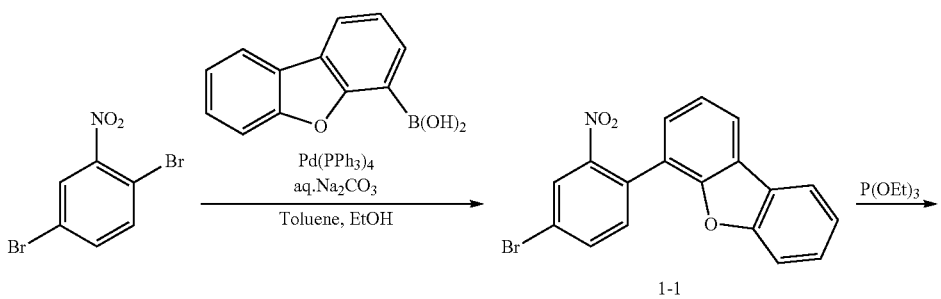

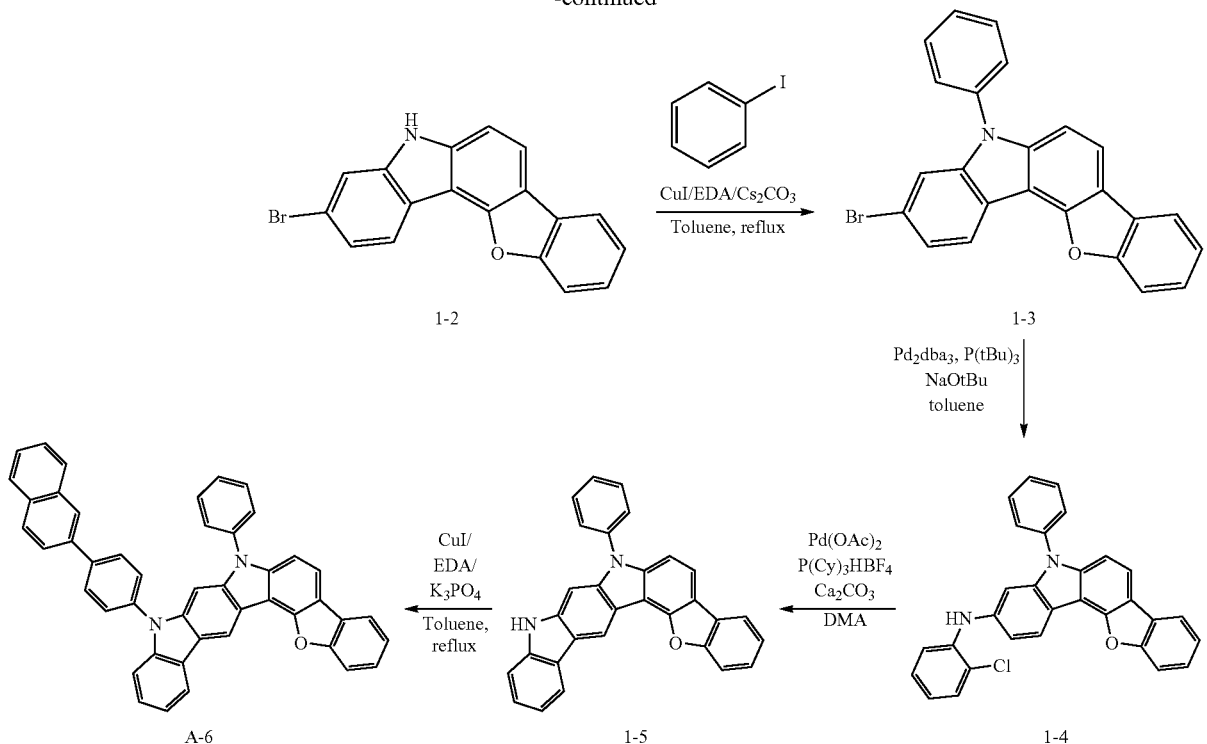

1) Preparation of Compound 1-1

After introducing 2,5-dibromo-nitrobenzene (70 g, 249 mmol), 4-dibenzofuran boronic acid (53 g, 249 mmol), tetrakis(triphenylphosphine)palladium (5.7 g, 4.98 mmol), sodium carbonate (53 g, 498 mmol), toluene (750 mL), and ethanol (250 mL) into a reaction vessel, distilled water (250 mL) was added to the mixture. The mixture was stirred at 120° C. for 3 hours. After completion of the reaction, the mixture was washed with distilled water, and extracted with ethyl acetate. The obtained organic layer was dried with magnesium sulfate, and the solvent was removed by rotary evaporator. The resultant was subjected to column chromatography to obtain compound 1-1 (60 g, yield 65%).

2) Preparation of Compound 1-3

After introducing compound 1-1 (60 g, 163 mmol), triethylphosphite (400 mL), and o-dichlorobenzene (400 mL) into a reaction vessel, the mixture was under reflux overnight. The reaction mixture was distilled under reduced pressure, and the solvent was removed therefrom to obtain compound 1-2, which was used for the next reaction without further purification. After adding iodobenzene (36 mL, 326 mmol), copper(I) iodide (15.5 g, 81.5 mmol), ethylene diamine (10 mL, 163 mmol), cesium carbonate (80 g, 245 mmol), and toluene (800 mL) to the reaction vessel containing compound 1-2, the mixture was stirred under reflux at 140° C. for 6 hours. After completion of the reaction, the mixture was washed with distilled water and extracted with ethyl acetate. The obtained organic layer was dried with magnesium sulfate, and the solvent was removed by rotary evaporator. The resultant was purified by column chromatography to obtain compound 1-3 (27 g, yield 41%).

3) Preparation of Compound 1-4

After introducing compound 1-3 (27.1 g, 65.7 mmol), 2-chloroaniline (13.7 mL, 131.4 mmol), tris(dibenzylidene acetone)dipalladium(0) (1.2 g, 1.31 mmol), tri(t-butyl)phosphine (1.5 mL, 3.3 mmol, 50 wt % xylene solution), sodium t-butoxide (12.5 g, 131.4 mmol), and o-xylene (350 mL) into a reaction vessel, the mixture was under reflux for 3 hours. The reaction mixture was cooled to room temperature, diluted with ethyl acetate, washed with water several times, and dried with anhydrous magnesium sulfate to remove moisture. The resultant was distilled under reduced pressure, and purified by column chromatography to obtain compound 1-4 (23.8 g, yield 79%).

4) Preparation of Compound 1-5

After introducing compound 1-4 (23.8 g, 51.9 mmol), palladium(II)acetate (0.6 g, 2.6 mmol), tricyclohexylphosphine tetrafluoroborate (1.9 g, 5.19 mmol), cesium carbonate (51 g, 156 mmol), and N,N-dimethylacetylamide (250 mL) into a reaction vessel, the mixture was under reflux for 1 hour. The reaction mixture was cooled to room temperature, diluted with ethyl acetate, washed with water several times, and dried with anhydrous magnesium sulfate to remove moisture. The resultant was distilled under reduced pressure, and purified by column chromatography to obtain compound 1-5 (9.5 g, yield 43%).

5) Preparation of Compound A-6

After introducing compound 1-5 (9.5 g, 22.5 mmol), 2-(4-bromophenyl)naphthalene (7.6 g, 27 mmol), copper(I) iodide (2.1 g, 11.25 mmol), ethylene diamine (3 mL, 45 mmol), potassium phosphate (10 g, 45 mmol), and toluene (120 mL) into a reaction vessel, the mixture was stirred under reflux at 140° C. for 6 hours. After completion of the reaction, the mixture was washed with distilled water and extracted with ethyl acetate. The obtained organic layer was dried with magnesium sulfate, and the solvent was removed by rotary evaporator. The resultant was purified by column chromatography to obtain compound A-6 (11.4 g, yield 81%).

| | MW | UV | PL | M.P |
|---|---|---|---|---|
| A-6 | 624 | 307 nm | 394 nm | 361° C. |

[Device Example 1] OLED Using the Organic Electroluminescent Compound of the Present Disclosure OLED was produced using the organic electroluminescent compound of the present disclosure as follows. A transparent electrode indium tin oxide (ITO) thin film (10 Ω/sq) on a glass substrate for an organic light-emitting diode (OLED) (Geomatec) was subjected to an ultrasonic washing with trichloroethylene, acetone, ethanol, and distilled water sequentially, and was then stored in isopropanol. The ITO substrate was then mounted on a substrate holder of a vacuum vapor depositing apparatus. $N^4,N^{4'}$-diphenyl-$N^4$, $N^{4'}$-bis(9-phenyl-9H-carbazole-3-yl)-[1,1'-biphenyl]-4,4'-diamine (HI-1) was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby forming a first hole injection layer having a thickness of 80 nm on the ITO substrate. Dipyrazino[2,3-f:2',3'-h]quinoxaline-2,3,6,7,10,11-hexacarbonitrile (HI-2) was then introduced into another cell of said vacuum vapor depositing apparatus, and evaporated by applying electric current to the cell, thereby forming a second hole injection layer having a thickness of 5 nm on the first hole injection layer. N-([1,1'-biphenyl-4-yl)-9,9-dimethyl-N-(4-(9-phenyl-9H-carbazole-3-yl)phenyl)-9H-fluorene-2-amine (HT-1) was introduced into one cell of the vacuum vapor depositing apparatus, and evaporated by applying electric current to the cell, thereby forming a first hole transport layer having a thickness of 10 nm on the second hole injection layer. N,N-di([1,1'-biphenyl]-4-yl)-4'-(9H-carbazole-9-yl)-[1,1'-biphenyl]-4-amine (HT-2) was introduced into another cell of the vacuum vapor depositing apparatus, and evaporated by applying electric current to the cell, thereby forming a second hole transport layer having a thickness of 60 nm on the first hole transport layer. Thereafter, compound A-35 was introduced into one cell of the vacuum vapor depositing apparatus as a host, and compound D-96 was introduced into another cell as a dopant. The two materials were evaporated at different rates, so that the dopant was deposited in a doping amount of 3 wt % based on the total amount of the host and dopant to form a light-emitting layer having a thickness of 40 nm on the hole transport layer. ET-2 and lithium quinolate (EI-1) were introduced into two cells of the vacuum vapor depositing apparatus, respectively, and evaporated at 1:1 rate to form an electron transport layer having a thickness of 30 nm on the light-emitting layer. After depositing lithium quinolate as an electron injection layer having a thickness of 2 nm, an Al cathode having a thickness of 80 nm was then deposited by another vacuum vapor deposition apparatus on the electron injection layer to produce OLED. The produced OLED showed a red emission having a luminance of 1,000 cd/m² at a driving voltage of 3.8V. The minimum time taken to be reduced to 97% of the luminance at 5,000 nit was 35 hours.

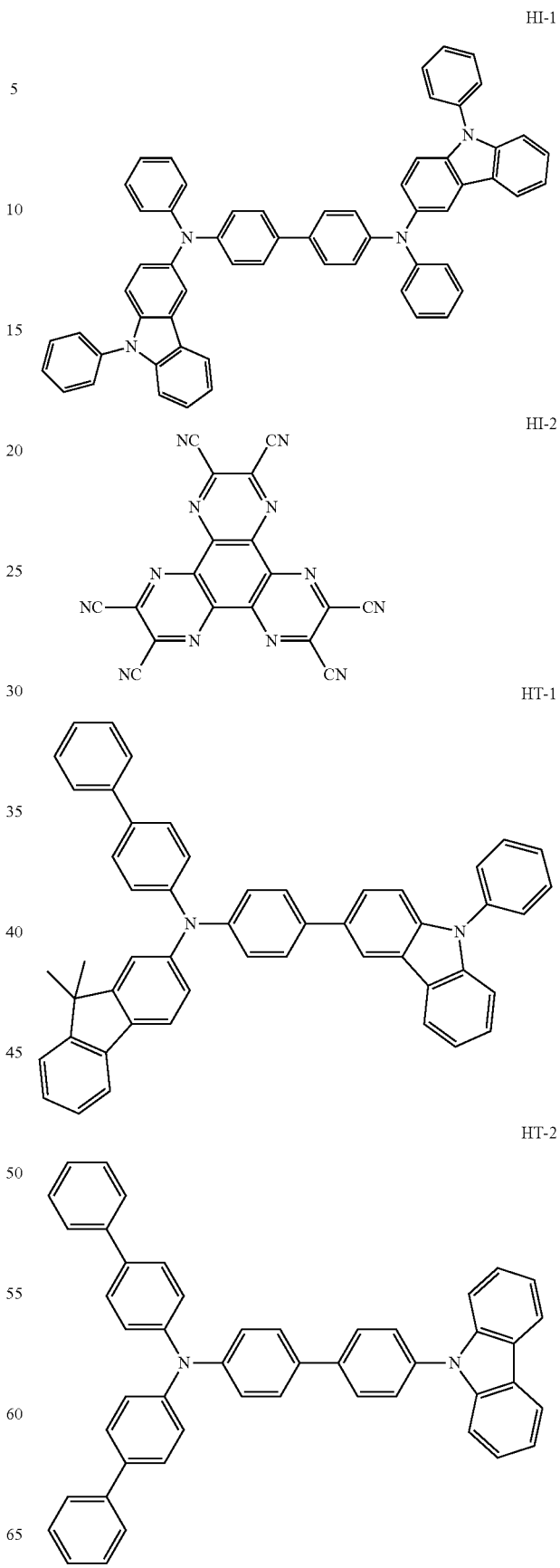

ET-1

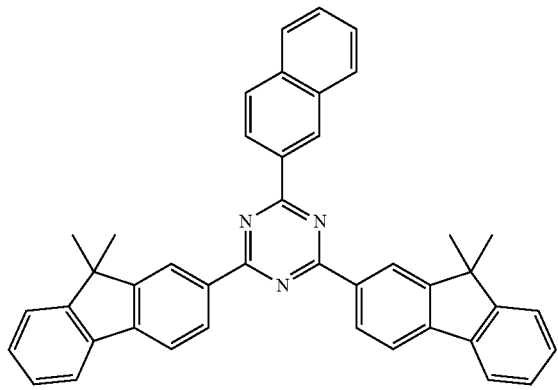

ET-2

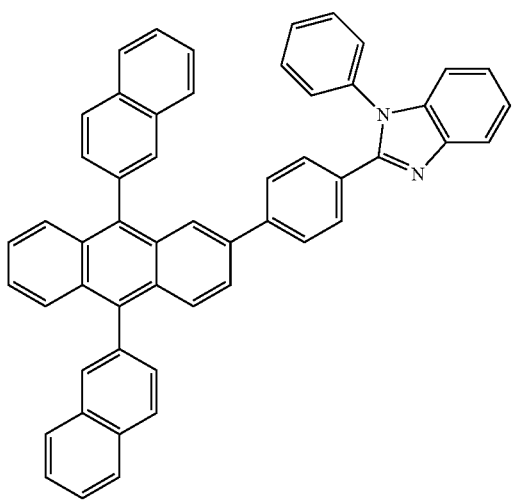

EI-1

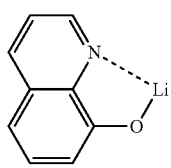

[Device Example 2] OLED Using the Compound of the Present Disclosure

OLED was produced in the same manner as in Device Example 1, except that compound A-53 was used as a host of the light-emitting material, and ET-1 was used for an electron transport layer instead of ET-2. The produced OLED showed a red emission having a luminance of 1,000 cd/m², and a current efficiency of 27.3 cd/A at a driving voltage of 3.8 V. The minimum time taken to be reduced to 97% of the luminance at 5,000 nit was 42 hours.

[Device Example 3] OLED Using the Compound of the Present Disclosure

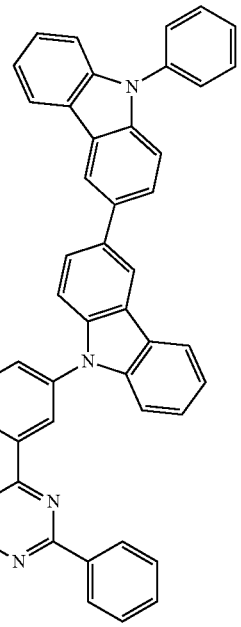

H-1

OLED was produced using the electroluminescent material of the present disclosure as follows. A transparent electrode indium tin oxide (ITO) thin film (10 Ω/sq) on a glass substrate for an organic light-emitting diode (OLED) (Geomatec) was subjected to an ultrasonic washing with trichloroethylene, acetone, ethanol and distilled water sequentially, and was then stored in isopropanol. The ITO substrate was then mounted on a substrate holder of a vacuum vapor depositing apparatus. $N^4,N^{4'}$-diphenyl-$N^4$, $N^{4'}$-bis(9-phenyl-9H-carbazole-3-yl)-[1,1'-biphenyl]-4,4'-diamine (HI-1) was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby forming a first hole injection layer having a thickness of 80 nm on the ITO substrate. Dipyrazino[2,3-f:2',3'-h]quinoxaline-2,3,6,7,10,11-hexacarbonitrile (HI-2) was then introduced into another cell of said vacuum vapor depositing apparatus, and evaporated by applying electric current to the cell, thereby forming a second hole injection layer having a thickness of 3 nm on the first hole injection layer. N-([1,1'-biphenyl]-4-yl)-9,9-dimethyl-N-(4-(9-phenyl-9H-carbazole-3-yl)phenyl)-9H-fluorene-2-amine (HT-1) was introduced into one cell of the vacuum vapor depositing apparatus, and evaporated by applying electric current to the cell, thereby forming a first hole transport layer having a thickness of 10 nm on the second hole injection layer. Compound A-6 was introduced into another cell of the vacuum vapor depositing apparatus, and evaporated by applying electric current to the cell, thereby forming a second hole transport layer having a thickness of 30 nm on the first hole transport layer. Thereafter, compound H-1 was introduced into one cell of the vacuum vapor depositing apparatus as a host, and compound D-1 was introduced into another cell as a dopant. The two materials were evaporated at different rates, so that the dopant was deposited in a doping amount of 15 wt % based on the total amount of the host and dopant to form a light-emitting layer having a thickness of 40 nm on the second hole transport layer. 2,4-bis(9,9-dimethyl-9H-fluoren-2-yl)-6-(naphthalen-2-yl)-1,3,5-triazine (ET-1) and lithium quinolate (EI-1) were introduced into two cells of the vacuum vapor depositing apparatus, respectively, and evaporated at 5:5 rate to form an electron transport layer having a thickness of 35 nm on the light-emitting layer. After depositing lithium quinolate (EI-1) as an electron injection layer having a thickness of 2 nm, an Al cathode having a thickness of 80 nm was then deposited by another vacuum vapor deposition apparatus on the electron injection layer to produce OLED. The produced OLED showed a green emission having a luminance of 1,000 cd/m$^2$ and a current density of 1.8 mA/cm$^2$.

[Device Example 4] OLED Using the Compound of the Present Disclosure

C-2

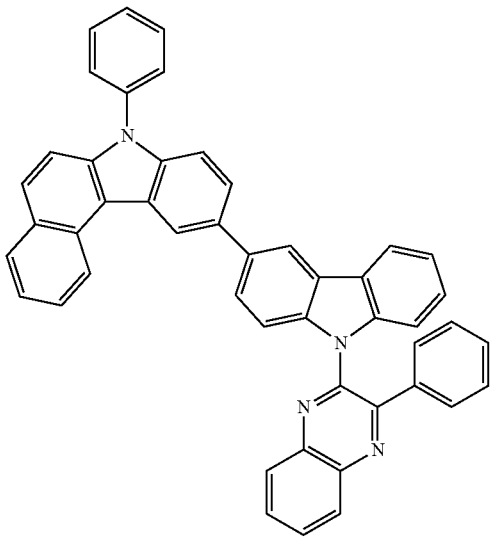

OLED was produced in the same manner as in Device Example 1, except that the thickness of the first hole injection layer was 90 nm which is 10 nm thicker than the thickness of 80 nm of Device Example 1; compound A-6 was used to form a second hole transport layer having a thickness of 60 nm; compound C-2 was introduced into one cell of the vacuum vapor depositing apparatus as a host, and compound D-96 was introduced into another cell as a dopant; and the host and the dopant were evaporated at different rates, so that the dopant was deposited in a doping amount of 3 wt % based on the total amount of the host and dopant to form a light-emitting layer having a thickness of 40 nm on the second hole transport layer. The produced OLED showed a red emission having a luminance of 1,100 cd/m$^2$, and a current density of 4.3 mA/cm$^2$.

[Device Example 5] OLED Using the Compound of the Present Disclosure

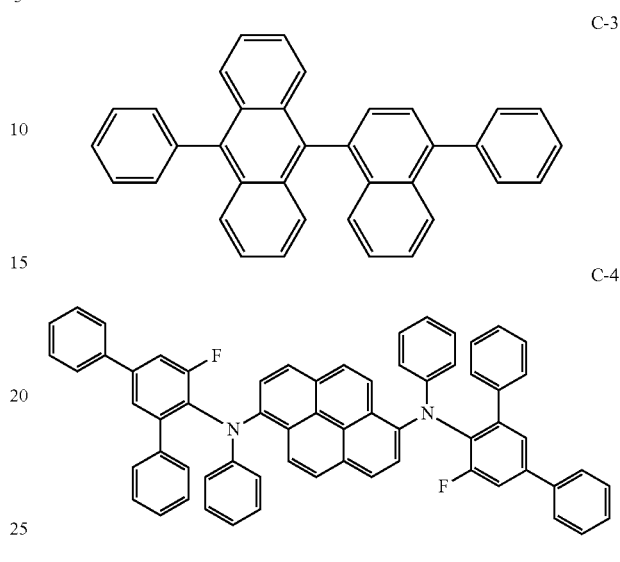

C-3

C-4

OLED was produced in the same manner as in Device Example 1, except that the thickness of the first hole injection layer was 60 nm which is 20 nm thinner than the thickness of 80 nm of Device Example 1; the thickness of the first hole transport layer was 20 nm which is 10 nm thicker than the thickness of 10 nm of Device Example 1; compound A-6 was used to form a second hole transport layer having a thickness of 5 nm; compound C-3 was introduced into one cell of the vacuum vapor depositing apparatus as a host, and compound C-4 was introduced into another cell as a dopant; and the host and the dopant were evaporated at different rates, so that the dopant was deposited in a doping amount of 2 wt % based on the total amount of the host and dopant to form a light-emitting layer having a thickness of 20 nm on the second hole transport layer. The produced OLED showed a blue emission having a luminance of 1,000 cd/m$^2$, and a current density of 15.9 mA/cm$^2$.

[Comparative Example 1] OLED Using a Conventional Organic Electroluminescent Material OLED was produced in the same manner as in Device Example 3, except that N-([1,1'-biphenyl]-4-yl)-9,9-dimethyl-N-(4-(9-phenyl-9H-carbazole-3-yl)phenyl)-9H-fluorene-2-amine (HT-1) was used to form a second hole transport layer having a thickness of 30 nm. The produced OLED showed a green emission having a luminance of 9,000 cd/m$^2$, and a current density of 21.9 mA/cm$^2$.

[Comparative Example 2] OLED Using a Conventional Organic Electroluminescent Material OLED was produced in the same manner as in Device Example 4, except that N-([1,1'-biphenyl]-4-yl)-9,9-dimethyl-N-(4-(9-phenyl-9H-carbazole-3-yl)phenyl)-9H-fluorene-2-amine (HT-1) was used to form a second hole transport layer having a thickness of 60 nm. The produced OLED showed a red emission having a luminance of 6,000 cd/m$^2$, and a current density of 31.3 mA/cm$^2$.

[Comparative Example 3] OLED Using a Conventional Organic Electroluminescent Material OLED was produced in the same manner as in Device Example 5, except that N-([1,1'-biphenyl]-4-yl)-9,9-dimethyl-N-(4-(9-phenyl-9H-carbazole-3-yl)phenyl)-9H-fluorene-2-amine (HT-1) was used to form a second hole transport layer having a thickness of 5 nm. The produced OLED showed a blue emission having a luminance of 2,000 cd/m$^2$, and a current density of 43.5 mA/cm$^2$.

[Comparative Example 4] OLED Using a Conventional Organic Electroluminescent Material OLED was produced in the same manner as in Device Example 1, except that 4,4'-di(9H-carbazole-9-yl)-1,1'-biphenyl was used as a host of light-emitting material, and ET-1 was used for an electron transport layer instead of ET-2. The produced OLED showed a red emission having a luminance of 1,000 cd/m$^2$, and a current efficiency of 17.4 cd/A at a driving voltage of 10.3 V. The minimum time taken to be reduced to 97% of the luminance at 5,000 nit was 0 hours (died suddenly).

The working examples above confirm that the compounds for an organic electronic material of the present disclosure have better luminous characteristics than conventional materials. The device employing the compound for an organic electronic material of the present disclosure shows excellence in luminous characteristics, hole-related characteristics, and lifespan.

The invention claimed is:
1. An organic electroluminescent compound represented by formula 1:

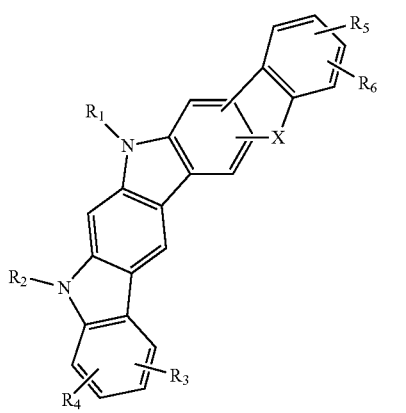

(1)

wherein
X represents —S—;
R$_1$ and R$_2$ each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl wherein the (3- to 30-membered)heteroaryl is selected from the group consisting of furyl, thiophenyl, pyrrolyl, imidazolyl, pyrazolyl, thiazolyl, thiadiazolyl, isothiazolyl, isoxazolyl, oxazolyl, oxadiazolyl, tetrazinyl, triazolyl, tetrazolyl, furazanyl, pyridyl, pyrazinyl, pyridazinyl, benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl and dihydroacridinyl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent(s) to form a (3- to 30-membered), mono- or polycyclic, alicyclic or aromatic ring whose carbon atom(s) may be replaced with at least one hetero atom selected from nitrogen, oxygen, and sulfur;
the substituents on the substituted aryl of R$_1$ and R$_2$ are at least one selected from the group consisting of deuterium, a halogen, a cyano, a carboxy, a nitro, a hydroxyl, a (C1-C30)alkyl, a halo(C1-C30)alkyl, a (C1-C30)alkoxy, a (C1-C30)alkylthio, a (C3-C30)cycloalkyl, a 3- to 7-membered heterocycloalkyl, a (C6-C30)aryloxy, a (C6-C30)arylthio, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl;
R$_3$ to R$_6$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di- (C6-C30)arylamino, or a substituted or unsubstituted (C1-C30)alkyl (C6-C30)arylamino; or may be linked to an adjacent substituent(s) to form a (3- to 30-membered), mono- or polycyclic, alicyclic or aromatic ring whose carbon atom(s) may be replaced with at least one hetero atom selected from nitrogen, oxygen, and sulfur; and
the heteroaryl contains at least one hetero atom selected from B, N, O, S, Si, and P.
2. The organic electroluminescent compound according to claim 1, wherein the substituents for the substituted alkyl, the substituted heteroaryl, the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted mono- or polycyclic, alicyclic or aromatic ring of R$_1$ to R$_6$, and the substituents for the substituted aryl of R$_3$ to R$_6$, each independently, are at least one selected from the group consisting of deuterium, a halogen, a cyano, a carboxy, a nitro, a hydroxy, a (C1-C30)alkyl, a halo(C1-C30)alkyl, a (C1-C30)alkoxy, a (C1-C30)alkylthio, a (C3-C30)cycloalkyl, a 3- to 7-membered heterocycloalkyl, a (C6-C30)aryloxy, a (C6-C30)arylthio, a 3- to 30-membered heteroaryl unsubstituted or substituted with a (C6-C30)aryl or a di(C6-C30)arylamino, a (C6-C30)aryl unsubstituted or substituted with a 3- to 30-membered heteroaryl or a di(C6-C30)arylamino, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

3. The organic electroluminescent compound according to claim 1, wherein the compound of formula 1 is represented by any one of the following formulae 2 to 7:

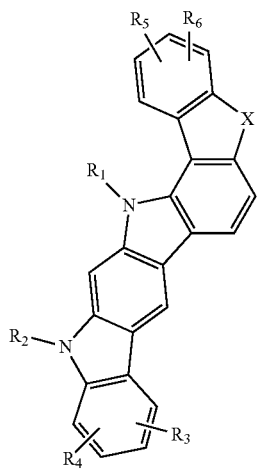

(2)

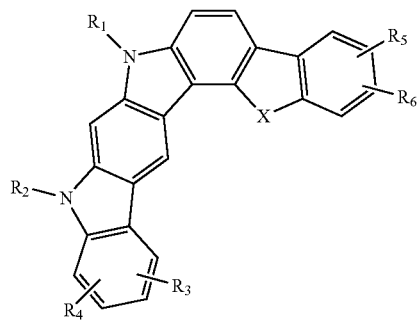

(3)

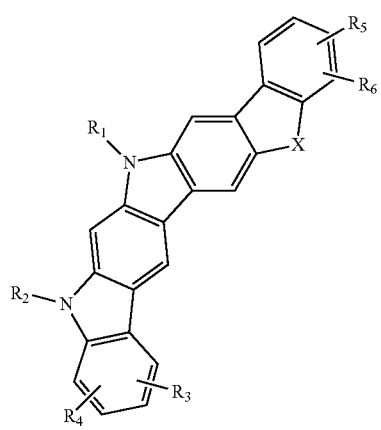

(4)

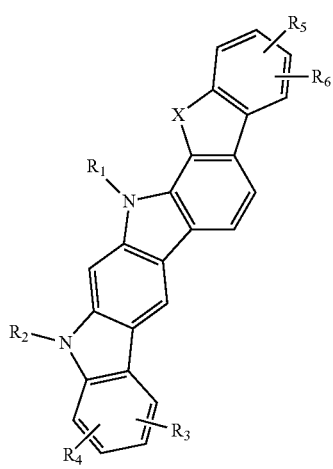

(5)

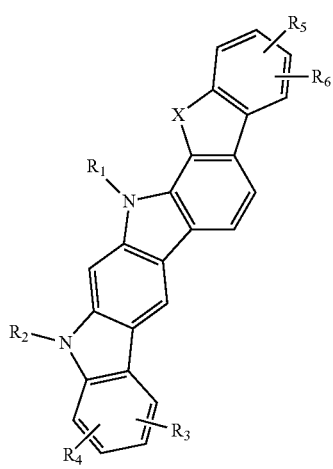

(6)

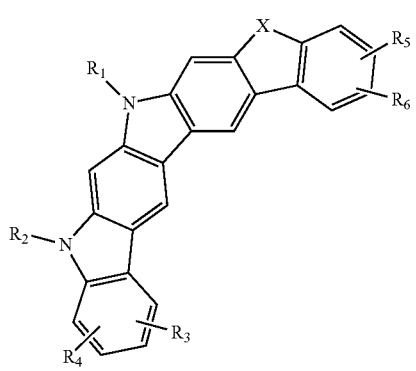

(7)

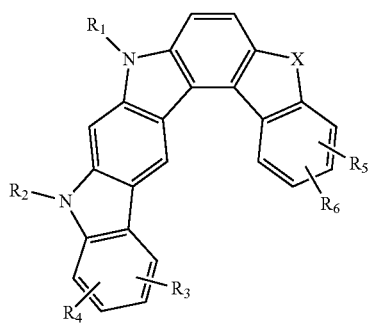

wherein X, and $R_1$ to $R_6$ are as defined in claim 1.

4. The organic electroluminescent compound according to claim 1, wherein $R_1$ and $R_2$, each independently, represent hydrogen, a substituted or unsubstituted (C6-C30)aryl, or a substituted or unsubstituted 5- to 30-membered heteroaryl wherein the (3- to 30-membered)heteroaryl is selected from the group consisting of furyl, thiophenyl, pyrrolyl, imidazolyl, pyrazolyl, thiazolyl, thiadiazolyl, isothiazolyl, isoxazolyl, oxazolyl, oxadiazolyl, tetrazinyl, triazolyl, tetrazolyl, furazanyl, pyridyl, pyrazinyl, pyridazinyl, benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl and dihydroacridinyl.

5. The organic electroluminescent compound according to claim 1, wherein $R_1$ represents hydrogen or the group represented by formula 8; and $R_2$ represents hydrogen, or the group represented by formula 9:

$$*-L_1-Ar_1 \quad (8)$$

$$*-L_2-Ar_2 \quad (9)$$

wherein $L_1$ and $L_2$, each independently, represent a single bond, a substituted or unsubstituted (C6-C30)arylene, or a substituted or unsubstituted 3- to 30-membered heteroarylene;

$Ar_1$ and $Ar_2$, each independently, represent a substituted or unsubstituted (C6-C30)aryl, or a substituted or unsubstituted 3- to 30-membered heteroaryl wherein the (3- to 30-membered)heteroaryl is selected from the group consisting of furyl, thiophenyl, pyrrolyl, imidazolyl, pyrazolyl, thiazolyl, thiadiazolyl, isothiazolyl, isoxazolyl, oxazolyl, oxadiazolyl, tetrazinyl, triazolyl, tetrazolyl, furazanyl, pyridyl, pyrazinyl, pyridazinyl, benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl and dihydroacridinyl; and the heteroaryl contains at least one hetero atom selected from B, N, O, S, Si, and P.

6. An organic electroluminescent selected from the group consisting of:

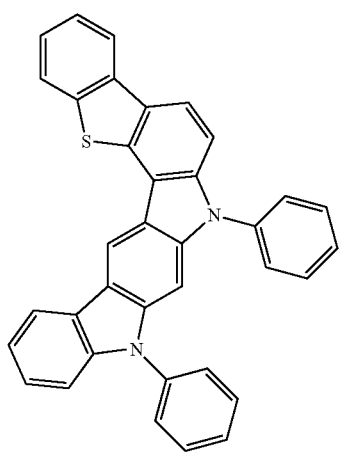

A-57

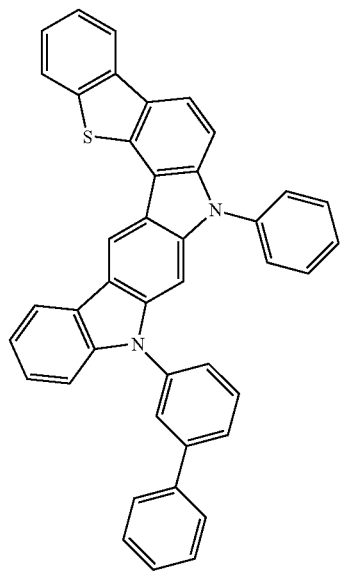

A-58

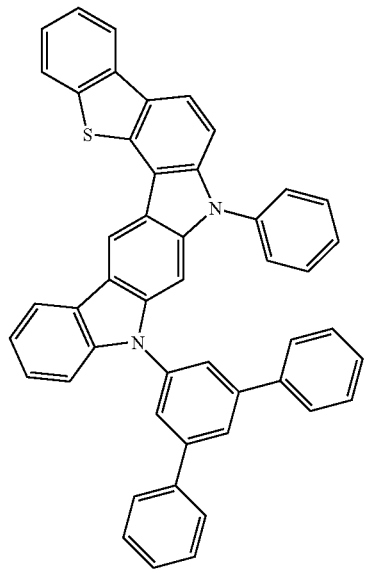

A-59

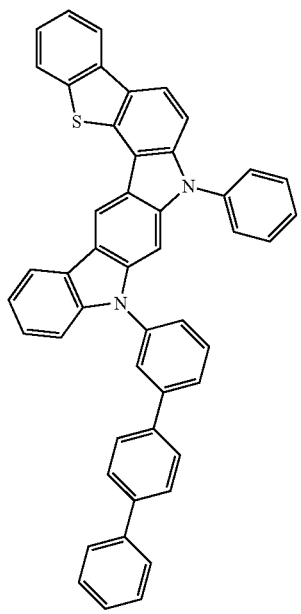
A-60
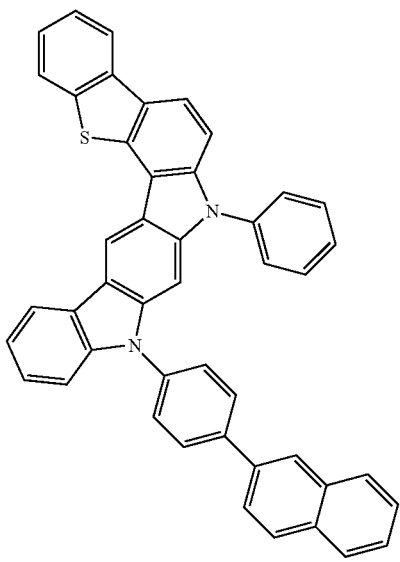
A-62
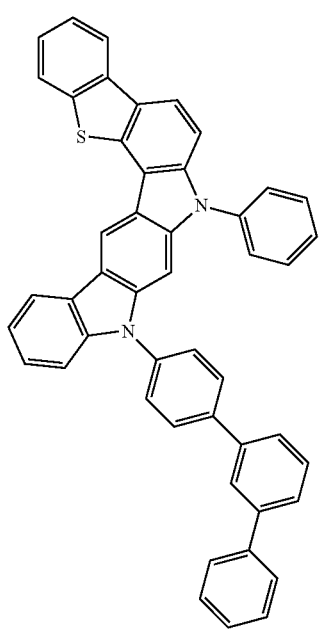
A-61
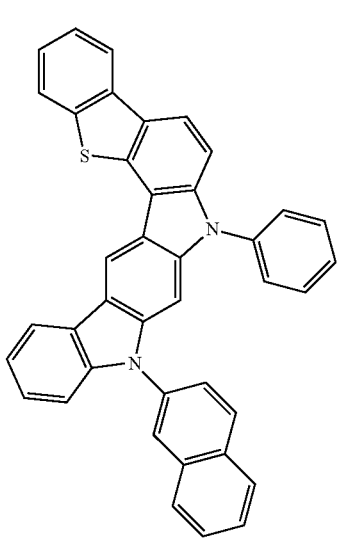
A-63

-continued
A-64
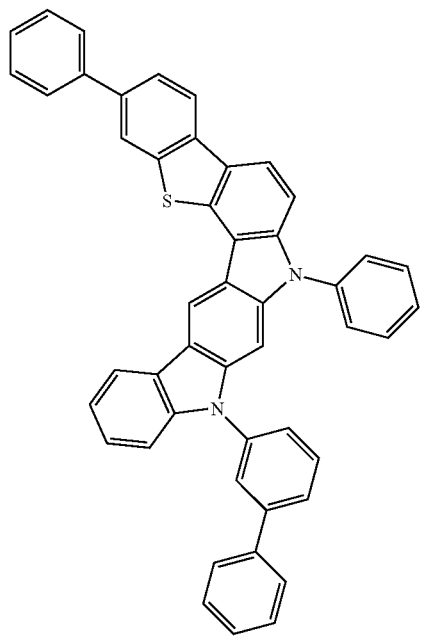
A-65
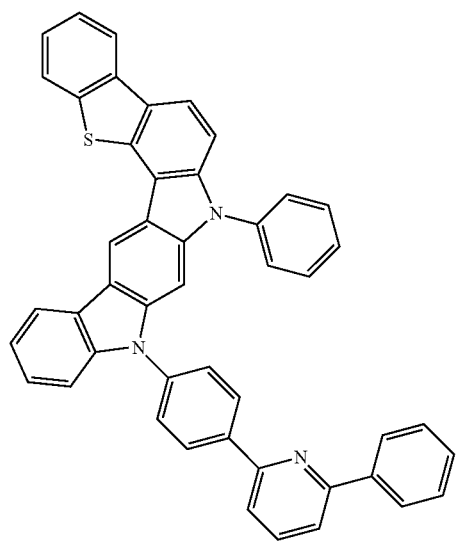
A-66
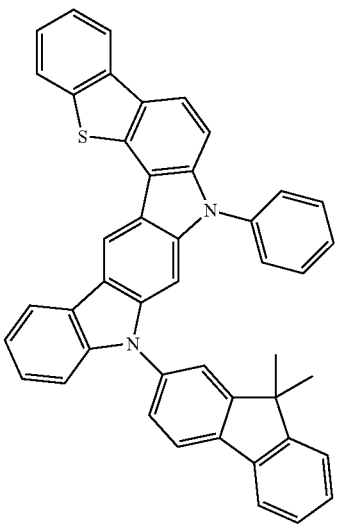
A-67
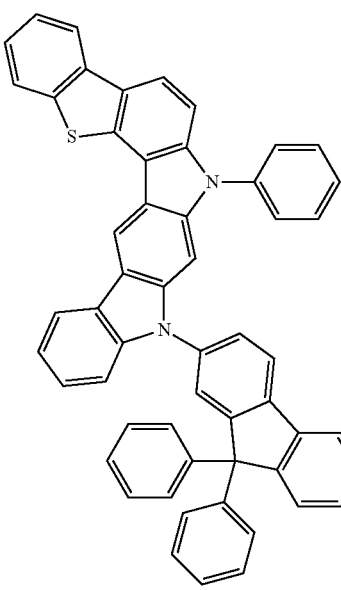
A-68
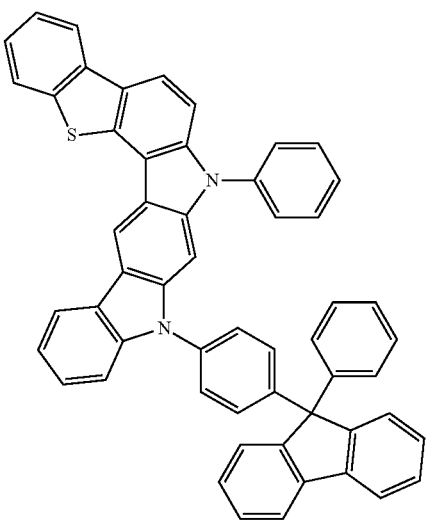

A-69
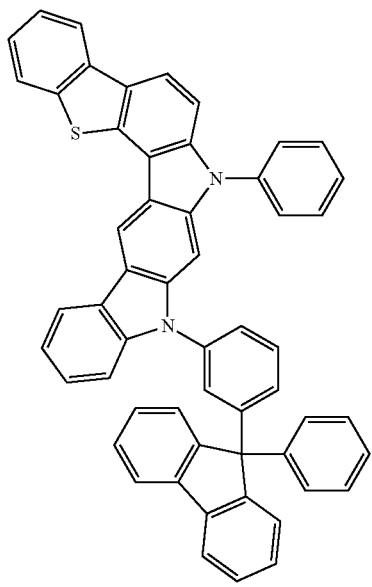
A-70
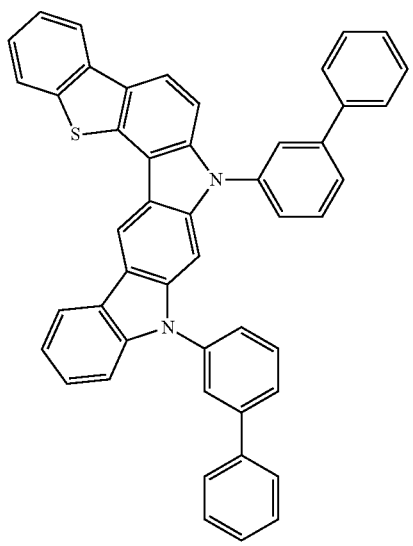
A-71
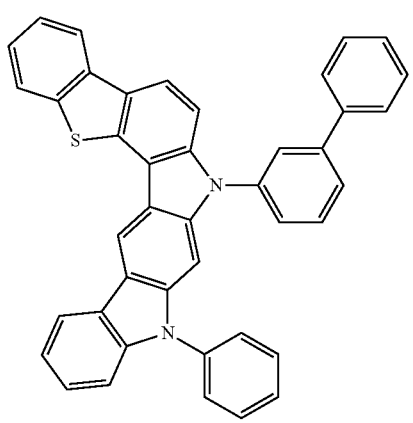
A-72
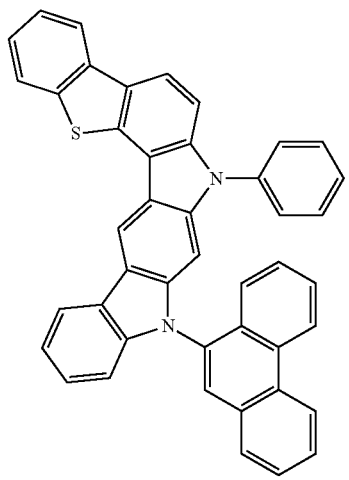
A-73
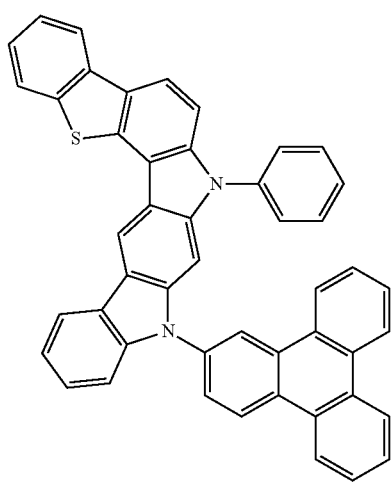
A-74
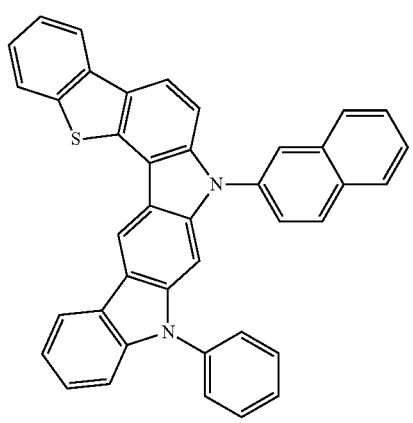

-continued
A-75
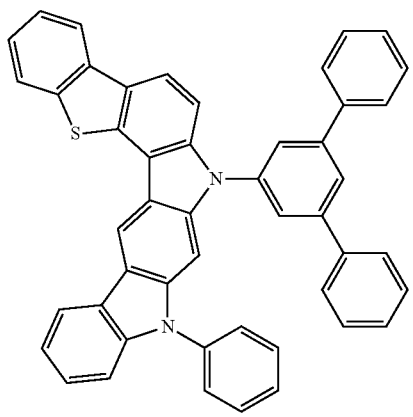
A-76
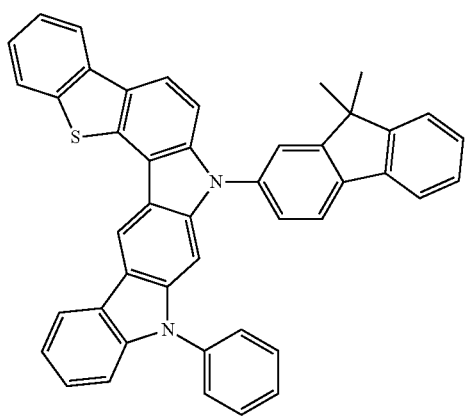
A-77
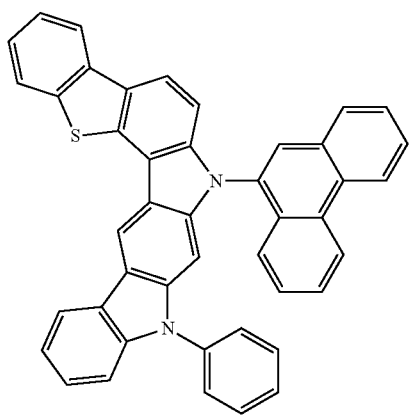
-continued
A-78
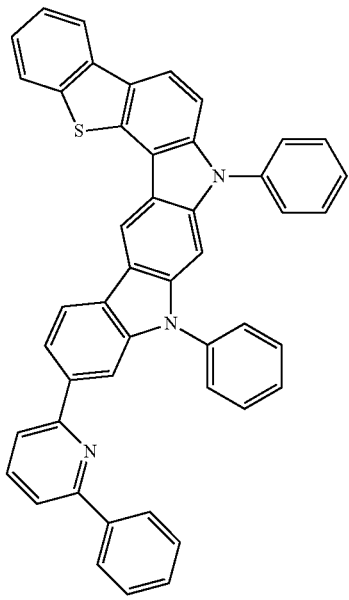
A-79
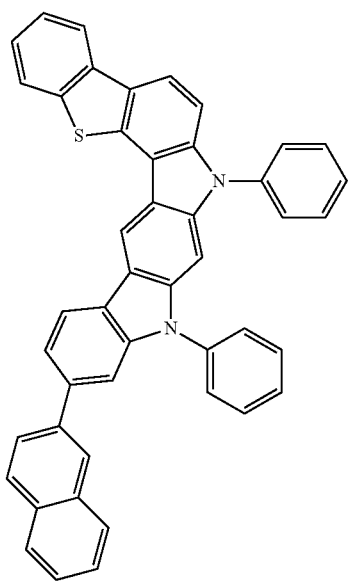
A-80
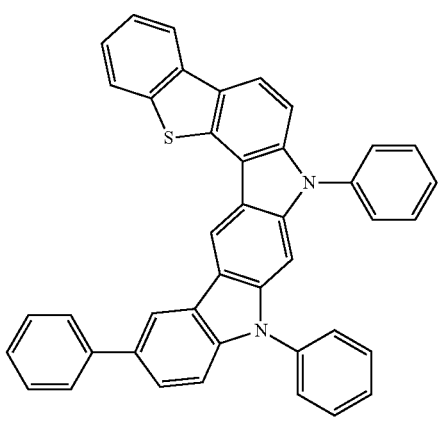

A-81
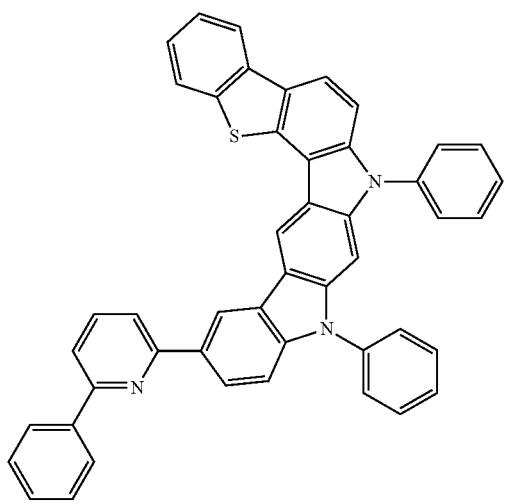
A-82
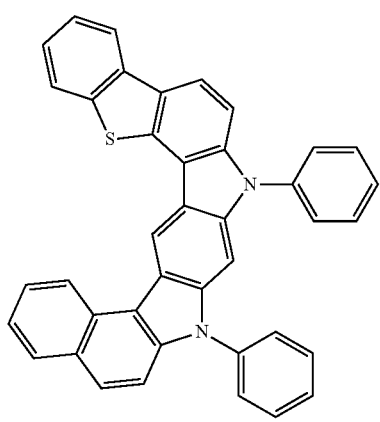
A-83
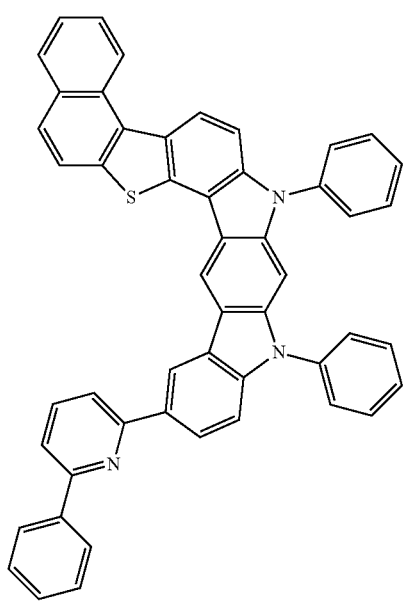
A-89
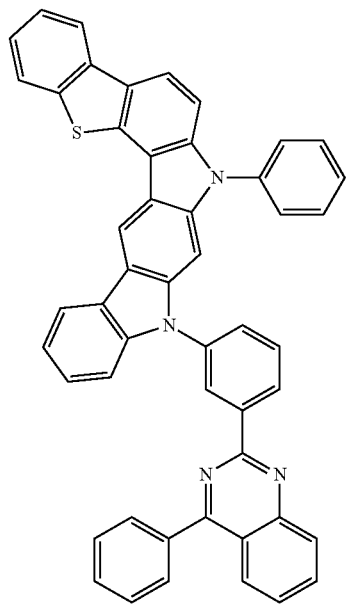
A-90
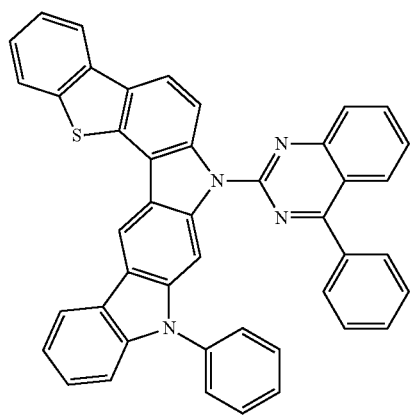
A-91
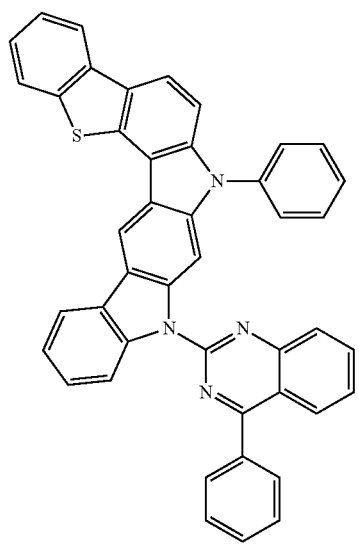

A-92
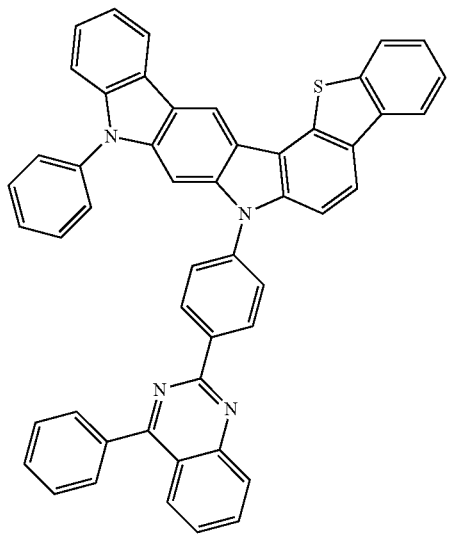
A-95
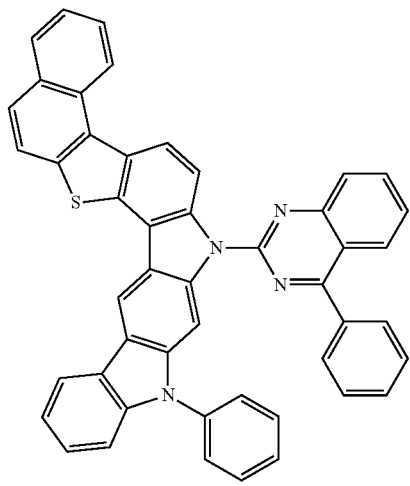
A-93
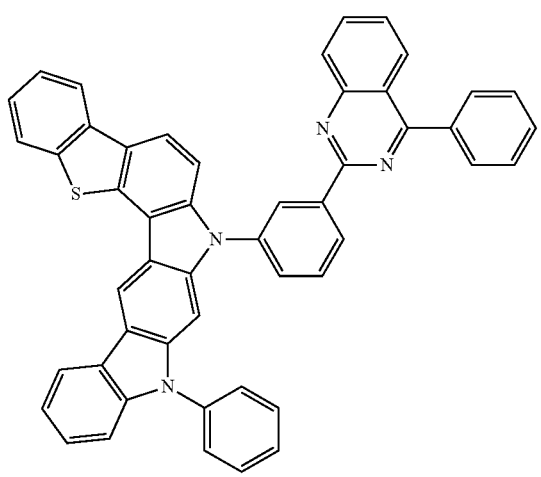
A-96
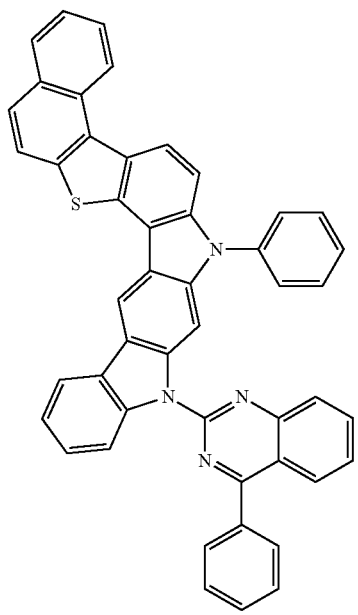
A-94
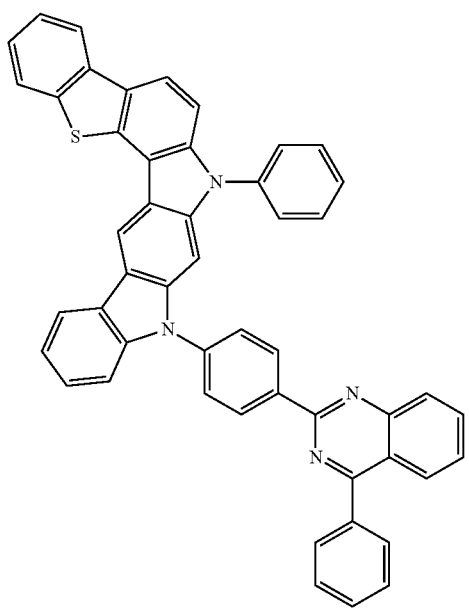
A-97
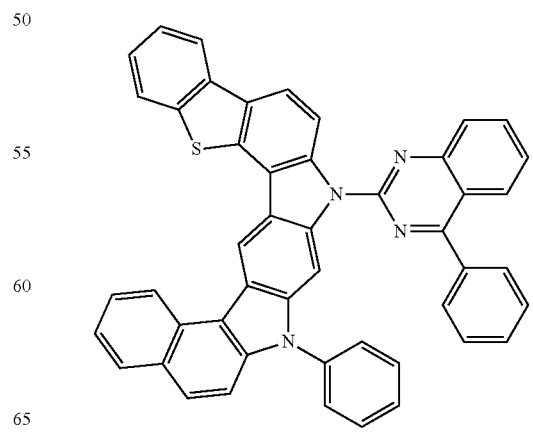

A-98
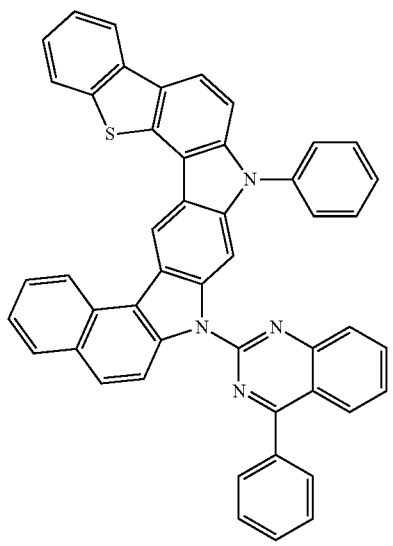
A-99
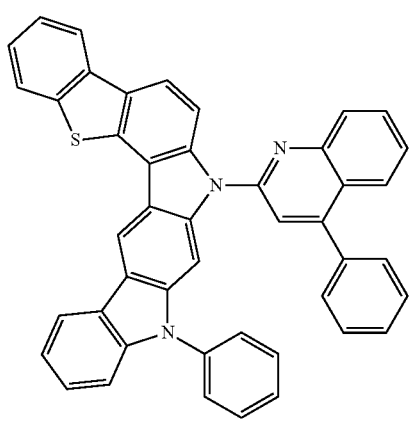
A-100
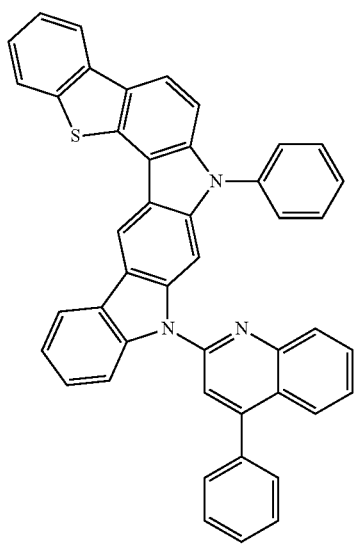
A-101
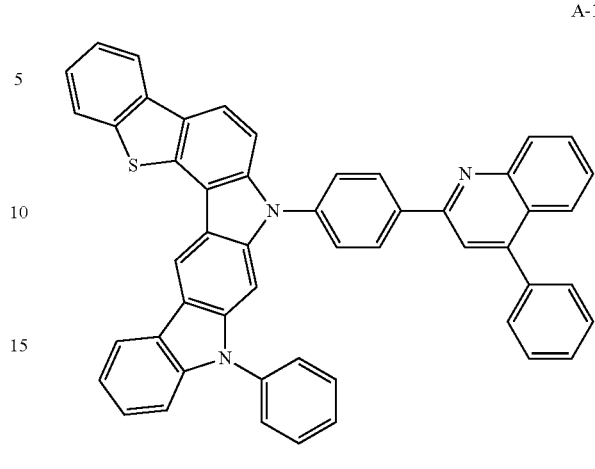
A-102
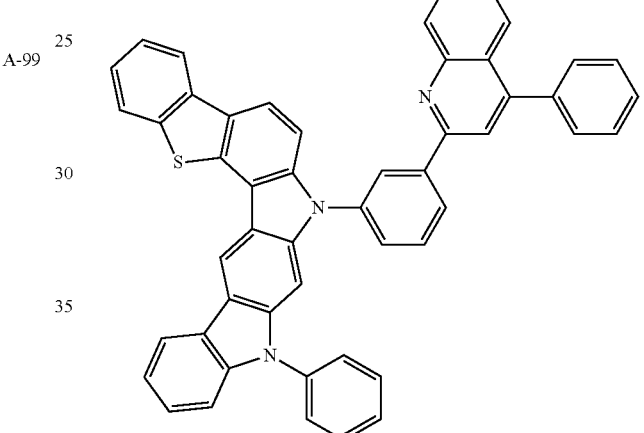
A-103
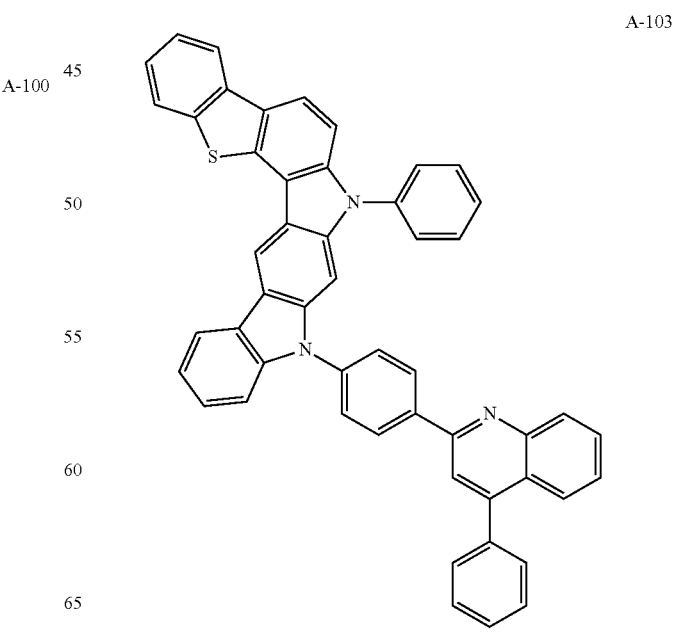

-continued
A-104
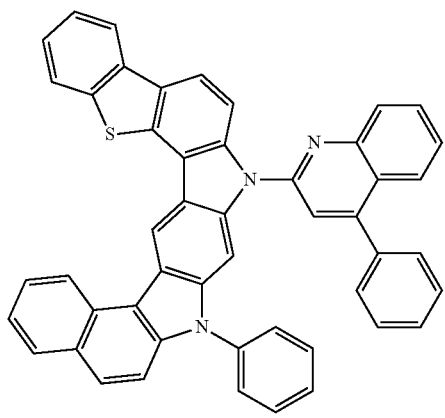
A-105
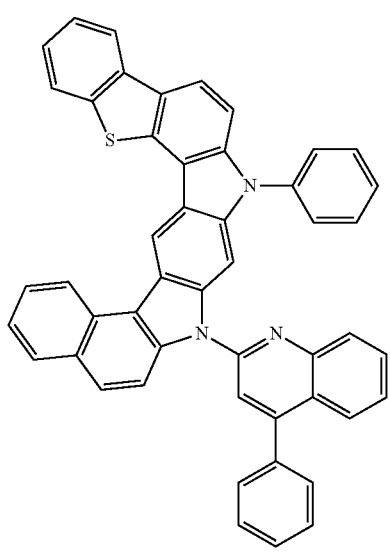
A-106
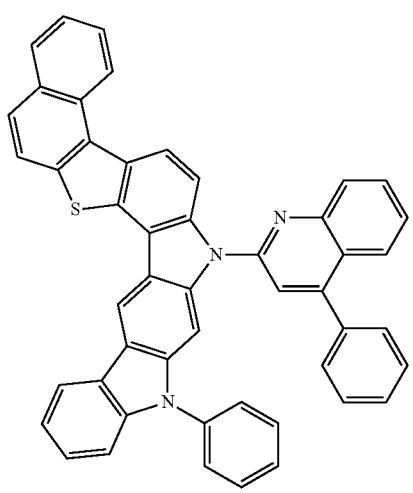
-continued
A-107
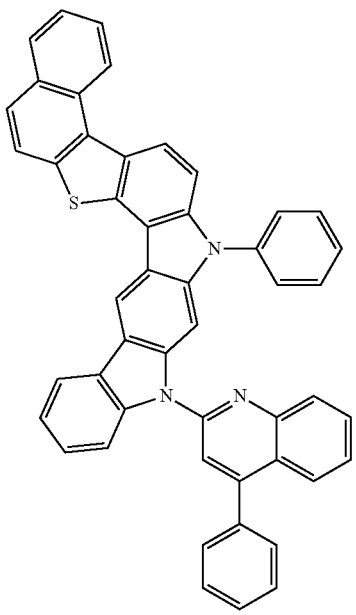
A-108
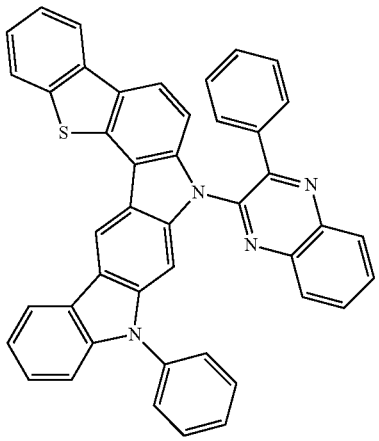
A-109
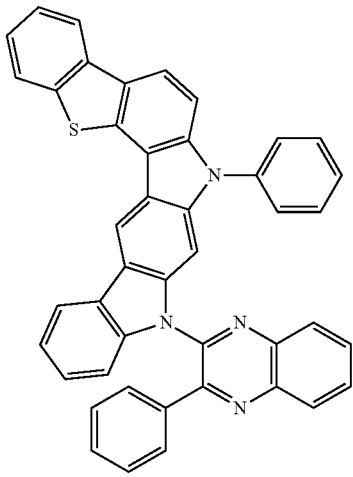

A-110
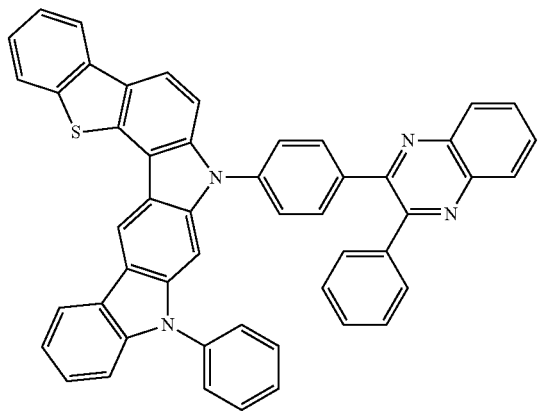
A-111
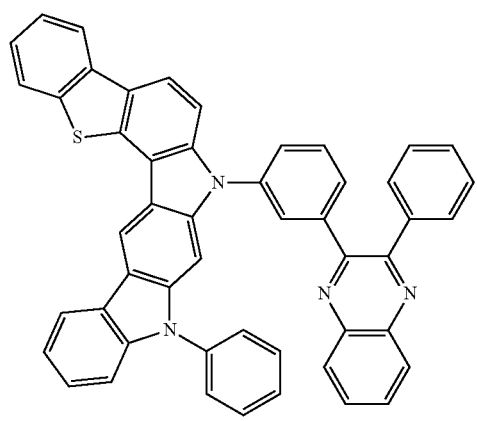
A-112
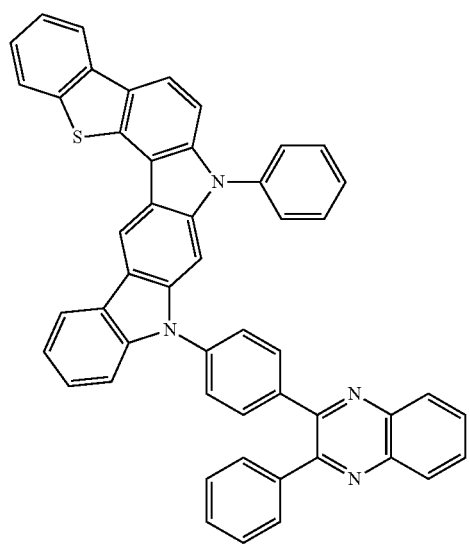
A-129
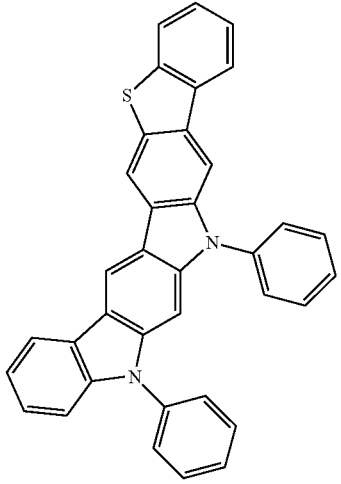
A-130
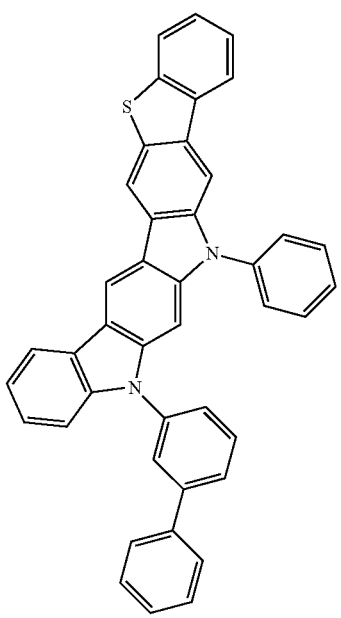

A-131
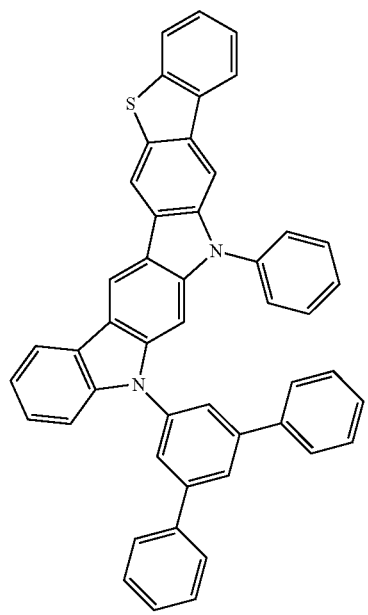
A-132
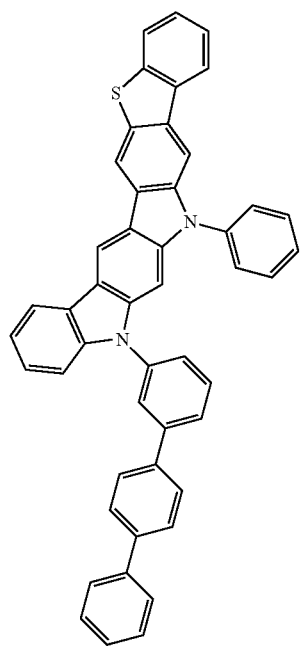
A-133
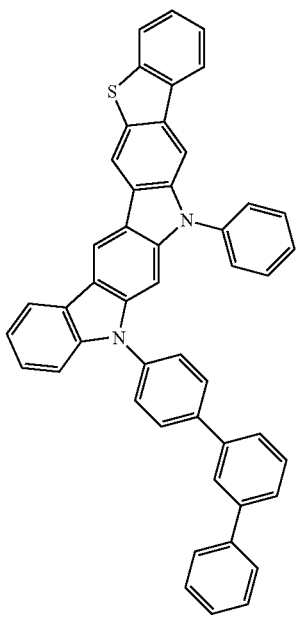
A-134
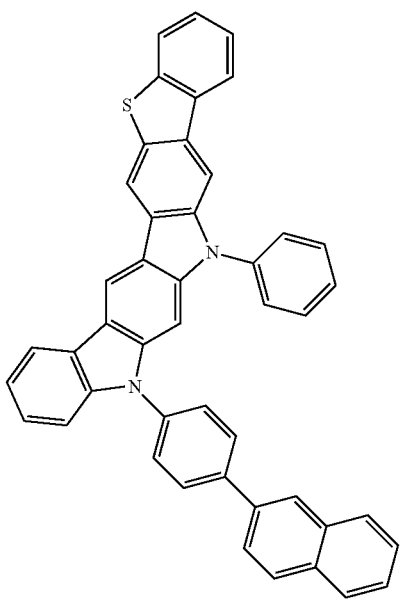

A-135
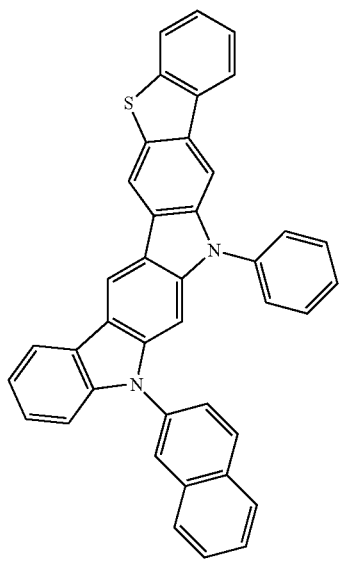
A-137
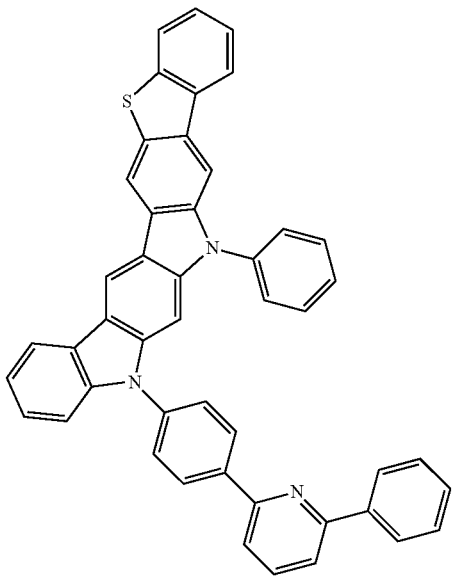
A-136
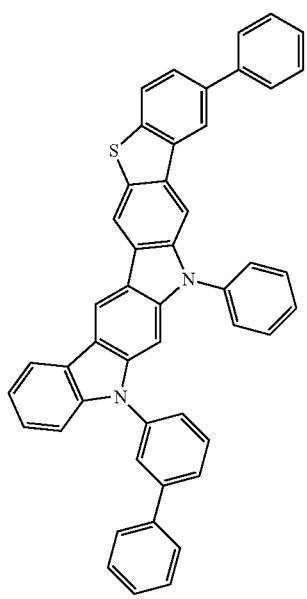
A-138
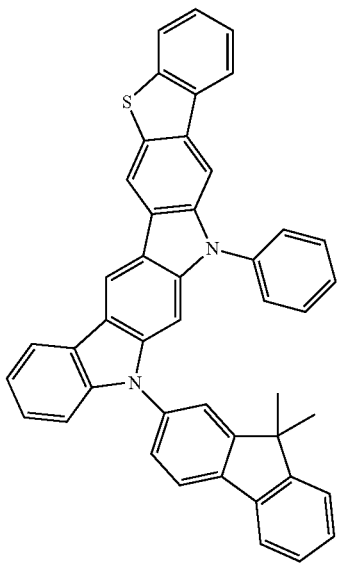

A-139
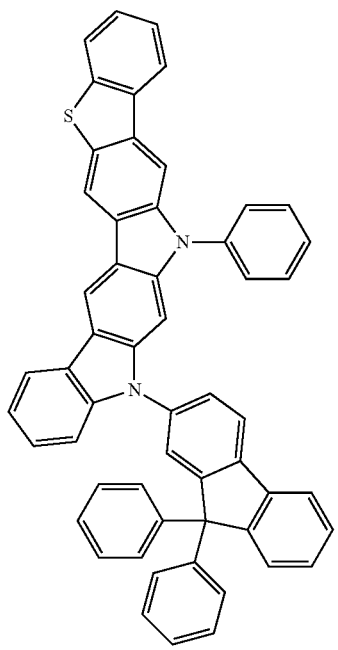
A-140
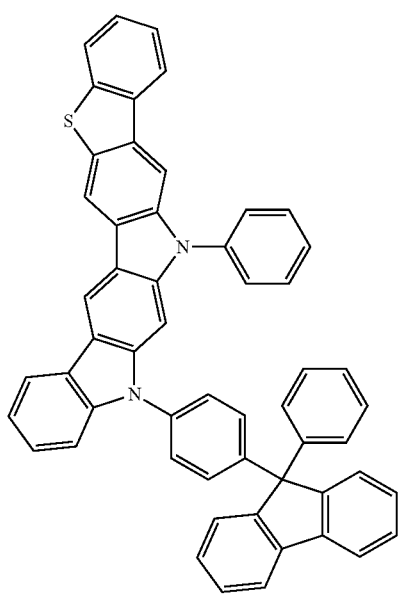
A-141
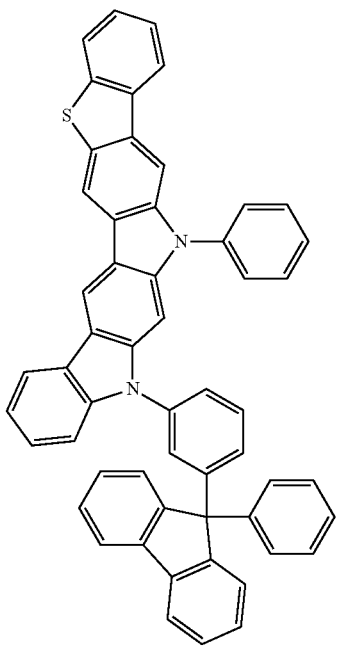
A-142
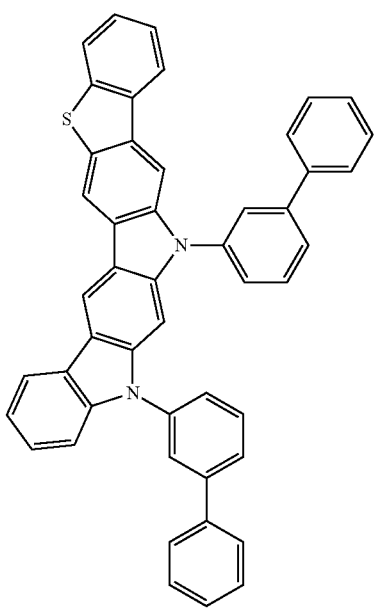

-continued
A-143
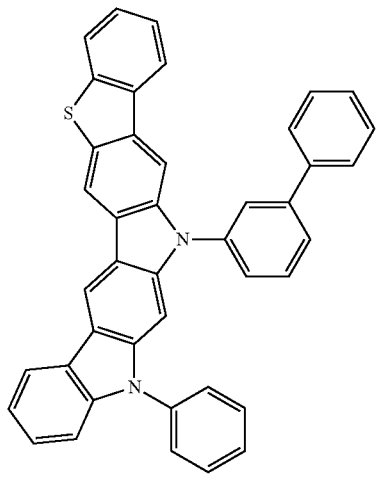
A-144
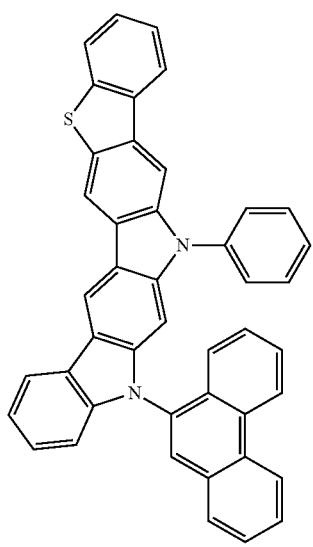
A-147
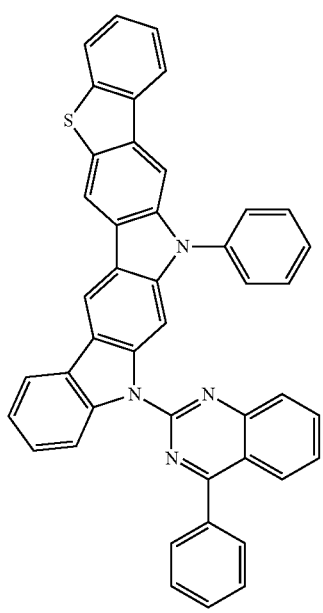
-continued
A-148
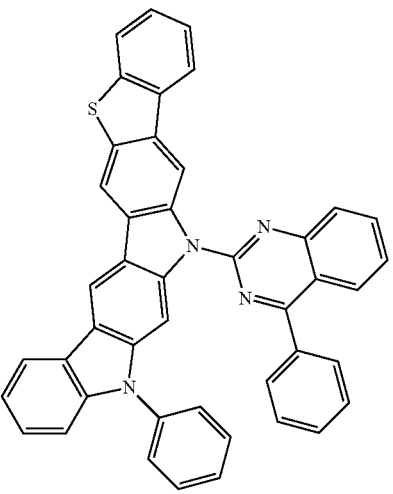
A-165
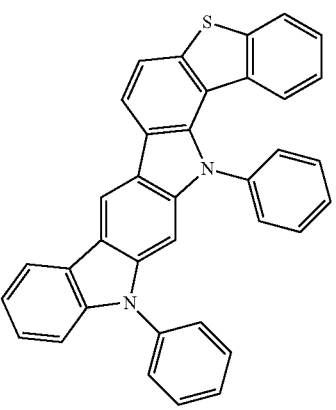
A-166
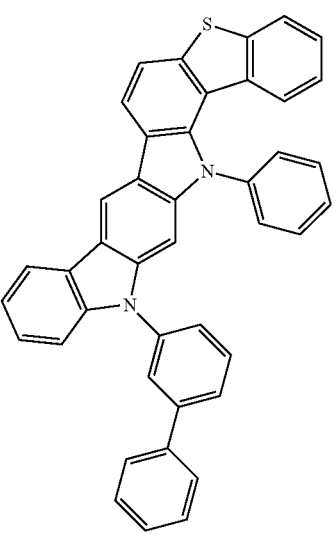

A-167
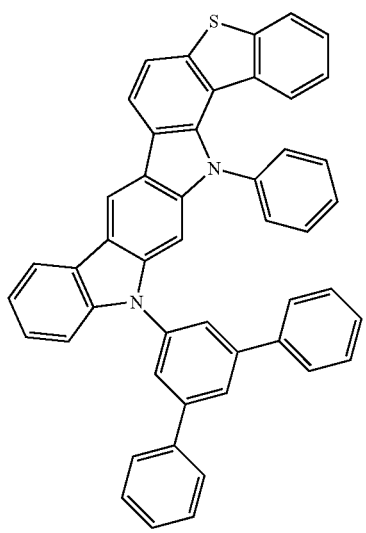
A-168
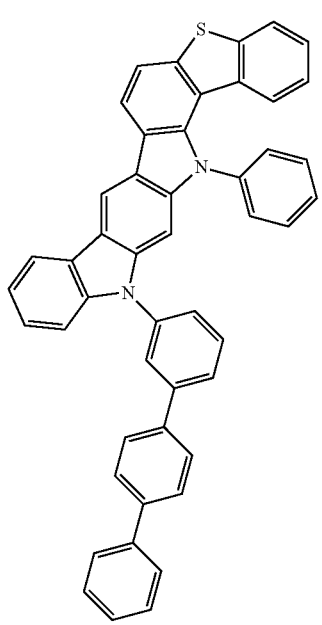
A-169
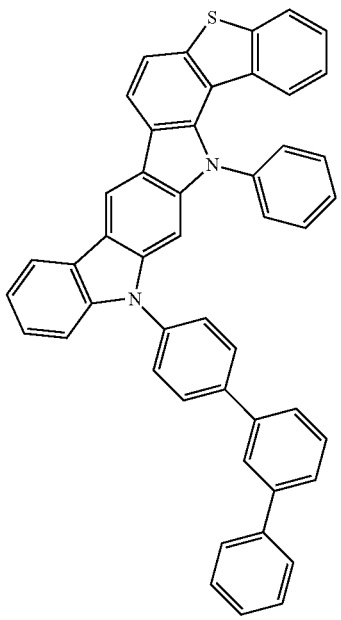
A-170
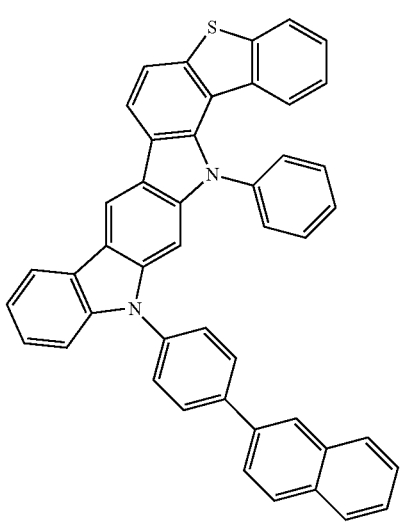
A-171
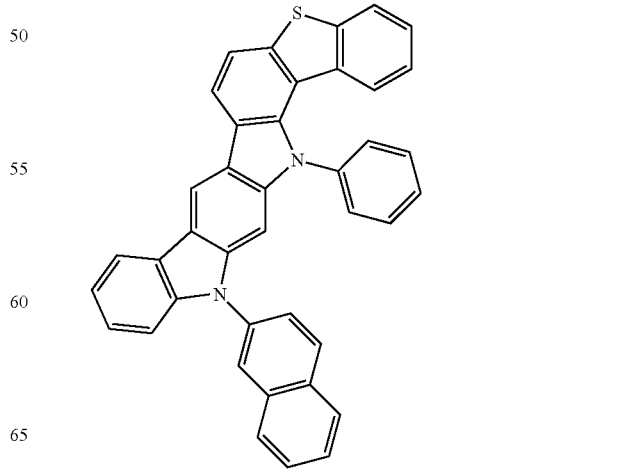

A-172
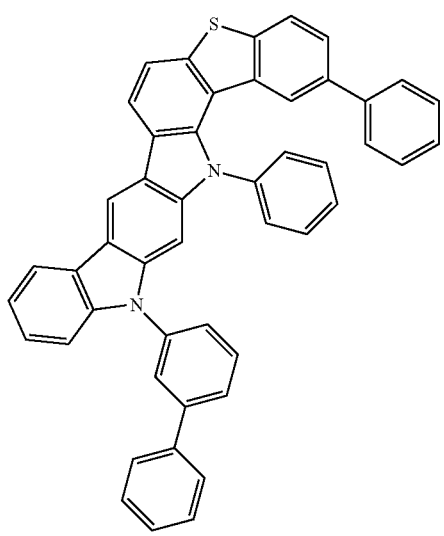
A-173
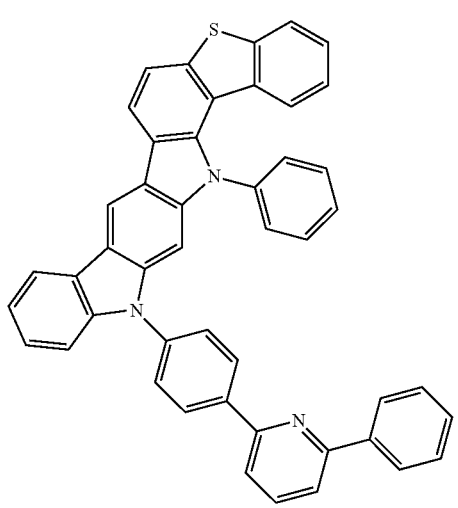
A-174
A-175
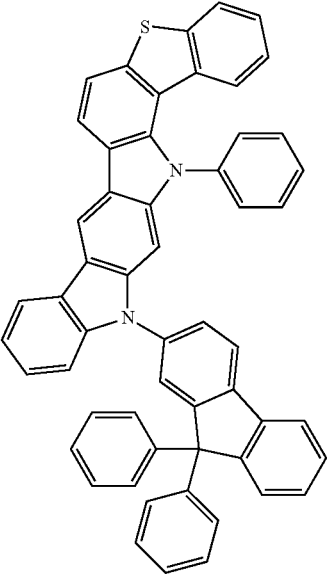
A-176
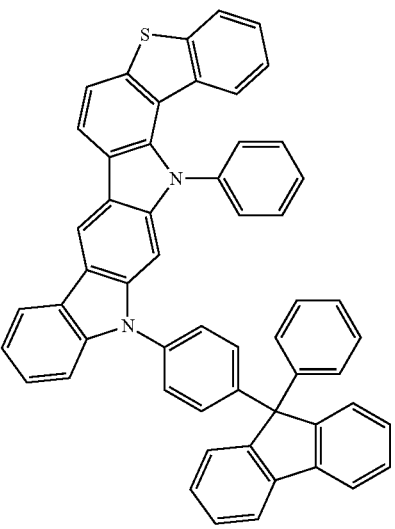

A-177
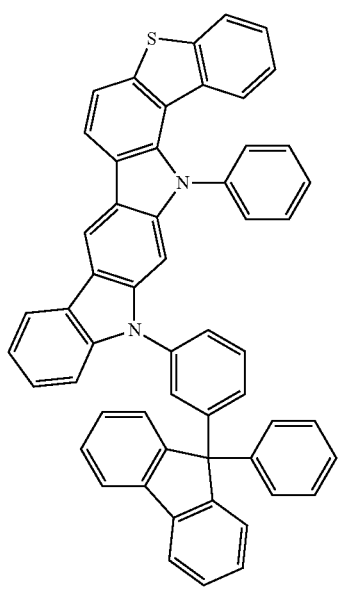
A-178
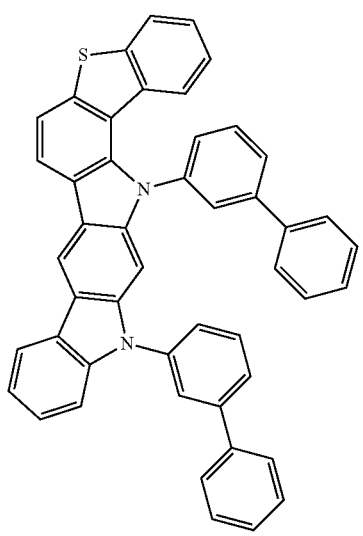
A-179
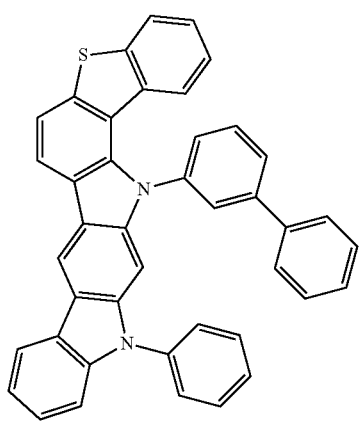
A-180
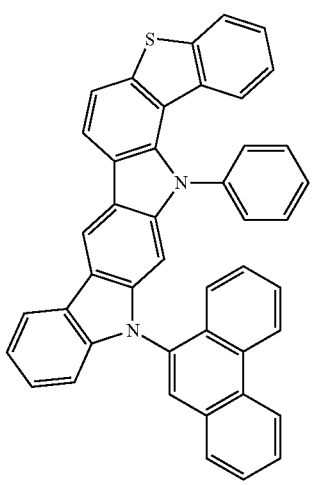
A-183
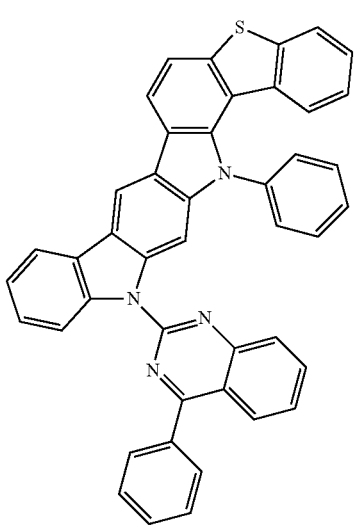
A-184
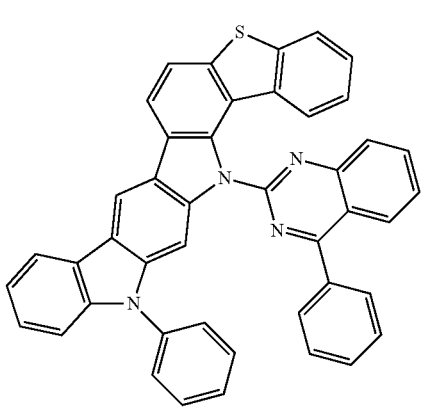

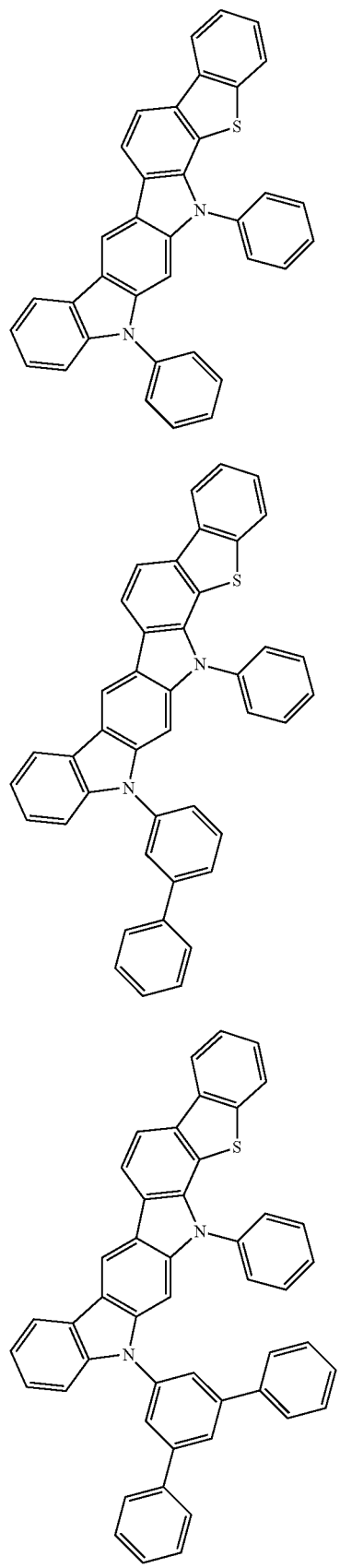
A-242
A-243
A-244
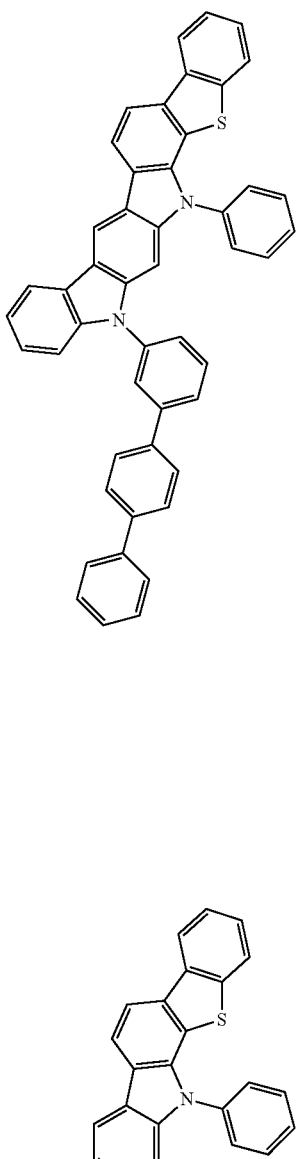
A-245
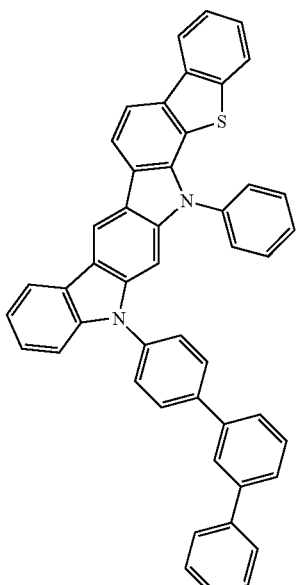
A-246
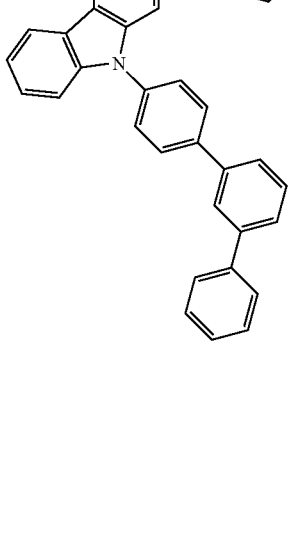

-continued
A-247
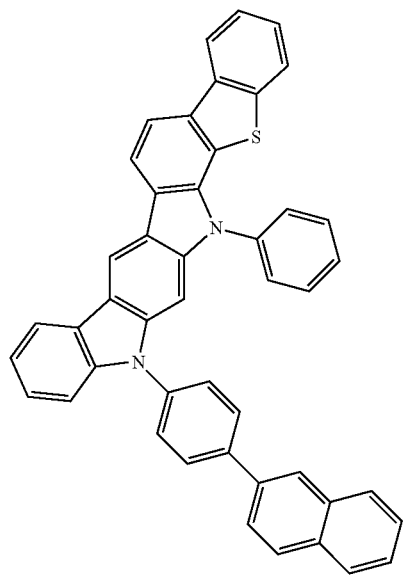
A-248
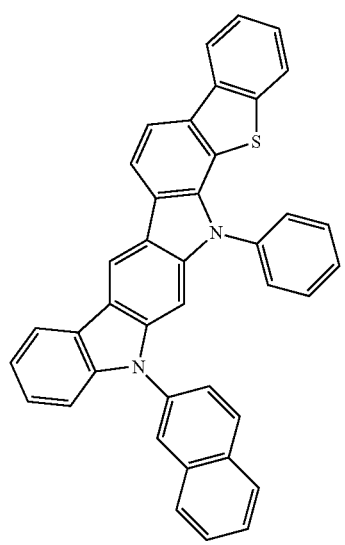
A-249
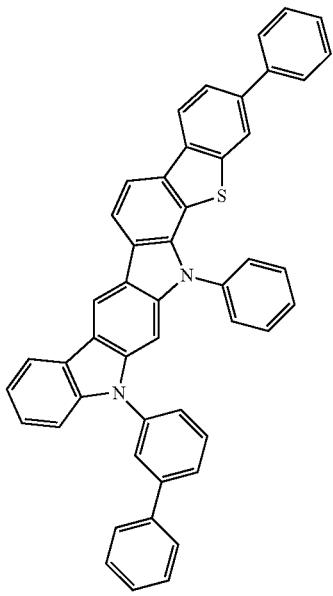
A-250
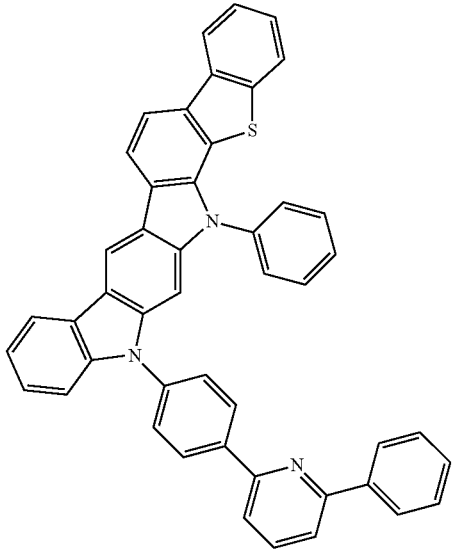

A-251
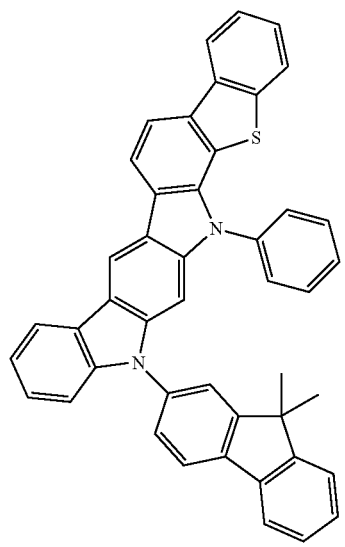
A-252
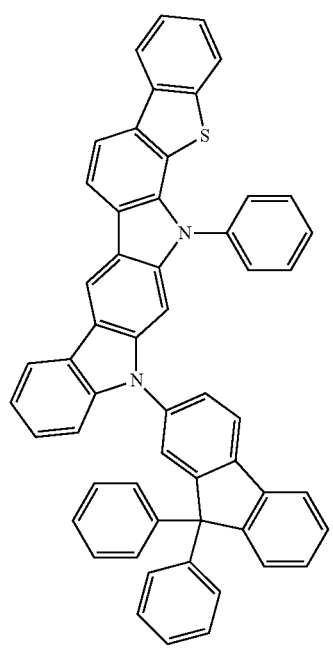
A-253
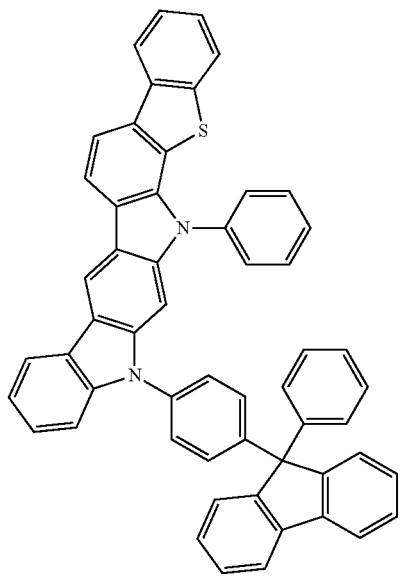
A-254
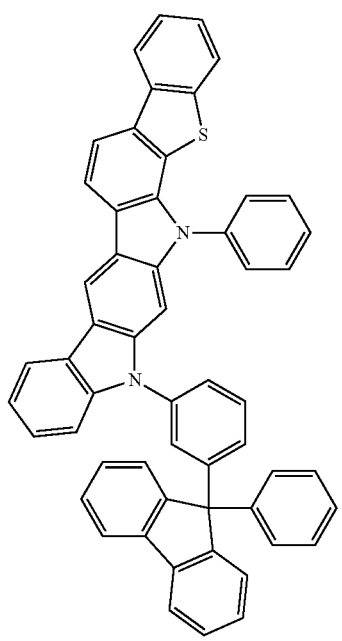

-continued
A-255
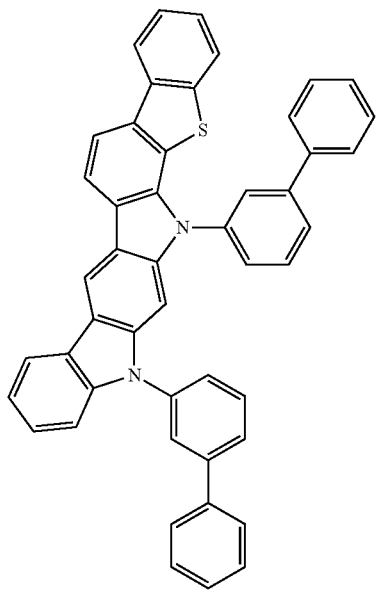
A-256
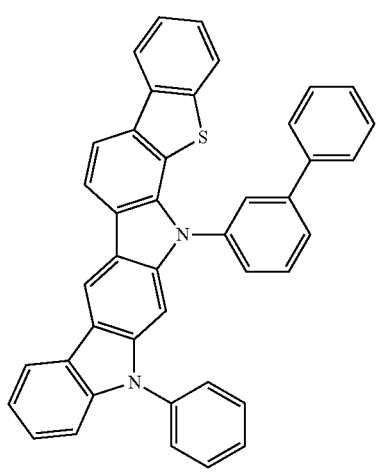
A-257
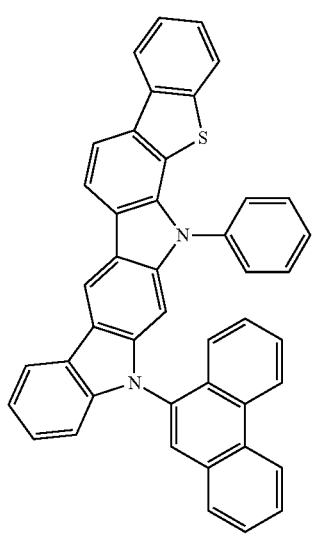
-continued
A-258
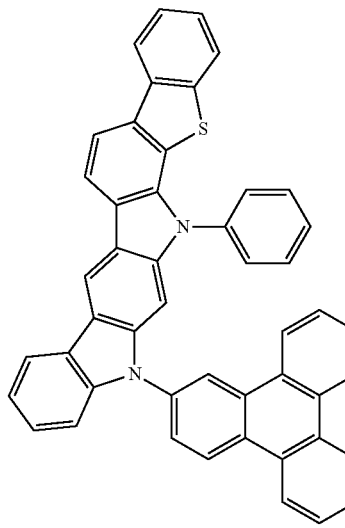
A-259
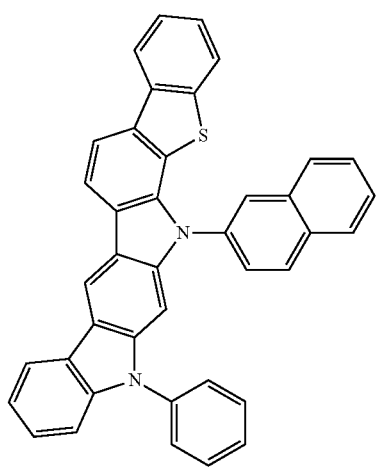
A-260
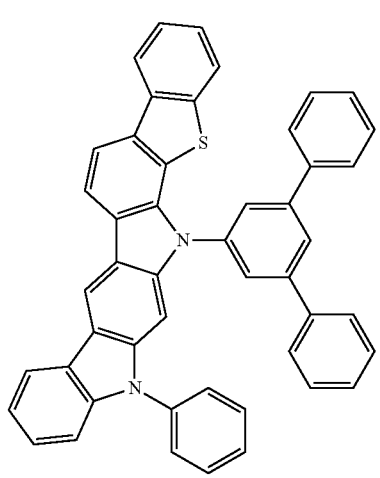

A-261
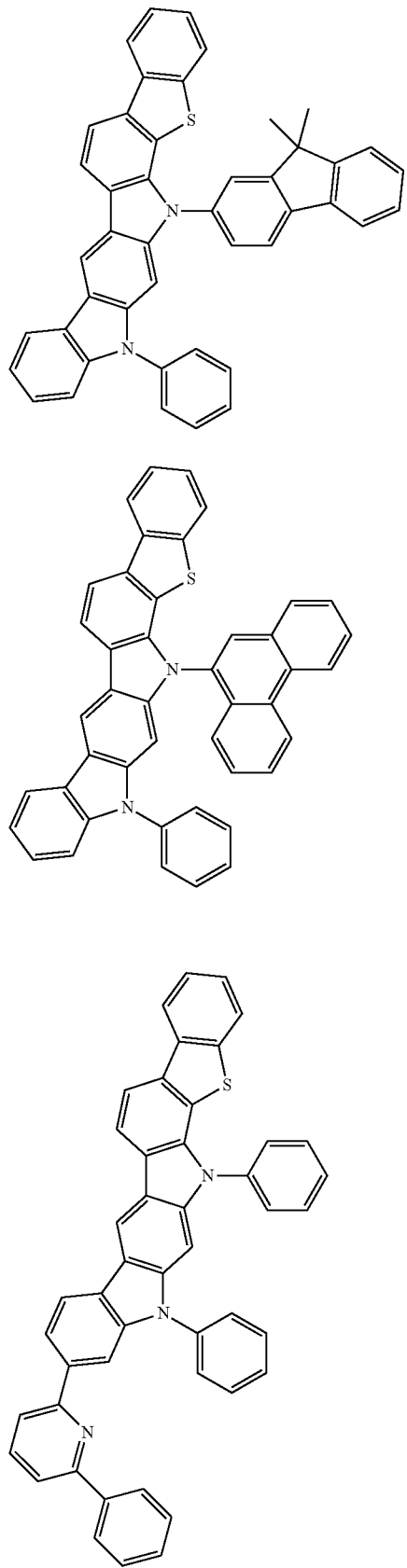
A-262
A-263
A-264
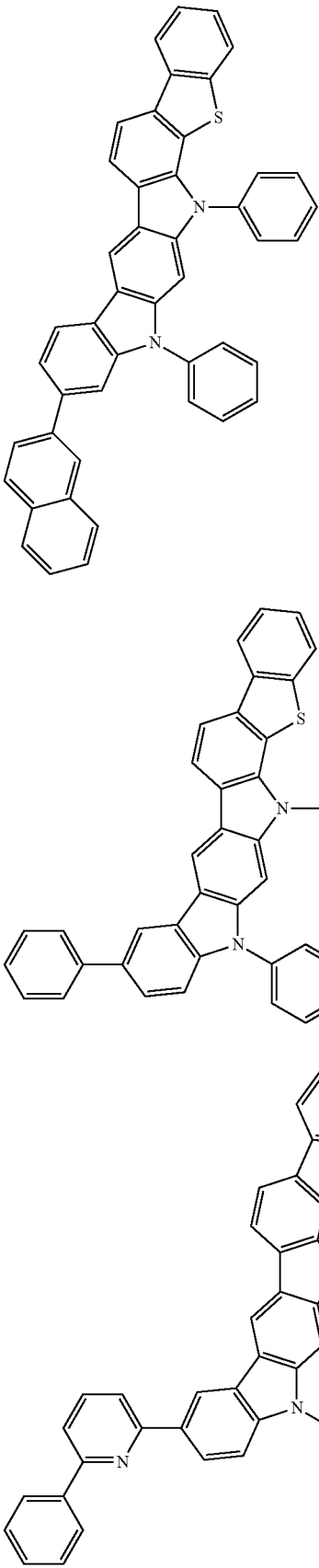
A-265
A-266

A-267 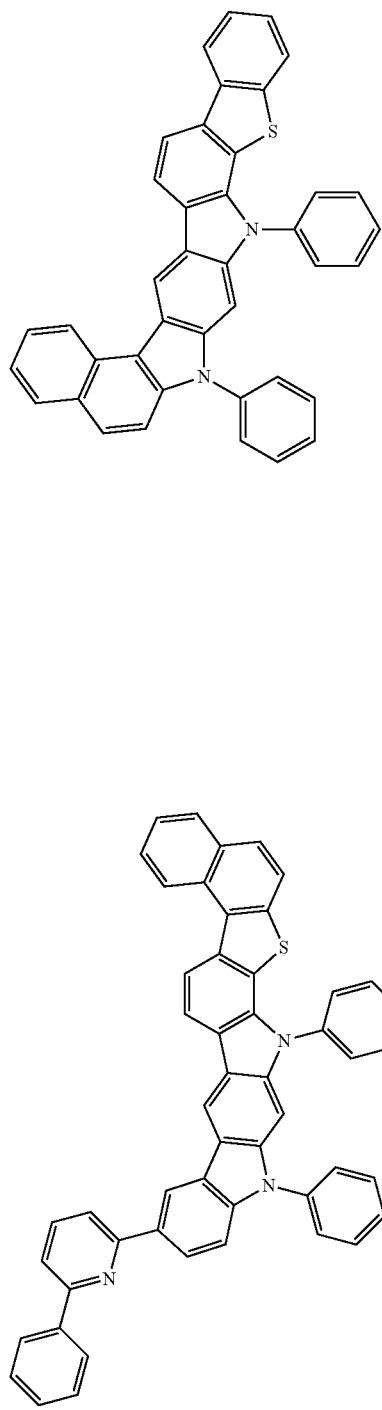
A-268
A-274 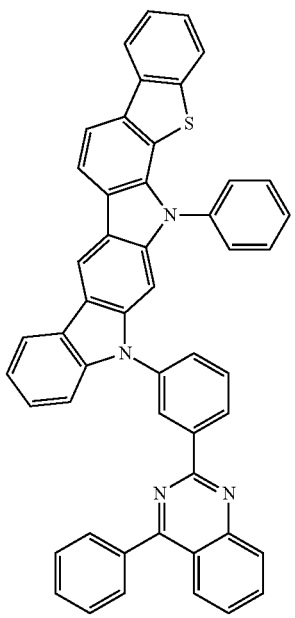
A-275 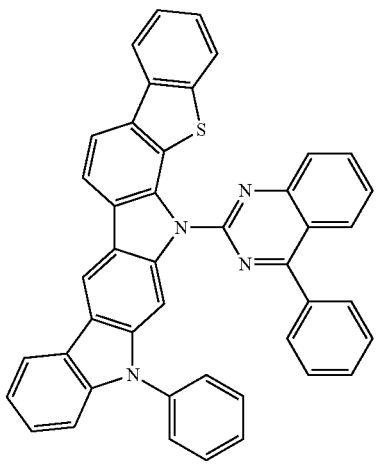
A-276 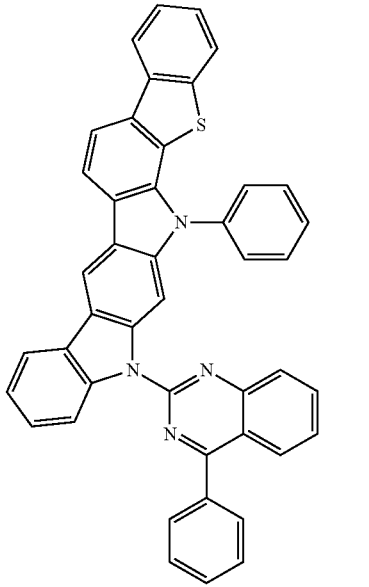

-continued
A-277
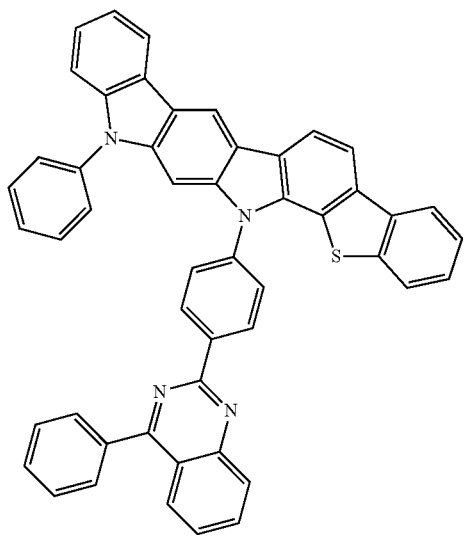
A-278
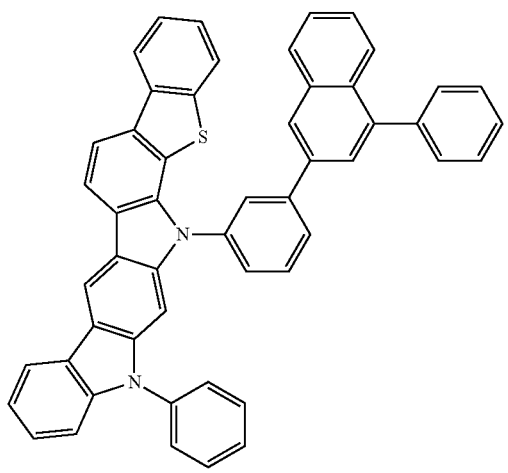
A-279
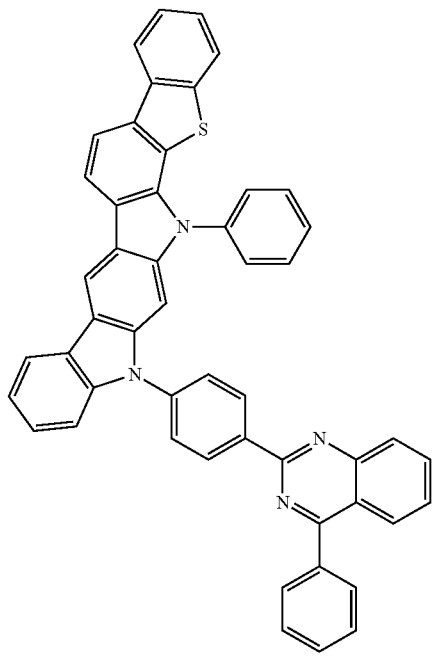
A-280
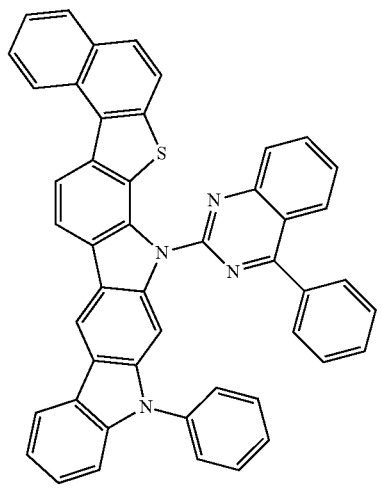

A-281
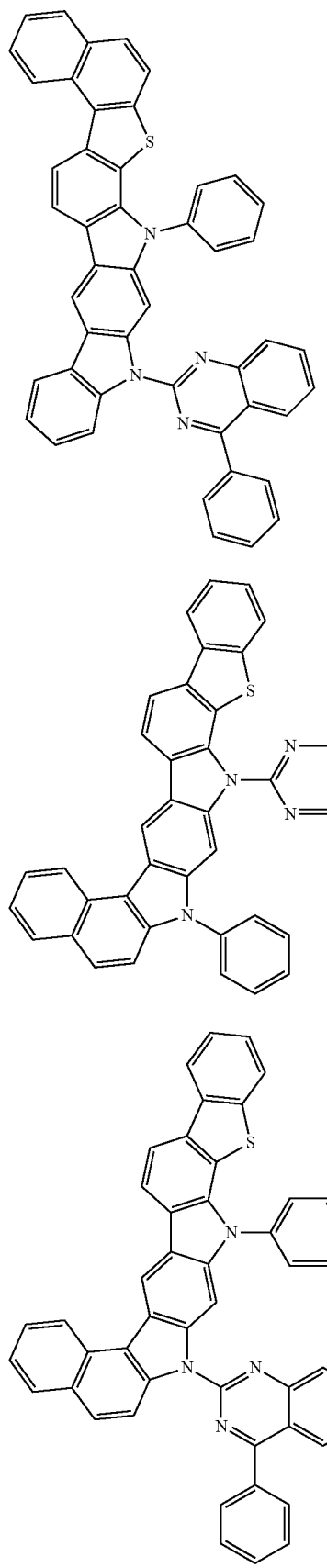
A-282
A-283
A-284
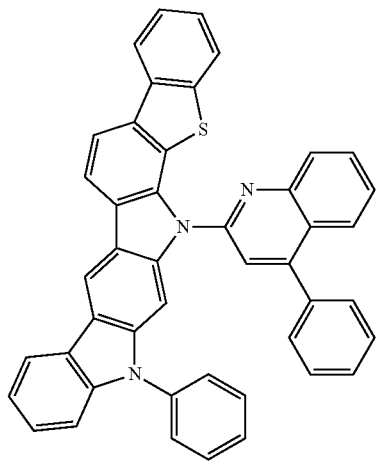
A-285
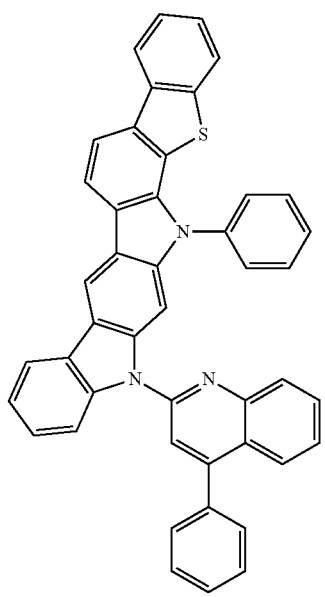
A-286
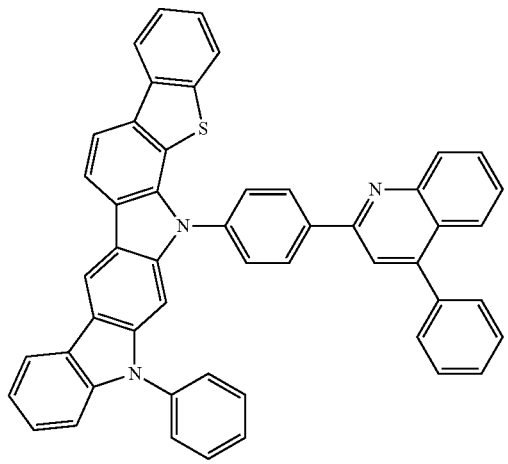

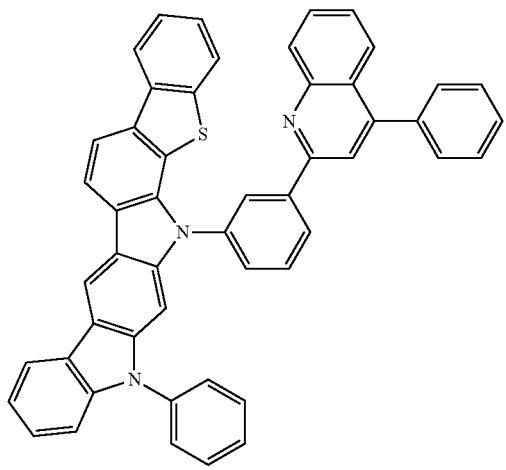
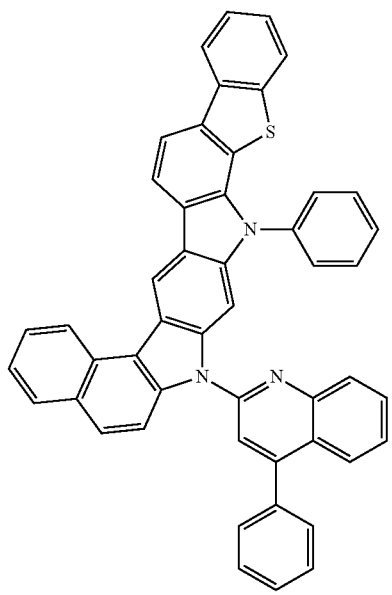

-continued
A-292
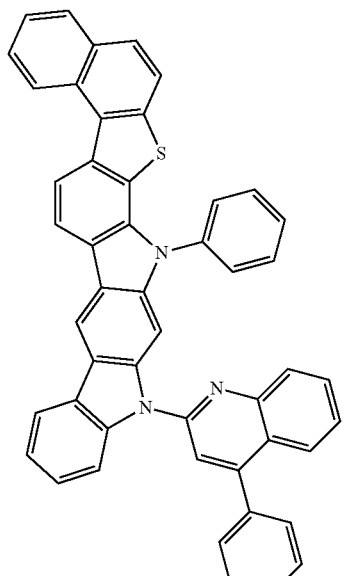
A-293
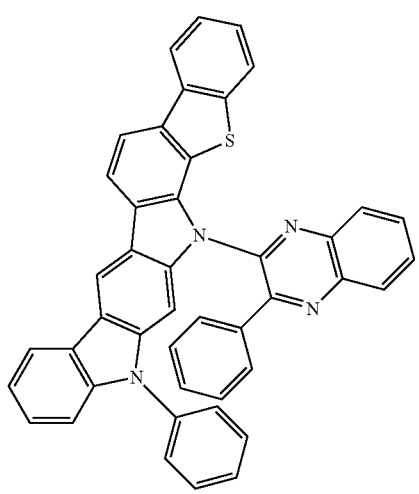
A-294
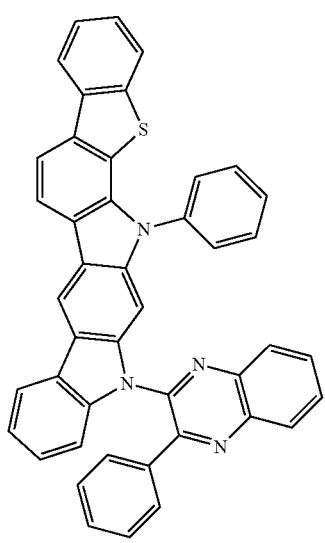
-continued
A-295
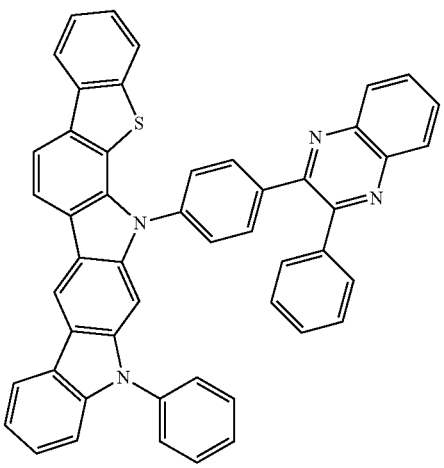
A-296
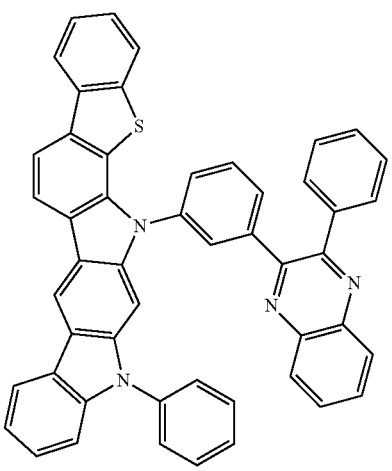
A-297
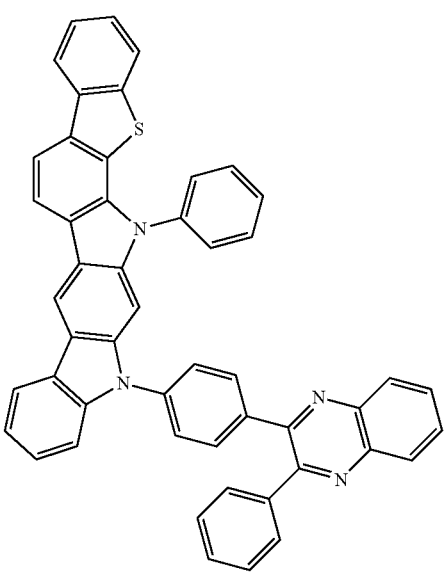

A-314
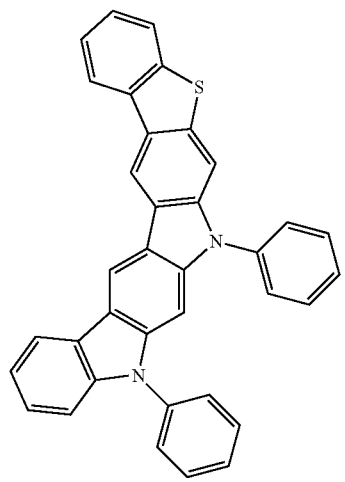
A-315
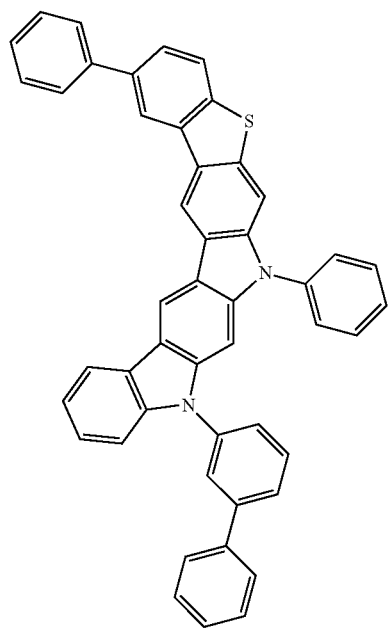
A-316
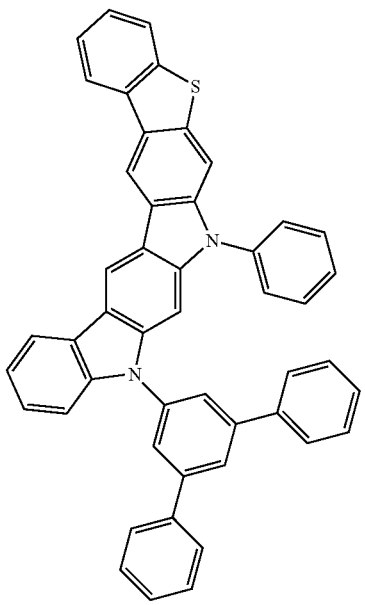
A-317
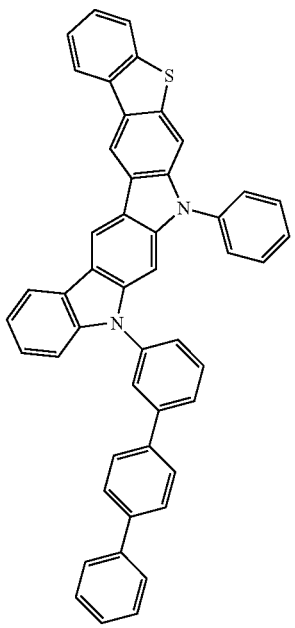

A-318
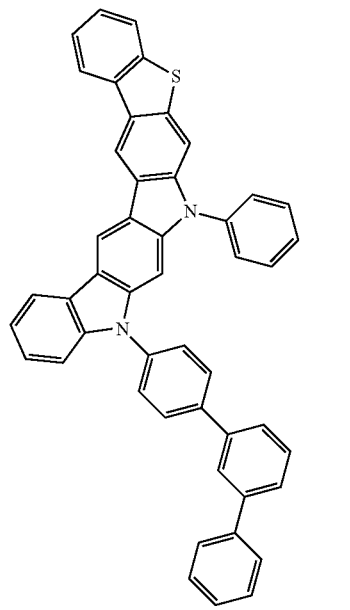
A-320
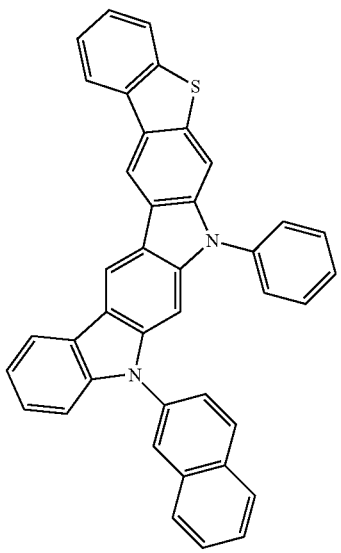
A-319
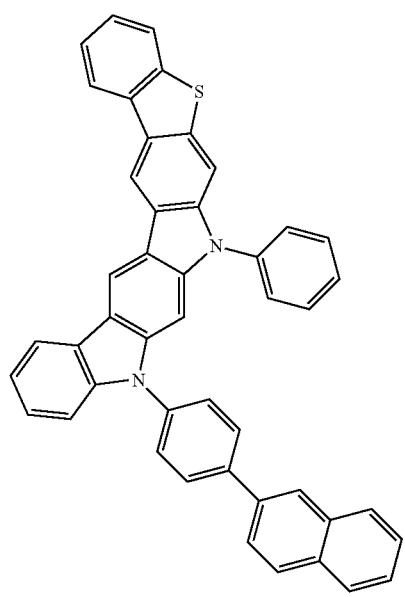
A-321
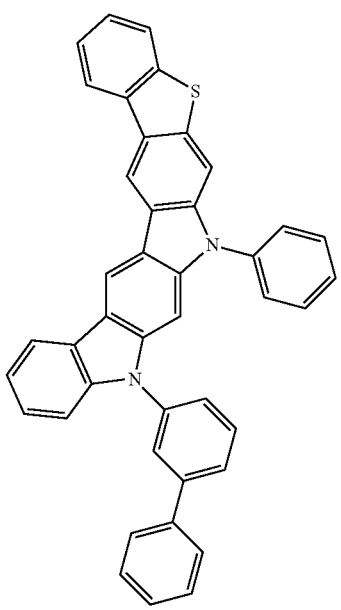

A-322
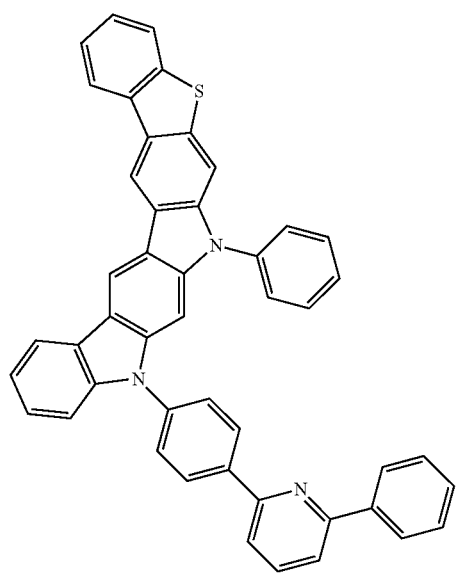
A-323
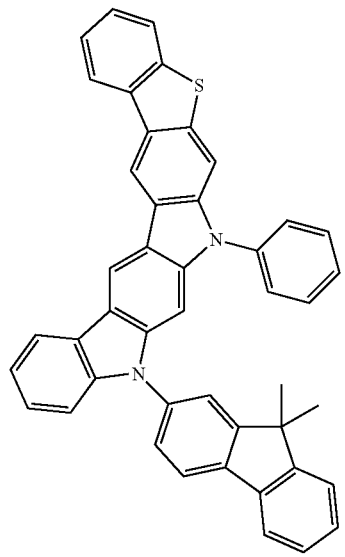
A-324
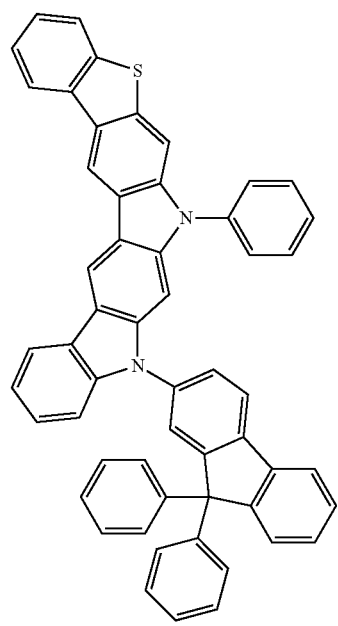
A-325

315
-continued
A-326
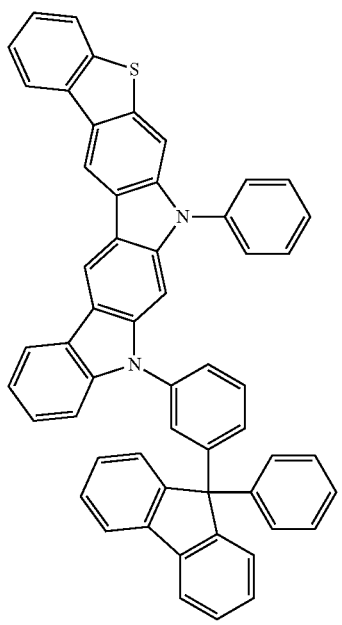
A-327
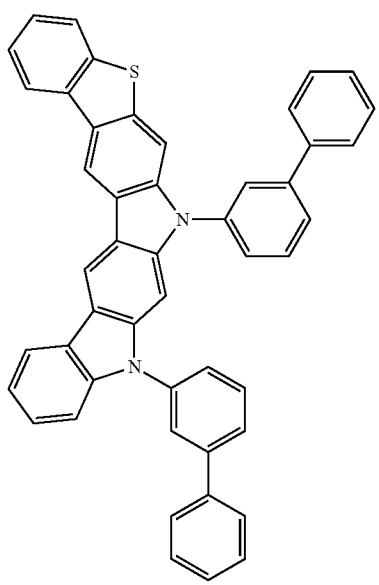
A-328
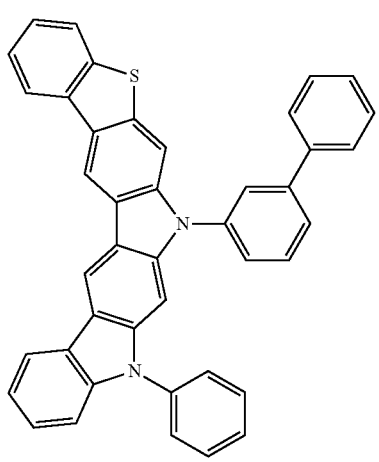
316
-continued
A-329
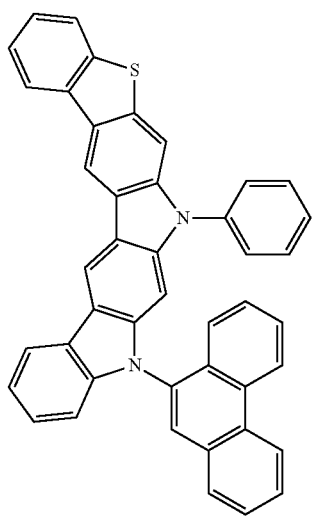
A-332
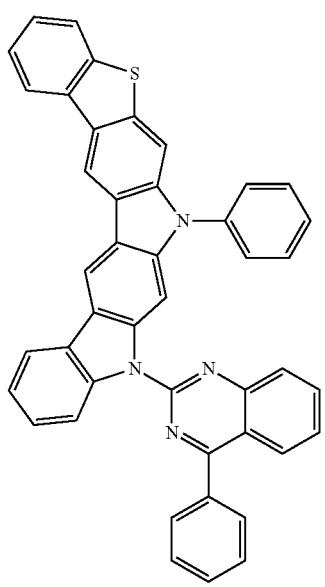
A-333
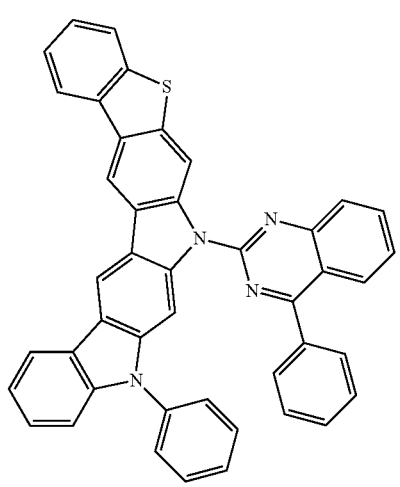

A-350
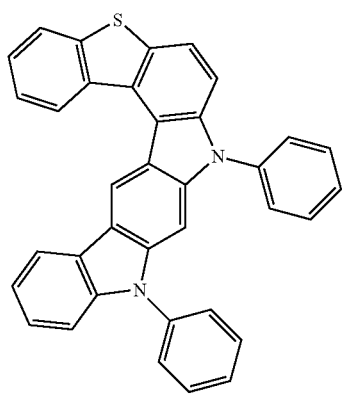
A-351
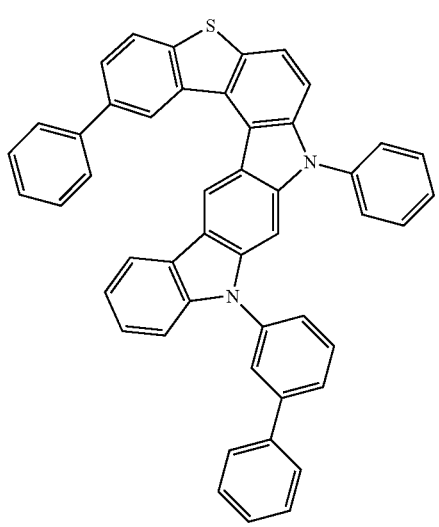
A-352
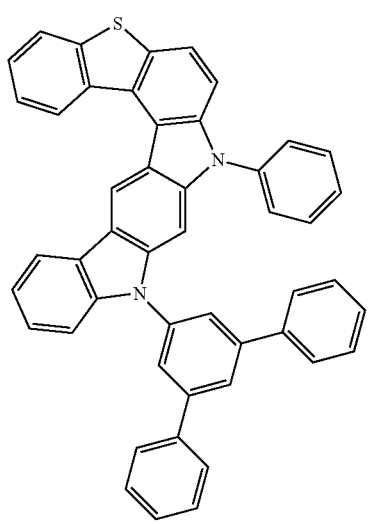
A-353
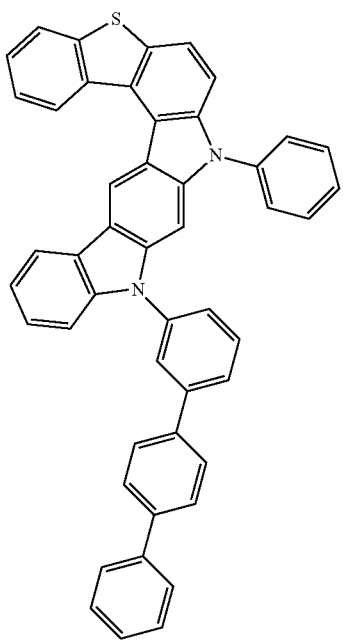
A-354
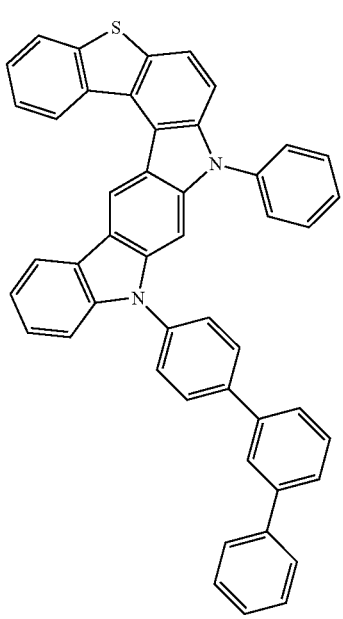

-continued
A-355
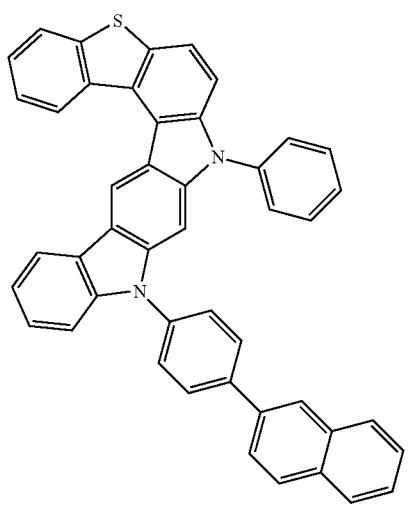
A-356
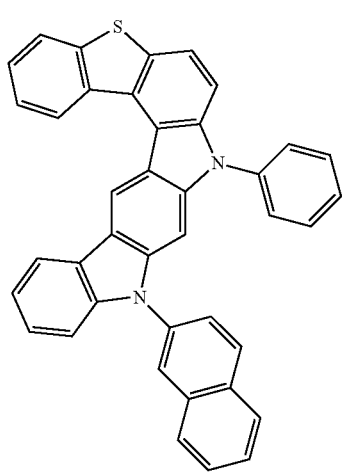
A-357
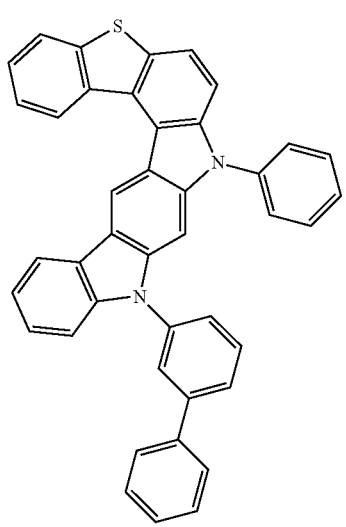
-continued
A-358
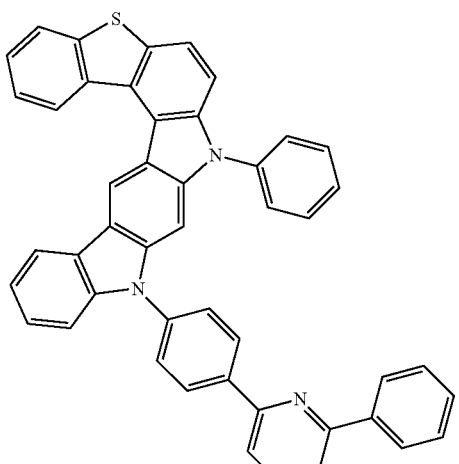
A-359
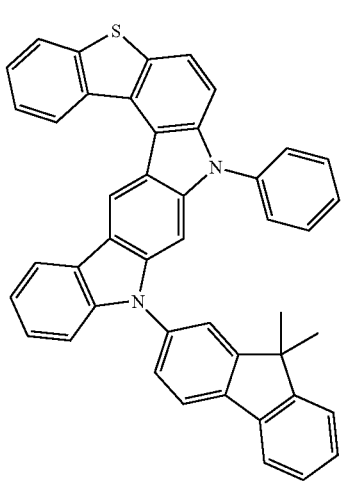
A-360
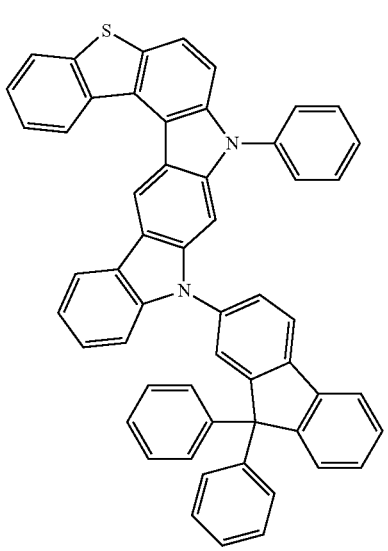

-continued
A-361
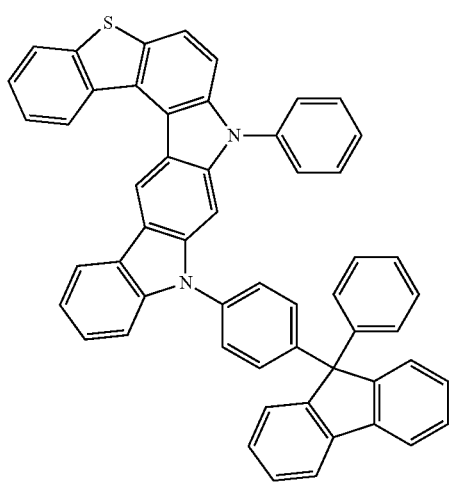
A-362
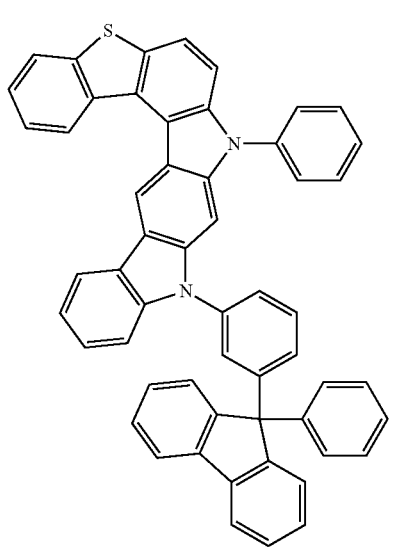
A-363
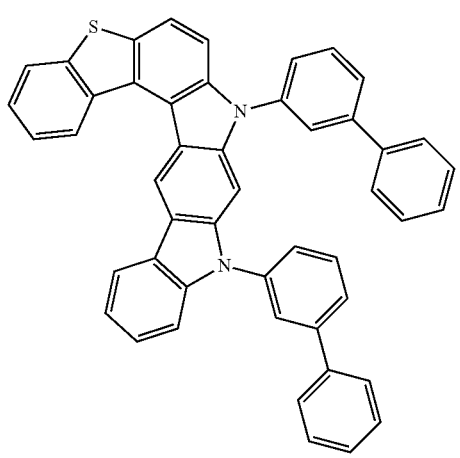
A-364
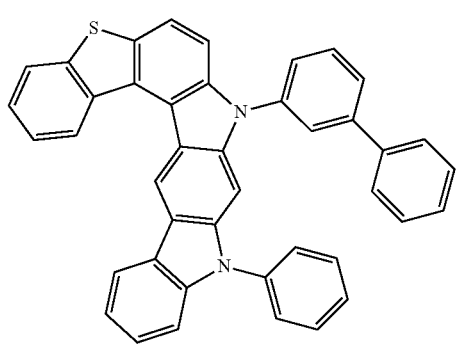
A-365
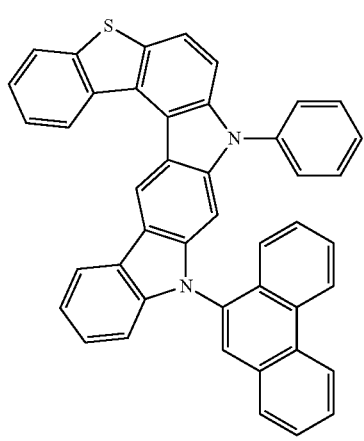
A-368
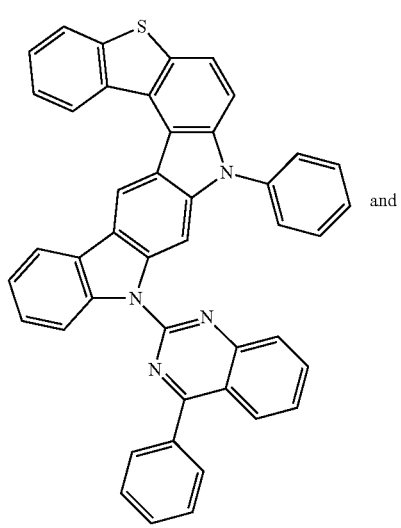
and A-369
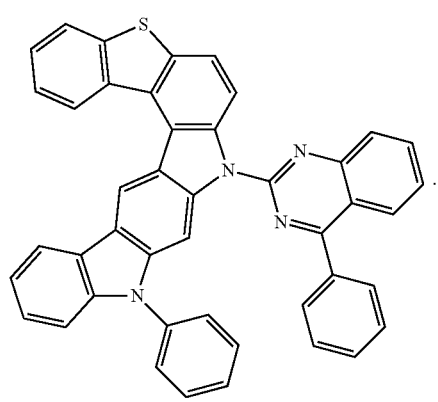
7. An organic electroluminescent device comprising the organic electroluminescent compound according to claim 1.
* * * * *